(12) United States Patent
Fan et al.

(10) Patent No.: US 11,608,336 B2
(45) Date of Patent: Mar. 21, 2023

(54) PRODRUGS OF FUSED-BICYCLIC C5AR ANTAGONISTS

(71) Applicant: CHEMOCENTRYX, INC., Mountain View, CA (US)

(72) Inventors: Pingchen Fan, Fremont, CA (US); Rebecca M. Lui, Mountain View, CA (US); Rajinder Singh, Belmont, CA (US); Venkat Reddy Mali, Cupertino, CA (US); Yibin Zeng, Foster City, CA (US); Penglie Zhang, Foster City, CA (US)

(73) Assignee: CHEMOCENTRYX, INC., San Carlos, CA (US)

( * ) Notice: Subject to any disclaimer, the term of this patent is extended or adjusted under 35 U.S.C. 154(b) by 314 days.

(21) Appl. No.: 16/982,817

(22) PCT Filed: Apr. 1, 2019

(86) PCT No.: PCT/US2019/025165
§ 371 (c)(1),
(2) Date: Sep. 21, 2020

(87) PCT Pub. No.: WO2019/195159
PCT Pub. Date: Oct. 10, 2019

(65) Prior Publication Data
US 2021/0052612 A1  Feb. 25, 2021

Related U.S. Application Data

(60) Provisional application No. 62/651,512, filed on Apr. 2, 2018.

(51) Int. Cl.
*C07D 471/04* (2006.01)
*C07D 487/04* (2006.01)
(Continued)

(52) U.S. Cl.
CPC .......... *C07D 471/04* (2013.01); *A61K 9/0019* (2013.01); *A61K 31/4162* (2013.01);
(Continued)

(58) Field of Classification Search
CPC ...... C07D 471/04; C07D 519/00; A61P 37/02
See application file for complete search history.

(56) References Cited

U.S. PATENT DOCUMENTS 4,925,846 A  5/1990  Deacon et al.
6,893,659 B2  5/2005  Abramovici et al.
(Continued)

FOREIGN PATENT DOCUMENTS

CN    103421006 A    12/2013
WO    02/49993 A3    2/2002
(Continued)

OTHER PUBLICATIONS

International Search Report dated Jul. 19, 2019 corresponding to PCT/US2019/025165 filed Apr. 1, 2019; 14 pages.
(Continued)

*Primary Examiner* — Erich A Leeser
(74) *Attorney, Agent, or Firm* — Mintz Levin Cohn Ferris Glovsky and Popeo PC

(57) ABSTRACT

The present disclosure provides, inter alia, Compounds of Formulae IA, IB, IC, IIA, IIB and IIC or pharmaceutically acceptable salts thereof that are modulators of the C5a receptor. Also provided are pharmaceutical compositions and methods of use including the treatment of diseases or disorders involving pathologic activation from C5a and non-pharmaceutical applications.

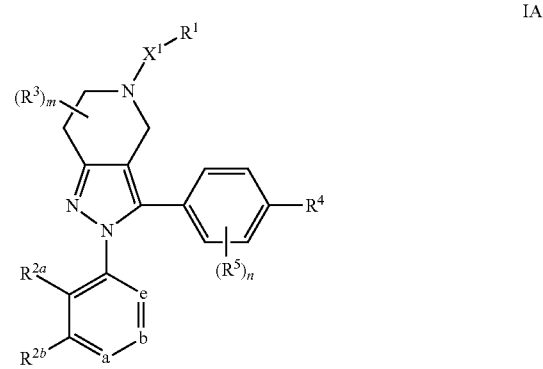

IA

IB

IC (Continued)

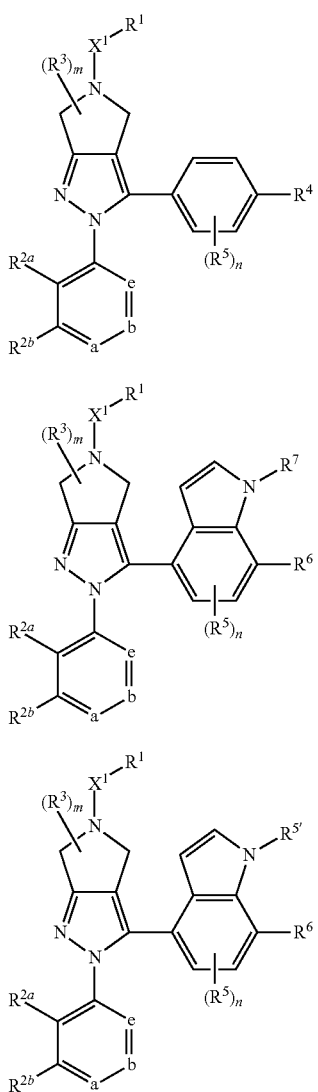

(52) U.S. Cl.
CPC .......... *A61K 31/506* (2013.01); *A61K 31/675* (2013.01); *A61P 9/10* (2018.01); *A61P 9/14* (2018.01); *A61P 11/00* (2018.01); *A61P 13/12* (2018.01); *A61P 19/02* (2018.01); *A61P 27/02* (2018.01); *A61P 35/00* (2018.01); *A61P 37/06* (2018.01); *C07D 487/04* (2013.01); *C07F 9/6561* (2013.01); *A61K 45/06* (2013.01)

(56) References Cited

U.S. PATENT DOCUMENTS

| | | | |
|---|---|---|---|
| 7,145,012 B2 | 12/2006 | Carpino | |
| 7,230,024 B2 | 6/2007 | Carpino et al. | |
| 7,531,531 B2 | 5/2009 | Fancelli et al. | |
| 7,541,354 B2 | 6/2009 | Fancelli et al. | |
| 7,902,179 B2 | 3/2011 | Tanaka et al. | |
| 8,445,515 B2 | 5/2013 | Fan et al. | |
| 8,846,949 B2 | 9/2014 | Winters et al. | |
| 8,883,808 B2 | 11/2014 | Bonaventure et al. | |
| 8,906,938 B2 | 12/2014 | Fan et al. | |
| 9,126,939 B2 | 9/2015 | Fan et al. | |
| 9,573,897 B2 | 2/2017 | Fan et al. | |
| 10,035,768 B2 | 7/2018 | Fan et al. | |
| 10,329,314 B2 | 6/2019 | Fan et al. | |
| 10,562,896 B2* | 2/2020 | Fan | C07D 519/00 |
| 10,683,294 B2* | 6/2020 | Fan | C07D 487/04 |
| 10,759,807 B2 | 9/2020 | Fan et al. | |
| 10,828,285 B2 | 11/2020 | Fan et al. | |
| 11,384,079 B2* | 7/2022 | Fan | A61P 37/02 |
| 11,478,460 B2 | 10/2022 | Fan et al. | |
| 11,479,553 B2 | 10/2022 | Fan et al. | |
| 11,485,737 B2 | 11/2022 | Fan et al. | |
| 2004/0116425 A1 | 6/2004 | Li et al. | |
| 2004/0147546 A1 | 7/2004 | Tanaka et al. | |
| 2004/0214855 A1 | 10/2004 | Carpino et al. | |
| 2004/0214856 A1 | 10/2004 | Carpino et al. | |
| 2006/0205948 A1* | 9/2006 | Carpino | A61P 1/00 548/310.7 |
| 2007/0112015 A1 | 5/2007 | Hurt et al. | |
| 2008/0267887 A1 | 10/2008 | Yuan et al. | |
| 2010/0311753 A1 | 12/2010 | Fan et al. | |
| 2011/0275639 A1 | 11/2011 | Fan et al. | |
| 2012/0149734 A1 | 6/2012 | Biftu et al. | |
| 2013/0184253 A1 | 7/2013 | Adams et al. | |
| 2014/0051688 A1 | 2/2014 | Winters et al. | |
| 2015/0141425 A1 | 5/2015 | Fan et al. | |
| 2017/0065604 A1 | 3/2017 | Fan et al. | |
| 2017/0114017 A1 | 4/2017 | Fan et al. | |
| 2019/0060321 A1 | 2/2019 | Fan et al. | |
| 2019/0062275 A1 | 2/2019 | Fan et al. | |
| 2019/0300526 A1 | 10/2019 | Fan et al. | |
| 2021/0009594 A1* | 1/2021 | Fan | C07D 487/04 |

FOREIGN PATENT DOCUMENTS

| | | |
|---|---|---|
| WO | 02/49993 A2 | 6/2002 |
| WO | 03/029187 A1 | 4/2003 |
| WO | 03/082826 A1 | 10/2003 |
| WO | 03/082828 A1 | 10/2003 |
| WO | 03/084524 A1 | 10/2003 |
| WO | 2004/018460 A1 | 3/2004 |
| WO | 2004/043925 A2 | 5/2004 |
| WO | 2004/043925 A3 | 5/2004 |
| WO | 2004/094421 A1 | 11/2004 |
| WO | 2004/094429 A1 | 11/2004 |
| WO | 2004/100975 A1 | 11/2004 |
| WO | 2005/007087 A2 | 1/2005 |
| WO | 2005/007087 A3 | 1/2005 |
| WO | 2009/155565 A1 | 12/2009 |
| WO | 2010/075257 A1 | 7/2010 |
| WO | 2011/163640 A2 | 12/2011 |
| WO | 2013/016197 A1 | 1/2013 |
| WO | 2014/028805 A1 | 2/2014 |
| WO | 2015/086512 A1 | 6/2015 |
| WO | 2017/176620 A2 | 10/2017 |

43 Claims, 2 Drawing Sheets

(51) Int. Cl.

| | |
|---|---|
| *A61P 19/02* | (2006.01) |
| *A61P 27/02* | (2006.01) |
| *A61P 9/10* | (2006.01) |
| *A61P 37/06* | (2006.01) |
| *A61P 13/12* | (2006.01) |
| *A61P 11/00* | (2006.01) |
| *A61P 9/14* | (2006.01) |
| *A61P 35/00* | (2006.01) |
| *A61K 9/00* | (2006.01) |
| *A61K 45/06* | (2006.01) |
| *A61K 31/4162* | (2006.01) |
| *A61K 31/506* | (2006.01) |
| *A61K 31/675* | (2006.01) |
| *C07F 9/6561* | (2006.01) |

(56) References Cited

FOREIGN PATENT DOCUMENTS

| WO | 2018/222598 A1 | 12/2018 |
| WO | 2018/222601 A1 | 12/2018 |
| WO | 2019/126424 A1 | 6/2019 |
| WO | 2019/126431 A1 | 6/2019 |

OTHER PUBLICATIONS

Strachan, Anna J. et al., "A New Small Molecule C5a Receptor Antagonist Inhibits the Reverse-Passive Arthus Reaction and Endotoxic Shock in Rats," *The Journal of Immunology* (Accepted for publication Apr. 6, 2000); 164:6560-6565.

Woodruff, Trent M. et al., "A Potent Human C5a Receptor Antagonist Protects against Disease Pathology in a Rat Model of Inflammatory Bowel Disease," *The Journal of Immunology* (Accepted for publication Sep. 9, 2003); 171:5514-5520.

U.S. Appl. No. 17/735,283, filed May 3, 2022, Fan et al.

U.S. Appl. No. 17/931,801, filed Sep. 13, 2022, Fan et al.

International Search Report and Written Opinion dated Aug. 24, 2018 corresponding to PCT/US2018/034905 filed May 29, 2018 (13 pages).

International Search Report and Written Opinion dated Aug. 23, 2018 corresponding to PCT/US2018/034908 filed May 29, 2018 (13 pages).

International Search Report and Written Opinion dated Mar. 25, 2019 corresponding to PCT/US2018/066667 filed Dec. 20, 2018 (7 pages).

International Search Report and Written Opinion dated Mar. 22, 2019 corresponding to PCT/US2018/066677 filed Dec. 20, 2018 (7 pages).

Extended European Search Report completed Aug. 27, 2020 corresponding to EP 18809537 (4 pages).

Extended European Search Report completed Aug. 27, 2020 corresponding to EP 18809125 (4 pages).

Extended European Search Report completed Apr. 19, 2021 corresponding to EP 18890906 (6 pages).

Extended European Search Report completed May 7, 2021 corresponding to EP 18890906 (8 pages).

Extended European Search Report dated Dec. 1, 2021 corresponding to EP19782402.2 filed Apr. 1, 2019; 8 pages.

An, GuiPeng et al., "Role of C5a-C5aR axis in the development of atherosclerosis," *Sci China Life Sci* (2014; accepted Jul. 8, 2014) 57:790-794.

Bao, Lihua et al., "C5a promotes development of experimental lupus nephritis which can be blocked with a specific receptor antagonist," *Eur. J. Immunol.* (Jun. 20, 2005); 35:2496-2506.

Cravedi, P. et al., "Immune Cell-Derived C3a and C5a Costimulate Human T Cell Alloimmunity," *Am. J. Transplant* (Jun. 27, 2013); 13(10):2530-2539.

Darling, Victoria R. et al., "Immunological Effects and Therapeutic Role of C5a in Cancer," *Expert Rev Clin Immunol.* (Feb. 1, 2015); 11(2):255-263.

Guo, Ren-Feng et al., "Role of C5a in Inflammatory Responses," *Annu. Rev. Immunol.* (Jan. 7, 2005); 23:821-852.

Huber-Lang, Markus S. et al., "Role of Complement in Multi-Organ Dysfunction," *The Complement System*, Abstract, (© 2004; Print/DOI: 10.1007/1-4020-8056-5_22); pp. 465-480.

Lee, Hyun et al., "Receptors for complement C5a. The importance of C5aR and the enigmatic role of C5L2," *Immunology and Cell Biology* (Jan. 29, 2008); 86:153-160.

Lu, Yi et al., "C5a stimulates the proliferation of breast cancer cells via akt-dependent RGC-32 gene activation," *Oncology Reports* (2014; Accepted Aug. 14, 2014); 32:2817-2823.

Pandey, Manoj Kumar, "Molecular Basis for Downregulation of C5a-Mediated Inflammation by IgG1 Immune Complexes in Allergy and Asthma," *Curr Allergy Asthma Rep* (Sep. 8, 2013) 13:596-606.

Seow, Vernon et al., "Inflammatory Responses Induced by Lipopolysaccharide Are Amplified in Primary Human Monocytes but Suppressed in Macrophages by Complement Protein C5a," *J Immunol* (2013; prepublished online Sep. 16, 2013) 191:4308-4316.

Winters, Michael P. et al., "Discovery and SAR of novel tetrahydropyrrolo[3,4-c]pyrazoles as inhibitors of the N-type calcium channel," *Bioorg. Med. Chem. Lett.* (avail online Mar. 27, 2014); 24:2053-2056.

\* cited by examiner

PRODRUGS OF FUSED-BICYCLIC C5AR ANTAGONISTS

CROSS-REFERENCES TO RELATED APPLICATIONS

This application claims the benefit of priority under 35 U.S.C. § 119(e) to U.S. Provisional Application Ser. No. 62/651,512 filed Apr. 2, 2018, the disclosure of which is incorporated herein by reference in its entirety.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The complement system plays a central role in the clearance of immune complexes and in immune responses to infectious agents, foreign antigens, virus infected cells and tumor cells. Inappropriate or excessive activation of the complement system can lead to harmful, and even potentially life-threatening consequences due to severe inflammation and resulting tissue destruction. These consequences are clinically manifested in various disorders including septic shock; myocardial, as well as, intestinal ischemia/reperfusion injury; graft rejection; organ failure; nephritis; pathological inflammation; and autoimmune diseases.

The complement system is composed of a group of proteins that are normally present in the serum in an inactive state. Activation of the complement system encompasses mainly three distinct pathways, i.e., the classical, the alternative, and the lectin pathway (V. M. Holers, *In Clinical Immunology: Principles and Practice*, ed. R. R. Rich, Mosby Press; 1996, 363-391): 1) The classical pathway is a calcium/magnesium-dependent cascade, which is normally activated by the formation of antigen-antibody complexes. It can also be activated in an antibody-independent manner by the binding of C-reactive protein, complexed with ligand, and by many pathogens including gram-negative bacteria. 2) The alternative pathway is a magnesium-dependent cascade which is activated by deposition and activation of C3 on certain susceptible surfaces (e.g. cell wall polysaccharides of yeast and bacteria, and certain biopolymer materials). 3) The lectin pathway involves the initial binding of mannose-binding lectin and the subsequent activation of C2 and C4, which are common to the classical pathway (Matsushita, M. et al., *J. Exp. Med.* 176: 1497-1502 (1992); Suankratay, C. et al., *J. Immunol.* 160: 3006-3013 (1998)).

The activation of the complement pathway generates biologically active fragments of complement proteins, e.g. C3a, C4a and C5a anaphylatoxins and C5b-9 membrane attack complexes (MAC), all which mediate inflammatory responses by affecting leukocyte chemotaxis; activating macrophages, neutrophils, platelets, mast cells and endothelial cells; and increasing vascular permeability, cytolysis and tissue injury.

Complement C5a is one of the most potent proinflammatory mediators of the complement system. (The anaphylactic C5a peptide is 100 times more potent, on a molar basis, in eliciting inflammatory responses than C3a.) C5a is the activated form of C5 (190 kD, molecular weight). C5a is present in human serum at approximately 80 µg/ml (Kohler, P. F. et al, *J. Immunol.* 99: 1211-1216 (1967)). It is composed of two polypeptide chains, α and β, with approximate molecular weights of 115 kD and 75 kD, respectively (Tack, B. F. et al., *Biochemistry* 18: 1490-1497 (1979)). Biosynthesized as a single-chain promolecule, C5 is enzymatically cleaved into a two-chain structure during processing and secretion. After cleavage, the two chains are held together by at least one disulphide bond as well as noncovalent interactions (Ooi, Y. M. et al, *J. Immunol.* 124: 2494-2498 (1980)).

C5 is cleaved into the C5a and C5b fragments during activation of the complement pathways. The convertase enzymes responsible for C5 activation are multi-subunit complexes of C4b, C2a, and C3b for the classical pathway and of $(C3b)_2$, Bb, and P for the alternative pathway (Goldlust, M. B. et al., *J. Immunol.* 113: 998-1007 (1974); Schreiber, R. D. et al, *Proc. Natl. Acad. Sci.* 75: 3948-3952 (1978)). C5 is activated by cleavage at position 74-75 (Arg-Leu) in the α-chain. After activation, the 11.2 kD, 74 amino acid peptide C5a from the amino-terminus portion of the α-chain is released. Both C5a and C3a are potent stimulators of neutrophils and monocytes (Schindler, R. et al., *Blood* 76: 1631-1638 (1990); Haeffner-Cavaillon, N. et al., *J. Immunol.* 138: 794-700 (1987); Cavaillon, J. M. et al., *Eur. J. Immunol.* 20: 253-257 (1990)).

In addition to its anaphylatoxic properties, C5a induces chemotactic migration of neutrophils (Ward, P. A. et al., *J. Immunol.* 102: 93-99 (1969)), eosinophils (Kay, A. B. et al., *Immunol.* 24: 969-976 (1973)), basophils (Lett-Brown, M. A. et al., *J. Immunol.* 117: 246-252 1976)), and monocytes (Snyderman, R. et al., *Proc. Soc. Exp. Biol. Med.* 138: 387-390 1971)). Both C5a and C5b-9 activate endothelial cells to express adhesion molecules essential for sequestration of activated leukocytes, which mediate tissue inflammation and injury (Foreman, K. E. et al., *J. Clin. Invest.* 94: 1147-1155 (1994); Foreman, K. E. et al., *Inflammation* 20: 1-9 (1996); Rollins, S. A. et al., *Transplantation* 69: 1959-1967 (2000)). C5a also mediates inflammatory reactions by causing smooth muscle contraction, increasing vascular permeability, inducing basophil and mast cell degranulation and inducing release of lysosomal proteases and oxidative free radicals (Gerard, C. et al., *Ann. Rev. Immunol.* 12: 775-808 (1994)). Furthermore, C5a modulates the hepatic acute-phase gene expression and augments the overall immune response by increasing the production of TNF-α, IL-1-β, IL-6, IL-8, prostaglandins and leukotrienes (Lambris, J. D. et al., *In: The Human Complement System in Health and Disease*, Volanakis, J. E. ed., Marcel Dekker, New York, pp. 83-118).

The anaphylactic and chemotactic effects of C5a are believed to be mediated through its interaction with the C5a receptor. The human C5a receptor (C5aR) is a 52 kD membrane bound G protein-coupled receptor, and is expressed on neutrophils, monocytes, basophils, eosinophils, hepatocytes, lung smooth muscle and endothelial cells, and renal glomerular tissues (Van-Epps, D. E. et al., *J. Immunol.* 132: 2862-2867 (1984); Haviland, D. L. et al., *J. Immunol.* 154:1861-1869 (1995); Wetsel, R. A., *Immunol. Leff.* 44: 183-187 (1995); Buchner, R. R. et al, *Immunol.* 155: 308-315 (1995); Chenoweth, D. E. et al, *Proc. Natl. Acad. Sci.* 75: 3943-3947 (1978); Zwirner, J. et al., *Mol. Immunol.*

36:877-884 (1999)). The ligand-binding site of C5aR is complex and consists of at least two physically separable binding domains. One binds the C5a amino terminus (amino acids 1-20) and disulfide-linked core (amino acids 21-61), while the second binds the C5a carboxy-terminal end (amino acids 62-74) (Wetsel, R. A., Curr. Opin. Immunol. 7: 48-53 (1995)).

C5a plays important roles in inflammation and tissue injury. In cardiopulmonary bypass and hemodialysis, C5a is formed as a result of activation of the alternative complement pathway when human blood makes contact with the artificial surface of the heart-lung machine or kidney dialysis machine (Howard, R. J. et al., Arch. Surg. 123: 1496-1501 (1988); Kirklin, J. K. et al., J. Cardiovasc. Surg. 86: 845-857 (1983); Craddock, P. R. et at, N. Engl. J. Med. 296: 769-774 (1977)). C5a causes increased capillary permeability and edema, bronchoconstriction, pulmonary vasoconstriction, leukocyte and platelet activation and infiltration to tissues, in particular the lung (Czermak, B. J. et al., J. Leukoc. Biol. 64: 40-48 (1998)). Administration of an anti-C5a monoclonal antibody was shown to reduce cardiopulmonary bypass and cardioplegia-induced coronary endothelial dysfunction (Tofukuji, M. et al., J. Thorac. Cardiovasc. Surg. 116: 1060-1068 (1998)).

C5a is also involved in acute respiratory distress syndrome (ARDS), Chronic Obstructive Pulmonary Disorder (COPD) and multiple organ failure (MOF) (Hack, C. E. et al., Am. J. Med. 1989: 86: 20-26; Hammerschmidt D E et al Lancet 1980; 1: 947-949; Heideman M. et al. J. Trauma 1984; 4: 1038-1043; Marc, M M, et al., Am. J. Respir. Cell and Mol. Biol., 2004: 31: 216-219). C5a augments monocyte production of two important pro-inflammatory cytokines, TNF-α and IL-1. C5a has also been shown to play an important role in the development of tissue injury, and particularly pulmonary injury, in animal models of septic shock (Smedegard Get al. Am. J. Pathol. 1989; 135: 489-497; Markus, S., et at, FASEB Journal (2001), 15: 568-570). In sepsis models using rats, pigs and non-human primates, anti-05a antibodies administered to the animals before treatment with endotoxin or E. coli resulted in decreased tissue injury, as well as decreased production of IL-6 (Smedegard, G. et al., Am. J. Pathol. 135: 489-497 (1989); Hopken, U. et at, Eur. J. Immunol. 26: 1103-1109 (1996); Stevens, J. H. et at, J Clin. Invest. 77: 1812-1816 (1986)). More importantly, blockade or C5a with anti-05a polyclonal antibodies has been shown to significantly improve survival rates in a caecal ligation/puncture model of sepsis in rats (Czermak, B. J. et al., Nat. Med. 5: 788-792 (1999)). This model share many aspects of the clinical manifestation of sepsis in humans. (Parker, S. J. et al., Br. J. Surg. 88: 22-30 (2001)). In the same sepsis model, anti-05a antibodies were shown to inhibit apoptosis of thymocytes (Guo, R. F. et al., J. Clin. Invest. 106: 1271-1280 (2000)) and prevent MOF (Huber-Lang, M. et al., J. Immunol. 166: 1193-1199 (2001)). Anti-C5a antibodies were also protective in a cobra venom factor model of lung injury in rats, and in immune complex-induced lung injury (Mulligan, M. S. et al. J. Clin. Invest. 98: 503-512 (1996)). The importance of C5a in immune complex-mediated lung injury was later confirmed in mice (Bozic, C. R. et al., Science 26: 1103-1109 (1996)).

C5a is found to be a major mediator in myocardial ischemia-reperfusion injury. Complement depletion reduced myocardial infarct size in mice (Weisman, H. F. et al., Science 249: 146-151 (1990)), and treatment with anti-05a antibodies reduced injury in a rat model of hindlimb ischemia-reperfusion (Bless, N. M. et al., Am. J. Physiol. 276: L57-L63 (1999)). Reperfusion injury during myocardial infarction was also markedly reduced in pigs that were retreated with a monoclonal anti-05a IgG (Amsterdam, E. A. et al., Am. J. Physiol. 268:H448-H457 (1995)). A recombinant human C5aR antagonist reduces infarct size in a porcine model of surgical revascularization (Riley, R. D. et al., J. Thorac. Cardiovasc. Surg. 120: 350-358 (2000)).

C5a driven neutrophils also contribute to many bullous diseases (e.g., bullous pemphigoid, pemphigus vulgaris and pemphigus foliaceus). These are chronic and recurring inflammatory disorders clinically characterized by sterile blisters that appear in the sub-epidermal space of the skin and mucosa. While autoantibodies to keratinocytes located at the cutaneous basement membranes are believed to underlie the detachment of epidermal basal keratinocytes from the underlying basement membrane, blisters are also characterized by accumulation of neutrophils in both the upper dermal layers and within the blister cavities. In experimental models a reduction of neutrophils or absence of complement (total or C5-selective) can inhibit formation of sub-epidermal blisters, even in the presence of high auto-antibody titers.

Complement levels are elevated in patients with rheumatoid arthritis (Jose, P. J. et al., Ann. Rheum. Dis. 49: 747-752 (1990); Grant, E. P., et al., J. of Exp. Med., 196(11): 1461-1471, (2002)), lupus nephritis (Bao, L., et al., Eur. J. of Immunol, 35(8), 2496-2506, (2005)) and systemic lupus erythematosus (SLE) (Porcel, J. M. et al., Clin. Immunol. Immunopathol. 74: 283-288 (1995)). C5a levels correlate with the severity of the disease state. Collagen-induced arthritis in mice and rats resembles the rheumatoid arthritic disease in human. Mice deficient in the C5a receptor demonstrated a complete protection from arthritis induced by injection of monoclonal anti-collagen Abs (Banda, N. K., et al., J. of Immunol., 2003, 171: 2109-2115). Therefore, inhibition of C5a and/or C5a receptor (C5aR) could be useful in treating these chronic diseases.

The complement system is believed to be activated in patients with inflammatory bowel disease (IBD) and is thought to play a role in the disease pathogenesis. Activated complement products were found at the luminal face of surface epithelial cells, as well as in the muscularis mucosa and submucosal blood vessels in IBD patients (Woodruff, T. M., et al., J of Immunol., 2003, 171: 5514-5520).

C5aR expression is upregulated on reactive astrocytes, microglia, and endothelial cells in an inflamed human central nervous system (Gasque, P. et al., Am. J. Pathol. 150: 31-41 (1997)). C5a might be involved in neurodegenerative diseases, such as Alzheimer disease (Mukherjee, P. et al., J. Neuroimmunol. 105: 124-130 (2000); O'Barr, S. et al., J. Neuroimmunol. (2000) 105: 87-94; Farkas, I., et al. J. Immunol. (2003) 170:5764-5771), Parkinson's disease, Pick disease and transmissible spongiform encephalopathies. Activation of neuronal C5aR may induce apoptosis (Farkas I et al. J. Physiol. 1998; 507: 679-687). Therefore, inhibition of C5a and/or C5aR could also be useful in treating neurodegenerative diseases.

There is some evidence that C5a production worsens inflammation associated with atopic dermatitis (Neuber, K., et al., Immunology 73:83-87, (1991)), and chronic urticaria (Kaplan, A. P., J. Allergy Clin. Immunol. 114; 465-474, (2004).

Psoriasis is now known to be a T cell-mediated disease (Gottlieb, E. L. et al., Nat. Med. 1: 442-447 (1995)). However, neutrophils and mast cells may also be involved in the pathogenesis of the disease (Terui, T. et al., Exp. Dermatol. 9: 1-10; 2000); Werfel, T. et al., Arch. Dermatol. Res. 289: 83-86 (1997)). Neutrophil accumulation under the stratum corneum is observed in the highly inflamed areas of psoriatic plaques, and psoriatic lesion (scale) extracts contain highly elevated levels of C5a and exhibit potent chemotactic activity towards neutrophils, an effect that can be inhibited by addition of a C5a antibody. T cells and neutrophils are chemo-attracted by C5a (Nataf, S. et al., *J. Immunol.* 162: 4018-4023 (1999); Tsuji, R. F. et al, *J. Immunol.* 165: 1588-1598 (2000); Cavaillon, J. M. et al, *Eur. J. Immunol.* 20: 253-257 (1990)). Additionally expression of C5aR has been demonstrated in plasmacytoid dendritic cells (pDC) isolated from lesions of cutaneous lupus erythematous and these cells were shown to display chemotactic behavior towards C5a, suggesting that blockade of C5aR on pDC might be efficacious in reducing pDC infiltration into inflamed skin in both SLE and psoriasis. Therefore C5a could be an important therapeutic target for treatment of psoriasis.

Immunoglobulin G-containing immune complexes (IC) contribute to the pathophysiology in a number of autoimmune diseases, such as systemic lupus erthyematosus, rheumatoid arthritis, Sjogren's disease, Goodpasture's syndrome, and hypersensitivity pneumonitis (Madaio, M. P., *Semin. Nephrol.* 19: 48-56 (1999); Korganow, A. S. et al., *Immunity* 10: 451-459 (1999); Bolten, W. K., *Kidney Int.* 50: 1754-1760 (1996); Ando, M. et al., *Curr. Opin. Pulm. Med.* 3: 391-399 (1997)). These diseases are highly heterogeneous and generally affect one or more of the following organs: skin, blood vessels, joints, kidneys, heart, lungs, nervous system and liver (including cirrhosis and liver fibrosis). The classical animal model for the inflammatory response in these IC diseases is the Arthus reaction, which features the infiltration of polymorphonuclear cells, hemorrhage, and plasma exudation (Arthus, M., C. R. *Soc. Biol.* 55: 817-824 (1903)). Recent studies show that C5aR deficient mice are protected from tissue injury induced by IC (Kohl, J. et al., *Mot Immunol.* 36: 893-903 (1999); Baumann, U. et al., *J. Immunol.* 164: 1065-1070 (2000)). The results are consistent with the observation that a small peptidic anti-05aR antagonist inhibits the inflammatory response caused by IC deposition (Strachan, A. J. et al., *J. Immunol.* 164: 6560-6565 (2000)). Together with its receptor, C5a plays an important role in the pathogenesis of IC diseases. Inhibitors of C5a and C5aR could be useful to treat these diseases.

Descripton of Related Art:

Non-peptide based C5a receptor antagonist have been reported as being effective for treating endotoxic shock in rats (Stracham, A. J., et al., *J. of Immunol.* (2000), 164(12): 6560-6565); and for treating IBD in a rat model (Woodruff, T. M., et al., *J. of Immunol.*, 2003, 171: 5514-5520). Non-peptide based C5a receptor modulators also have been described in the patent literature by Neurogen Corporation, (e.g., WO2004/043925, WO2004/018460, WO2005/007087, WO03/082826, WO03/08828, WO02/49993, WO03/084524); Dompe S.P.A. (WO02/029187); The University of Queenland (WO2004/100975); and ChemoCentryx (WO2010/075257).

There is considerable experimental evidence in the literature that implicates increased levels of C5a with a number of diseases and disorders, in particular in autoimmune and inflammatory diseases and disorders. Thus, there remains a need in the art for new small organic molecule modulators, e.g., agonists, preferably antagonists, partial agonists, of the C5a receptor (C5aR) that are useful for inhibiting pathogenic events, e.g., chemotaxis, associated with increased levels anaphylatoxin activity. The present invention fulfills this and other needs.

BRIEF SUMMARY OF THE INVENTION

In one aspect, the present invention provide compounds of Formulae (IA), (IB), (IC), (IIA), (IIB), and (IIC):

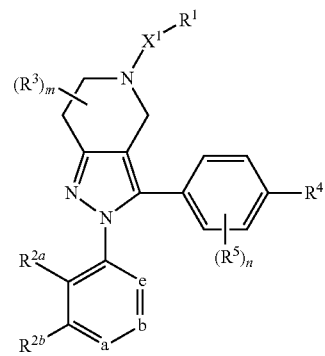

IA

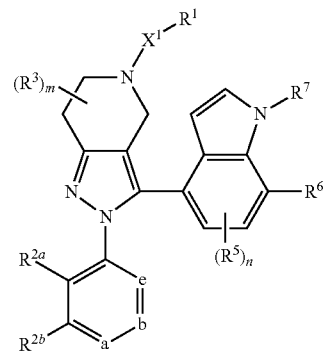

IB

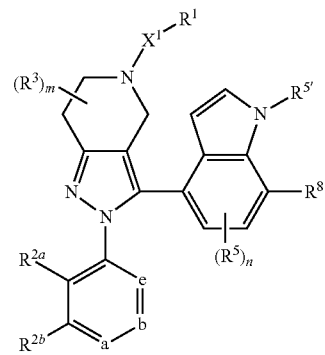

IC

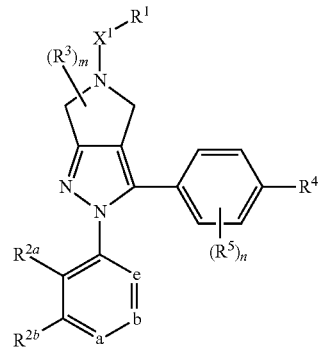

IIA

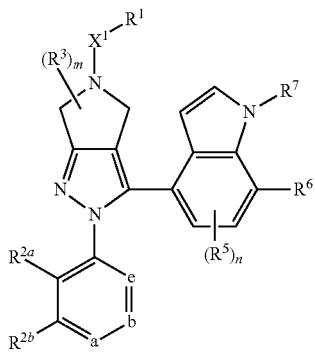

IIB

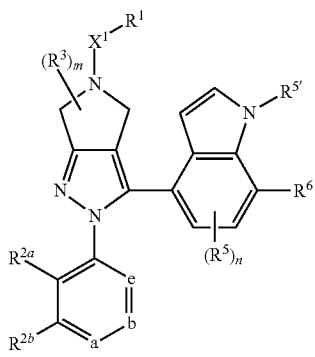

IIC or a pharmaceutically acceptable salt thereof, wherein the symbols, letters and subscripts n, m, a, b, e, $X^1$, $R^1$, $R^{2a}$, $R^{2b}$, $R^3$, $R^4$, $R^5$, $R^6$, $R^7$ and $R^8$ have the meanings provided in the description below.

In addition to the compounds provided herein, the present invention further provides pharmaceutical compositions containing one or more of these compounds, as well as methods for the use of these compounds in therapeutic methods, primarily to treat diseases associated C5a signaling activity.

In yet another aspect, the present invention provides methods of diagnosing disease in an individual. In these methods, the compounds provided herein are administered in labeled form to a subject, followed by diagnostic imaging to determine the presence or absence of C5aR and/or the localization of cells expressing a C5aR receptor. In a related aspect, a method of diagnosing disease is carried out by contacting a tissue or blood sample with a labeled compound as provided herein and determining the presence, absence, amount, or localization of C5aR in the sample.

DETAILED DESCRIPTION OF THE INVENTION

Abbreviation and Definitions

Figure 1:
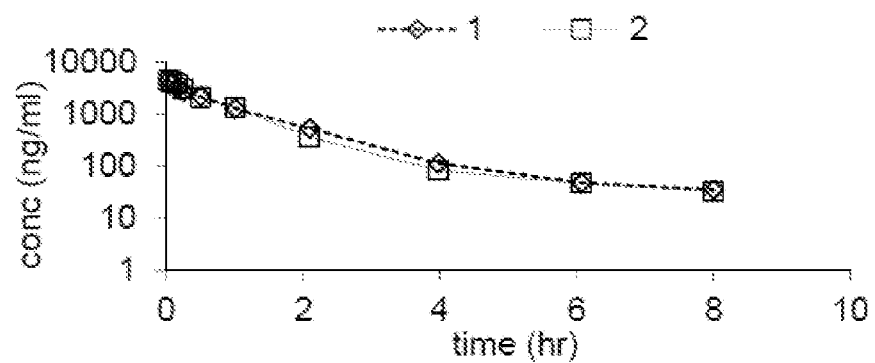
FIG. 1 shows release of active compound intermediate 4 from the compound of Example 1 (0.5 mg/kg mole equiv., AUC=4,160 ng.hr/mL).

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), isobutenyl, 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrhydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, and —CH=CH—N($CH_3$)—$CH_3$. Up to two heteroatoms may be consecutive, such as, for example, —$CH_2$—NH—OCH$_3$ and —$CH_2$—O—Si($CH_3$)$_3$. Similarly, the terms "heteroalkenyl" and "heteroalkynyl" by itself or in combination with another term, means, unless otherwise stated, an alkenyl group or alkynyl group, respectively, that contains the stated number of carbons and having from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group.

The term "heteroalkylene" by itself or as part of another substituent means a divalent radical, saturated or unsaturated or polyunsaturated, derived from heteroalkyl, as exemplified by —CH$_2$—CH$_2$—S—CH$_2$CH$_2$— and —CH$_2$—S—CH$_2$—CH$_2$—NH—CH$_2$—, —O—CH$_2$—CH=CH—, —CH$_2$—CH=C(H)CH$_2$—O—CH$_2$— and —S—CH$_2$—C≡C—. For heteroalkylene groups, heteroatoms can also occupy either or both of the chain termini (e.g., alkyleneoxy, alkylenedioxy, alkyleneamino, alkylenediamino, and the like).

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

The term "hydroxyalkyl" is used in its conventional sense, and refers to branched or straight chain alkyl group substituted with at least one hydroxyl group. The hydroxyl group may be at any position in the alkyl group. For example, the term "C$_{1-4}$ hydroxylalkyl" is meant to include hydroxymethyl, hydroxyethyl, hydroxypropyl, hydroxyisopropyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "C$_{1-4}$haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzooxazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, pyrrolopyridyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention.

Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "prodrug component" refers to a group that provides desired properties to a compound which improve, for example, the compound's stability, circulation time in vivo, or solubility. A compound bearing a prodrug component is metabolized (generally via hydrolysis or enzymatically) following administration to a subject—resulting in an active compound.

Compounds with a prodrug component may only become active upon cleavage, but compounds with a prodrug component may have activity in their unreacted forms. Additionally, a prodrug component itself may be active. Examples of prodrug components contemplated in this disclosure include, but are not limited to, phosphate, phosphomethyl, hydroxymethyl, amino acid, dipeptide and tripeptide moieties. Further embodiments contemplated are further described herein.

The term "amino acid" refers to naturally occurring and non-natural amino acids. Non-natural amino acids refer to compounds that have the same basic chemical structure as a naturally occurring amino acid, i.e., an a carbon that is bound to a hydrogen, a carboxyl group, an amino group, and an R group, such as, but not limited to, homoserine, norleucine, methionine sulfoxide, methionine methyl sulfonium. Such analogs have modified R groups (such as, 2,5-diaminopentanoic acid) or modified peptide backbones, but retain the same basic chemical structure as a naturally occurring amino acid. The amino acids of the present disclosure include N-methylated and N-acylated moieties. When the terminal group of the amino acid is an N atom, it may be di-methylated.

As used herein, a wavy line, that intersects a single, double or triple bond in any chemical structure depicted herein, represent the point attachment of the single, double, or triple bond to the remainder of the molecule.

Description of the Embodiments

Compounds

In one aspect, the present invention provides compounds of Formulae (IA), (IB), (IC), (IIA), (IIB), and (IIC):

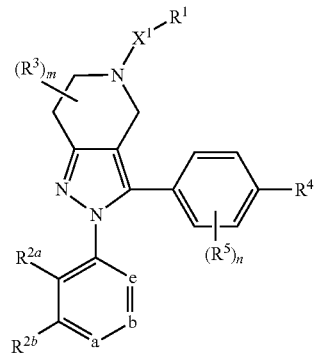

IA

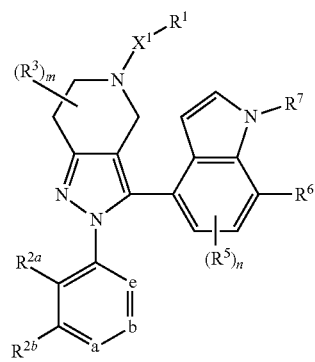

IB

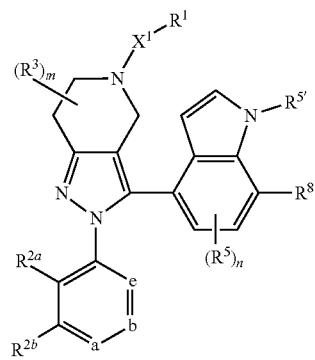

IC

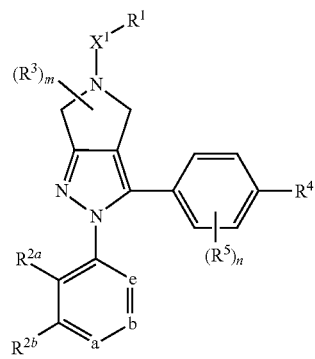

IIA

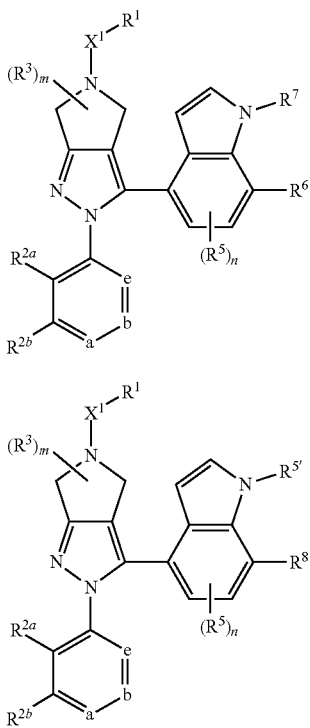

or a pharmaceutically acceptable salt thereof, wherein,
ring vertex a is N or $C(R^{2c})$, ring vertex b is N or $C(R^{2d})$, and ring vertex e is N or $C(R^{2e})$, wherein no more than one of a, b and e is N;

$X^1$ is selected from the group consisting of a bond, $C_{1-8}$ alkylene, C(O), C(O)—$C_{1-4}$ alkylene, and $S(O)_2$;

$R^1$ is selected from the group consisting of
a) 5- to 10-membered heteroaryl having from 1 to 4 heteroatoms as ring vertices selected from N, O and S;
b) $C_{6-10}$ aryl;
c) $C_{3-8}$ cycloalkyl;
d) 4- to 8-membered heterocycloalkyl having from 1 to 2 heteroatoms as ring vertices selected from N, O and S; and
e) $C_{1-8}$ alkyl, $C_{1-8}$ alkoxy, $C_{1-8}$haloalkyl, —C(O)$NR^{1a}R^{1b}$, and —$CO_2R^{1a}$; wherein $R^{1a}$ and $R^{1b}$ are each independently selected from the group consisting of hydrogen, $C_{1-8}$ alkyl, $C_{6-10}$ aryl, and —$C_{1-6}$ alkylene-$C_{6-10}$ aryl;

wherein the group —$X^1$—$R^1$ is optionally substituted with 1 to 5 $R^x$ substituents;

$R^{2a}$ and $R^{2c}$ are each independently selected from the group consisting of hydrogen, $C_{1-6}$ alkyl, $C_{1-6}$ alkoxy, —S—$C_{1-6}$ alkyl, —$C_{1-6}$ alkyl-O—$C_{1-6}$ alkyl, —$C_{1-6}$alkyl-S—$C_{1-6}$ alkyl, CN, and halogen, and at least one of $R^{2a}$ and $R^{2e}$ is other than hydrogen;

$R^{2b}$, $R^{2c}$, and $R^{2d}$ are each independently selected from the group consisting of hydrogen, $C_{1-6}$ alkyl, $C_{1-6}$ alkoxy, $C_{1-6}$ haloalkyl, haloalkyl, —S—$C_{1-6}$ alkyl, —$C_{1-6}$ alkyl-O—$C_{1-6}$ alkyl, —$C_{1-6}$ alkyl-S—$C_{1-6}$ alkyl, cyano, and halogen;

each $R^3$ is independently selected from the group consisting of hydroxyl, $C_{1-4}$ alkyl, $C_{1-4}$ haloalkyl and $C_{1-4}$ hydroxyalkyl, and optionally two $R^3$ groups on the same carbon atom are combined to form oxo (=O), and optionally two $R^3$ groups and the carbon atoms they are attached to form a 3-6 membered ring with 0-2 heteroatoms as ring members selected from O, N, and S;

$R^4$ is a member selected from the group consisting of: —$NHP^1$, —$NHC(O)NHP^1$, —$CH_2NHP^1$ and —$CH_2NHC(O)NHP^1$;

each $R^5$ is independently selected from the group consisting of $C_{1-8}$ alkyl, $C_{1-8}$ alkoxy, $C_{1-8}$ haloalkyl, $C_{1-8}$ haloalkoxy, $C_{1-8}$ hydroxyalkyl, halogen, OH, CN, $C(O)R^{5a}$ and $CO_2R^{5a}$;

$R^{5'}$ is a member selected from the group consisting of hydrogen, $C_{1-8}$ alkyl, $C_{1-8}$ haloalkyl, $C_{1-8}$ hydroxyalkyl, $C(O)R^{5a}$ and $CO_2R^{5a}$; wherein each $R^{5a}$ is independently selected from the group consisting of hydrogen, $C_{1-4}$ alkyl, and $C_{1-4}$ haloalkyl;

$R^6$ is a member selected from the group consisting of hydrogen, $C_{1-6}$ alkyl, $C_{1-6}$ alkoxy, $C_{1-6}$ haloalkyl, —S—$C_{1-6}$ alkyl, —$C_{1-6}$ alkyl-O—$C_{1-6}$ alkyl, —$C_{1-6}$ alkyl-S—$C_{1-6}$ alkyl, cyano, and halogen;

$R^7$ is $P^1$; and $R^8$ is —$CH_2OP^1$;

each $P^1$ is a prodrug component;

each $R^x$ is independently selected from the group consisting of halogen, CN, $C_{1-4}$ alkyl, $C_{1-4}$ alkoxy, $C_{1-4}$ haloalkyl, $C_{1-4}$ haloalkoxy, $C_{1-4}$ hydroxyalkyl, $C_{2-4}$ alkenyl, $C_{3-6}$ cycloalkyl, $CO_2$—$C_{1-4}$ alkyl, and $CONH_2$;

the subscript m is 0, 1, 2, 3 or 4; and the subscript n is 0, 1, 2 or 3.

In one group of embodiments, the compounds provided herein have Formula (IA). In another group of embodiments, the compounds provided herein have Formula (IB). In still another group of embodiments, the compounds provided herein have Formula (IC). In yet another group of embodiments, the compounds provided herein have Formula (IIA). In another group of embodiments, the compounds provided herein have Formula (IIB). In still another group of embodiments, the compounds provided herein have Formula (IIC).

In some embodiments for the compounds of formula (IA), (IB), (IC), (IIA), (IIB), (IIC), or a pharmaceutically acceptable salt thereof, as well as any of the groups of embodiments noted above, $P^1$ is selected from the group consisting of:

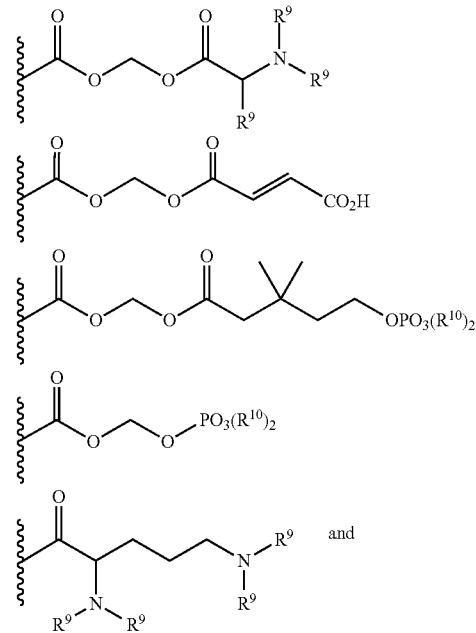

-continued

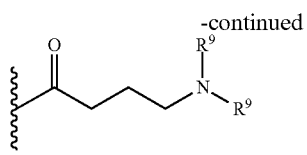

wherein each $R^9$ is independently selected from the group consisting of H and $C_{1-3}$ alkyl; and
each $R^{10}$ is independently selected from the group consisting of H, $C_{1-3}$ alkyl, phenyl, and benzyl.

In some embodiments for the compounds of formula (IA), (IB), (IC), (IIA), (IIB), (IIC), or a pharmaceutically acceptable salt thereof, as well as any of the groups of embodiments noted above, $P^1$ is selected from the group consisting of:

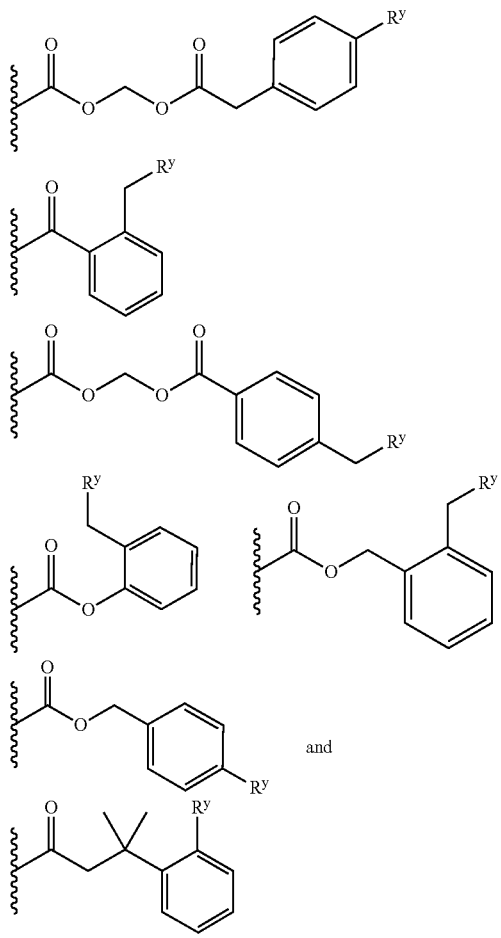

and wherein
each $R^y$ is independently selected from the group consisting of
—OP(O)(OB$^{y1}$)$_2$, —OC(O)CH$_2$N(R$^{y2}$)$_2$, —N(R$^{y2}$)$_2$, and piperazine;
each $R^{y1}$ is independently selected form the group consisting of H, $C_{1-3}$ alkyl, and benzyl;
each $R^{y2}$ is independently H or $C_{1-3}$ alkyl; and
each phenyl ring bearing an $R^y$ or —CH$_2$R$^y$ substituent is further substituted with from 0 to 3 members independently selected from the group consisting of nitro, halogen, CN, CF$_3$, $C_{1-4}$ alkyl, $C_{1-4}$ alkoxy, $C_{1-4}$ haloalkyl, $C_{1-4}$ haloalkoxy, and $C_{1-4}$ hydroxyalkyl.

In some embodiments for the compounds of formula (IA), (IB), (IC), (IIA), (IIB), (IIC), or a pharmaceutically acceptable salt thereof, as well as any of the groups of embodiments noted above, $P^1$ is selected from the group consisting of —CH$_2$OH, —P(O)(OR$^{10}$)$_2$, and —CH$_2$—O—P(O)(OR$^{10}$)$_2$, wherein each $R^{10}$ is independently selected from the group consisting of H, $C_{1-3}$ alkyl, phenyl, and benzyl, In some embodiments for the compounds of formula (IA), (IB), (IC), (IIA), (IIB), (IIC), or a pharmaceutically acceptable salt thereof, as well as any of the groups of embodiments noted above, $P^1$ is selected from the group consisting of an amino acid, a dipeptide, and a tripeptide. In some embodiments, the amino acid, dipeptide, or tripeptide are natural amino acids. In some embodiments the amino acid, dipeptide, or tripeptide moieties are independently selected from the group consisting of glycine, alanine, valine, leucine, isoleucine, lysine, cysteine, aspartate, glutamate, histidine, and phenylalanine, wherein the N atom of each amino acid unit may be methylated or acylated.

The amino acids of the present disclosure can be covalently linked to the remainder of the molecule via any suitable means. Suitable linkages include, but are not limited to, amide formation between an amine group a hydroxyl group, ester formation between a carboxylic acid group and a hydroxyl group, and sulfonamide formation (N—S linkage) between a thio group and an amino group. Typically, amino acids are covalently linked to the remainder of the molecule via the alpha amino group or the alpha carboxylic acid; however, when the R group of the amino acid includes a functional group, this may also serve as the linkage point. For example, the carboxylic acid of a glutamate may service as the linkage point to the remainder of the molecule. Similarly, the thiol of a cysteine may also serve as the linkage point to the remainder of the molecule.

In some embodiments for the compounds of formula (IA), (IB), (IC), (IIA), (IIB), (IIC), or a pharmaceutically acceptable salt thereof, as well as any of the groups of embodiments noted above, $P^1$ is selected from the group consisting of:

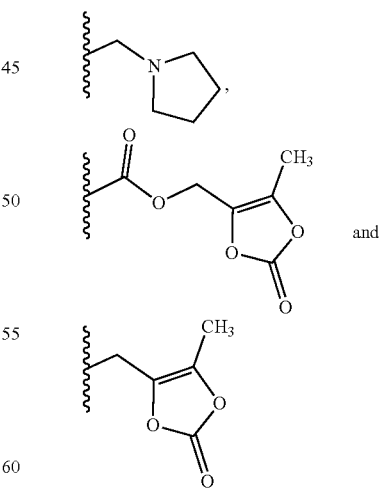

With reference to the compounds of formula (IA), (IB), (IC), (IIA), (IIB), (IIC), or a pharmaceutically acceptable salt thereof, as well as any of the groups of embodiments noted above, in certain selected embodiments, $X^1$ is a bond; in other selected embodiments, $X^1$ is C(O); in still other selected embodiments, $X^1$ is $C_{1-8}$ alkylene; in yet other selected embodiments, $X^1$ is $C(O)$—$C_{1-4}$ alkylene or $S(O)_2$.

With reference to the compounds of formula (IA), (IB), (IC), (IIA), (IIB), (IIC), or a pharmaceutically acceptable salt thereof, as well as any of the groups or selected embodiments noted above, in some further embodiments, wherein $R^1$ is a 5- to 10-membered heteroaryl having from 1 to 4 heteroatoms as ring vertices selected from N, O and S; and wherein the group —$X^1$—$R^1$ is optionally substituted with 1 to 4 $R^x$ substituents. In still further embodiments, $R^1$ is selected from the group consisting of pyrazolyl, pyridyl, pyrimidinyl, imidazolyl, thiazolyl, thiadiazolyl and pyrazinyl; and wherein the group —$X^1$—$R^1$ is optionally substituted with 1 to 4 IV substituents.

With reference to the compounds of formula (IA), (IB), (IC), (IIA), (IIB), (IIC), or a pharmaceutically acceptable salt thereof, as well as any of the groups or selected embodiments noted above, in some further embodiments, wherein $R^1$ is $C_{6-10}$ aryl; and wherein the group —$X^1$—$R^1$ is optionally substituted with 1 to 4 IV substituents. In still further embodiments, $R^1$ is phenyl; and wherein the group —$X^1$—$R^1$ is optionally substituted with 1 to 4 $R^x$ substituents.

With reference to the compounds of formula (IA), (IB), (IC), (IIA), (IIB), (IIC), or a pharmaceutically acceptable salt thereof, as well as any of the groups or selected embodiments noted above, in some further embodiments, $R^1$ is $C_{3-8}$ cycloalkyl; and wherein the group —$X^1$—$R^1$ is optionally substituted with 1 to 4 $R^x$ substituents. In still further embodiments, $R^1$ is selected from the group consisting of cyclobutyl, cyclopentyl and cyclohexyl; and wherein the group —$X^1$—$R^1$ is optionally substituted with 1 to 4 $R^x$ substituents.

With reference to the compounds of formula (IA), (IB), (IC), (IIA), (IIB), (IIC), or a pharmaceutically acceptable salt thereof, as well as any of the groups or selected embodiments noted above, in some further embodiments, $R^1$ is a 4- to 8-membered heterocycloalkyl having from 1 to 2 heteroatoms as ring vertices selected from N, O and S; and wherein the group —$X^1$—$R^1$ is optionally substituted with 1 to 4 $R^x$ substituents. In still further selected embodiments, $R^1$ is selected from the group consisting of oxetanyl, tetrahydrofuranyl, tetrahydropyranyl and morpholinyl; and wherein the group —$X^1$—$R^1$ is optionally substituted with 1 to 4 $R^x$ substituents.

With reference to the compounds of formula (IA), (IB), (IC), (IIA), (IIB), (IIC), or a pharmaceutically acceptable salt thereof, as well as any of the groups or selected embodiments noted above, in some further embodiments, $R^1$ is selected from the group consisting of $C_{1-8}$ alkyl, $C_{1-8}$ alkoxy, $C_{1-8}$ haloalkyl, —$C(O)NR^{1a}R^{1b}$, and —$CO_2R^{1a}$; wherein $R^{1a}$ and $R^{1b}$ are each independently selected from the group consisting of hydrogen, $C_{1-8}$ alkyl, $C_{6-10}$ aryl, and —$C_{1-6}$ alkylene-$C_{6-10}$ aryl; and wherein the group —$X^1$—$R^1$ is optionally substituted with 1 to 4 $R^x$ substituents.

With reference to the compounds of formula (IA), (IB), (IC), (IIA), (IIB), (IIC), or a pharmaceutically acceptable salt thereof, as well as any of the groups or selected embodiments noted above, in some further embodiments, $R^1$ is selected from the group consisting of phenyl, pyridyl, pyrimidinyl, and pyrazinyl; and wherein the group —$X^1$—$R^1$ is optionally substituted with 1 to 4 $R^x$ substituents.

With reference to the compounds of formula (IA), (IB), (IC), (IIA), (IIB), (IIC), or a pharmaceutically acceptable salt thereof, as well as any of the embodiments noted above, in some further embodiments, ring vertices a and b are CH; $R^{2b}$ is H; ring vertex e is $C(R^{2e})$, and $R^{2a}$ and $R^{2c}$ are independently selected from the group consisting of $C_{1-6}$ alkyl, $C_{1-6}$ alkoxy, $C_{1-6}$ haloalkyl, —O—$C_{1-6}$ haloalkyl, —S—$C_{1-6}$ alkyl, —$C_{1-6}$ alkyl-O—$C_{1-6}$ alkyl, —$C_{1-6}$ alkyl-S—$C_{1-6}$ alkyl, CN, and halogen.

With reference to the compounds of formula (IA), (IB), (IC), (IIA), (IIB), (IIC), or a pharmaceutically acceptable salt thereof, as well as any of the embodiments noted above, in some further embodiments, ring vertices a and b are CH; $R^{2b}$ is H; ring vertex e is $C(R^{2e})$, and $R^{2a}$ and $R^{2e}$ are independently selected from the group consisting of $C_{1-6}$ alkyl, $C_{1-6}$ alkoxy and halogen.

With reference to the compounds of formula (IA), (IB), (IC), (IIA), (IIB), (IIC), or a pharmaceutically acceptable salt thereof, as well as any of the embodiments noted above, in some further embodiments, the subscript n is 0, 1 or 2 and each $R^5$, when present, is selected from the group consisting of F, Cl, CN, $C_{1-4}$ alkyl and $C_{1-4}$ alkoxy. In still further selected embodiments, the subscript n is 0, 1 or 2 and each $R^5$, when present, is selected from the group consisting of F, Cl, CN, $CH_3$ and $OCH_3$.

With reference to the compounds of formula (IA), (IB), (IC), (IIA), (IIB), (IIC), or a pharmaceutically acceptable salt thereof, as well as any of the embodiments noted above, in some further embodiments, the subscript m is 0, 1 or 2 and each $R^3$, when present, is $C_{1-4}$ alkyl.

In a particular group of embodiments of the compounds of formula (IA), (IB), (IC), (IIA), (IIB), (IIC), or a pharmaceutically acceptable salt thereof, $R^1$ is selected from the group consisting of phenyl or pyridyl, wherein the group —$X^1$—$R^1$ is optionally substituted with 1 to 4 $R^x$ substituents; ring vertices a and b are CH; $R^{2b}$ is H; ring vertex e is $C(R^{2e})$, and $R^{2a}$ and $R^{2e}$ are independently selected from the group consisting of $C_{1-6}$ alkyl, $C_{1-6}$ alkoxy and halogen; m is 0, 1 or 2 and each $R^3$, when present, is $CH_3$, n is 0, 1 or 2 and each $R^5$, when present, is selected from the group consisting of F, Cl, CN, $CH_3$ and $OCH_3$.

In some embodiments of the compounds of formula (IA), (IB), (IC), (IIA), (IIB), (IIC), or a pharmaceutically acceptable salt thereof, $R^1$ is selected from the group consisting of

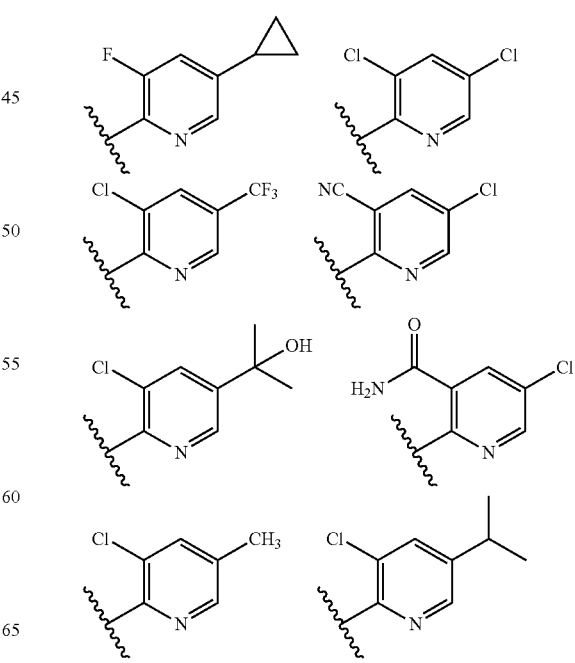

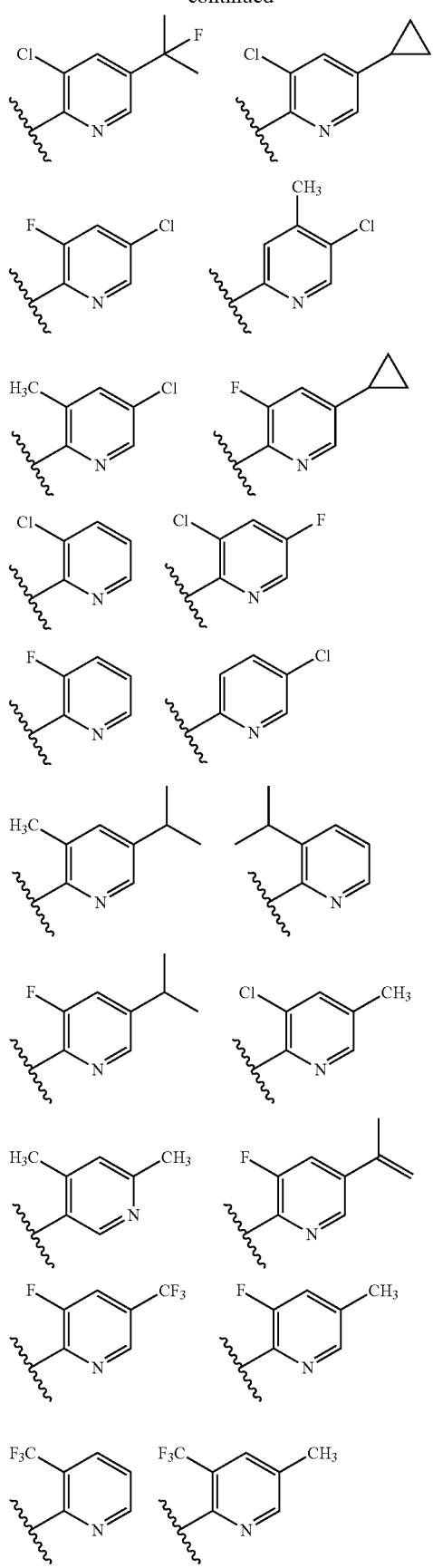
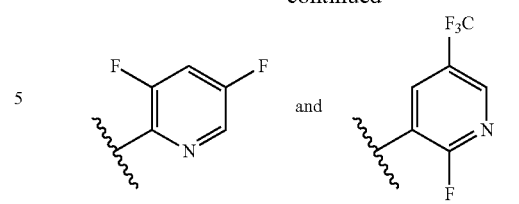
In some embodiments of the compounds of formula (IA), (IB), (IC), (IIA), (IIB), (IIC), or a pharmaceutically acceptable salt thereof, —X$^1$—R$^1$ is selected from the group consisting of:
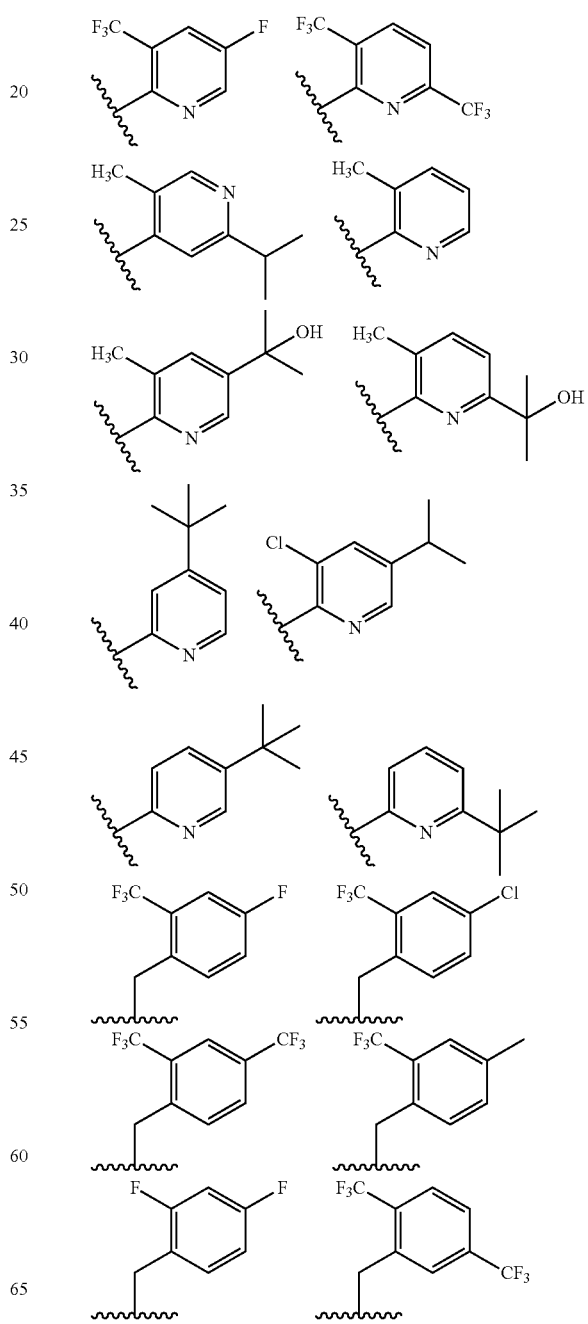

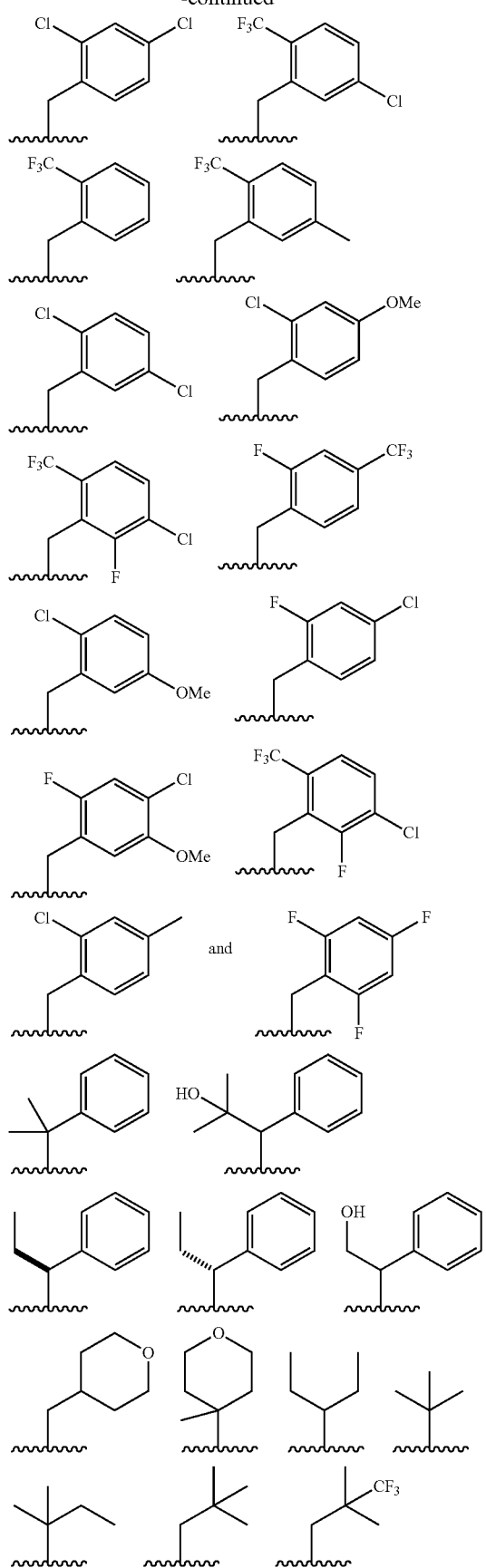
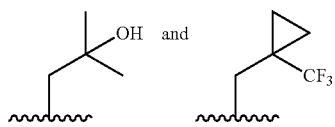
In some embodiments of the compounds of formula (IA), (IB), (IC), (IIA), (IIB), (IIC), or a pharmaceutically acceptable salt thereof, R¹ is selected from the group consisting of:
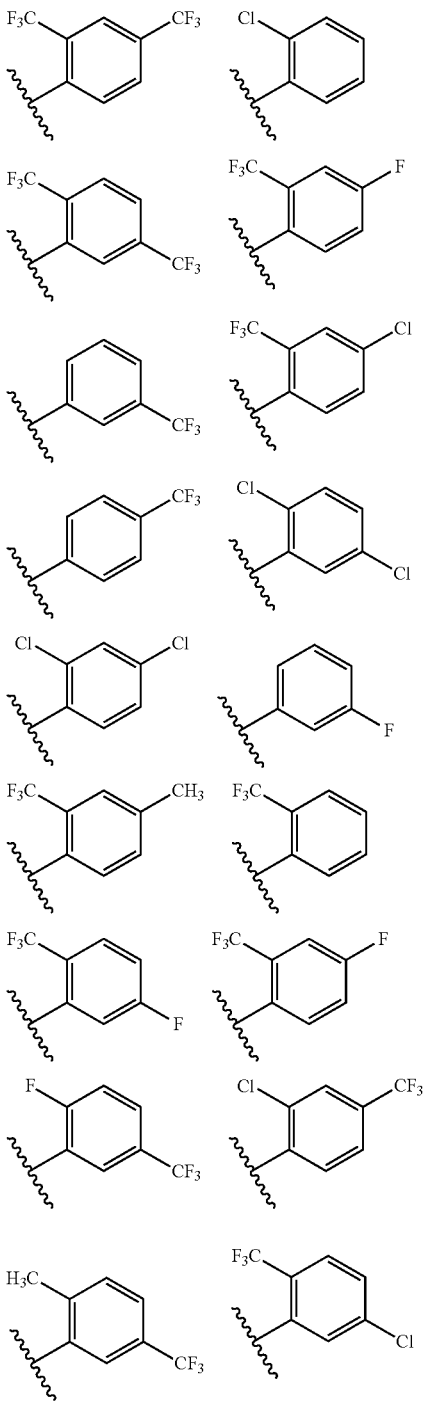

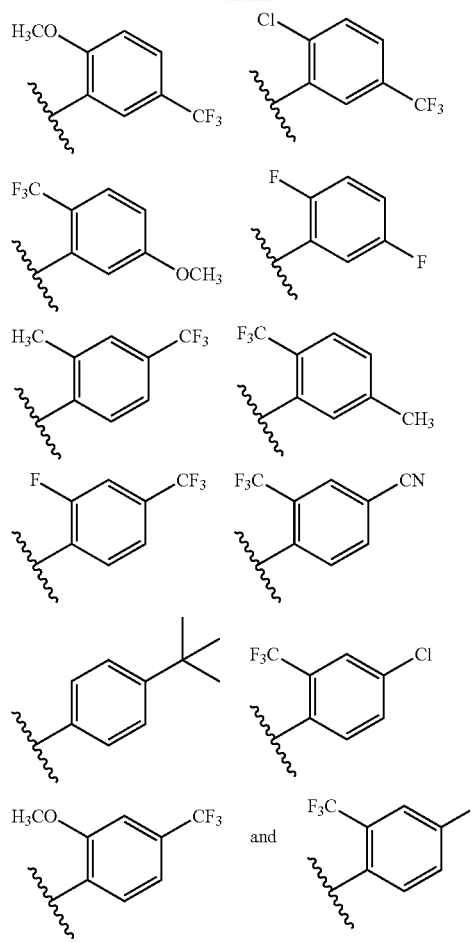
In some embodiments of the compounds of formula (IA), (IB), (IC), (IIA), (IIB), (IIC), or a pharmaceutically acceptable salt thereof, R¹ is selected from the group consisting of:
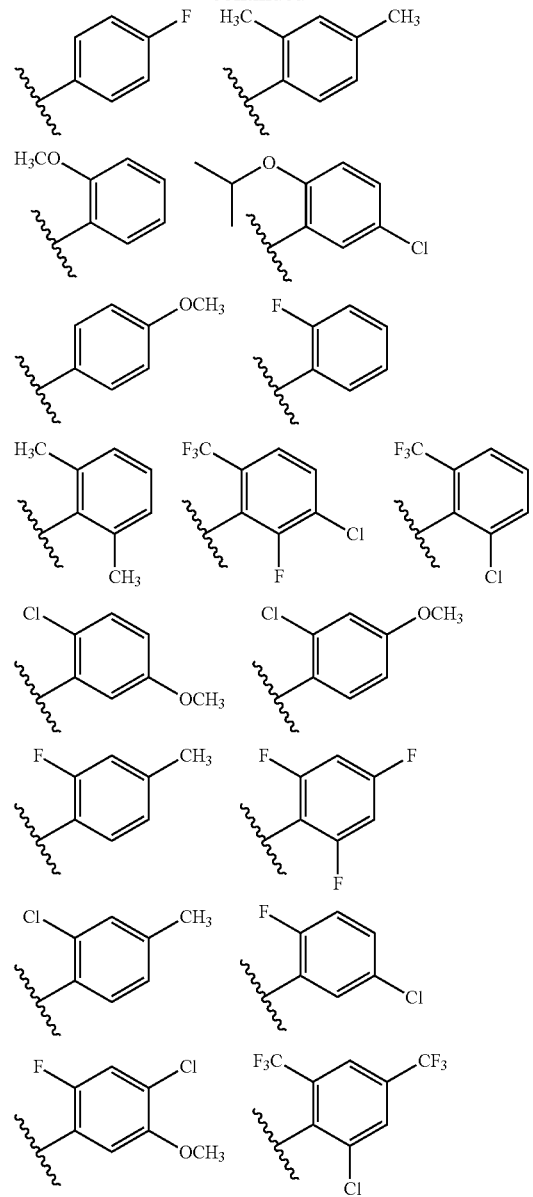
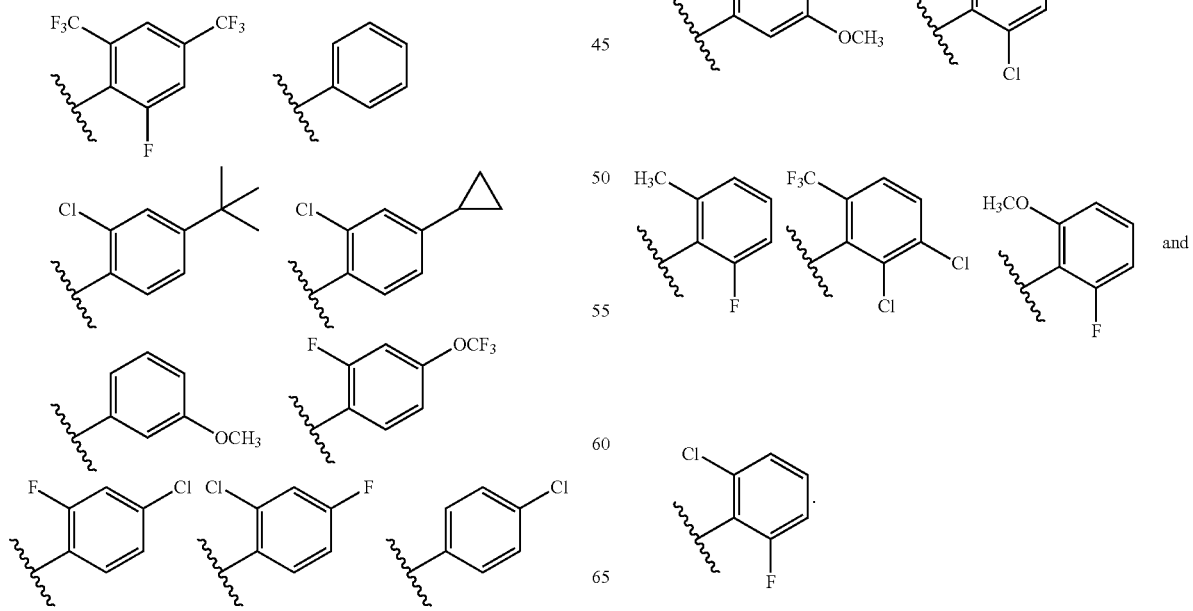

In some embodiments of the compounds of formula (IA), (IB), (IC), (IIA), (IIB), (IIC), or a pharmaceutically acceptable salt thereof, $R^1$ is selected from the group consisting of:

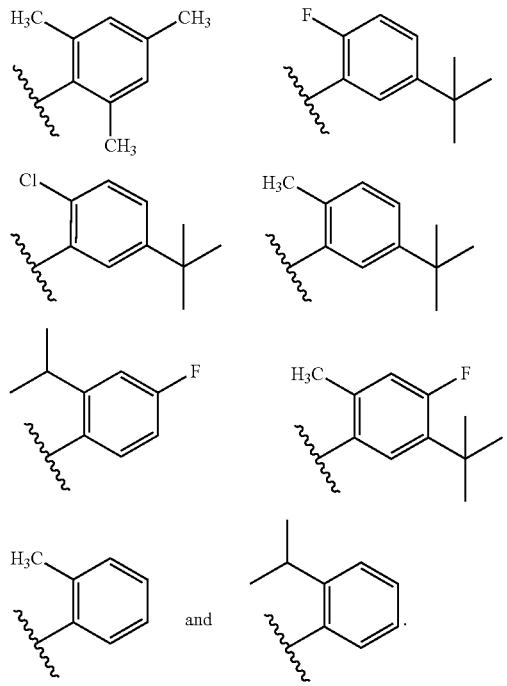

With reference to the compounds of formula (IA), (IB), (IC), (IIA), (IIB), (IIC), or a pharmaceutically acceptable salt thereof, as well as any of the embodiments noted above, in

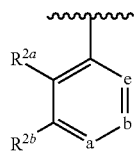

some further embodiments, the group is selected from the group consisting of

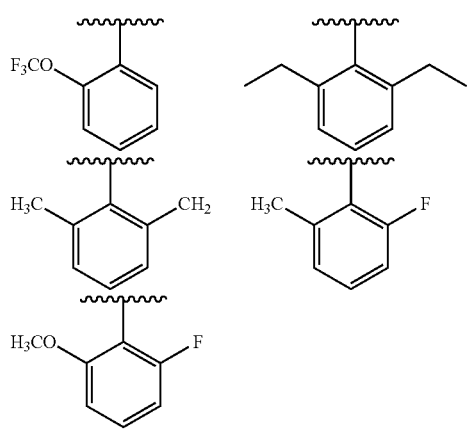

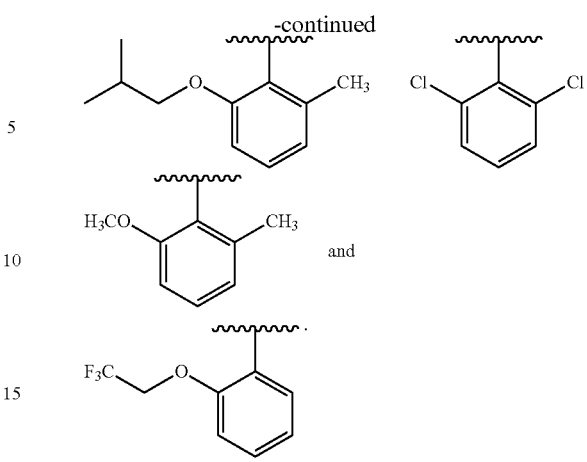

With reference to the compounds of formula (IA), (IB), (IC), (IIA), (IIB), (IIC), or a pharmaceutically acceptable salt thereof, as well as any of the embodiments noted above, in some further embodiments, wherein n is 0.

With reference to the compounds of formula (IA), (IB), (IC), (IIA), (IIB), (IIC), or a pharmaceutically acceptable salt thereof, as well as any of the embodiments noted above, in some further embodiments, the subscript n is 2 and the two $R^3$ groups are on the same carbon atom and are combined to form oxo (=O).

In some embodiments, the compound of the present disclosure is a compound described in the Examples section and the accompanying Tables.

Preparation of Compounds

Certain compounds of the invention can be prepared following methodology as described in the Examples section of this document. In addition, the syntheses of certain intermediate compounds that are useful in the preparation of compounds of the invention are also described.

Pharmaceutical Compositions

In addition to the compounds provided above, compositions for modulating C5a activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxy-ethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

The compounds of this invention may also be coupled a carrier that is a suitable polymers as targetable drug carriers.

Such polymers can include polyvinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the compounds of the invention may be coupled to a carrier that is a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like. In one embodiment of the invention, the compound of the invention is coupled to a polymer or semipermeable polymer matrix that is formed as a stent or stert-graft device.

The pharmaceutical compositions of the present disclosure may be formulated with one or more additional therapeutic agents. The one or more additional therapeutic agent is selected from the group consisting of corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetyl-mannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, C3 aR modulators, C5aR2 modulators, T cell receptor antagonists, PD-1 inhibitors, PD-L1 inhibitors, TIGIT inhibitors, TIM-3 inhibitors, LAG-3 inhibitors, VISTA inhibitors, STING agonists, IDO inhibitors, adenosine receptor modulators, CD39 inhibitors, CD73 inhibitors, antagonists of the chemokine receptors, especially CXCR1, CXCR2, CXCR3, CXCR4, CXCR7, CCR1, CCR2, CCR3, CCR4, CCR5, CCR7, CCR7, CCR9, CX3CR1 and CXCR6, and combinations thereof.

In some embodiments, the one or more additional therapeutic agent is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIIB-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, LT-1951, OMS721, ALN-CC5, ACH-4471, AMY-101, Acthar gel, and CD4+CD25+ regulatory T-cells, MEDI7814, P32, P59, pembrolizumab, nivolumab, atezolizumab, avelumab, durvalumab, CCX354, CCX721, CCX9588, CCX140, CCX872, CCX598, CCX6239, CCX587, CCX624, CCX282, CCX025, CCX507, CCX430, CCX765, CCX758, CCX771, CCX662, CCX650, and combinations thereof. Further discussions of combination therapy are included in the "Methods of Use" section of this application.

Methods of Use

The compounds of the invention may be used as agonists, (preferably) antagonists, partial agonists, inverse agonists, of C5a receptors in a variety of contexts, both in vitro and in vivo. In one embodiment, the compounds of the invention are C5aR antagonist that can be used to inhibit the binding of C5a receptor ligand (e.g., C5a) to C5a receptor in vitro or in vivo. In general, such methods comprise the step of contacting a C5a receptor with a sufficient amount of one or more C5a receptor modulators as provided herein, in the presence of C5a receptor ligand in aqueous solution and under conditions otherwise suitable for binding of the ligand to C5a receptor. The C5a receptor may be present in suspension (e.g., in an isolated membrane or cell preparation), in a cultured or isolated cell, or in a tissue or organ.

Preferably, the amount of C5a receptor modulator contacted with the receptor should be sufficient to inhibit C5a binding to C5a receptor in vitro as measured, for example, using a radioligand binding assay, calcium mobilization assay, or chemotaxis assay as described herein.

In one embodiment of the invention, the C5a modulators of the invention are used to modulate, preferably inhibit, the signal-transducing activity of a C5a receptor, for example, by contacting one or more compound(s) of the invention with a C5a receptor (either in vitro or in vivo) under conditions suitable for binding of the modulator(s) to the receptor. The receptor may be present in solution or suspension, in a cultured or isolated cell preparation or within a patient. Any modulation of the signal transducing activity may be assessed by detecting an effect on calcium ion calcium mobilization or by detecting an effect on C5a receptor-mediated cellular chemotaxis. In general, an effective amount of C5a modulator(s) is an amount sufficient to modulate C5a receptor signal transducing activity in vitro within a calcium mobilization assay or C5a receptor-mediated cellular chemotaxis within a migration assay.

When compounds of the invention are used to inhibit C5a receptor-mediated cellular chemotaxis, preferably leukocyte (e.g., neutrophil) chemotaxis, in an in vitro chemotaxis assay, such methods comprise contacting white blood cells (particularly primate white blood cells, especially human white blood cells) with one or more compounds of the invention. Preferably the concentration is sufficient to inhibit chemotaxis of white blood cells in an in vitro chemotaxis assay, so that the levels of chemotaxis observed in a control assay are significantly higher, as described above, than the levels observed in an assay to which a compound of the invention has been added.

In another embodiment, the compounds of the present invention further can be used for treating patients suffering from conditions that are responsive to C5a receptor modulation. As used herein, the term "treating" or "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). As used herein, a condition is considered "responsive to C5a receptor modulation" if modulation of C5a receptor activity results in the reduction of inappropriate activity of a C5a receptor. As used herein, the term "patients" include primates (especially humans), domesticated companion animals (such as dogs, cats, horses, and the like) and livestock (such as cattle, pigs, sheep, and the like), with dosages as described herein.

Conditions that can be Treated by C5a Modulation:

Autoimmune disorders—e.g., Rheumatoid arthritis, systemic lupus erythematosus, Guillain-Barre syndrome, pancreatitis, lupus nephritis, lupus glomerulonephritis, psoriasis, Crohn's disease, vasculitis, irritable bowel syndrome, dermatomyositis, multiple sclerosis, bronchial asthma, dense deposit disease, pemphigus, pemphigoid, scleroderma, myasthenia gravis, autoimmune hemolytic and thrombocytopenic states, Goodpasture's syndrome (and associated glomerulonephritis and pulmonary hemorrhage), C3-glomerulopathy, C3-glomerulonephritis, membranoproliferative glomerulonephritis, Kawasaki disease, IGs nephropathy, immunovasculitis, tissue graft rejection, graft versus host disease, hyperacute rejection of transplanted organs; and the like.

Inflammatory disorders and related conditions—e.g., Neutropenia, sepsis, septic shock, Alzheimer's disease, multiple sclerosis, neutrophilia, stroke, inflammatory bowel disease (IBD), inflammation associated with severe burns, lung injury, and ischemia-reperfusion injury, osteoarthritis, as well as acute (adult) respiratory distress syndrome (ARDS), chronic pulmonary obstructive disorder (COPD), systemic inflammatory response syndrome (SIRS), atopic dermatitis, psoriasis, chronic urticaria and multiple organ dysfunction syndrome (MODS) Hemolytic uremic syndrome, atypical hemolytic uremic syndrome (aHUS). Also included are pathologic sequellae associated with insulin-dependent diabetes mellitus (including diabetic retinopathy), lupus nephropathy, Heyman nephritis, membranous nephritis and other forms of glomerulonephritis, contact sensitivity responses, and inflammation resulting from contact of blood with artificial surfaces that can cause complement activation, as occurs, for example, during extracorporeal circulation of blood (e.g., during hemodialysis or via a heart-lung machine, for example, in association with vascular surgery such as coronary artery bypass grafting or heart valve replacement), or in association with contact with other artificial vessel or container surfaces (e.g., ventricular assist devices, artificial heart machines, transfusion tubing, blood storage bags, plasmapheresis, plateletpheresis, and the like). Also included are diseases related to ischemia/reperfusion injury, such as those resulting from transplants, including solid organ transplant, and syndromes such as ischemic reperfusion injury, ischemic colitis and cardiac ischemia. Compounds of the instant invention may also be useful in the treatment of age-related macular degeneration (Hageman et al, *P.N.A.S.* 102: 7227-7232, 2005).

Cardiovascular and Cerebrovascular Disorders—e.g., myocardial infarction, coronary thrombosis, vascular occlusion, post-surgical vascular reocclusion, atherosclerosis, traumatic central nervous system injury, and ischemic heart disease. In one embodiment, an effective amount of a compound of the invention may be administered to a patient at risk for myocardial infarction or thrombosis (i.e., a patient who has one or more recognized risk factor for myocardial infarction or thrombosis, such as, but not limited to, obesity, smoking, high blood pressure, hypercholesterolemia, previous or genetic history of myocardial infarction or thrombosis) in order reduce the risk of myocardial infarction or thrombosis.

Oncologic Diseases or Disorders—e.g., melanoma, lung cancer, lymphoma, sarcoma, carcinoma, fibrosarcoma, liposarcoma, chondrosarcoma, osteogenic sarcoma, angiosarcoma, lymphangiosarcoma, synovioma, mesothelioma, meningioma, leukemia, lymphoma, leiomyosarcoma, rhabdomyosarcoma, squamous cell carcinoma, basal cell carcinoma, adenocarcinoma, papillary carcinoma, cystadenocarcinoma, bronchogenic carcinoma, renal cell carcinoma, hepatocellular carcinoma, transitional cell carcinoma, choriocarcinoma, seminoma, embryonal carcinoma, wilm's tumor, pleomorphic adenoma, liver cell papilloma, renal tubular adenoma, cystadenoma, papilloma, adenoma, leiomyoma, rhabdomyoma, hemangioma, lymphangioma, osteoma, chondroma, lipoma and fibroma.

Diseases of Vasculitis—Vasculitic diseases are characterized by inflammation of the vessels. Infiltration of leukocytes leads to destruction of the vessel walls, and the complement pathway is believed to play a major role in initiating leukocyte migration as well as the resultant damage manifested at the site of inflammation (Vasculitis, Second Edition, Edited by Ball and Bridges, Oxford University Press, pp 47-53, 2008). The compounds provided in the present invention can be used to treat leukoclastic vasculitis, Anti-neutrophil cytoplasmic antibody (ANCA) associated vasculitis, immune vasculitis Wegener's granulomatosis, microscopic polyangiitis, Churg-Strauss syndrome, Henoch-Schonlein purpura, polyateritis nodosa, Rapidly Progressive Glomerulonephritis (RPGN), cryoglobulinaemia, giant cell arteritis (GCA), Behcet's disease and Takayasu's arteritis (TAK).

HIV infection and AIDS—C5a receptor modulators provided herein may be used to inhibit HIV infection, delay AIDS progression or decrease the severity of symptoms or HIV infection and AIDS.

Neurodegenerative disorders and related diseases—Within further aspects, C5a antagonists provided herein may be used to treat Alzheimer's disease, multiple sclerosis, and cognitive function decline associated with cardiopulmonary bypass surgery and related procedures.

In one embodiment of the invention, the compounds of the invention can be used for the treatment of diseases selected from the group consisting of sepsis (and associated disorders), COPD, rheumatoid arthritis, lupus nephritis and multiple sclerosis.

Treatment methods provided herein include, in general, administration to a patient an effective amount of one or more compounds provided herein. Suitable patients include those patients suffering from or susceptible to (i.e., prophylactic treatment) a disorder or disease identified herein. Typical patients for treatment as described herein include mammals, particularly primates, especially humans. Other suitable patients include domesticated companion animals such as a dog, cat, horse, and the like, or a livestock animal such as cattle, pig, sheep and the like.

In general, treatment methods provided herein comprise administering to a patient an effective amount of a compound one or more compounds provided herein. In a preferred embodiment, the compound(s) of the invention are preferably administered to a patient (e.g., a human) orally or topically. The effective amount may be an amount sufficient to modulate C5a receptor activity and/or an amount sufficient to reduce or alleviate the symptoms presented by the patient. Preferably, the amount administered is sufficient to yield a plasma concentration of the compound (or its active metabolite, if the compound is a pro-drug) high enough to detectably inhibit white blood cell (e.g., neutrophil) chemotaxis in vitro. Treatment regimens may vary depending on the compound used and the particular condition to be treated; for treatment of most disorders, a frequency of administration of 4 times daily or less is preferred. In general, a dosage regimen of 2 times daily is more preferred, with once a day dosing particularly preferred. It will be understood, however, that the specific dose level and treatment regimen for any particular patient will depend upon a variety of factors including the activity of the specific compound employed, the age, body weight, general health, sex, diet, time of administration, route of administration, rate of excretion, drug combination (i.e., other drugs being administered to the patient) and the severity of the particular disease undergoing therapy, as well as the judgment of the prescribing medical practitioner. In general, the use of the minimum dose sufficient to provide effective therapy is preferred. Patients may generally be monitored for therapeutic effectiveness using medical or veterinary criteria suitable for the condition being treated or prevented.

Dosage levels of the order of from about 0.1 mg to about 140 mg per kilogram of body weight per day are useful in the treatment or preventions of conditions involving pathogenic C5a activity (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. For compounds administered orally, transdermally, intravaneously, or subcutaneously, it is preferred that sufficient amount of the compound be administered to achieve a serum concentration of 5 ng (nanograms)/mL-10 µg (micrograms)/mL serum, more preferably sufficient compound to achieve a serum concentration of 20 ng-1 µg/ml serum should be administered, most preferably sufficient compound to achieve a serum concentration of 50 ng/ml-200 ng/ml serum should be administered. For direct injection into the synovium (for the treatment of arthritis) sufficient compounds should be administered to achieve a local concentration of approximately 1 micromolar.

Frequency of dosage may also vary depending on the compound used and the particular disease treated. However, for treatment of most disorders, a dosage regimen of 4 times daily, three times daily, or less is preferred, with a dosage regimen of once daily or 2 times daily being particularly preferred. It will be understood, however, that the specific dose level for any particular patient will depend upon a variety of factors including the activity of the specific compound employed, the age, body weight, general health, sex, diet, time of administration, route of administration, and rate of excretion, drug combination (i.e., other drugs being administered to the patient), the severity of the particular disease undergoing therapy, and other factors, including the judgment of the prescribing medical practitioner.

Combination Therapy

The presently disclosed compounds may be used in combination with one or more additional therapeutic agents that are used in the treatment, prevention, suppression or amelioration of the diseases or conditions for which compounds and compositions of the present invention are useful. Such one or more additional therapeutic agents may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention.

Examples of the one or more additional therapeutic agents are corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, C3aR modulators, C5aR2 modulators, T cell receptor antagonists, PD-1 inhibitors, PD-L1 inhibitors, TIGIT inhibitors, TIM-3 inhibitors, LAG-3 inhibitors, VISTA inhibitors, STING agonists, IDO inhibitors, adenosine receptor modulators, CD39 inhibitors, CD73 inhibitors, antagonists of the chemokine receptors, especially CXCR1, CXCR2, CXCR3, CXCR4, CXCR7, CCR1, CCR2, CCR3, CCR4, CCR5, CCR7, CCR7, CCR9, CX3CR1 and CXCR6, and combinations thereof.

In some embodiments, the additional therapeutic agent used in the therapeutic methods herein, is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIIB-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, LT-1951, OMS721, ALN-CCS, ACH-4471, AMY-101, Acthar gel, and CD4+CD25+ regulatory T-cells, MEDI7814, P32, P59, pembrolizumab, nivolumab, atezolizumab, avelumab, durvalumab, CCX354, CCX721, CCX9588, CCX140, CCX872, CCX598, CCX6239, CCX587, CCX624, CCX282, CCX025, CCX507, CCX430, CCX765, CCX758, CCX771, CCX662, CCX650, and combinations thereof.

The disease or disorder being treated will determine which additional therapeutic agent or therapeutic agents are most appropriately administered in combination with the compounds of the present invention—such determination can be made by a person of skill in the art.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

Non-Pharmaceutical Applications

In another aspect of the invention, the compounds of the invention can be used in a variety of non-pharmaceutical in vitro and in vivo application. For example, the compounds of the invention may be labeled and used as probes for the detection and localization of C5a receptor (cell preparations or tissue sections samples). The compounds of the invention may also be used as positive controls in assays for C5a receptor activity, i.e., as standards for determining the ability of a candidate agent to bind to C5a receptor, or as radiotracers for positron emission tomography (PET) imaging or for single photon emission computerized tomography (SPECT). Such methods can be used to characterize C5a receptors in living subjects. For example, a C5a receptor modulator may be labeled using any of a variety of well known techniques (e.g., radiolabeled with a radionuclide such as tritium), and incubated with a sample for a suitable incubation time (e.g., determined by first assaying a time course of binding). Following incubation, unbound compound is removed (e.g., by washing), and bound compound detected using any method suitable for the label employed (e.g., autoradiography or scintillation counting for radiolabeled compounds; spectroscopic methods may be used to detect luminescent groups and fluorescent groups). As a control, a matched sample containing labeled compound and a greater (e.g., 10-fold greater) amount of unlabeled compound may be processed in the same manner. A greater amount of detectable label remaining in the test sample than in the control indicates the presence of C5a receptor in the sample. Detection assays, including receptor autoradiography (receptor mapping) of C5a receptor in cultured cells or tissue samples may be performed as described by Kuhar in sections 8.1.1 to 8.1.9 of Current Protocols in Pharmacology (1998) John Wiley & Sons, New York.

The compounds provided herein may also be used within a variety of well known cell separation methods. For example, modulators may be linked to the interior surface of a tissue culture plate or other support, for use as affinity ligands for immobilizing and thereby isolating, C5a receptors (e.g., isolating receptor-expressing cells) in vitro. In one preferred application, a modulator linked to a fluorescent marker, such as fluorescein, is contacted with the cells, which are then analyzed (or isolated) by fluorescence activated cell sorting (FACS).

EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 mM NH$_4$OAc in acetonitrile/water as delivery system.

The following abbreviations are used in the Examples and throughout the description of the invention:
EtOH: Ethanol
EtONa: Sodium ethoxide
THF: Tetrahydrofuran
TLC: Thin layer chromatography
MeOH: Methanol Compounds within the scope of this invention can be synthesized as described below, using a variety of reactions known to the skilled artisan. One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Synthesis of intermediate 1: 3-(6-chloro-7-methoxy-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine

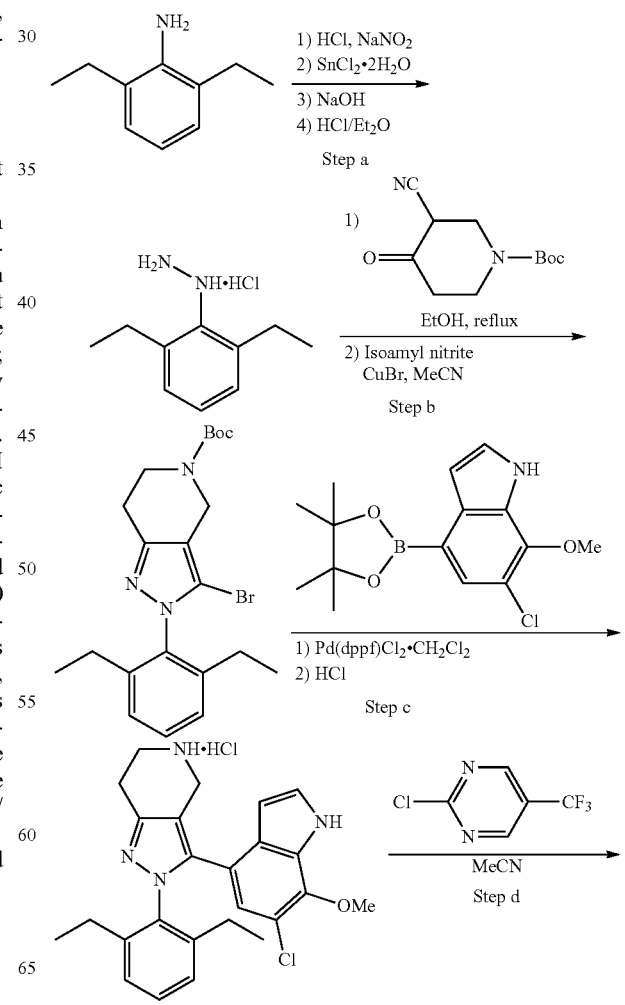

-continued

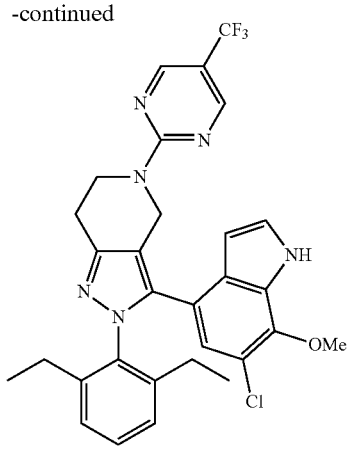

Caution: Diazonium Formation could be Potentially Dangerous, Please Handle with Care and Wear Proper Personal Protective Equipment!

Step a: To a 250 mL flask charged with 90 mL of concentrated hydrochloric acid under magnetic stirring was added 2,6-diethylaniline (10.0 g, 67.0 mmol). The resulting mixture was stirred for 30 min and cooled with an ice-salt bath until the internal temperature reached −5° C. A solution of sodium nitrite (5.5 g, 80.0 mmol) in water (60 mL) was added slowly to the above mixture while maintaining the internal temperature below 5° C.

Separately, tin(II) chloride dihydrate (31.6 g, 140.0 mmol) was added to a 500 mL 3-neck round bottom flask charged with concentrated hydrochloric acid (60 mL) under mechanical stirring. The resulting solution was then cooled with an ice bath.

The diazonium slurry was then filtered into the 500 mL flask containing the cooled tin chloride solution with vigorous stirring. After 90 min, the reaction mixture was transferred to a 500 mL Erlenmeyer flask and the flask was rinsed with water (20 mL) and chloroform (8 mL). The combined mixture was stirred overnight at room temperature. The entire liquid layer was decanted to give a wet solid. The recovered material was dried in vacuo for one day and then transferred to a 500 mL 3-neck round bottom flask equipped with an overhead mechanical stirrer and stirred with ether (180 mL). The resulting mixture was cooled in an ice bath, and NaOH solution (10 N, 30 mL) was added slowly to the above mixture while maintaining the inner temperature below 12° C. After the addition, the mixture was allowed to stand for 2 h on ice. The ether layer was decanted into a 500 mL flask and a stream of hydrogen chloride gas was bubbled into the ether solution while stirring. The resulting precipitate was collected by filtration to afford (2,6-diethylphenyl)hydrazine hydrochloride. MS: (ES) m/z calculated for $C_{10}H_{17}N_2$ $[M+H]^+$ 165.1, found 165.1.

Step b: N,N-diisopropylethylamine (8 mL, 46.0 mmol) was added to a mixture of (2,6-diethylphenyl)hydrazine hydrochloride (8 g, 39.9 mmol), tert-butyl 3-cyano-4-oxopiperidine-1-carboxylate (5 g, 22.3 mmol) and EtOH (60 mL) in a 250 mL round bottom flask under magnetic stirring. The resulting mixture was stirred under reflux for 3 h. Glacial acetic acid (12 mL, 208 mmol) was added and the mixture was stirred under reflux for another 2 h. The solvent was removed under reduced pressure and the residue was dissolved in EtOAc and washed with NaOH solution (2 N), brine, and dried over $MgSO_4$. The solvent was removed under reduced pressure and the residue was purified by silica gel flash chromatography (5 to 55% EtOAc in hexanes) to give tert-butyl 3-amino-2-(2,6-diethylphenyl)-6,7-dihydro-2H-pyrazolo[4,3-c]pyridine-5(4H)-carboxylate. MS: (ES) m/z calculated for $C_{21}H_{31}N_4O_2$ $[M+H]^+$ 371.2, found 371.2.

Caution: Diazonium Formation could be Potentially Dangerous, Please Handle with Care and Wear Proper Personal Protective Equipment!

Isopentyl nitrite (4 mL, 28.6 mmol) was added slowly at room temperature to a mixture of tert-butyl 3-amino-2-(2,6-diethylphenyl)-6,7-dihydro-2H-pyrazolo[4,3-c]pyridine-5(4H)-carboxylate (3 g, 8.1 mmol), CuBr (4 g, 27.9 mmol) and MeCN (50 mL) in a 250 mL round bottom flask under magnetic stirring. The resulting mixture was stirred at room temperature for 1 h, diluted with EtOAc, filtered through Celite, washed with saturated $NH_4Cl$ solution, and dried over $MgSO_4$. The solvent was removed under reduced pressure and the residue was purified by silica gel flash chromatography (2 to 25% EtOAc in hexanes) to give tert-butyl 3-bromo-2-(2,6-diethylphenyl)-6,7-dihydro-2H-pyrazolo[4,3-c]pyridine-5(4H)-carboxylate. MS: (ES) m/z calculated for $C_{21}H_{29}BrN_3O_2$ $[M+H]^+$ 434.1, found 434.2.

Step c: Iodomethane (1.5 mL, 24 mmol) was added to a suspension of 4-bromo-2-chloro-6-nitrophenol (3.2 g, 12.7 mmol) and $K_2CO_3$ (3 g, 21.7 mmol) in DMF (40 mL) in a 250 mL round bottom flask under magnetic stirring. The resulting mixture was stirred at 45° C. for 4 h, diluted with EtOAc, washed with brine, and dried over $MgSO_4$. The solvent was removed under reduced pressure and the residue was purified by silica gel flash chromatography (2 to 25% EtOAc in hexanes) to give 5-bromo-1-chloro-2-methoxy-3-nitrobenzene. MS: (ES) m/z calculated for $C_7H_6BrClNO_3$ $[M+H]^+$ 265.9, found 265.9.

A solution of vinylmagenesium bromide in THF (1 M, 40 mL, 40 mmol) was added rapidly to a solution of 5-bromo-1-chloro-2-methoxy-3-nitrobenzene (3.2 g, 12 mmol) in anhydrous THF (40 mL) under $N_2$ and vigorous stirring at −60° C. The reaction mixture was allowed to warm to −30° C. over 1.5 h. The reaction was quenched with saturated aqueous $NH_4Cl$ solution and the mixture was allowed to warm up to room temperature over 1 h. The reaction mixture was diluted with EtOAc, washed with brine and dried over $MgSO_4$. The solvent was removed under reduced pressure and the residue was purified by silica gel flash chromatography (2 to 20% EtOAc in hexanes) to give 4-bromo-6-chloro-7-methoxy-1H-indole. MS: (ES) m/z calculated for $C_9H_8BrClNO$ $[M+H]^+$ 259.9, found 259.9.

To a suspension of 4-bromo-6-chloro-7-methoxy-1H-indole (1.2 g, 4.6 mmol), 4,4,4',4',5,5,5',5'-octamethyl-2,2'-bi (1,3,2-dioxaborolane) (2.4 g, 9.5 mmol), and KOAc (2.3 g, 23.4 mmol) in DMSO (10 mL) was added $Pd(dppf)Cl_2$ complex with dichloromethane (600 mg, 0.73 mmol). The reaction mixture was degassed ($N_2$) for 2 min and stirred at 120° C. for 2 h. The reaction mixture was diluted with EtOAc, filtered through Celite, washed with brine and dried over $MgSO_4$. The solvent was removed under reduced pressure and the residue was purified by silica gel flash chromatography (5 to 20% EtOAc in hexanes) to give 6-chloro-7-methoxy-4-(4,4,5,5-tetramethyl-1,3,2-dioxaborolan-2-yl)-1H-indole. MS: (ES) m/z calculated for $C_{15}H_{20}BClNO_3$ $[M+H]^+$ 308.1, found 308.1.

To a suspension of tert-butyl 3-bromo-2-(2,6-diethylphenyl)-6,7-dihydro-2H-pyrazolo[4,3-c]pyridine-5(4H)-carboxylate (600 mg, 1.4 mmol), 6-chloro-7-methoxy-4-(4,4,5,5-tetramethyl-1,3,2-dioxaborolan-2-yl)-1H-indole (550 mg, 1.8 mmol), and $K_2CO_3$ (500 mg, 3.6 mmol) in p-dioxane (6 mL) and $H_2O$ (1 mL) was added $Pd(dppf)Cl_2$ complex with dichloromethane (300 mg, 0.37 mmol). The reaction mixture was degassed (N₂) for 2 min and stirred under N₂ at 100° C. for 2 h. The reaction mixture was diluted with EtOAc, filtered through Celite, washed with brine and dried over MgSO₄. The solvent was removed under reduced pressure and the residue was purified by silica gel flash chromatography (5 to 20% EtOAc in hexanes) to give tert-butyl 3-(6-chloro-7-methoxy-1H-indol-4-yl)-2-(2,6-diethylphenyl)-6,7-dihydro-2H-pyrazolo[4,3-c]pyridine-5 (4H)-carboxylate. MS: (ES) m/z calculated for C₃₀H₃₆ClN₄O₃ [M+H]⁺ 535.2.1, found 535.2.

The above tert-butyl 3-(6-chloro-7-methoxy-1H-indol-4-yl)-2-(2,6-diethylphenyl)-6,7-dihydro-2H-pyrazolo[4,3-c]pyridine-5(4H)-carboxylate was dissolved in dichloromethane (5 mL) and charged with 4 N HCl in dioxane (5 mL, 20 mmol). The resulting mixture was stirred at room temperature for 2 h. After the reaction was complete, the solvent was evaporated in vacuo to give 3-(6-chloro-7-methoxy-1H-indol-4-yl)-2-(2,6-diethylphenyl)-4,5,6,7-tetrahydro-2H-pyrazolo[4,3-c]pyridine hydrochloride. MS: (ES) m/z calculated for C₂₅H₂₉ClN₄O [M+H]⁺ 435.2, found 435.2.

Step d: N,N-diisopropylethylamine (0.2 mL, 1.15 mmol) was added to a suspension of 3-(6-chloro-7-methoxy-1H-indol-4-yl)-2-(2,6-diethylphenyl)-4,5,6,7-tetrahydro-2H-pyrazolo[4,3-c]pyridine hydrochloride (100 mg, 0.21 mmol), 2-chloro-5-(trifluoromethyl)pyrimidine (45 mg, 0.25 mmol), and Li₂CO₃ (20 mg, 0.27 mmol) in MeCN (10 mL) under magnetic stirring. The resulting mixture was stirred at 75° C. for 30 min. After cooling to room temperature, the reaction mixture was diluted with EtOAc, washed with brine and dried over MgSO₄. The solvent was removed under reduced pressure and the residue was purified by preparative TLC (40% EtOAc in hexanes) followed by trituration in MeOH to afford 3-(6-chloro-7-methoxy-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine. ¹H NMR (400 MHz, CDCl₃) δ 8.48 (s, 2H), 8.46 (s, 1H), 7.06-7.27 (m, 4H), 6.62 (d, J=1.0 Hz, 1H), 6.42-6.49 (m, 1H), 4.83 (s, 2H), 4.36 (t, J=5.7 Hz, 2H), 4.00 (s, 3H), 3.03 (t, J=5.7 Hz, 2H), 2.10-2.40 (m, 4H), 0.80-1.08 (m, 6H). MS: (ES) m/z calculated for C₃₀H₂₉ClF₃N₆O [M+H]⁺ 581.2, found 581.2.

Synthesis of intermediate 2: [4-[2-(2,6-diethylphenyl)-5-[5-(trifluoromethyl)pyrimidin-2-yl]-6,7-dihydro-4H-pyrazolo[4,3-c]pyridin-3-yl]-5-fluoro-1H-indol-7-yl]methanol

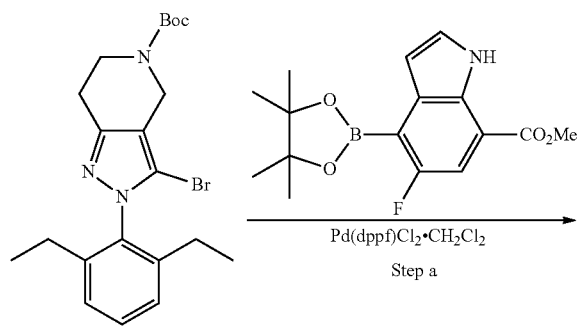

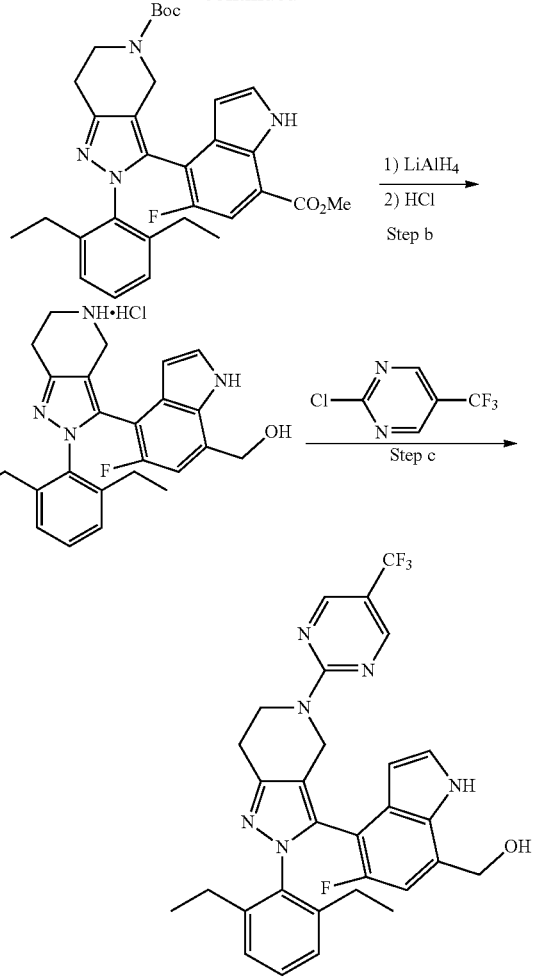

Step a: Vinylmagnesium bromide solution in THF (1 M, 341 mL, 341 mmol) was added to a solution of 4-bromo-5-fluoro-2-nitrobenzoic acid (15.0 g, 56.8 mmol) in anhydrous THF (200 mL) under N₂ at −50° C. The reaction mixture was stirred at the same temperature and allowed to warm to −40° C. over 1.5 h. The reaction mixture was quenched with saturated aqueous NH₄Cl solution and allowed to warm up to room temperature over 1 h. The reaction mixture was acidified with 1 N aqueous HCl, diluted with EtOAc, washed with brine and dried over Na₂SO₄. The solvent was removed under reduced pressure to give a crude residue.

The above crude residue was stirred in a mixture of H2504 (25 mL) in MeOH (250 mL) at reflux for 5 h. It was then cooled to room temperature and concentrated under reduced pressure. The obtained residue was diluted with EtOAc and brine. The organic layer was separated, dried with Na₂SO₄, concentrated under reduced pressure and purified by silica gel flash chromatography (0 to 50% EtOAc in hexanes) to give methyl 4-bromo-5-fluoro-1H-indole-7-carboxylate. MS: (ES) m/z calculated for C₁₀H₈BrFNO₂ [M+H]⁺ 271.9, found 271.9.

To a suspension of methyl 4-bromo-5-fluoro-1H-indole-7-carboxylate (0.900 g, 3.3 mmol), 4,4,4',4',5,5,5',5'-octamethyl-2,2'-bi(1,3,2-dioxaborolane) (1.51 g, 5.94 mmol), and KOAc (1.62 g, 16.5 mmol) in DMSO (19 mL) was added Pd(dppf)Cl₂ complex with dichloromethane (400 mg, 0.49 mmol). The reaction mixture was degassed (N₂) for 2 min and stirred at 115° C. for 1.5 h. The reaction mixture was diluted with EtOAc, filtered through Celite, washed with brine and dried over Na₂SO₄. The solvent was removed under reduced pressure and the residue was purified by silica gel flash chromatography (0 to 100% CH₂Cl₂/hexanes) to give methyl 5-fluoro-4-(4,4,5,5-tetramethyl-1,3,2-dioxaborolan-2-yl)-1H-indole-7-carboxylate. MS: (ES) m/z calculated for C₁₆H₂₀BFNO₄ [M+H]⁺ 320.1, found 320.1.

To a suspension of tert-butyl 3-bromo-2-(2,6-diethylphenyl)-6,7-dihydro-2H-pyrazolo[4,3-c]pyridine-5(4H)-carboxylate (1.00 g, 2.31 mmol), methyl 5-fluoro-4-(4,4,5,5-tetramethyl-1,3,2-dioxaborolan-2-yl)-1H-indole-7-carboxylate (740 mg, 2.31 mmol) and K₂CO₃ (1.28 g, 9.24 mmol) in p-dioxane (14 mL) and water (2.5 mL) was added Pd(dppf)Cl₂ complex with dichloromethane (400 mg, 0.49 mmol). The reaction mixture was degassed (N₂) for 2 min and stirred under N₂ at 100° C. for 2.5 h. The reaction mixture was diluted with EtOAc, washed with aqueous NaHCO₃ and dried over Na₂SO₄. The solvent was removed under reduced pressure and the residue was purified by silica gel flash chromatography (0 to 70% EtOAc in hexanes) to give tert-butyl 2-(2,6-diethylphenyl)-3-(5-fluoro-7-methoxycarbonyl-1H-indol-4-yl)-6,7-dihydro-4H-pyrazolo[4,3-c]pyridine-5-carboxylate. MS: (ES) m/z calculated for C₃₁H₃₆FN₄O₄ [M+H]⁺ 547.2, found 547.2.

Step b: The above tert-butyl 2-(2,6-diethylphenyl)-3-(5-fluoro-7-methoxycarbonyl-1H-indol-4-yl)-6,7-dihydro-4H-pyrazolo[4,3-c]pyridine-5-carboxylate (1.00 g, 1.83 mmol) was dissolved in THF (35 mL) and charged with a solution of LiAlH₄ in ether (1 M, 2.7 mL) at 0° C. The resulting mixture was stirred at 0° C. for 40 min. It was then quenched with water, diluted with IPA/CHCl₃ (1:3), washed with brine and dried over Na₂SO₄. The solvent was removed under reduced pressure and the residue was purified by silica gel flash chromatography (0 to 90% EtOAc in hexanes) to give tert-butyl 2-(2,6-diethylphenyl)-3-[5-fluoro-7-(hydroxymethyl)-1H-indol-4-yl]-6,7-dihydro-4H-pyrazolo[4,3-c]pyridine-5-carboxylate. MS: (ES) m/z calculated for C₃₀H₃₆FN₄O₃ [M+H]⁺ 519.2, found 519.2.

The above tert-butyl 2-(2,6-diethylphenyl)-3-(5-fluoro-7-(hydroxymethyl)-1H-indol-4-yl]-6,7-dihydro-4H-pyrazolo[4,3-c]pyridine-5-carboxylate (650 mg, 1.25 mmol) was dissolved in dichloromethane (13 mL) and charged with 4 N HCl in dioxane (35 mL, 140 mmol). The resulting mixture was stirred at room temperature for 1.5 h. After the reaction was complete, the solvent was evaporated in vacuo to give [4-[2-(2,6-diethylphenyl)-4,5,6,7-tetrahydropyrazolo[4,3-c]pyridin-3-yl]-5-fluoro-1H-indol-7-yl]methanol hydrochloride. MS: (ES) m/z calculated for C₂₅H₂₈FN₄O [M+H]⁺ 419.2, found 419.2.

Step c: Triethylamine (1.50 mL, 10.7 mmol) was added to a suspension of [4-[2-(2,6-diethylphenyl)-4,5,6,7-tetrahydropyrazolo[4,3-c]pyridin-3-yl]-5-fluoro-1H-indol-7-yl]methanol hydrochloride (600 mg, 1.32 mmol) and 2-chloro-5-(trifluoromethyl)pyrimidine (350 mg, 1.9 mmol) in MeCN (70 mL). The resulting mixture was stirred at 80° C. for 30 min. After cooling to room temperature, the reaction mixture was diluted with EtOAc, washed with aqueous NaHCO₃ and dried over Na₂SO₄. The solvent was removed under reduced pressure and the residue was purified by silica gel flash chromatography (0 to 90% EtOAc in hexanes) to afford [4-[2-(2,6-diethylphenyl)-5-[5-(trifluoromethyl)pyrimidin-2-yl]-6,7-dihydro-4H-pyrazolo[4,3-c]pyridin-3-yl]-5-fluoro-1H-indol-7-yl]methanol. ¹H NMR (400 MHz, CDCl₃) δ 9.05 (br s, 1H), 8.47 (br s, 2H), 7.27 (m, 1H), 7.16 (m, 2H), 6.86 (d, J=7.26 Hz, 1H), 6.56 (d, J=10.0 Hz, 1H), 6.37 (t, J=2.6 Hz, 1H), 4.88 (m, 3H), 4.68 (d, J=16.4 Hz, 1H), 4.43 (m, 1H), 4.29 (m, 1H), 3.04 (t, J=6.0 Hz, 2H), 2.38-2.58 (m, 3H), 2.17 (sextet, J=7.3 Hz, 1H), 1.94 (sextet, J=7.3 Hz, 1H), 1.21 (t, J=7.4 Hz, 3H), 0.75 (t, J=7.4 Hz, 3H). MS: (ES) m/z calculated for C₃₀H₂₉F₄N₆O [M+H]⁺ 565.2, found 565.2.

Synthesis of intermediate 3: 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)urea

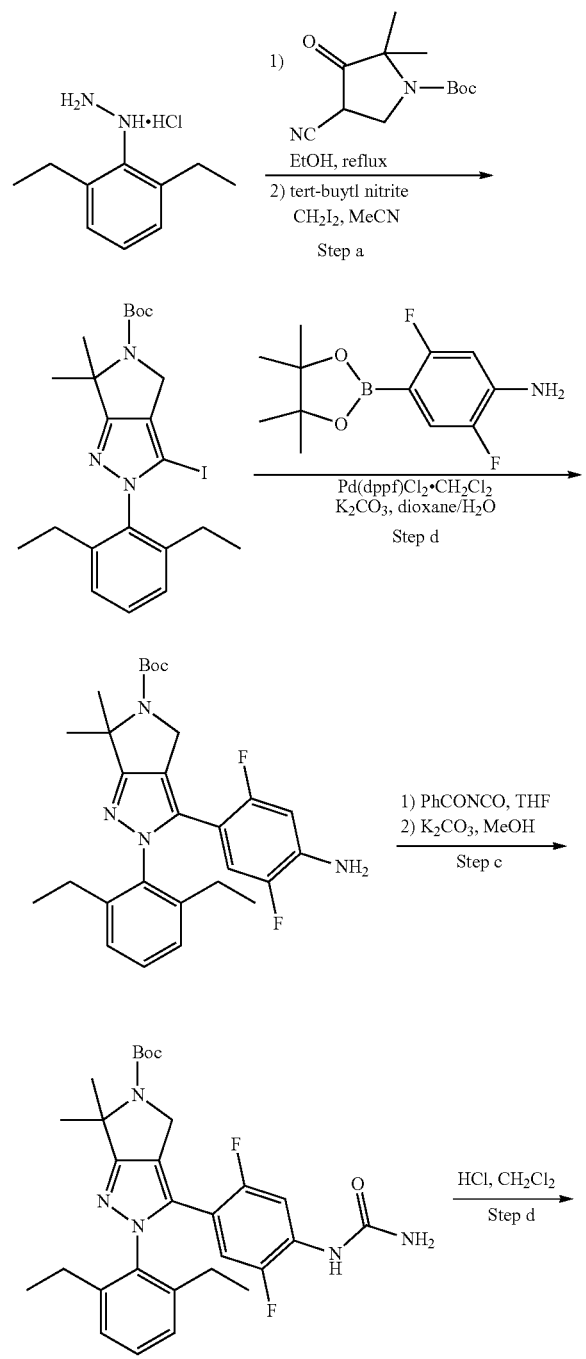

-continued

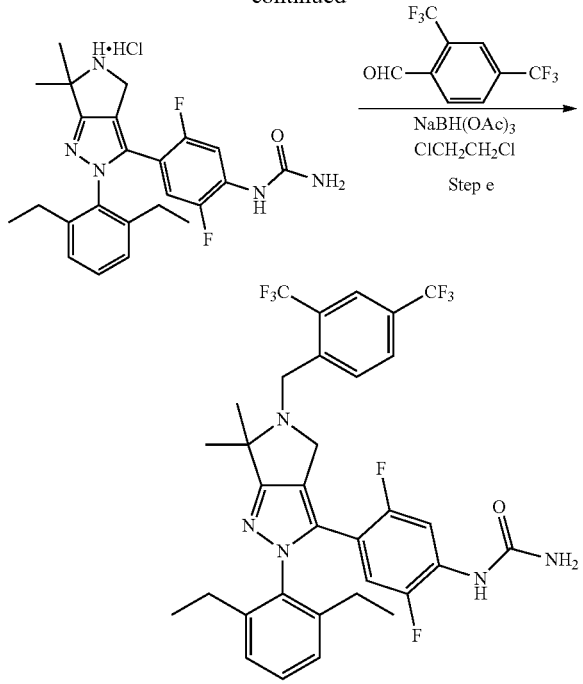

Step a: Pyridine (4.0 mL, 49.5 mmol) was added to a mixture of (2,6-diethylphenyl)hydrazine hydrochloride (5.0 g, 24.9 mmol), tert-butyl 4-cyano-2,2-dimethyl-3-oxopyrrolidine-1-carboxylate (5.0 g, 21.0 mmol) and EtOH (60 mL) in a 250 mL round bottom flask under magnetic stirring. The resulting mixture was stirred at 70° C. for 24 h. The solvent was removed under reduced pressure, and the residue was diluted with EtOAc and washed with aqueous citric acid solution, saturated aqueous NaHCO$_3$ solution, brine, and dried over MgSO$_4$. The solvent was removed under reduced pressure and the residue was crystallized from cyclohexane to give tert-butyl 3-amino-2-(2,6-diethylphenyl)-6,6-dimethyl-2,6-dihydropyrrolo[3,4-c]pyrazole-5(4H)-carboxylate. MS: (ES) m/z calculated for $C_{22}H_{33}N_4O_2$ [M+H]$^+$ 385.2, found 385.2.

Caution: Diazonium Formation could be Potentially Dangerous, Please Handle with Care and Wear Proper Personal Protective Equipment!

Tert-butyl nitrite (0.5 mL, 3.8 mmol) was added slowly at room temperature to a mixture of tert-butyl 3-amino-2-(2,6-diethylphenyl)-6,6-dimethyl-2,6-dihydropyrrolo[3,4-c]pyrazole-5(4H)-carboxylate (1 g, 2.6 mmol), diiodomethane (1.5 mL, 18.6 mmol) and MeCN (15 mL) in a 100 mL round bottom flask under magnetic stirring. The resulting mixture was stirred at 45° C. for 3 h before it was diluted with toluene, washed with saturated NH$_4$Cl solution/NH$_4$OH (3:1), brine, and dried over MgSO$_4$. The solvent was removed under reduced pressure and the residue was purified by silica gel flash chromatography (2 to 25% EtOAc in hexanes) to give tert-butyl 2-(2,6-diethylphenyl)-3-iodo-6,6-dimethyl-2,6-dihydropyrrolo[3,4-c]pyrazole-5(4H)-carboxylate. MS: (ES) m/z calculated for $C_{22}H_{31}IN_3O_2$ [M+H]$^+$ 496.1, found 496.2.

Step b: A mixture of 4-bromo-2,5-difluoroaniline (1.5 g, 7.2 mmol), 4,4,4',4',5,5,5',5'-octamethyl-2,2'-bi(1,3,2-dioxaborolane) (2.2 g, 8.7 mmol), KOAc (1.8 g, 18.3 mmol) and Pd(dppf)Cl$_2$ complex with dichloromethane (580 mg, 0.7 mmol) in dioxane (12 mL) was stirred at 95° C. for 2 h under nitrogen. The mixture was then cooled to room temperature and filtered over Celite. The filtrate was collected, concentrated under reduced pressure, and purified by silica gel flash chromatography (0 to 50% EtOAc in hexanes) to give 2,5-difluoro-4-(4,4,5,5-tetramethyl-1,3,2-dioxaborolan-2-yl)aniline. MS: (ES) m/z calculated for $C_{12}H_{17}BF_2NO_2$ [M+H]$^+$ 256.1, found 256.2.

To a suspension of tert-butyl 2-(2,6-diethylphenyl)-3-iodo-6,6-dimethyl-2,6-dihydropyrrolo[3,4-c]pyrazole-5(4H)-carboxylate (0.7 g, 1.4 mmol), 2,5-difluoro-4-(4,4,5,5-tetramethyl-1,3,2-dioxaborolan-2-yl)aniline (0.7 g, 2.7 mmol), K$_2$CO$_3$ (1.3 g, 7.2 mmol) in dioxane (10 mL) and water (2 mL) was added Pd(dppf)Cl$_2$ complex with dichloromethane (300.0 mg, 0.37 mmol). The reaction mixture was degassed (N$_2$) for 2 min and stirred under N$_2$ at 100° C. for 2 h. The reaction mixture was diluted with EtOAc, filtered through Celite, washed with brine, dried over MgSO$_4$, and filtered. The solvent was removed under reduced pressure and the residue was purified by silica gel flash chromatography (2 to 10% EtOAc in hexanes) to give tert-butyl 3-(4-amino-2,5-difluorophenyl)-2-(2,6-diethylphenyl)-6,6-dimethyl-2,6-dihydropyrrolo[3,4-c]pyrazole-5(4H)-carboxylate. MS: (ES) m/z calculated for $C_{28}H_{35}F_2N_4O_2$ [M+H]$^+$ 497.3, found 497.5.

Step c: A mixture of tert-butyl 3-(4-amino-2,5-difluorophenyl)-2-(2,6-diethylphenyl)-6,6-dimethyl-2,6-dihydropyrrolo[3,4-c]pyrazole-5(4H)-carboxylate (0.5 g, 1.0 mmol) and benzoyl isocyanate (0.5 g, 3.4 mmol) in THF (10 mL) was stirred for 3 h at room temperature. The mixture was concentrated under reduced pressure to obtain tert-butyl 3-(4-(3-benzoylureido)-2,5-difluorophenyl)-2-(2,6-diethylphenyl)-6,6-dimethyl-2,6-dihydropyrrolo[3,4-c]pyrazole-5(4H)-carboxylate.

A mixture of tert-butyl 3-(4-(3-benzoylureido)-2,5-difluorophenyl)-2-(2,6-diethylphenyl)-6,6-dimethyl-2,6-dihydropyrrolo[3,4-c]pyrazole-5(4H)-carboxylate (~1.0 mmol, from above) and K$_2$CO$_3$ (1.3 g, 7.2 mmol) in MeOH (15 mL) was stirred for 2 h at room temperature followed by 20 min at 50° C. The mixture was extracted with EtOAc. The organic layer was separated, dried over MgSO$_4$, concentrated under reduced pressure and purified by silica gel flash chromatography (10 to 50% EtOAc in hexanes) to afford tert-butyl 2-(2,6-diethylphenyl)-3-(2,5-difluoro-4-ureidophenyl)-6,6-dimethyl-2,6-dihydropyrrolo[3,4-c]pyrazole-5(4H)-carboxylate. MS: m/z calculated for $C_{29}H_{36}F_2N_5O_3$ [M+H]$^+$ 540.3, found 540.3.

Step d: The above tert-butyl 2-(2,6-diethylphenyl)-3-iodo-6,6-dimethyl-2,6-dihydropyrrolo[3,4-c]pyrazole-5(4H)-carboxylate was dissolved in dichloromethane (10 mL) and charged with 4 N HCl in dioxane (5 mL, 20 mmol). The resulting mixture was stirred at room temperature for 12 h. Upon completion, the solvent was evaporated in vacuo to give 1-(4-(2-(2,6-diethylphenyl)-6,6-dimethyl-2,4,5,6-tetrahydropyrrolo[3,4-c]pyrazol-3-yl)-2,5-difluorophenyl)urea hydrochloride. MS: (ES) m/z calculated for $C_{24}H_{28}F_2N_5O$ [M+H]$^+$ 440.2, found 440.3.

Step e: N,N-diisopropylethylamine (0.2 mL, 1.2 mmol) was added to a suspension 1-(4-(2-(2,6-diethylphenyl)-6,6-dimethyl-2,4,5,6-tetrahydropyrrolo[3,4-c]pyrazol-3-yl)-2,5-difluorophenyl)urea hydrochloride (0.1 g, 0.2 mmol), and 2,4-bis(trifluoromethyl)benzaldehyde (0.2 g, 0.8 mmol) in 1,2-dichloroethane (10 mL) under magnetic stirring. After stirring at room temperature for 10 min, NaBH(OAc)$_3$ (0.3 g, 1.4 mmol) was added in portions. The resulting mixture was stirred at 45° C. for 2 h. After cooling to room temperature, the reaction mixture was diluted with EtOAc, washed with aqueous NaHCO$_3$ solution, brine and dried over MgSO$_4$. The solvent was removed under reduced pressure and the residue was purified by preparative TLC (50% EtOAc in hexanes) followed by HPLC (MeCN/H$_2$O, with 0.1% TFA) to give 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)urea. $^1$H NMR (400 MHz, CDCl$_3$) δ 8.18 (d, J=8.3 Hz, 1H), 7.88-7.98 (m, 2H), 7.75-7.83 (m, 1H), 7.31 (t, J=7.7 Hz, 1H), 7.14 (d, J=7.7 Hz, 2H), 6.79-6.85 (br, 1H), 6.40 (dd, J=6.5, 12.1 Hz, 1H), 4.79 (s, 2H), 4.13 (s, 2H), 3.74 (s, 2H), 2.20-2.34 (m, 4H), 1.51 (s, 6H), 1.06 (t, J=7.6 Hz, 6H). MS: (ES) m/z calculated for C$_{33}$H$_{32}$F$_8$N$_5$O [M+H]$^+$ 666.2, found 666.2.

Synthesis of intermediate 4: 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole

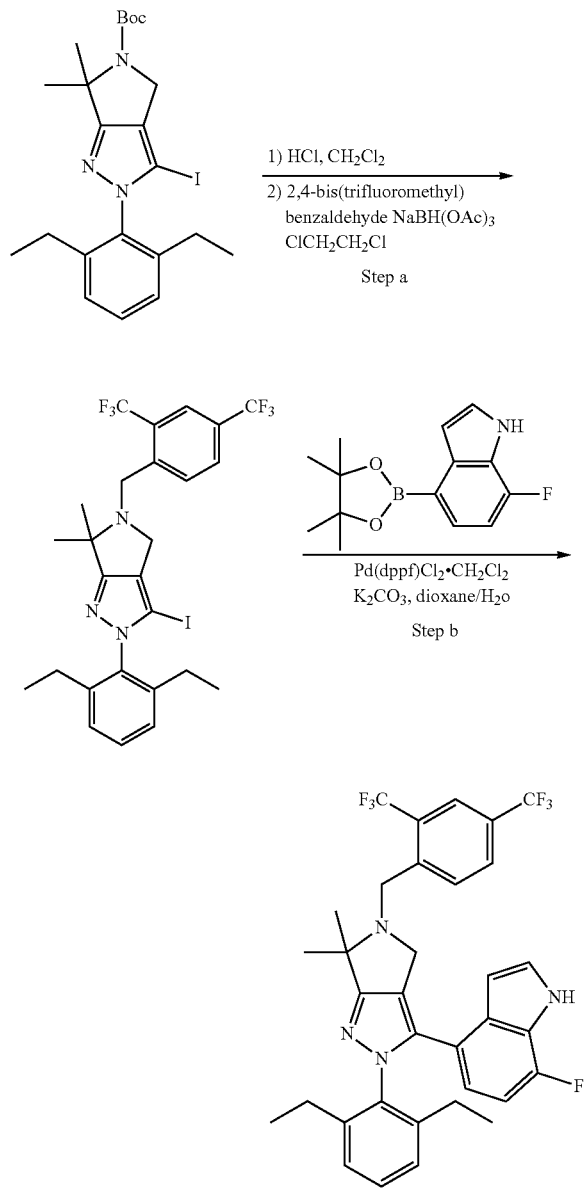

Step a: The above tert-butyl 2-(2,6-diethylphenyl)-3-iodo-6,6-dimethyl-2,6-dihydropyrrolo[3,4-c]pyrazole-5(4H)-carboxylate was dissolved in dichloromethane (10 mL) and charged with 4 N HCl in dioxane (5 mL, 20 mmol). The resulting mixture was stirred at room temperature for 12 h. Upon completion, the solvent was evaporated in vacuo to give 2-(2,6-diethylphenyl)-3-iodo-6,6-dimethyl-2,4,5,6-tetrahydropyrrolo[3,4-c]pyrazole hydrochloride. MS: (ES) m/z calculated for C$_{17}$H$_{23}$IN$_3$ [M+H]$^+$ 396.1, found 396.2.

N,N-diisopropylethylamine (0.3 mL, 1.73 mmol) was added to a suspension of 2-(2,6-diethylphenyl)-3-iodo-6,6-dimethyl-2,4,5,6-tetrahydropyrrolo[3,4-c]pyrazole hydrochloride (680 mg, 1.57 mmol), and 2,4-bis(trifluoromethyl)benzaldehyde (800 mg, 3.3 mmol) in 1,2-dichloroethane (10 mL) under magnetic stirring. After stirring at room temperature for 10 min, NaBH(OAc)$_3$ (800 mg, 3.77 mmol) was added in portions. The resulting mixture was stirred at 45° C. for 2 h. After cooling to room temperature, the reaction mixture was diluted with EtOAc, washed with aqueous NaHCO$_3$ solution, brine and dried over MgSO$_4$. The solvent was removed under reduced pressure and the residue was purified by silica gel flash chromatography (2 to 25% EtOAc in hexanes) to give 5-(2,4-bis(trifluoromethyl)benzyl)-2-(2,6-diethylphenyl)-3-iodo-6,6-dimethyl-2,4,5,6-tetrahydropyrrolo[3,4-c]pyrazole. MS: (ES) m/z calculated for C$_{26}$H$_{27}$F$_6$IN$_3$ [M+H]$^+$ 622.1, found 622.1.

Step b: To a suspension of 4-bromo-7-fluoro-1H-indole (1.00 g, 4.67 mmol), bis(pinacolato)diboron (1.31 g, 5.14 mmol) and KOAc (1.15 g, 11.7 mmol) in dioxane (15 mL) was added Pd(dppf)Cl$_2$ complex with dichloromethane (416 mg, 0.51 mmol). The reaction mixture was degassed with N$_2$ for 2 min and stirred at 100° C. for 2 h. The reaction mixture was cooled to room temperature, diluted with EtOAc, and filtered through Celite. The solvent was removed under reduced pressure and the residue was purified by silica gel flash chromatography (0 to 30% EtOAc in hexanes) to give 7-fluoro-4-(4,4,5,5-tetramethyl-1,3,2-dioxaborolan-2-yl)-1H-indole. MS: (ES) m/z calculated for C$_{14}$H$_{18}$I$_3$FNO$_2$ [M+H]$^+$ 262.1, found 262.1.

A mixture of 5-(2,4-bis(trifluoromethyl)benzyl)-3-iodo-2-(2,6-diethylphenyl)-6,6-dimethyl-2,4,5,6-tetrahydropyrrolo[3,4-c]pyrazole (200 mg, 0.32 mmol), 7-fluoro-4-(4,4,5,5-tetramethyl-1,3,2-dioxaborolan-2-yl)-1H-indole (150 mg, 0.57 mmol), K$_2$CO$_3$ (276 mg, 2.0 mmol) and Pd(dppf)Cl$_2$ complex with dichloromethane (60 mg, 0.07 mmol) in dioxane (6 mL) and water (1 mL) was stirred at 100° C. for 5 h under N$_2$. The mixture was cooled to room temperature, diluted with EtOAc, and filtered through a plug of Celite. The filtrate was collected, concentrated in vacuo and the residue was purified by silica gel flash chromatography (0 to 50% EtOAc in hexanes) to yield 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole.

$^1$H NMR (400 MHz, CDCl$_3$) δ 8.44 (s, 1H), 8.19 (d, J=8.0 Hz, 1H), 7.86 (s, 1H), 7.75 (d, J=8.4 Hz, 1H), 7.22 (m, 2H), 7.07 (d, J=7.6 Hz, 2H), 6.61 (m, 1H), 6.47 (m, 2H), 4.15 (s, 2H), 3.71 (s, 2H), 2.37 (m, 2H), 2.22 (m, 2H), 1.56 (s, 6H), 1.00 (t, J=7.6 Hz, 6H). MS: (ES) m/z calculated for C$_{34}$H$_{32}$F$_7$N$_4$ [M+H]$^+$ 629.2, found 629.2.

Example 1: Synthesis of (phosphonooxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

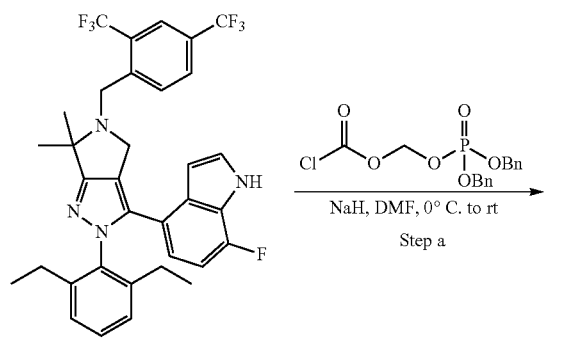

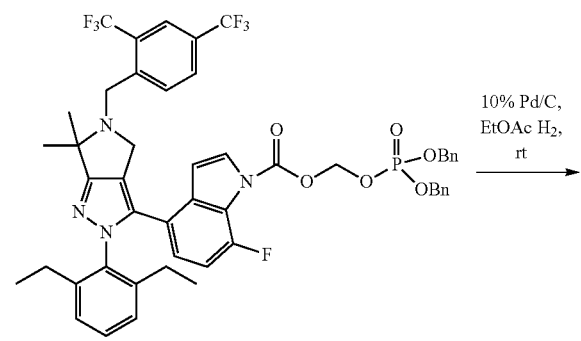

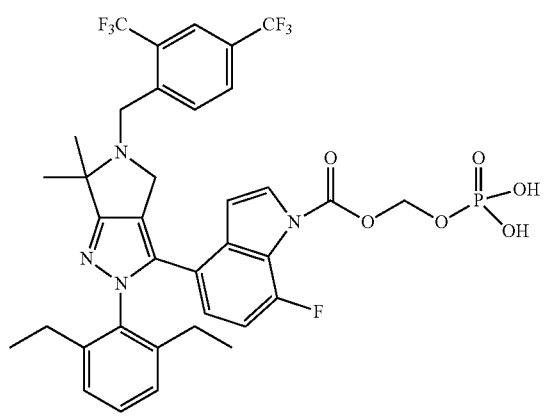

Step a: To a stirred solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (240 mg, 0.35 mmol) in DMF was added NaH (60%, 60 mg, 1.5 mmol) at 0° C. The mixture was stirred at 0° C. for 10 min, followed by addition of dibenzyloxyphosphoryloxymethyl carbonochloridate (263 mg, 0.71 mmol) at 0° C. The resulting mixture was stirred and allowed to warm up to room temperature over 30 min. After completion of the reaction, the reaction was quenched with water, extracted with EtOAc, dried over $Mg_2SO_4$ and concentrated in vacuo. The crude product was purified by silica gel chromatography (10 to 50% EtOAc in hexanes) to give ((bis(benzyloxy)phosphoryl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for $C_{50}H_{47}F_7N_4O_6P$ $[M+H]^+$ 963.3, found 963.3.

Step b: To a solution of ((bis(benzyloxy)phosphoryl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (79 mg, 0.08 mmol) in ethyl acetate (40 mL) was added 10% Pd/C (100 mg), and hydrogenated under 45 psi for 20 min. The reaction mixture was filtered through Celite, rinsed with 1:1 EtOAc/MeOH (15 mL), and concentrated to dryness. The residue was purified by HPLC (MeCN/$H_2O$, with 0.1% TFA) to give (phosphonooxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, $d_6$-DMSO) δ 8.13 (d, J=8.2 Hz, 1H), 8.01 (d, J=8.2 Hz, 1H), 7.95 (s, 1H), 7.80 (d, J=4.8 Hz, 1H), 7.30 (t, J=7.8 Hz, 1H), 7.12 (d, J=7.8 Hz, 2H), 6.95 (dd, J=8.6, 12.1 Hz, 1H), 6.56-6.66 (m, 2H), 5.70 (d, J=14.4 Hz, 2H), 4.15 (s, 2H), 3.60 (s, 2H), 3.35 (br, 2H), 2.14-2.22 (m, 4H), 1.47 (s, 6H), 0.90 (t, J=7.6 Hz, 6H). MS: (ES) m/z calculated for $C_{36}H_{35}F_7N_4O_6P$ $[M+H]^+$ 783.2, found 783.2.

Example 2: Synthesis of (S)-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)-L-cysteine

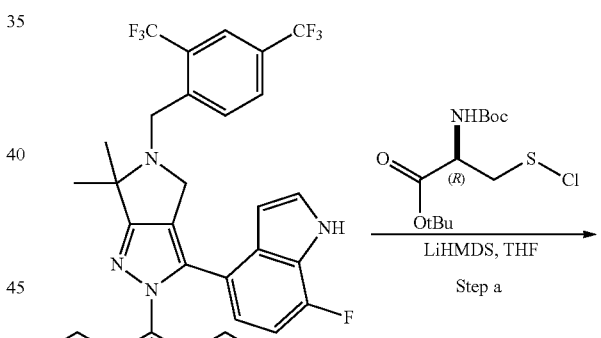

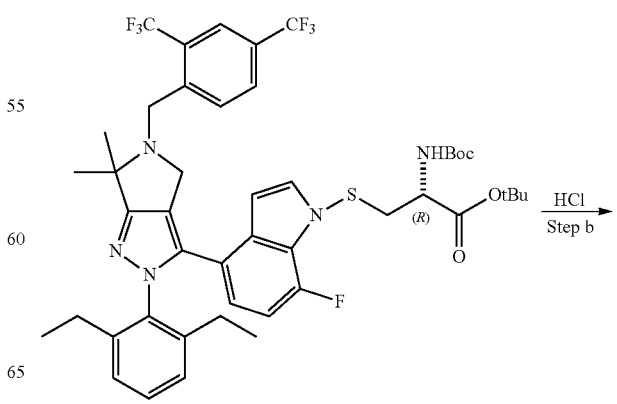

-continued

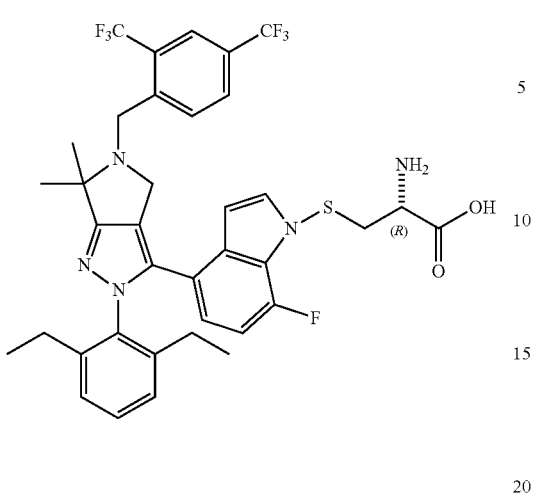

Step a: To a stirred solution of di-tert-butyl 3,3'-disulfanediyl(2R,2'R)-bis(2-((tert-butoxycarbonyl)amino)propanoate) (830 mg, 1.5 mmol) in dichloroethane (6 mL) at 0° C. was added thionyl chloride (0.14 mL, 1.9 mmol). The mixture was stirred at 0° C. for 15 min to form tert-butyl N-(tert-butoxycarbonyl)-S-chloro-L-cysteinate which was used directly in the next step.

To a stirred solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (240 mg, 0.35 mmol) in THF (10 mL) under $N_2$ at −45° C. was added 1 M LiHMDS solution in THF (0.8 mL, 0.8 mmol). After stirring for 15 min at −45° C., tert-butyl N-(tert-butoxycarbonyl)-S-chloro-L-cysteinate formed above (~1.5 mmol) was added. The resulting mixture was stirred and allowed to warm to room temperature over 30 min. After completion, the reaction was quenched with water, extracted with EtOAc, dried over $MgSO_4$ and concentrated in vacuo. The crude product was purified by silica gel chromatography (10 to 50% EtOAc in hexanes) to give tert-butyl (S)-(4-(5-(2,4-(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-O—N-(tert-butoxycarbonyl)-L-cysteinate. MS: (ES) m/z calculated for $C_{46}H_{53}F_7N_5O_4S$ [M+H]+ 904.4, found 904.5.

Step b: To a solution of tert-butyl (S)-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)-N-(tert-butoxycarbonyl)-L-cysteinate (220 mg, 0.24 mmol) in dichloromethane (6 mL) was added 4 N HCl in dioxane (5 mL, 20 mmol). The resulting mixture was stirred at room temperature overnight. After completion, the mixture was concentrated in vacuo. The residue was by HPLC (MeCN/$H_2O$, with 0.1% TFA) to give (S)-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)-L-cysteine. $^1$H NMR (400 MHz, $CD_3OD$) δ 8.24 (d, J=7.6 Hz, 1H), 7.98-8.10 (m, 2H), 7.63-7.66 (m, 2H), 7.22-7.37 (m, 2H), 6.97-7.03 (m, 1H), 6.63-6.68 (m, 1H), 6.43-6.47 (m, 1H), 4.71-4.86 (m, 5H), 4.07-4.27 (m, 3H), 3.14-3.33 (m, 2H), 2.37-2.49 (m, 2H), 2.02-2.26 (m, 2H), 1.85-1.94 (m, 6H), 1.25-1.42 (m, 3H), 0.77-0.84 (m, 3H). MS: (ES) m/z calculated for $C_{37}H_{37}F_7N_5O_2S$ [M+H]+ 748.3, found 748.2.

Example 3: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)phosphonic acid

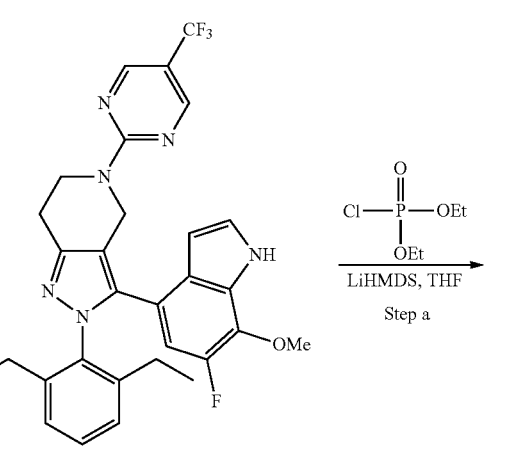

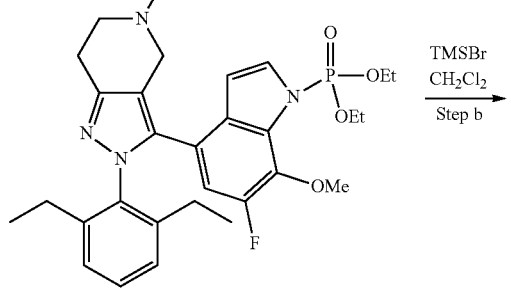

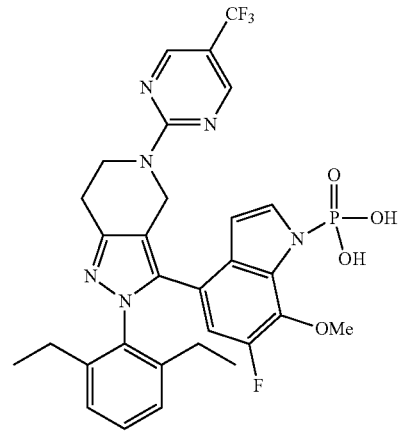

Step a: To a stirred solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (230 mg, 0.4 mmol) in THF (10 mL) under $N_2$ at −70° C. was added 1 M LiHMDS solution in THF (0.6 mL, 0.6 mmol). After stirring 15 min at −70° C., diethyl phosphorochloridate (0.1 mL, 0.8 mmol) was added. The resulting mixture was allowed to warm to room temperature over 1 h. After completion, the mixture was quenched with water, extracted with EtOAc, washed with saturated aqueous NaHCO₃ solution, dried over MgSO₄ and concentrated in vacuo. The crude product was purified by silica gel chromatography (5 to 25% EtOAc in hexanes) to give diethyl (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)phosphonate. MS: (ES) m/z calculated for $C_{34}H_{38}F_4N_6O_4P$ [M+H]⁺ 701.3, found 701.3.

Step b: To a solution of diethyl (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)phosphonate (75 mg, 0.11 mmol) in dichloromethane (6 mL) at 0° C. was added TMSBr (0.2 mL, 1.5 mmol). The resulting mixture was allowed to warm to room temperature over 1 h, and then stirred at 40° C. overnight. After completion, the reaction mixture was concentrated in vacuo. The residue was purified by HPLC (MeCN/H₂O, with 0.1% TFA) to give (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)phosphonic acid. ¹H NMR (400 MHz, CD₃OD) δ 8.58 (s, 2H), 7.68 (dd, J=2.5, 3.5 Hz, 1H), 7.32 (t, J=7.7 Hz, 1H), 7.16 (br, 2H), 6.49-6.57 (m, 2H), 4.82-4.90 (m, 4H), 4.39 (s, 2H), 3.99 (s, 3H), 2.98 (t, J=5.9 Hz, 2H), 2.05-2.42 (m, 4H), 0.78-1.25 (m, 6H). MS: (ES) m/z calculated for $C_{30}H_{30}F_4N_6O_4P$ [M+H]⁺ 645.2, found 645.4.

Example 4: Synthesis of (phosphonooxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

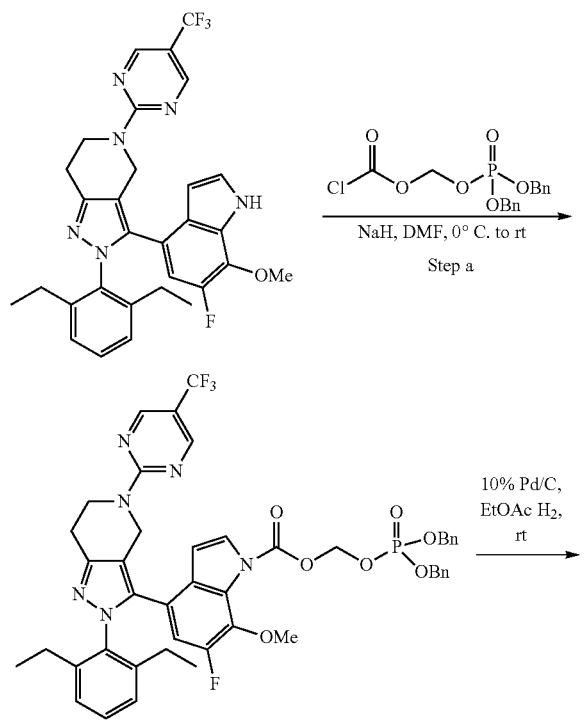

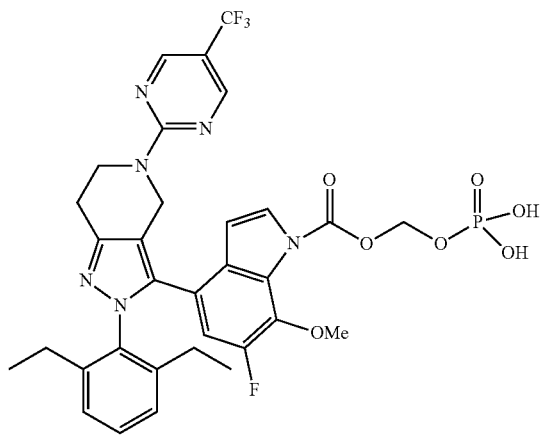

Step a: To a stirred solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (570 mg, 1.0 mmol) in DMF was added NaH (60%, 60 mg, 1.5 mmol) at 0° C. The mixture was stirred at 0° C. for 10 min, followed by addition of dibenzyloxyphosphoryloxymethyl carbonochloridate (526 mg, 1.42 mmol). The resulting mixture was stirred and allowed to warm to room temperature over 30 min. After completion, the mixture was quenched with water, extracted with EtOAc, dried over MgSO₄ and concentrated in vacuo. The crude product was purified by silica gel chromatography (10 to 100% EtOAc in hexanes) to give ((bis(benzyloxy)phosphoryl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. MS: (ES) m/z calculated for $C_{46}H_{44}F_4N_6O_7P$ [M+H]⁺ 899.3, found 899.3.

Step b: To a solution of ((bis(benzyloxy)phosphoryl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (120 mg, 0.13 mmol) in ethyl acetate (45 mL) was added 10% Pd/C (200 mg), and hydrogenated under 50 psi for 20 min. The reaction mixture was filtered through Celite, rinsed with 1:1 EtOAc/MeOH (15 mL), concentrated to dryness. The residue was purified by HPLC (MeCN/H₂O, with 0.1% TFA) to give (phosphonooxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. ¹H NMR (400 MHz, CD₃OD) δ 8.58 (s, 2H), 7.87 (d, J=3.9 Hz, 1H), 7.33 (t, J=7.6 Hz, 1H), 7.16 (br s, 2H), 6.59-6.64 (m, 2H), 5.87 (d, J=14.4 Hz, 2H), 4.74-4.86 (m, 4H), 4.39 (s, 2H), 3.97 (s, 3H), 2.98 (t, J=5.7 Hz, 2H), 2.05-2.42 (m, 4H), 0.76-1.28 (m, 6H). MS: (ES) m/z calculated for $C_{32}H_{32}F_4N_6O_7P$ [M+H]⁺ 719.2, found 719.2.

Example 5: Synthesis of (E)-4-(((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)oxy)methoxy)-4-oxobut-2-enoic acid

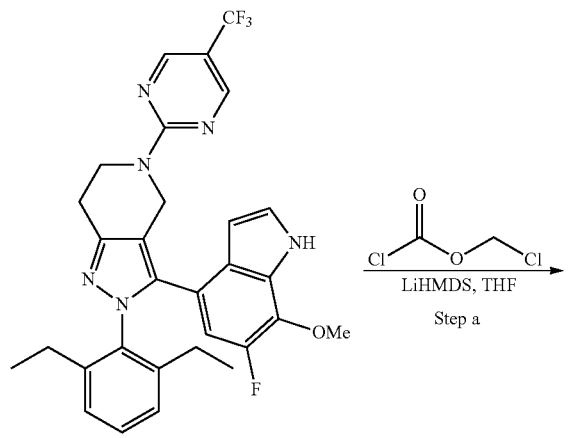

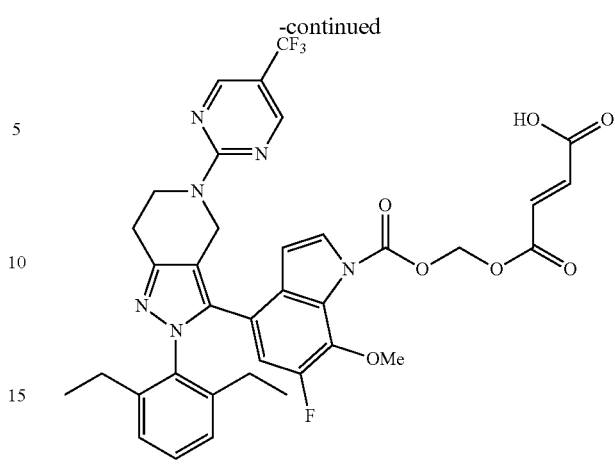

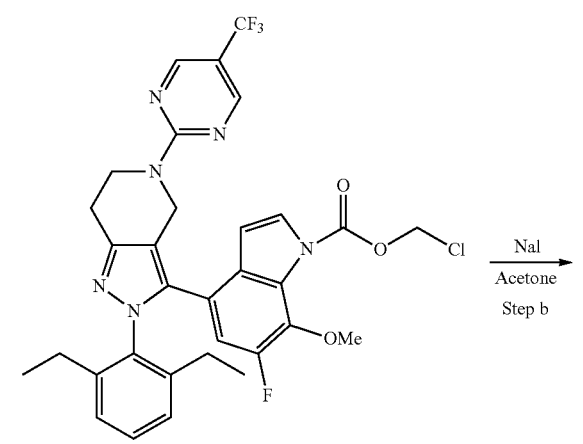

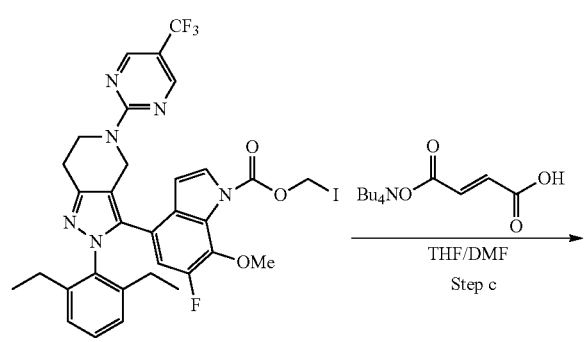

Step a: To a stirred solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (280 mg, 0.5 mmol) in THF (10 mL) at −78° C. was added 1 M LiHMDS solution in THF (0.8 mL, 0.8 mmol). The mixture was stirred at −78° C. for 15 min, followed by addition of chloromethyl carbonochloridate (80 4, 0.9 mmol). The resulting mixture was stirred and allowed to warm up to room temperature over 30 min. After completion, the mixture was quenched with saturated aqueous NH$_4$Cl solution, extracted with EtOAc, dried over Mg$_2$SO$_4$ and concentrated in vacuo to give chloromethyl 4-(2-(2,6-diethylphenyl)-5-(5-[4,3-c]pyridin-3-yl)-6-fluoro-7-methoxy-1H-indole-1-carboxylate, which was directly in the next step. MS: (ES) m/z calculated for C$_{32}$H$_{30}$ClF$_4$N$_6$O$_3$ [M+H]$^+$ 657.2, found 657.2.

Step a: NaI (350 mg, 2.33 mmol) was added to a stirred solution of chloromethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (300 mg, 0.46 mmol) in acetone (10 mL) at room temperature. The resulting mixture was stirred at 45° C. overnight. After completion, the mixture was quenched with brine, extracted with EtOAc, dried over MgSO$_4$ and concentrated in vacuo. The crude product was purified by silica gel chromatography (5 to 25% EtOAc in hexanes) to give iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. MS: (ES) m/z calculated for C$_{32}$H$_{30}$F$_4$IN$_6$O$_3$ [M+H]$^+$ 749.1, found 749.2.

Step c: To a solution of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (50 mg, 0.07 mmol) in THF (5 mL) at 0° C. was added fumaric acid tetrabutylammonium salt (25 mg, 0.07 mmol) in DMF (1 mL). The resulting mixture was allowed to warm to room temperature over 1 h. After completion, the mixture was concentrated in vacuo. The residue was purified by HPLC (MeCN/H$_2$O, with 0.1% TFA) to give (E)-4-(((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)oxy)methoxy)-4-oxobut-2-enoic acid. $^1$H NMR (400 MHz, CD$_3$OD) δ 8.58 (s, 2H), 7.87 (d, J=3.9 Hz, 1H), 7.33 (t, J=7.6 Hz, 1H), 7.16 (br s, 2H), 6.59-6.64 (m, 2H), 5.87 (d, J=14.4 Hz, 2H), 4.74-4.86 (m, 4H), 4.39 (s, 2H), 3.97 (s, 3H), 2.98 (t, J=5.7 Hz, 2H), 2.05-2.42 (m, 4H), 0.76-1.28 (m, 6H). MS: (ES) m/z calculated for C$_{36}$H$_{33}$F$_4$N$_6$O$_7$ [M+H]$^+$ 737.2, found 737.2.

Example 6: Synthesis of ((dimethylglycyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

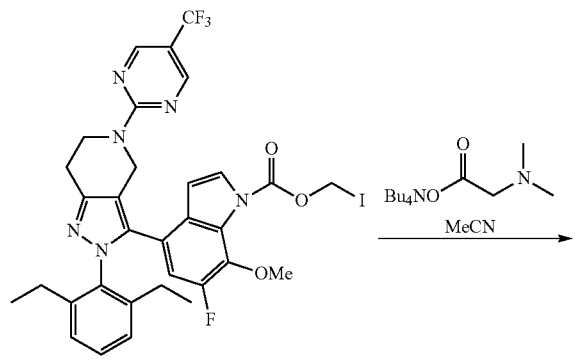

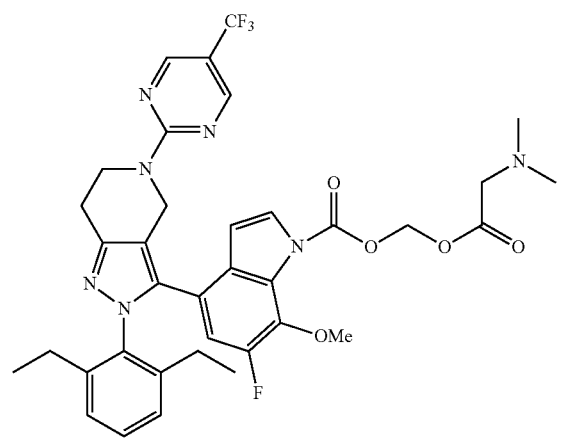

To a solution of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (40 mg, 0.06 mmol) in MeCN (5 mL) at 0° C. was added tetrabutylammonium dimethylglycinate (20 mg, 0.06 mmol) in DMF (1 mL). The resulting mixture was allowed to warm to room temperature over 1 h. After completion, the mixture was quenched with 1 N HCl (0.1 mL, 0.1 mmol) and purified by HPLC (MeCN/H$_2$O, with 0.1% TFA) to give ((dimethylglycyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate as TFA salt. $^1$H NMR (400 MHz, CD$_3$OD) δ 8.59 (s, 2H), 7.92 (d, J=3.9 Hz, 1H), 7.34 (t, J=7.6 Hz, 1H), 7.17 (br s, 2H), 6.63-6.74 (m, 2H), 5.83 (s, 2H), 4.81-4.88 (br s, 1H), 4.46 (s, 2H), 4.39 (s, 2H), 3.97 (s, 3H), 3.45 (s, 5H), 2.95-3.03 (m, 5H), 2.05-2.42 (m, 4H), 0.76-1.28 (m, 6H). MS: (ES) m/z calculated for C$_{36}$H$_{38}$F$_4$N$_7$O$_5$ [M+H]$^+$ 724.2, found 724.2.

Example 7: Synthesis of ((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)carbamoyl)phosphoramidic acid

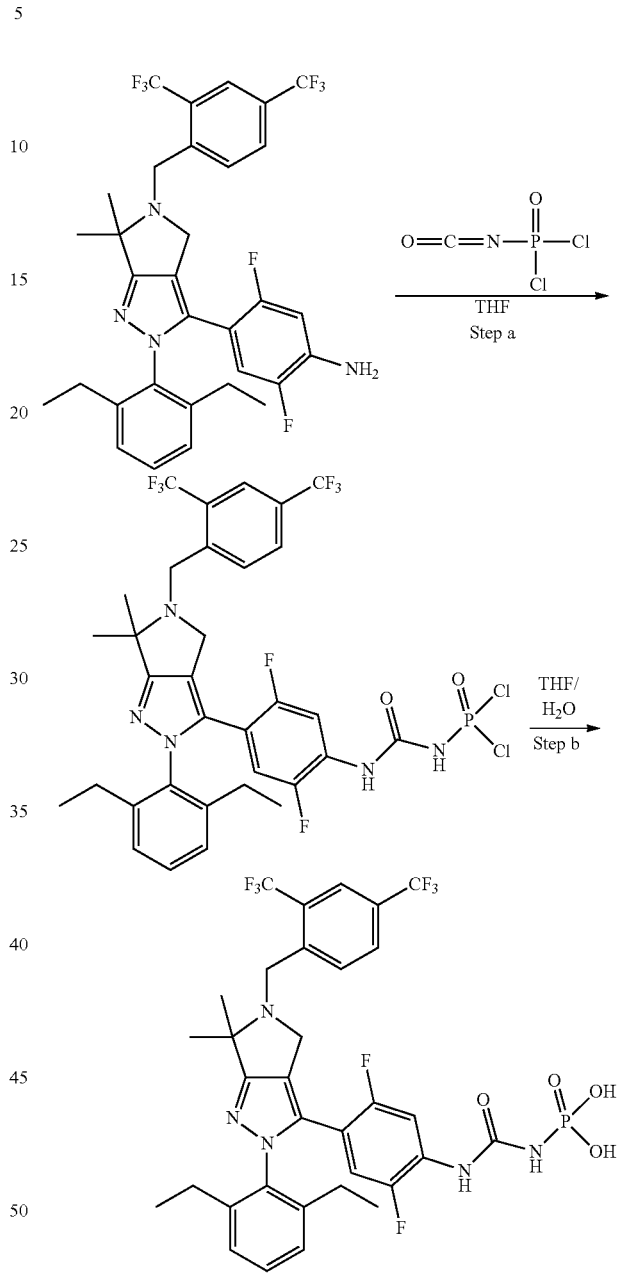

Step a: To a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluoroaniline (100 mg, 0.16 mmol) in THF (6 mL) at −50° C. was added phosphorisocyanatidic dichloride (0.04 mL, 0.41 mmol). The mixture was allowed to warm to room temperature over 1 h and then concentrated in vacuo. The residue was triturated with hexanes to to give ((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)carbamoyl)phosphoramidic dichloride which was used directly in the next step.

Step b: To a solution of the above ((4-(5-(2,4-bis(trifluoromethyl)benzyl)-2-(2,6-diethylphenyl)-6,6-dimethyl-2,4,5, 6-tetrahydropyrrolo[3,4-c]pyrazol-3-yl)-2,5-difluorophenyl)carbamoyl)phosphoramidic dichloride (~0.16 mmol) in THF (6 mL) at room temperature was added water (3 mL). The mixture was stirred at room temperature for 2 h, followed by addition of 1 N NaOH (0.5 mL, 0.5 mmol). The mixture was stirred for another 2 h. After completion, the mixture was purified by HPLC (MeCN/H$_2$O, with 0.1% TFA) to yield ((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)carbamoyl)phosphoramidic acid. $^1$H NMR (400 MHz, DMSO-d$_6$) δ 9.60 (br, 1H), 8.29 (s, 1H), 8.16 (d, J=8.2 Hz, 2H), 7.92-8.08 (m, 2H), 7.38 (d, J=7.9 Hz, 1H), 7.21 (d, J=7.7 Hz, 2H), 6.45 (dd, J=6.7, 11.9 Hz, 1H), 4.13 (s, 2H), 3.64 (s, 2H), 3.24-3.48 (br, 2H), 2.16 (q, J=7.6 Hz, 4H), 1.42 (s, 6H), 0.95 (t, J=7.6 Hz, 6H). MS: (ES) m/z calculated for C$_{33}$H$_{33}$F$_8$N$_5$O$_4$P [M+H]$^+$ 746.2, found 746.2.

Example 8: Synthesis of (((3,3-dimethyl-5-(phosphonooxy)pentanoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

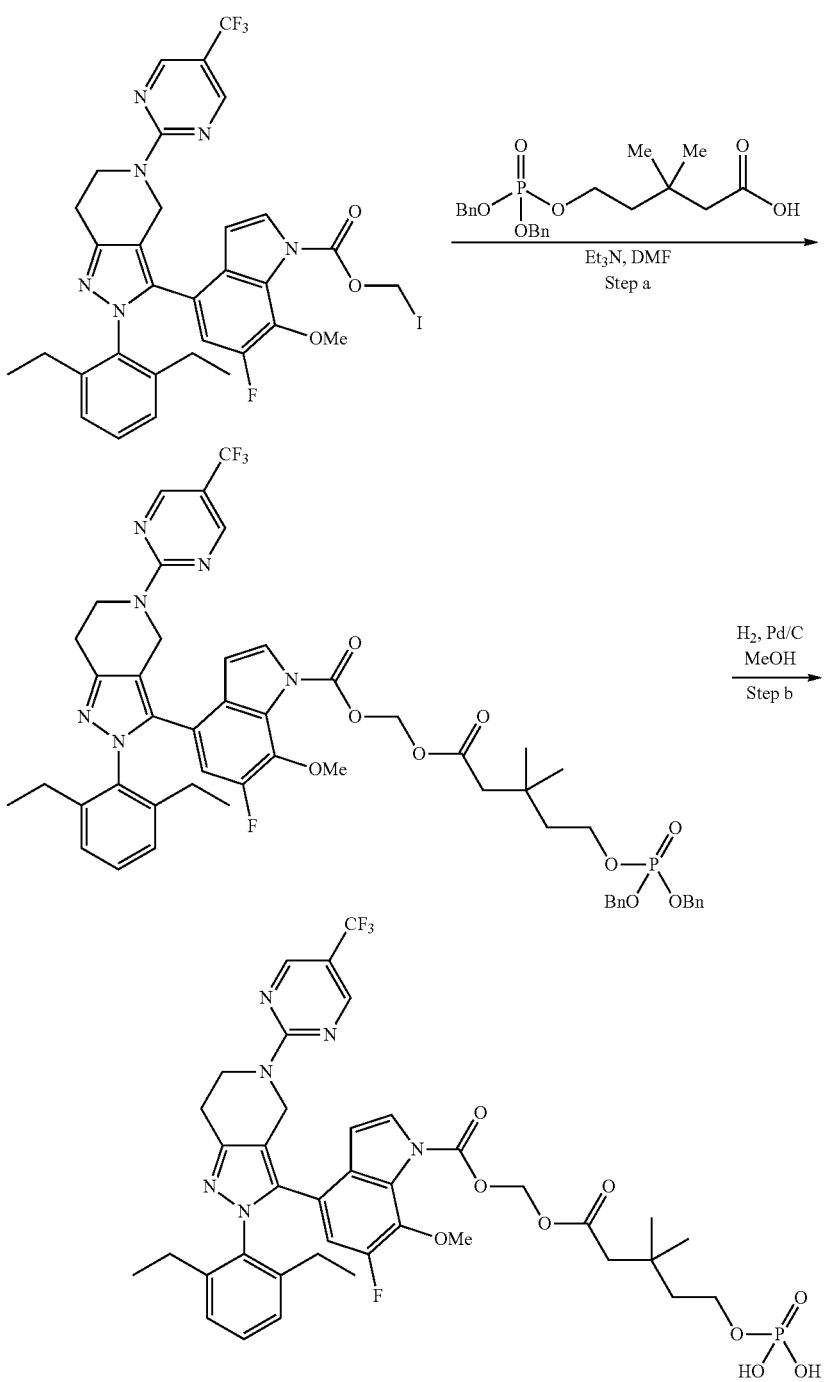

Step a: To a flask containing 4,4-dimethyldihydro-2H-pyran-2,6(3H)-dione (5 g, 35 mmol) in THF (140 mL) was added dropwise a 1 M solution of LiAlH$_4$ in THF (35 mL, 35 mmol). The mixture was heated at 75° C. for 2 h. Upon was completion, the reaction was quenched with H$_2$O and the mixture was filtered. The filtrate was concentrated to afford 3,3-dimethylpentane-1,5-diol.

To a solution of 3,3-dimethylpentane-1,5-diol (1 g, 7.6 mmol) in THF (15.6 mL) was added dropwise a 1 M solution of tBuOK (8.3 mL, 8.3 mmol) followed by tetrabenzyl-diphosphate (4.2 g, 7.8 mmol). After heating at 70° C. for 16 h, the mixture was concentrated and purified by silica gel column chromatography (0 to 100% EtOAc in hexanes) to yield dibenzyl (5-hydroxy-3,3-dimethylpentyl) phosphate. MS: (ES) m/z calculated for C$_{21}$H$_{29}$O$_5$P [M+H]$^+$ 393.2, found 393.1.

To a solution of dibenzyl (5-hydroxy-3,3-dimethylpentyl) phosphate (400 mg, 1 mmol), in DMF (10 mL) was added pyridinium dichromate (2.3 g, 6 mmol). The mixture was stirred at room temperature of 2 h then concentrated and purified by silica gel column chromatography (0 to 100% EtOAc in hexanes). The purified residue was dissolved in 10 mL of a 1:1 solution of tBuOH and H$_2$O. To the solution was added NaH$_2$PO$_4$ (0.61 g, 5 mmol), followed by sodium chlorite (0.46 g, 5 mmol) and a 2 M solution of 2-methyl-2-butene (5 mL, 10 mmol). The mixture was stirred at room temperature for 16 h. Upon completion, the mixture was concentrated in vacuo and the crude residue was purified by silica gel column chromatography (0 to 100% EtOAc in hexanes) to provide 5-((bis(benzyloxy)phosphoryl)oxy)-3,3-dimethylpentanoic acid. MS: (ES) m/z calculated for C$_{21}$H$_{27}$O$_6$P [M+H]$^+$ 407.2, found 407.1.

To a solution of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (70 mg, 0.09 mmol) in 0.2 mL of DMF was added 5-((bis(benzyloxy)phosphoryl)oxy)-3,3-dimethylpentanoic acid (54 mg, 0.13 mmol) followed by Et$_3$N (0.02 mL, 0.14 mmol). The mixture was stirred at room temperature for 2 h then concentrated in vacuo. The resulting residue was purified by silica gel column chromatography (0 to 100% EtOAc in hexanes) to produce (((5-((bis(benzyloxy)phosphoryl)oxy)-3,3-dimethylpentanoyl)oxy) methyl 4-(2-(2,6-diethylphenyl)-5-(5-(trifluoromethyl) pyrimidin-2-yl)-4,5,6,7-tetrahydro-2H-pyrazolo[4,3-c] pyridin-3-yl)-6-fluoro-7-methoxy-1H-indole-1-carboxylate.

Step b: To a solution of (((5-((bis(benzyloxy)phosphoryl) oxy)-3,3-dimethylpentanoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (50 mg, 0.05 mmol) in MeOH (1 mL) was added 10% Pd/C (6 mg, 0.005 mmol). The mixture was stirred under a H2 balloon for 1 h, then filtered through Celite, concentrated and purified by HPLC (MeCN/H$_2$O, with 0.1% TFA) to yield ((3,3-dimethyl-5-(phosphonooxy)pentanoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. $^1$H NMR (400 MHz, CDCl$_3$) δ 8.54 (s, 2H), 7.63 (d, J=3.9 Hz, 1H), 7.28 (t, J=7.7 Hz, 1H), 7.08 (d, J=7.6 Hz, 2H), 6.59 (d, J=12.1 Hz, 1H), 6.47 (d, J=3.8 Hz, 1H), 6.02 (s, 2H), 5.60 (br s, 2H), 4.76 (bs, 2H), 4.38 (t, J=5.9 Hz, 2H), 4.03 (dd, J=14.1, 7.1 Hz, 2H), 3.99 (s, 3H), 3.10 (t, J=3.1 Hz, 2H), 2.35 (s, 2H), 2.20 (br s, 4H), 1.74 (t, J=7.0 Hz, 2H), 1.05 (br s, 12H). MS: (ES) m/z calculated for C$_{39}$H$_{43}$FN$_6$O$_9$P [M+H]$^+$ 847.3, found 847.2.

Example 9: Synthesis of (3-fluoro-4-phosphonooxy-phenyl)methyl N-((4-(5-((2,4-bis(trifluoromethyl) phenyl)methyl)-2-(2,6-diethylphenyl)-6,6-dimethyl-4H-pyrrolo[3,4-c]pyrazol-3-yl)-2,5-difluorophenyl) carbamoyl]carbamate

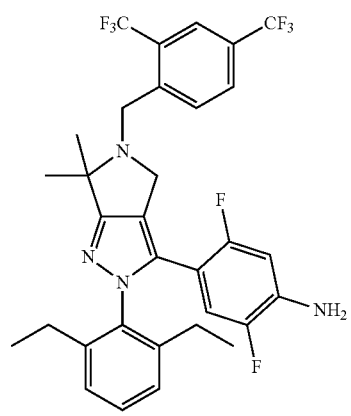
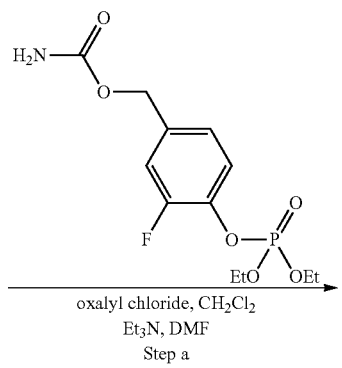

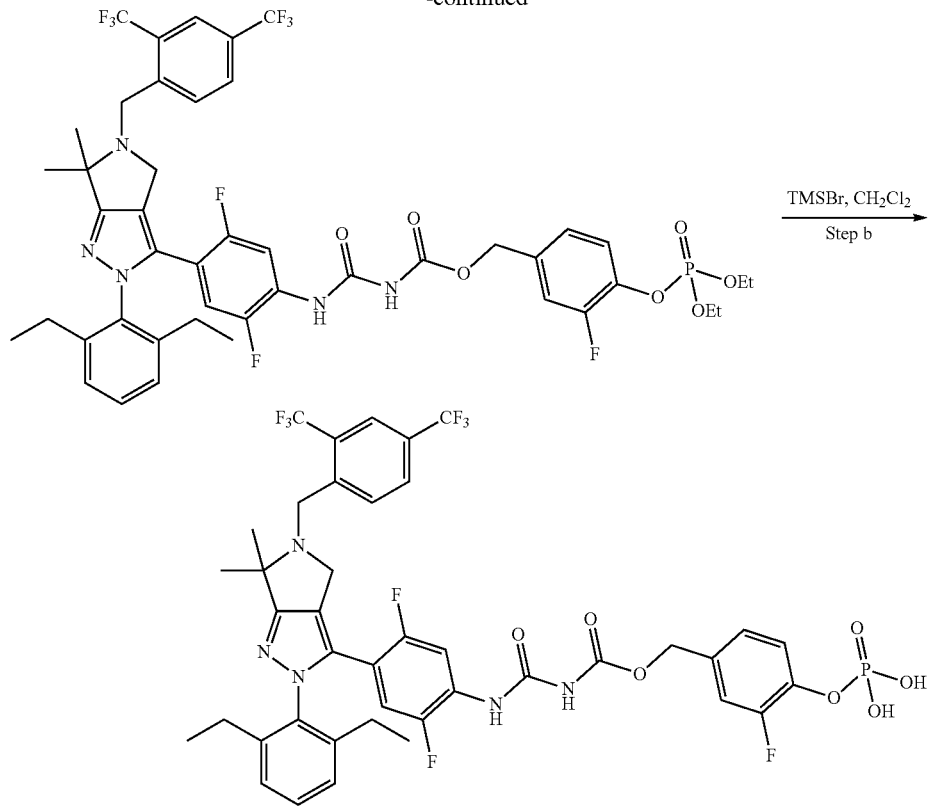

Step a: To a solution of 3-fluoro-4-hydroxybenzaldehyde (5 g, 35.7 mmol) in dichloromethane (36 mL) was added Et$_3$N (7.5 mL, 53.8 mmol) followed by diethylchlorophosphate (5.7 mL, 39.4 mmol). The mixture was stirred at room temperature for 3 h then quenched with H$_2$O. The organic and aqueous layers were separated and the aqueous layer was extracted with EtOAc. The organic layers were combined, dried with sodium sulfate, filtered and concentrated in vacuo. The resultant residue was purified by silica gel column chromatography to afford diethyl (2-fluoro-4-formylphenyl) phosphate. MS: (ES) m/z calculated for C$_{11}$H$_{14}$FO$_5$P [M+H]$^+$ 277.1, found 277.0.

To a solution of diethyl (2-fluoro-4-formylphenyl) phosphate (8.99 g, 32.5 mmol) in THF (32.5 mL) at −78° C. was added NaBH$_4$ (3.6 g, 97.3 mmol). After stirring at −78° C. for 1 h the reaction was quenched with H$_2$O. The organic and aqueous layers were separated and the aqueous layer was extracted with EtOAc. The organic layers were combined, dried with sodium sulfate, filtered and concentrated in vacuo. The residue was purified by silica gel column chromatography (85 to 100% EtOAc in hexanes) to produce diethyl (2-fluoro-4-(hydroxymethyl)phenyl) phosphate. MS: (ES) m/z calculated for C$_{11}$H$_{16}$FO$_5$P [M+H]$^+$ 279.1, found 279.0.

To a solution of diethyl (2-fluoro-4-(hydroxymethyl)phenyl) phosphate (1 g, 3.6 mmol) in THF (8.7 mL) at 0° C. was added diisopropylethylamine (0.76 mL, 4.4 mmol) and triphosgene (0.53 g, 1.8 mmol). After stirring at 0° C. for 1 h, NH$_4$OH (1.6 mL, 41 mmol) was added. The mixture was stirred at room temperature for 16 h then concentrated in vacuo and the residue was purified by silica gel column chromatography (0 to 100% EtOAc in hexanes) to provide 4-((diethoxyphosphoryl)oxy)-3-fluorobenzyl carbamate. MS: (ES) m/z calculated for C$_{12}$H$_{17}$FNO$_6$P [M+H]$^+$ 322.1, found 322.0.

To a solution of 4-((diethoxyphosphoryl)oxy)-3-fluorobenzyl carbamate (155 mg, 0.48 mmol) in dichloromethane (4.8 mL) at 0° C. was added oxalyl chloride (0.06 mL, 0.71 mmol). The mixture was heated at 40° C. for 16 h then concentrated in vacuo. The residue was dissolved in THF (2 mL) and added to a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluoroaniline (100 mg, 0.16 mmol) in THF (2 mL). The mixture was stirred at room temperature for 5 h then concentrated in vacuo. The residue was purified by silica gel column chromatography (0 to 100% EtOAc in hexanes) to give (4-diethoxyphosphoryloxy-3-fluorophenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate. MS: (ES) m/z calculated for C$_{45}$H$_{45}$F$_9$N$_5$O$_7$P [M+H]$^+$ 970.3, found 970.0.

Step b: To a solution of (4-diethoxyphosphoryloxy-3-fluorophenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate (77 mg, 0.08 mmol) in dichloromethane (1 mL) was added dropwise TMSBr (0.13 mL, 0.10 mmol). The mixture was stirred at room temperature for 16 h then concentrated in vacuo. The residue was purified on HPLC (MeCN/H$_2$O, with 0.1% TFA) to yield (3-fluoro-4-phosphonooxyphenyl)methyl N-44-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl) carbamate. $^1$H NMR (400 MHz, CD$_3$OD) δ 8.22 (d, J=8.2

Hz, 1H), 8.15 (s, 1H), 8.08-8.15 (m, 2H), 7.46 (dd, J=7.6, 7.9 Hz, 1H), 7.38 (dd, J=8.2, 8.2 Hz, 1H), 7.28 (d, J=7.6 Hz, 2H), 7.17 (d, J=11.0 Hz, 1H), 7.10 (d, J=8.6 Hz, 1H), 6.42 (dd, J=6.5, 11.5 Hz, 1H), 5.14 (s, 2H), 4.77 (s, 2H), 4.57 (s, 2H), 3.34 (s, 2H), 2.24 (q, J=7.7 Hz, 4H), 1.89 (s, 6H), 1.05 (t, J=7.2 Hz, 6H). MS: (ES) m/z calculated for $C_{41}H_{37}F_9N_5O_7P$ [M+H]$^+$ 914.2, found 914.1.

Example 10: Synthesis of 3-nitro-4-(phosphonooxy)benzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

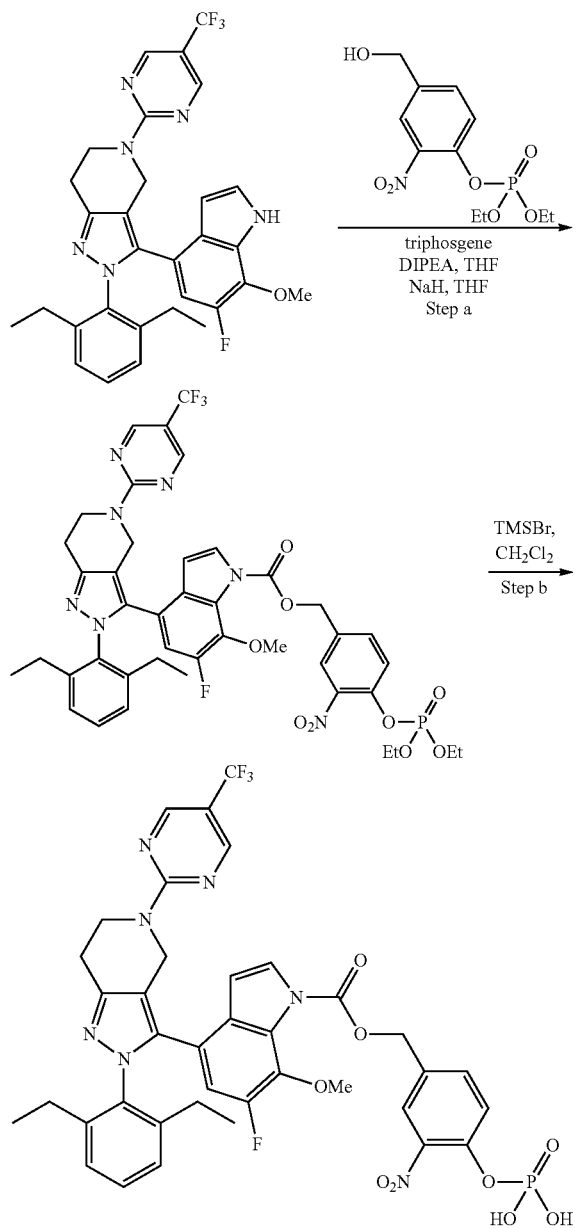

Step a: To a solution of 4-hydroxy-3-nitrobenzaldehyde (1 g, 6.0 mmol) in dichloromethane (6 mL) was added Et$_3$N (1.25 mL, 9.0 mmol) and diethylchlorophosphate (0.95 mL, 6.6 mmol). The mixture was stirred at room temperature for 16 h then quenched with H$_2$O. The organic and aqueous layers were separated and the aqueous layer was extracted with EtOAc. The organic layers were combined, dried with sodium sulfate, filtered and concentrated in vacuo. The residue was purified by silica gel column chromatography (0 to 100% EtOAc in hexanes) to afford diethyl (4-formyl-2-nitrophenyl) phosphate. MS: (ES) m/z calculated for $C_{11}H_{14}NO_7P$ [M+H]$^+$ 304.1, found 304.0.

To a solution of diethyl (4-formyl-2-nitrophenyl) phosphate (1.36 g, 4.5 mmol) in THF (4.5 mL) at −78° C. was added NaBH$_4$ (500 mg, 13.5 mmol). After stirring at −78° C. for 1 h the reaction was quenched with H$_2$O. The organic and aqueous layers were separated, and the aqueous layer was extracted with EtOAc. The organic layers were combined, dried with sodium sulfate, filtered, and concentrated. The resultant residue was purified by silica gel column chromatography (0 to 100% EtOAc in hexanes) to provide diethyl (4-(hydroxymethyl)-2-nitrophenyl)phosphate. MS: (ES) m/z calculated for $C_{11}H_{16}NO_7P$ [M+H]$^+$ 306.1, found 306.0.

To a solution of diethyl (4-(hydroxymethyl)-2-nitrophenyl)phosphate (100 mg, 0.33 mmol) in THF (1.6 mL) at 0° C. was added diisopropylethylamine (0.07 mL, 0.40 mmol) and triphosgene (50 mg, 0.17 mmol). After stirring at 0° C. for 1 h, the reaction was quenched with H$_2$O. The organic and aqueous layers were separated, and the aqueous layer was extracted with EtOAc. The organic layers were combined, dried with sodium sulfate, filtered and concentrated to afford the crude chloroformate intermediate.

To a solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (93 mg, 0.16 mmol) in THF (1 mL) at 0° C. was added NaH (13 mg, 0.32 mmol). After stirring at 0° C. for 30 min, a solution of the crude chloroformate (prepared above) in THF (0.5 mL), was added to the mixture. The solution was stirred at room temperature for 16 h. The reaction was quenched with H$_2$O. The organic and aqueous layers were separated, and the aqueous layer was extracted with EtOAc. The organic layers were combined, dried with sodium sulfate, filtered and concentrated in vacuo. The residue was purified by silica gel column chromatography (0 to 100% EtOAc in hexanes) to produce 4-((diethoxyphosphoryl)oxy)-3-nitrobenzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate.

Step b: To a solution of 4-((diethoxyphosphoryl)oxy)-3-nitrobenzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (128 mg, 0.14 mmol) in dichloromethane (1.4 mL) was added dropwise TMSBr (0.11 mL, 0.86 mmol). After stirring at room temperature for 5 h, an additional amount of TMSBr (0.11 mL, 0.86 mmol) was added to the mixture. The mixture was stirred at room temperature for 16 h, concentrated in vacuo and purified by HPLC (MeCN/H$_2$O, with 0.1% TFA) to yield 3-nitro-4-(phosphonooxy)benzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. $^1$H NMR (400 MHz, DMSO-d$_6$) δ 8.68 (s, 2H), 8.12 (dd, J=0.9, 2.3 Hz, 1H), 7.85 (d, J=3.8 Hz, 1H), 7.85 (dd, J=2.2, 8.6 Hz, 1H), 7.60 (dd, J=1.1, 8.5 Hz, 1H), 7.29 (t, J=7.6 Hz, 1H), 7.12 (br s, 2H), 6.62 (d, J=3.8 Hz, 1H), 6.55 (d, J=12.4 Hz, 1H), 5.48 (s, 2H), 4.76 (s, 2H), 4.30 (br s, 2H), 3.83 (d, J=1.2 Hz, 3H), 2.91 (t, J=6.0 Hz, 2H), 2.16 (br s, 4H), 2.04 (s, 2H), 0.91 (br s, 6H). MS: (ES) m/z calculated for $C_{38}H_{34}FN_7O_9P$ [M+H]$^+$ 840.2, found 840.0.

Example 11: Synthesis of 3-fluoro-4-(phosphonooxy)benzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

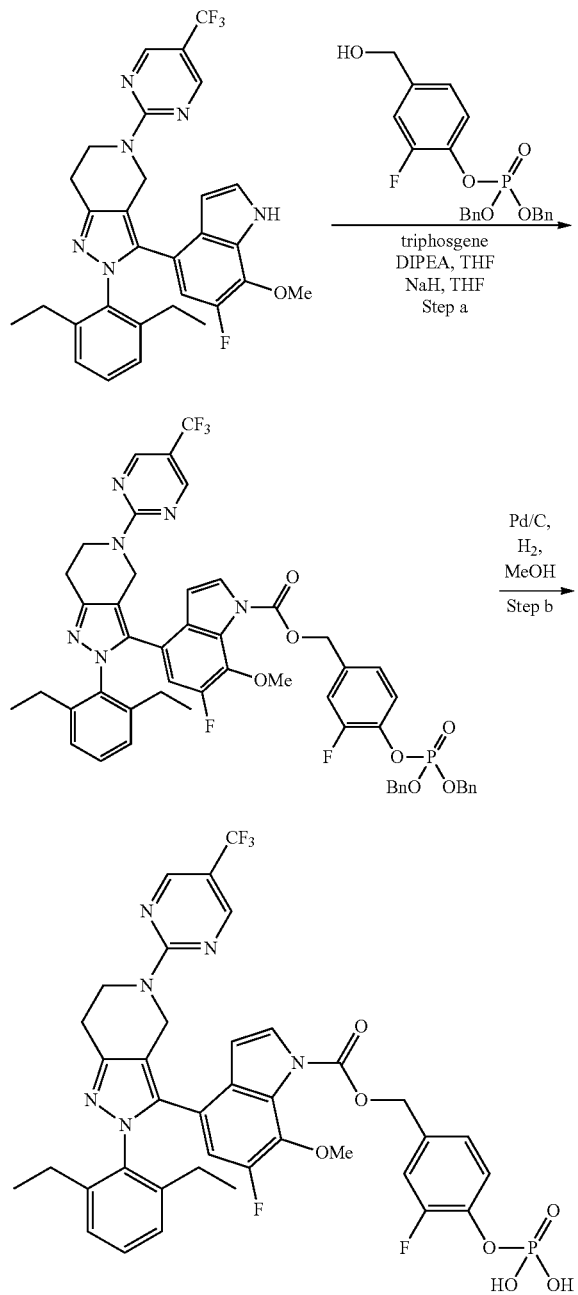 [SMILES: CCc1cccc(CC)c1-n1nc2c(c1-c1cc(F)c(OC)c3[nH]ccc13)CN(c1ncc(C(F)(F)F)cn1)CC2 ; O=P(OCc1ccccc1)(OCc1ccccc1)Oc1ccc(CO)cc1F ; CCc1cccc(CC)c1-n1nc2c(c1-c1cc(F)c(OC)c3c1ccn3C(=O)OCc1ccc(OP(=O)(OCc3ccccc3)OCc3ccccc3)c(F)c1)CN(c1ncc(C(F)(F)F)cn1)CC2 ; CCc1cccc(CC)c1-n1nc2c(c1-c1cc(F)c(OC)c3c1ccn3C(=O)OCc1ccc(OP(=O)(O)O)c(F)c1)CN(c1ncc(C(F)(F)F)cn1)CC2]

Step a: To a solution of 3-fluoro-4-hydroxybenzaldehyde (1 g, 7.1 mmol) in THF (32 mL) was added a 1 M solution of tBuOK in THF (7.6 mL, 7.6 mmol). The mixture was heated to 70° C. and tetrabenzylphosphate was added (4.0 g, 7.4 mmol). After 1 h at 70° C., hexanes was added to the mixture and the contents were filtered. The filtrate was concentrated in vacuo and the resulting residue was purified by silica gel column chromatography (0 to 100% EtOAc in hexanes) to produce dibenzyl (2-fluoro-4-formylphenyl) phosphate. MS: (ES) m/z calculated for $C_{21}H_{18}FO_5P$ [M+H]$^+$ 401.1, found 401.1.

To a solution of dibenzyl (2-fluoro-4-formylphenyl) phosphate (2.68 g, 6.7 mmol) in THF (6.7 mL) at −78° C. was added NaBH$_4$ (0.76 g, 20.5 mmol). After stirring at −78° C. for 1 h, the mixture was quenched with H$_2$O. The organic and aqueous layers were separated, and the aqueous layer was extracted with EtOAc. The combined organic layers were dried with sodium sulfate, filtered and concentrated in vacuo. The resulting residue was purified by silica gel column (0 to 100% EtOAc in hexanes) to provide dibenzyl (2-fluoro-4-(hydroxymethyl)phenyl)phosphate. MS: (ES) m/z calculated for $C_{21}H_{20}FO_5P$ [M+H]$^+$ 403.1, found 403.0.

To a solution of dibenzyl (2-fluoro-4-(hydroxymethyl) phenyl)phosphate (200 mg, 0.50 mmol) in THF (2.4 mL) at 0° C. was added diisopropylethylamine (0.1 mL, 0.57 mmol) and triphosgene (72 mg, 0.24 mmol). After stirring at 0° C. for 1 h, the reaction was quenched with H$_2$O. The organic and aqueous layers were separated, and the aqueous layer was extracted with EtOAc. The organic layers were combined, dried with sodium sulfate, filtered and concentrated to afford the crude chloroformate intermediate.

To a solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (70 mg, 0.12 mmol) in THF (1.2 mL) at 0° C. was added NaH (10 mg, 0.24 mmol). After stirring at 0° C. for 30 min, a solution of the crude chloroformate (prepared above) in THF (1.2 mL) was added to the mixture. The solution was stirred at 0° C. for 1 h then quenched with H$_2$O. The organic and aqueous layers were separated and the aqueous layer was extracted with EtOAc. The organic layers were combined, dried with sodium sulfate, filtered and concentrated in vacuo. The residue was purified by silica gel column chromatography (0 to 100% EtOAc in hexanes) to produce 4-((bis(benzyloxy) phosphoryl)oxy)-3-fluorobenzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate.

Step b: To a solution of 4-((bis(benzyloxy)phosphoryl) oxy)-3-fluorobenzyl 4-(2-(2,6-diethylphenyl)-5-(5-(trifluoromethyl)pyrimidin-2-yl)-4,5,6,7-tetrahydro-2H-pyrazolo [4,3-c]pyridin-3-yl)-6-fluoro-7-methoxy-1H-indole-1-carboxylate (100 mg, 0.10 mmol) in MeOH (1 mL) was added 10% Pd/C (10 mg, 0.01 mmol). The mixture was stirred under a H2 balloon for 1 h, then filtered through Celite, concentrated and purified by HPLC (MeCN/H$_2$O, with 0.1% TFA) to yield 3-fluoro-4-(phosphonooxy)benzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. $^1$H NMR (400 MHz, DMSO-d$_6$) δ 8.68 (s, 2H), 7.84 (s, 1H), 7.52-7.38 (m, 2H), 7.37-7.25 (m, 2H), 7.11 (br s, 2H), 6.62 (s, 1H), 6.54 (d, J=12.3 Hz, 1H), 5.40 (s, 2H), 4.76 (s, 2H), 4.30 (s, 2H), 3.83 (s, 3H), 2.90 (bs, 2H), 2.16 (br s, 4H), 2.04 (br s, 2H), 0.90 (br s, 6H). MS: (ES) m/z calculated for $C_{38}H_{34}F_5N_6O_7P$ [M+H]$^+$ 813.2, found 813.2.

Example 12: Synthesis of (2-(4-(phosphonooxy)phenyl)acetoxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

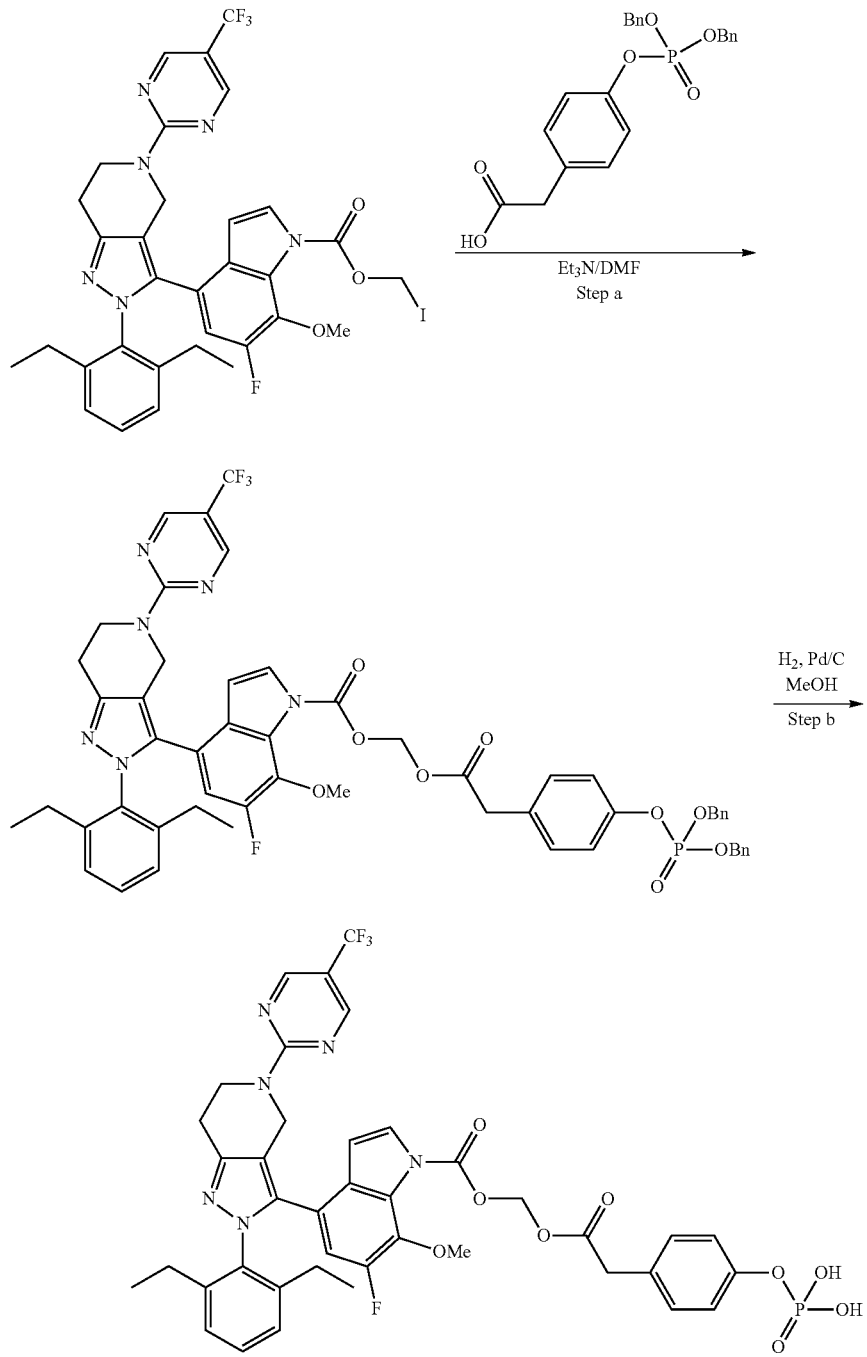 [SMILES: CCc1cccc(CC)c1-n1nc2c(c1-c1cc(F)c(OC)c3c1ccn3C(=O)OCI)CN(c1ncc(C(F)(F)F)cn1)CC2 ; O=C(O)Cc1ccc(OP(=O)(OCc2ccccc2)OCc2ccccc2)cc1 ; CCc1cccc(CC)c1-n1nc2c(c1-c1cc(F)c(OC)c3c1ccn3C(=O)OCOC(=O)Cc1ccc(OP(=O)(OCc3ccccc3)OCc3ccccc3)cc1)CN(c1ncc(C(F)(F)F)cn1)CC2 ; CCc1cccc(CC)c1-n1nc2c(c1-c1cc(F)c(OC)c3c1ccn3C(=O)OCOC(=O)Cc1ccc(OP(=O)(O)O)cc1)CN(c1ncc(C(F)(F)F)cn1)CC2]

Step a: To a flask containing ethyl 2-(4-hydroxyphenyl)acetate (1 g, 5.6 mmol) in THF (11 mL) was added dropwise a 1 M solution of tBuOK in THF (5.9 mL, 5.9 mmol) and tetrabenzyldiphosphate (3 g, 5.6 mmol). The mixture was heated at 70° C. for 2 h. An additional amount of 1.0 M tBuOK (1.2 mL, 1.2 mmol) and tetrabenzyldiphosphate (0.6 g, 1.1 mmol) was added. The mixture was heated for an additional 3 h. Upon completion, hexanes was added and the contents were filtered. The filtrate was concentrated and the residue was purified by silica gel column chromatography (0 to 100% EtOAc in hexanes) to afford ethyl 2-(4-((bis(benzyloxy)phosphoryl)oxy)phenyl)acetate. MS: (ES) m/z calculated for $C_{24}H_{25}O_6P$ [M+H]$^+$ 441.1, found 441.1.

To a solution of ethyl 2-(4-((bis(benzyloxy)phosphoryl)oxy)phenyl)acetate (1.54 g, 3.5 mmol) in THF (9 mL) was added dropwise a solution of LiOH (0.32 g, 7.6 mmol) in $H_2O$ (9 mL). The mixture was stirred at room temperature for 1 h. The reaction was quenched with 1 N HCl. The aqueous layer was extracted with EtOAc. The organic layers were combined, dried with sodium sulfate, filtered and concentrated. The residue was purified by silica gel column chromatography (0 to 100% EtOAc in hexanes) to yield 2-(4-((bis(benzyloxy)phosphoryl)oxy)phenyl)acetic acid. MS: (ES) m/z calculated for $C_{22}H_{21}O_6P$ [M+H]$^+$413.1, found 413.1.

To a solution of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (100 mg, 13 mmol) in DMF (0.5 mL) was added 2-(4-((bis(benzyloxy)phosphoryl)oxy)phenyl)acetic acid (82 mg, 20 mmol) and triethylamine (0.03 mL, 0.20 mmol). The mixture was stirred at room temperature for 16 h then concentrated. The residue was purified by silica gel column chromatography (0 to 100% EtOAc in hexanes) to provide (2-(4-((bis(benzyloxy)phosphoryl)oxy)phenyl)acetoxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate.

Step b: To a solution of (2-(4-((bis(benzyloxy)phosphoryl)oxy)phenyl)acetoxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (66 mg, 0.06 mmol) in MeOH (1 mL) was added 10% Pd/C (7 mg, 0.006 mmol). The mixture was stirred under a H2 balloon for 1 h, then filtered through Celite, concentrated and purified by HPLC (MeCN/H$_2$O, with 0.1% TFA) to yield (2-(4-(phosphonooxy)phenyl)acetoxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. $^1$H NMR (400 MHz, CDCl$_3$) δ 8.47 (s, 2H), 7.38 (d, J=3.8 Hz, 1H), 7.22-7.26 (m, 2H), 7.10 (d, J=7.7 Hz, 2H), 7.01-7.06 (m, 4H), 6.57 (d, J=12.1 Hz, 1H), 6.45 (d, J=3.8 Hz, 1H), 5.97 (s, 2H), 5.02 (br s, 2H), 4.77 (s, 2H), 4.36 (br s, 2H), 3.95 (s, 3H), 3.60 (s, 2H), 3.07 (br s, 2H), 2.05-2.35 (m, 4H), 0.99 (br s, 6H). MS: (ES) m/z calculated for $C_{40}H_{37}F_4N_6O_9P$ [M+H]$^+$ 853.2, found 853.0.

Example 13: Synthesis of (4-phosphonooxy-3-(trifluoromethyl)phenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate

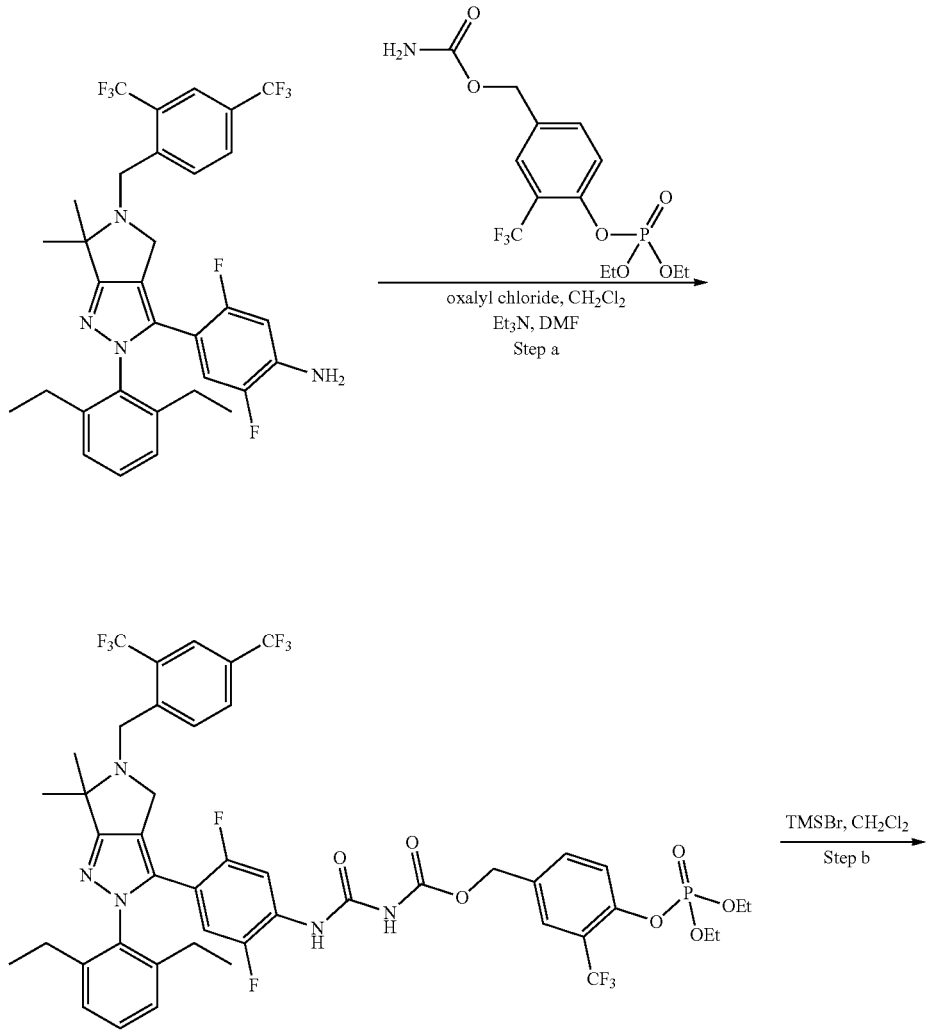

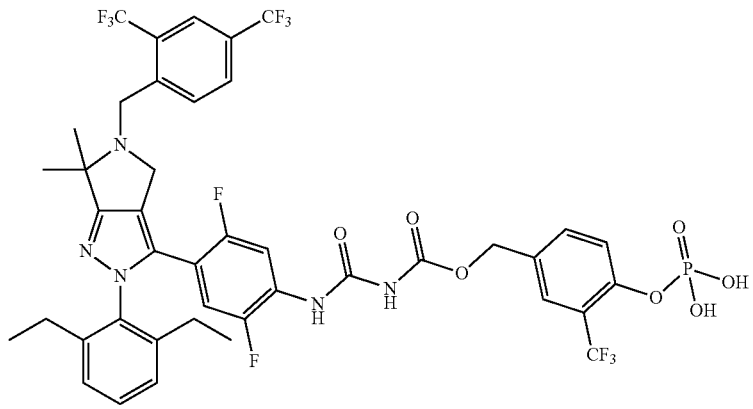

Step a: To a solution of 4-hydroxy-3-(trifluoromethyl)benzaldehyde (1 g, 0.53 mmol) in dichloromethane (10 mL) was added triethylamine (1.1 mL, 0.79 mmol) followed by diethylchlorophosphate (0.84 mL, 0.58 mmol). The mixture was stirred at room temperature for 1 h then concentrated in vacuo. The residue was purified by silica gel column chromatography (0 to 100% EtOAc in hexanes) to afford diethyl (4-formyl-2-(trifluoromethyl)phenyl)phosphate. MS: (ES) m/z calculated for $C_{12}H_{14}F_3O_5P$ [M+H]$^+$ 327.1, found 327.0.

To a solution of diethyl (4-formyl-2-(trifluoromethyl)phenyl)phosphate (1.43 g, 4.4 mmol) in THF (4.5 mL) at −78° C. was added NaBH$_4$ (0.49 g, 13.2 mmol). The reaction mixture was warmed to room temperature and stirred for 16 h. Upon completion, the reaction was quenched with H$_2$O. The organic and aqueous layers were separated, and the aqueous layer was extract with EtOAc. The organic layers were combined, dried with sodium sulfate, filtered and concentrated in vacuo. The residue was purified by silica gel column chromatography (85 to 100% EtOAc in hexanes) to produce diethyl (4-(hydroxymethyl)-2-(trifluoromethyl)phenyl)phosphate. MS: (ES) m/z calculated for $C_{12}H_{16}F_3O_5P$ [M+H]$^+$ 329.1, found 329.1.

To a solution of diethyl (4-(hydroxymethyl)-2-(trifluoromethyl)phenyl)phosphate (0.6 g, 1.8 mmol) in THF (4.4 mL) at 0° C. was added diisopropylethylamine (0.39 mL, 2.2 mmol) and triphosgene (0.27 mL, 0.9 mmol). After stirring at 0° C. for 1 h, NH$_4$OH (0.8 mL, 21 mmol) was added. The mixture was stirred at room temperature for 1 h then concentrated in vacuo and the residue was purified by silica gel column chromatography (0 to 100% EtOAc in hexanes) to provide 4-((diethoxyphosphoryloxy)-3-(trifluoromethyl) benzyl carbamate. MS: (ES) m/z calculated for $C_{13}H_{17}F_3NO_6P$ [M+H]$^+$ 372.1, found 372.0.

To a solution of 4-((diethoxyphosphoryl)oxy)-3-(trifluoromethyl)benzyl carbamate (240 mg, 0.65 mmol) in dichloromethane (2 mL) at 0° C. was added oxalyl chloride (0.09 mL, 1.0 mmol). The mixture was heated at 40° C. for 16 h then concentrated in vacuo. The residue was dissolved in 2 mL of THF and added to a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluoroaniline (200 mg, 0.32 mmol) in THF (4 mL). The mixture was stirred at room temperature for 5 h then concentrated in vacuo. The residue was purified by silica gel column chromatography (0 to 100% EtOAc in hexanes) to give (4-diethoxyphosphoryloxy-3-(trifluoromethyl)phenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate.

Step b: To a solution of (4-diethoxyphosphoryloxy-3-(trifluoromethyl)phenyl)methyl N-(4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate (176 mg, 0.17 mmol) in dichloromethane (1.7 mL) was added dropwise TMSBr (0.29 mL, 2 mmol). The mixture was stirred at room temperature for 16 h then concentrated in vacuo. The residue was purified on HPLC (MeCN/H$_2$O, with 0.1% TFA) to yield (4-phosphonooxy-3-(trifluoromethyl)phenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate. $^1$H NMR (400 MHz, DMSO-d$_6$) δ: 10.80 (s, 1H), 10.11 (s, 1H), 8.15 (s, 1H), 7.90-8.15 (m, 3H), 7.73 (bs, 1H), 7.63-7.69 (m, 1H), 7.54-7.61 (m, 1H), 7.35-7.42 (m, 1H), 7.18-7.24 (m, 2H), 6.49-6.58 (m, 1H), 5.19 (s, 2H), 4.13 (s, 2H), 3.65 (s, 2H), 2.07-2.23 (m, 4H), 1.30-1.40 (m, 6H), 0.88-1.03 (m, 6H). MS: (ES) m/z calculated for $C_{42}H_{37}F_{11}N_5O_7P$ [M+H]$^+$ 964.2, found 964.0.

Example 14: Synthesis of (3-nitro-4-phosphonooxy-phenyl)methyl N-((4-(5-(2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate Step a: To a solution of 4-hydroxy-3-nitrobenzaldehyde (1 g, 6.0 mmol) in dichloromethane (6 mL) was added Et₃N (1.25 mL, 9.0 mmol) and diethylchlorophosphate (0.95 mL, 6.6 mmol). The mixture was stirred at room temperature for 16 h then quenched with H₂O. The organic and aqueous layers were separated, and the aqueous layer was extracted

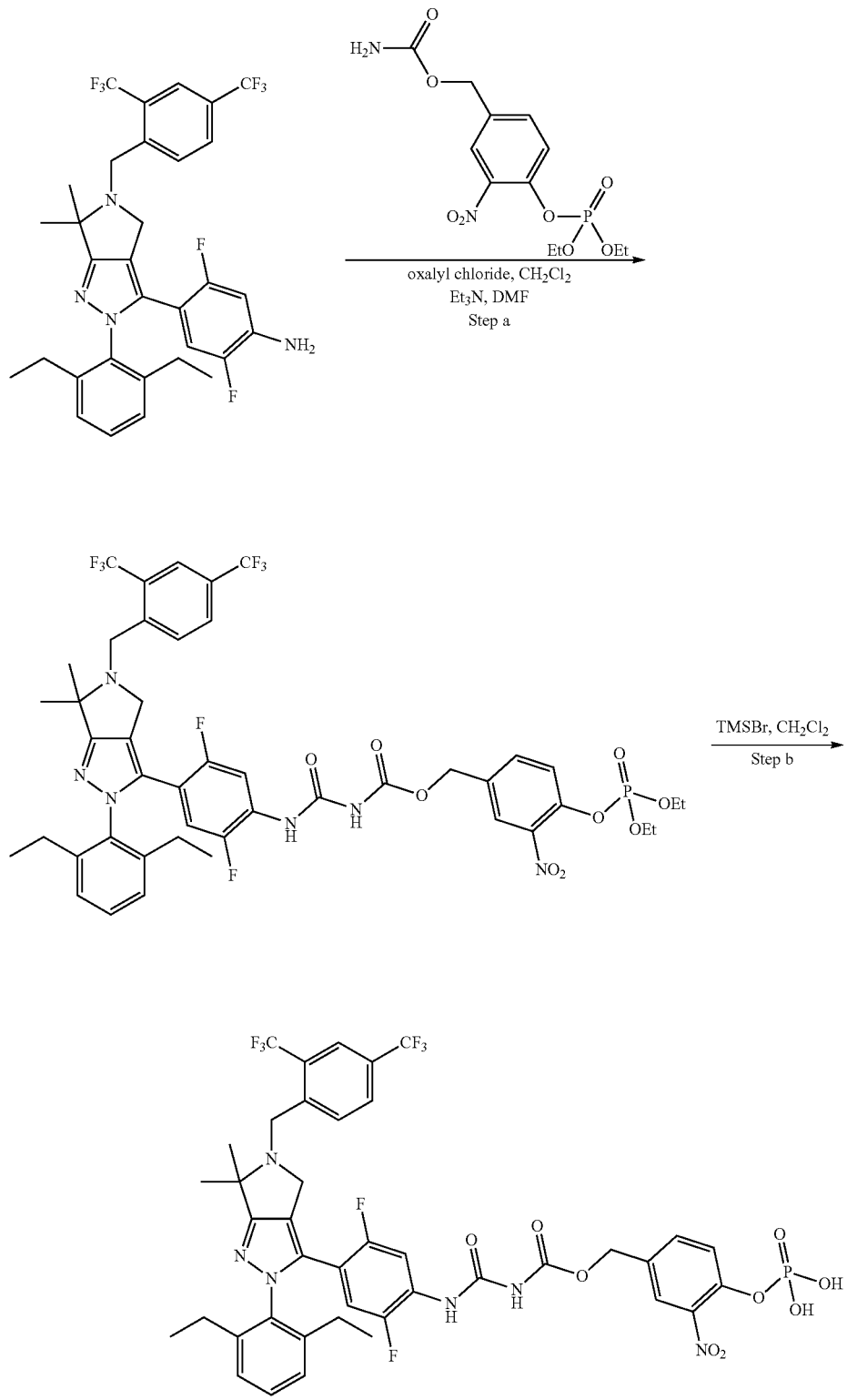

with EtOAc. The organic layers were combined, dried with sodium sulfate, filtered and concentrated in vacuo. The residue was purified by silica gel column chromatography (0 to 100% EtOAc in hexanes) to afford diethyl (4-formyl-2-nitrophenyl)phosphate. MS: (ES) m/z calculated for $C_{11}H_{14}NO_7P$ [M+H]$^+$ 304.1, found 304.0.

To a solution of diethyl (4-formyl-2-nitrophenyl)phosphate (1.36 g, 4.5 mmol) in THF (4.5 mL) at −78° C. was added NaBH$_4$ (500 mg, 13.5 mmol). After stirring at −78° C. for 1 h the reaction was quenched with H$_2$O. The organic and aqueous layers were separated, and the aqueous layer was extracted with EtOAc. The organic layers were combined, dried with sodium sulfate, filtered, and concentrated. The residue was purified by silica gel column chromatography (0 to 100% EtOAc in hexanes) to provide diethyl (4-(hydroxymethyl)-2-nitrophenyl)phosphate. MS: (ES) m/z calculated for $C_{11}H_{16}NO_7P$ [M+H]$^+$ 306.1, found 306.1.

To a solution of diethyl (4-(hydroxymethyl)-2-nitrophenyl)phosphate (200 mg, 0.66 mmol) in THF (1.6 mL) at 0° C. was added diisopropylethylamine (0.14 mL, 0.80 mmol) and triphosgene (100 mg, 0.34 mmol). After stirring at 0° C. for 1 h, NH$_4$OH (0.32 mL, 8.2 mmol) was added. The mixture was stirred at room temperature for 1 h then concentrated in vacuo and the residue was purified by silica gel column chromatography (0 to 100% EtOAc in hexanes) to provide 4-((diethoxyphosphoryl)oxy)-3-nitrobenzyl carbamate. MS: (ES) m/z calculated for $C_{12}H_{17}N_2O_8P$ [M+H]$^+$ 349.1, found 349.0.

To a solution of 4-((diethoxyphosphoryl)oxy)-3-(trifluoromethyl)benzyl carbamate (0.4 g, 1.2 mmol) in dichloromethane (11.5 mL) at 0° C. was added oxalyl chloride (0.15 mL, 1.8 mmol). The mixture was heated at 40° C. for 16 h then concentrated in vacuo. The residue was dissolved in THF (1 mL) and added to a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluoroaniline (200 mg, 0.32 mmol) in THF (5 mL). The mixture was stirred at room temperature for 3 h then concentrated in vacuo. The residue was purified by silica gel column chromatography (0 to 100% EtOAc in hexanes) to give (4-diethoxyphosphoryloxy-3-nitrophenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate.

Step b: To a solution of (4-diethoxyphosphoryloxy-3-nitrophenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl) carbamate (100 mg, 0.10 mmol) in dichloromethane (1 mL) was added dropwise TMSBr (0.09 mL, 0.6 mmol). After stirring at room temperature for 3 h, an additional amount of TMSBr (0.09 mL, 0.6 mmol) was added to the mixture. The mixture was stirred at room temperature for 16 h, concentrated in vacuo and purified by HPLC (MeCN/H$_2$O, with 0.1% TFA) to yield (3-nitro-4-phosphonooxyphenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate. $^1$H NMR (400 MHz, CD$_3$OD) δ: 8.25 (d, J=8.0 Hz, 1H), 8.16 (s, 2H), 8.01-8.12 (m, 1H), 7.82 (s, 1H), 7.54 (s, 2H), 7.46 (t, J=7.7 Hz, 1H), 7.28 (d, J=7.8 Hz, 2H), 6.38 (dd, J=7.6, 11.2 Hz, 1H), 5.20 (s, 2H), 4.81 (s, 2H), 4.66 (s, 2H), 2.25 (q, J=7.7 Hz, 4H), 1.92 (s, 6H), 1.05 (t, J=7.7 Hz, 6H). MS: (ES) m/z calculated for $C_{41}H_{37}F_8N_6O_9P$ [M+H]$^+$ 941.2, found 941.1

Example 15: Synthesis of 2-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)-5-fluorobenzyl dihydrogen phosphate

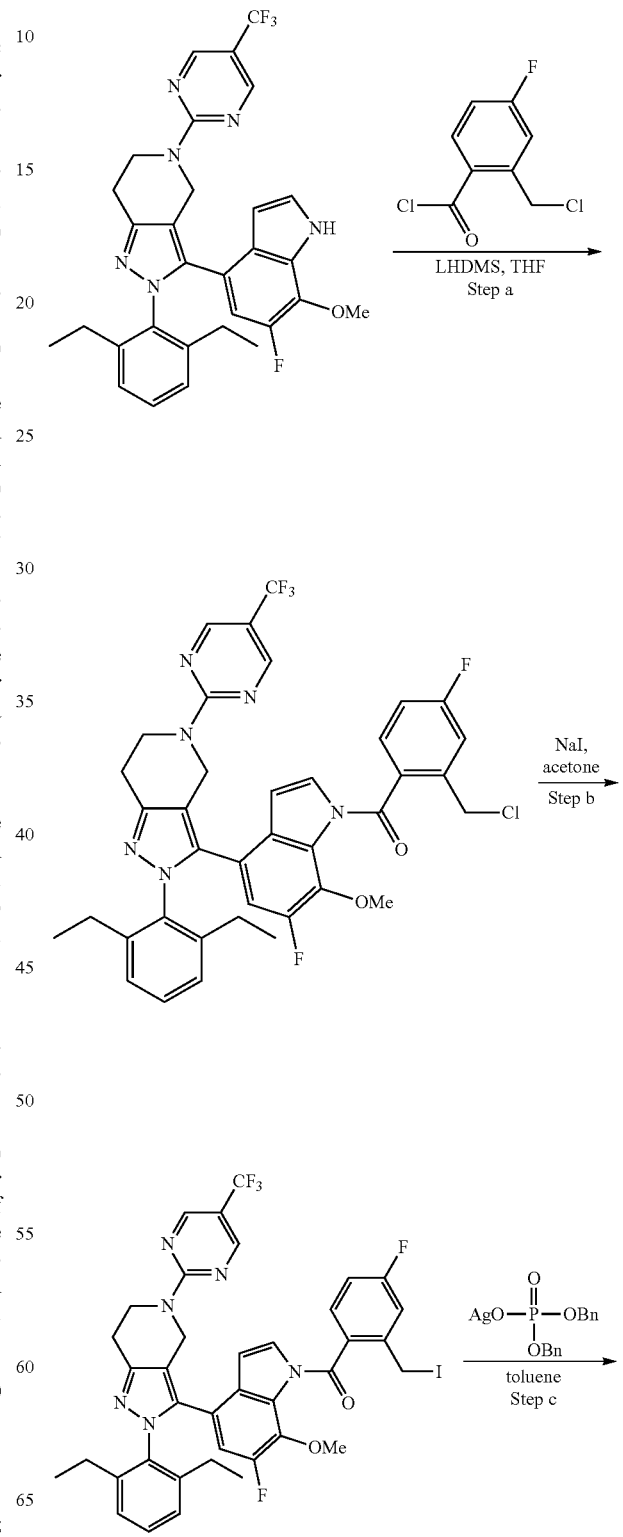

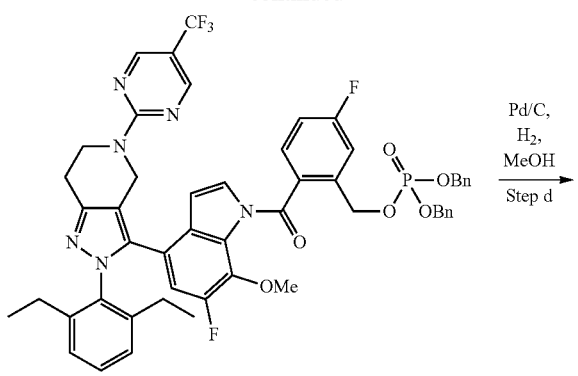

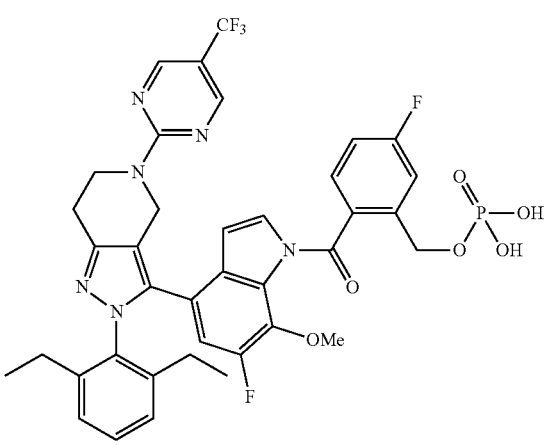 [SMILES: CCc1cccc(CC)c1-n1nc2c(c1-c1cc(F)c(OC)c3c1ccn3C(=O)c1ccc(F)cc1COP(=O)(O)O)CN(c1ncc(C(F)(F)F)cn1)CC2]

Step a: A vial containing 5-fluoroisobenzofuran-1(3H)-one (50 mg, 0.33 mmol), boric acid (2 mg, 0.03 mmol), and triethylbenzylammonium chloride (6 mg, 0.03 mmol) was heated at 110° C. To the mixture was added thionyl chloride (0.05 mL, 0.69 mmol). After stirring at 110° C. for 16 h, the contents were concentrated to give 2-(chloromethyl)-4-fluorobenzoyl chloride.

To a solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (46 mg, 0.08 mmol) in THF (0.5 mL) at −78° C. was added a 1 M solution of LHMDS in THF (0.12 mL, 0.12 mmol). The mixture was stirred at −78° C. for 30 min, warmed to 0° C. and stirred for 15 min, then cooled back down to −78° C. A solution of 2-(chloromethyl)-4-fluorobenzoyl chloride (0.33 mmol) in THF (0.5 mL) was added dropwise to the mixture. After stirring at room temperature for 16 h, the reaction was quenched with H$_2$O. The aqueous and organic layers were separated, and the aqueous layer was extracted with EtOAc. The organic layers were combined, dried with sodium sulfate, filtered and concentrated. The residue was purified by silica gel column chromatography (0 to 100% EtOAc in hexanes) to yield (2-(chloromethyl)-4-fluorophenyl)(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)methanone. MS: (ES) m/z calculated for C$_{38}$H$_{32}$ClF$_5$N$_6$O$_2$ [M+H]$^+$ 735.2, found 735.1.

Step b: To a solution of (2-(chloromethyl)-4-fluorophenyl)(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)methanone (48 mg, 0.065 mmol) in acetone (1 mL) was added sodium iodide (32 mg, 0.21 mmol). The mixture was heated at 70° C. for 1 h then concentrated in vacuo. The residue was purified by silica gel column chromatography (0 to 100% EtOAc in hexanes) to produce (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)(4-fluoro-2-(iodomethyl)phenyl)methanone. MS: (ES) m/z calculated for C$_{38}$H$_{32}$F$_5$IN$_6$O$_2$ [M+H]$^+$ 827.2, found 827.0.

Step c: To a solution of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)(4-fluoro-2-(iodomethyl)phenyl)methanone (26 mg, 0.031 mmol) in toluene (1 mL) was added silver dibenzylphosphate (24 mg, 0.062 mmol). The mixture was heated at 110° C. for 16 h then concentrated in vacuo. The residue was purified by silica gel column chromatography (0 to 100% EtOAc in hexanes) to provide dibenzyl (2-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)-5-fluorobenzyl) phosphate.

Step d: To a solution of dibenzyl (2-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)-5-fluorobenzyl) phosphate (17 mg, 0.017 mmol) in MeOH (1 mL) was added 10% Pd/C (2 mg). The mixture was stirred under a H2 balloon for 1 h, then filtered through Celite, concentrated and purified by HPLC (MeCN/H$_2$O, with 0.1% TFA) to yield 2-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)-5-fluorobenzyl dihydrogen phosphate. $^1$H NMR (400 MHz, CD$_3$OD) δ 8.58 (s, 2H), 7.60 (d, J=10.0 Hz, 1H), 7.49 (br s, 2H), 7.33 (t, J=7.6 Hz, 1H), 7.11-7.24 (m, 3H), 6.65 (s, 1H), 6.59 (d, J=13.0 Hz, 1H), 5.35 (d, J=7.3 Hz, 2H), 4.87 (s, 2H), 4.38 (s, 2H), 3.75 (s, 3H), 2.98 (s, 2H), 2.25 (br s, 4H), 1.02 (br s, 6H). MS: (ES) m/z calculated for C$_{38}$H$_{34}$F$_5$N$_6$O$_6$P [M+H]$^+$ 797.2, found 797.1.

Example 16: Synthesis of 2-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)benzyl dimethylglycinate

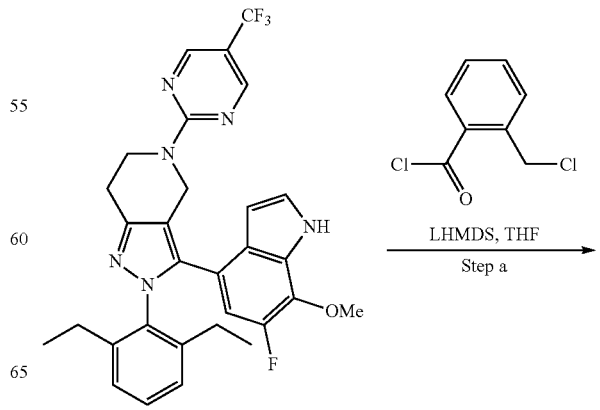

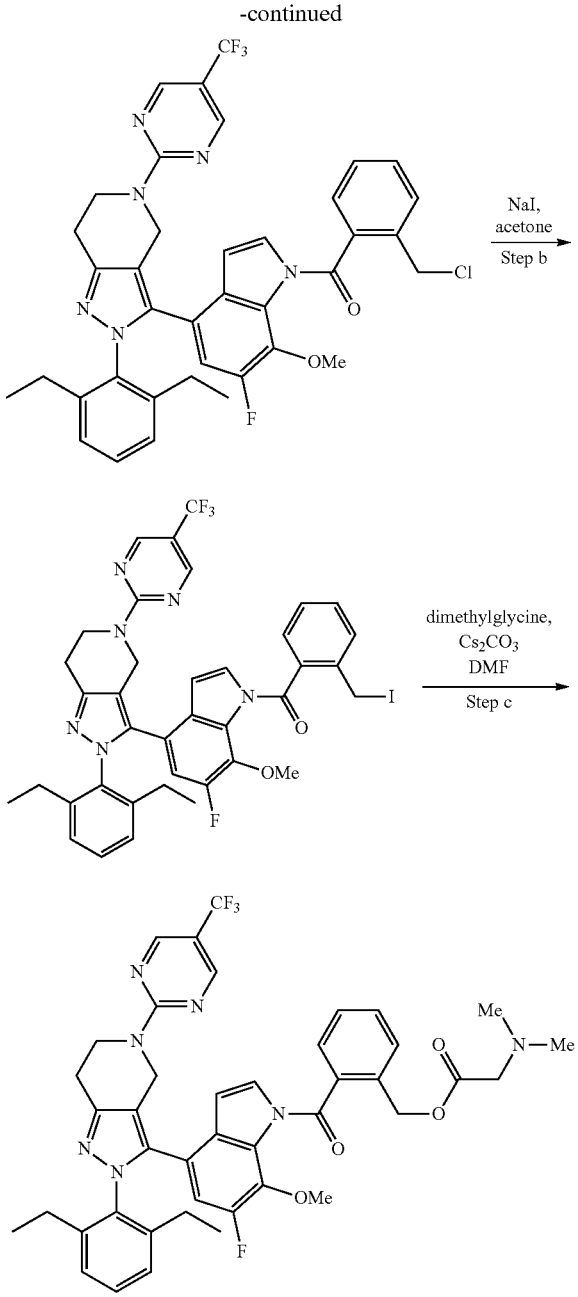

methoxy-1H-indol-1-yl)methanone. MS: (ES) m/z calculated for $C_{38}H_{33}ClF_4N_6O_2$ [M+H]$^+$ 717.2, found 717.0.

Step b: To a solution of (2-(chloromethyl)phenyl)(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)methanone (156 mg, 0.22 mmol) in acetone (2.2 mL) was added sodium iodide (129 mg, 0.9 mmol). After heating at 70° C. for 1 h, the reaction was quenched with H$_2$O. The aqueous and organic layers were separated, and the aqueous layer was extracted with EtOAc. The organic layers were combined, dried with sodium sulfate, filtered and concentrated.

The residue was purified by silica gel column chromatography (0 to 100% EtOAc in hexanes) to produce (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)(2-(iodomethyl)phenyl)methanone.

Step c: To a solution of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)(2-(iodomethyl)phenyl)methanone (76 mg, 0.094 mmol) in DMF (1 mL) at 0° C. was added Cs$_2$CO$_3$ (31 mg, 0.1 mmol) and dimethylglycine (10 mg, 0.1 mmol). After stirring at room temperature for 16 h, the reaction was quenched with H$_2$O. The aqueous and organic layers were separated, and the aqueous layer was extracted with EtOAc. The organic layers were combined, dried with sodium sulfate, filtered and concentrated. The residue was purified by HPLC (MeCN/H$_2$O, with 0.1% TFA) to provide 2-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carbonyl)benzyl dimethylglycinate. $^1$H NMR (400 MHz, CDCl$_3$) δ 8.54 (s, 2H), 7.65-7.81 (m, 4H), 7.31 (t, J=7.7 Hz, 1H), 7.22 (d, J=3.7 Hz, 1H), 7.11 (br s, 2H), 6.64 (d, J=12.7 Hz, 1H), 6.52 (d, J=3.7 Hz, 1H), 5.08 (s, 2H), 4.76 (s, 2H), 4.37 (s, 2H), 4.14 (s, 2H), 3.85 (s, 3H), 3.32 (s, 6H), 3.09 (t, J=5.9 Hz, 2H), 2.08 (br s, 4H), 1.04 (br s, 6H). MS: (ES) m/z calculated for $C_{42}H_{41}F_4N_7O_4$ [M+H]$^+$ 784.3, found 784.2.

Example 17: Synthesis of 3-chloro-4-(phosphonooxy)benzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

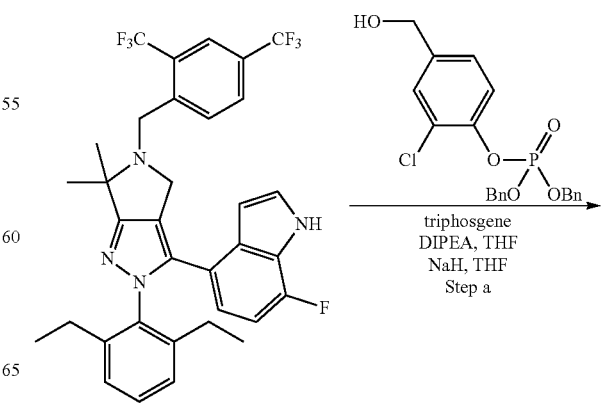

Step a: To a solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (500 mg, 0.9 mmol) in THF (8.8 mL) at −78° C. was added a 1 M solution of LHMDS in THF (0.98 mL, 0.98 mmol). After stirring at −78° C. for 30 min, 2-(chloromethyl)benzoyl chloride (0.25 mL, 1.78 mmol) was added to the mixture. After stirring at room temperature for 16 h, the reaction was quenched with H$_2$O. The aqueous and organic layers were separated, and the aqueous layer was extracted with EtOAc. The organic layers were combined, dried with sodium sulfate, filtered and concentrated. The residue was purified by silica gel column chromatography (0 to 100% EtOAc in hexanes) to yield (2-(chloromethyl)phenyl)(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-

-continued

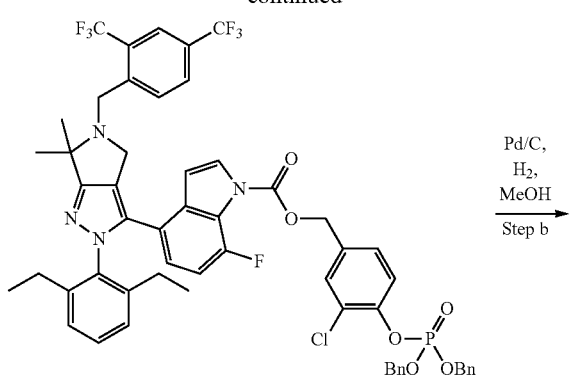

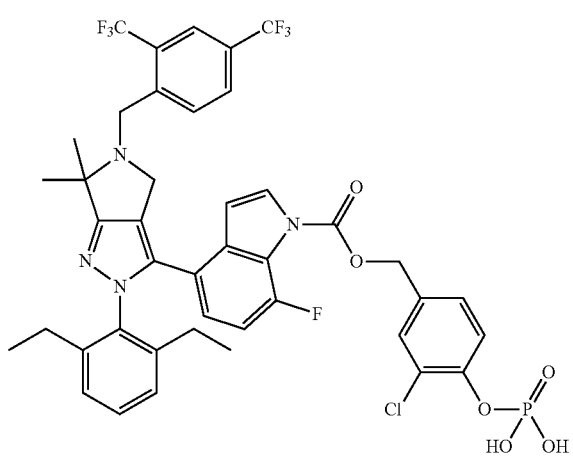

Step a: To a flask containing 3-chloro-4-hydroxybenzoic acid (5 g, 29 mmol) in MeOH (100 mL) was added dropwise thionyl chloride (7.4 mL, 102 mmol). The mixture was heated at 60° C. for 1 h then concentrated in vacuo. The crude residue was dissolved in THF (100 mL). To the solution was added LiAlH$_4$ (4.4 g, 110 mmol). After heating at 65° C. for 1 h, the reaction was quenched with 1 N HCl. The aqueous and organic layers were separated, and the aqueous layer was extracted with EtOAc. The organic layers were combined, dried with sodium sulfate, filtered and concentrated. The residue was purified by silica gel column chromatography (0 to 100% EtOAc in hexanes) to afford 2-chloro-4-(hydroxymethyl)phenol.

To a solution of 2-chloro-4-(hydroxymethyl)phenol (2 g, 12.7 mmol) in dioxane (25 mL) was added DDQ (2.87 g, 12.7 mmol). The mixture was stirred at room temperature for 4 h then filtered. The filtrate was washed with H$_2$O, then dried with sodium sulfate, filtered and concentrated. The residue was purified by silica gel column chromatography (0 to 100% EtOAc in hexanes) to yield 3-chloro-4-hydroxybenzaldehyde. MS: (ES) m/z calculated for $C_7H_5ClO_2$ [M+H]$^+$ 157.0, found 157.0.

To a flask containing 3-chloro-4-hydroxybenzaldehyde (1.4 g, 9.0 mmol) in THF (14.6 mL) was added dropwise a 1.0 M solution of tBuOK in THF (9.5 mL, 9.5 mmol) and tetrabenzyldiphosphate (4.8 g, 8.9 mmol). The mixture was heated at 70° C. for 2 h. Upon completion, hexanes was added and the contents were filtered. The filtrate was concentrated and the resultant residue was purified by silica gel column chromatography (0 to 100% EtOAc in hexanes) to afford dibenzyl (2-chloro-4-formylphenyl)phosphate. MS: (ES) m/z calculated for $C_{21}H_{18}ClO_5P$ [M+H]$^+$ 417.1, found 417.0.

To a solution of dibenzyl (2-chloro-4-formylphenyl)phosphate (2.75 g, 6.6 mmol) in THF (6.6 mL) at −78° C. was added NaBH$_4$ (0.73 g, 19.7 mmol). After stirring at −78° C. for 1 h, the reaction was quenched with H$_2$O. The organic and aqueous layers were separated, and the aqueous layer was extracted with EtOAc. The organic layers were combined, dried with sodium sulfate, filtered and concentrated in vacuo. The resultant residue was purified by silica gel column chromatography (0 to 100% EtOAc in hexanes) to produce dibenzyl (2-chloro-4-(hydroxymethyl)phenyl)phosphate. MS: (ES) m/z calculated for $C_{21}H_{20}ClO_5P$ [M+H]$^+$ 419.1, found 419.0.

To a solution of dibenzyl (2-chloro-4-(hydroxymethyl)phenyl)phosphate (250 mg, 0.6 mmol) in THF (3 mL) at 0° C. was added diisopropylethylamine (0.12 mL, 0.69 mmol) and triphosgene (92 mg, 0.3 mmol). After stirring at 0° C. for 1 h, the reaction was quenched with H$_2$O. The organic and aqueous layers were separated and the aqueous layer was extracted with EtOAc. The organic layers were combined, dried with sodium sulfate, filtered and concentrated to afford the crude chloroformate.

To a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (187 mg, 0.30 mmol) in THF (1.5 mL) at 0° C. was added NaH (24 mg, 0.60 mmol). After stirring at 0° C. for 30 min, a solution of the crude chloroformate (prepared above) in THF (1.5 mL), was added to the mixture. After stirring at 0° C. for 1 h, the reaction was quenched with H$_2$O. The organic and aqueous layers were separated and the aqueous layer was extracted with EtOAc. The organic layers were combined, dried with sodium sulfate, filtered and concentrated in vacuo. The residue was purified by silica gel column chromatography (0 to 100% EtOAc in hexanes) to produce 4-((bis(benzyloxy)phosphoryl)oxy)-3-chlorobenzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate.

Step b: To a solution of 4-((bis(benzyloxy)phosphoryl)oxy)-3-chlorobenzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (298 mg, 0.28 mmol) in MeOH (4 mL) was added 10% Pd/C (30 mg, 0.03 mmol). The mixture was stirred under a H2 balloon for 1 h, then filtered through Celite, concentrated and purified by HPLC (MeCN/H$_2$O, with 0.1% TFA) to yield 3-chloro-4-(phosphonooxy)benzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, CD$_3$OD) δ 8.12 (s, 1H), 8.04-8.12 (m, 2H), 7.83 (s, 1H), 7.55 (s, 1H), 7.51 (d, J=8.4 Hz, 1H), 7.33-7.37 (m, 2H), 7.17 (d, J=7.9 Hz, 2H), 6.82 (dd, J=10.2, 10.2 Hz, 1H), 6.67 (br s, 2H), 5.36 (s, 2H), 4.77 (s, 2H), 4.50 (s, 2H), 2.16-2.29 (m, 4H), 1.93 (br s, 6H), 0.99 (br s, 6H). MS: (ES) m/z calculated for $C_{42}H_{37}ClF_7N_4O_6P$ [M+H]$^+$ 893.2, found 893.1.

Example 18: Synthesis of 3-fluoro-4-(phosphonooxy)benzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

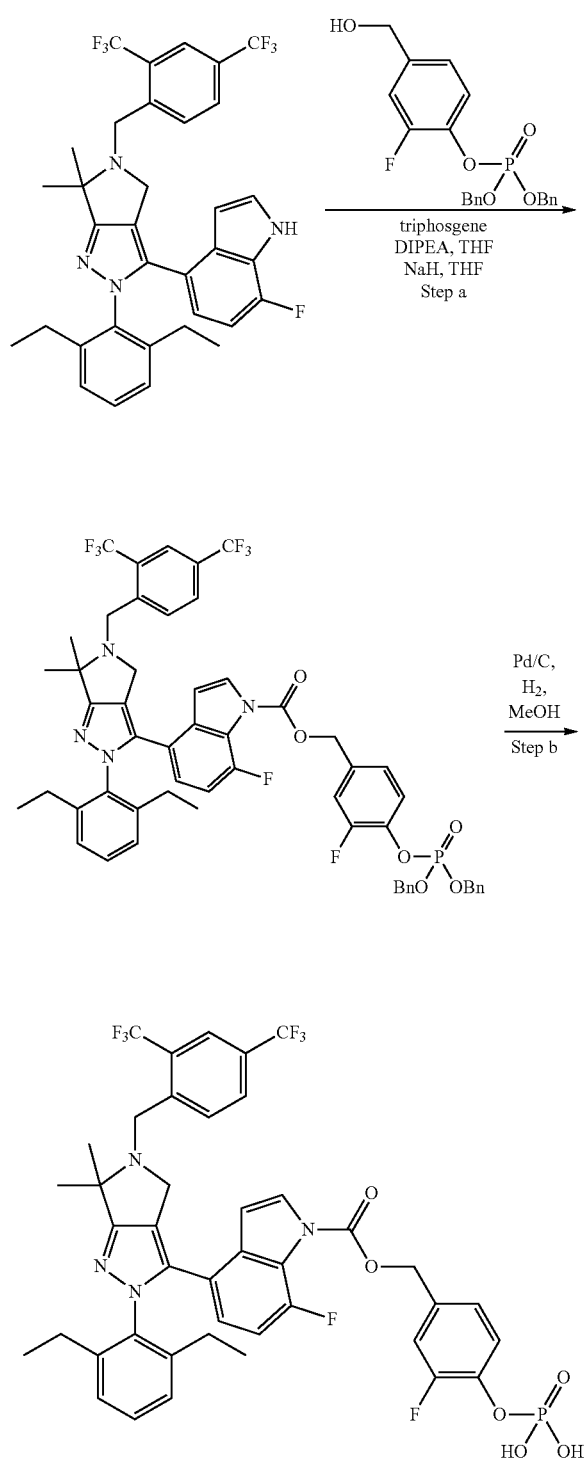

Step a: To a flask containing 3-fluoro-4-hydroxybenzaldehyde (1 g, 7.1 mmol) in THF (32 mL) was added dropwise a 1.0 M solution of tBuOK in THF (7.6 mL, 7.6 mmol) and tetrabenzyldiphosphate (4.0 g, 7.4 mmol). The mixture was heated at 70° C. for 1 h. Upon completion, hexanes was added and the contents were filtered. The filtrate was concentrated and the residue was purified by silica gel column chromatography (0 to 100% EtOAc in hexanes) to afford dibenzyl (2-fluoro-4-formylphenyl) phosphate. MS: (ES) m/z calculated for $C_{21}H_{18}FO_5P$ [M+H]$^+$ 401.1, found 401.1.

To a solution of dibenzyl (2-fluoro-4-formylphenyl) phosphate (2.68 g, 6.7 mmol) in THF (6.7 mL) at −78° C. was added NaBH$_4$ (0.76 g, 20.5 mmol). After stirring at −78° C. for 1 h, the reaction was quenched with H$_2$O. The organic and aqueous layers were separated, and the aqueous layer was extract with EtOAc. The organic layers were combined, dried with sodium sulfate, filtered and concentrated in vacuo. The residue was purified by silica gel column chromatography (0 to 100% EtOAc in hexanes) to produce dibenzyl (2-fluoro-4-(hydroxymethyl)phenyl) phosphate. MS: (ES) m/z calculated for $C_{21}H_{20}FO_5P$ [M+H]$^+$ 403.1, found 403.0.

To a solution of dibenzyl (2-fluoro-4-(hydroxymethyl)phenyl)phosphate (250 mg, 0.62 mmol) in THF (3 mL) at 0° C. was added diisopropylethylamine (0.12 mL, 0.69 mmol) and triphosgene (92 mg, 0.3 mmol). After stirring at room temperature for 30 min, the reaction was quenched with H$_2$O. The organic and aqueous layers were separated, and the aqueous layer was extracted with EtOAc. The organic layers were combined, dried with sodium sulfate, filtered and concentrated to afford the crude chloroformate.

To a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (195 mg, 0.31 mmol) in THF (1.5 mL) at 0° C. was added NaH (24 mg, 0.60 mmol). After stirring at room temperature for 30 min, a solution of the crude chloroformate (prepared above) in THF (1.5 mL), was added to the mixture. After stirring at room temperature for 16 h, the reaction was quenched with H$_2$O. The organic and aqueous layers were separated, and the aqueous layer was extracted with EtOAc. The organic layers were combined, dried with sodium sulfate, filtered and concentrated in vacuo. The residue was purified by silica gel column chromatography (0 to 100% EtOAc in hexanes) to produce 4-((bis(benzyloxy)phosphoryl)oxy)-3-fluorobenzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate.

Step b: To a solution of 4-((bis(benzyloxy)phosphoryl)oxy)-3-fluorobenzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (307 mg, 0.29 mmol) in EtOAc (1.5 mL) was added 10% Pd/C (30 mg, 0.03 mmol). The mixture was stirred under a H2 balloon for 3 h, then filtered through Celite, concentrated and purified by HPLC (MeCN/H$_2$O, with 0.1% TFA) to yield 3-fluoro-4-(phosphonooxy)benzyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, CD$_3$OD) δ: 8.13 (s, 1H), 8.05-8.11 (m, 2H), 7.83 (m, 1H), 7.44 (dd, J=8.4, 8.4 Hz, 1H), 7.30-7.37 (m, 2H), 7.23 (d, J=8.4 Hz, 1H), 7.17 (d, J=7.8 Hz, 2H), 6.83 (dd, J=10.4, 10.4 Hz, 1H), 6.67 (br s, 2H), 5.38 (s, 2H), 4.80 (s, 2H), 4.54 (s, 2H), 2.15-2.29 (m, 4H), 1.96 (br s, 6H), 0.99 (br s, 6H). MS: (ES) m/z calculated for $C_{42}H_{37}F_8N_4O_6P$ [M+H]$^+$ 877.2, found 877.1.

Example 19: Synthesis of 2-((phosphonooxy)methyl)phenyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

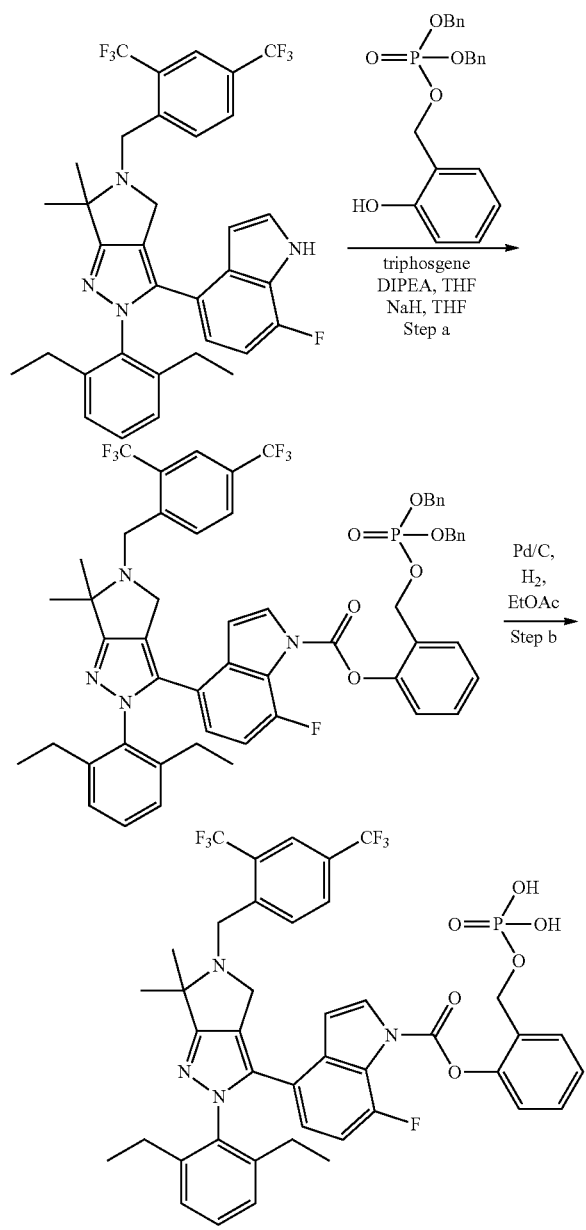

Step a: To a flask containing 2-hydroxybenzaldehyde (10 g, 82 mmol) in DMF (82 mL) was added dropwise imidazole (6.1 g, 90 mmol) and TBDMSCl (13.6 g, 90 mmol). After stirring at room temperature for 3 h, the reaction was quenched with $H_2O$. The mixture was extracted with EtOAc. The combined organic layers were dried with sodium sulfate, filtered and concentrated. The residue was purified by silica gel column chromatography (0-100% EtOAc in hexanes) to afford 2-((tert-butyldimethylsilyl)oxy)benzaldehyde. MS: (ES) m/z calculated for $C_{13}H_{20}O_2Si$ [M+H]$^+$ 237.1, found 237.1.

To a solution of 2-((tert-butyldimethylsilyl)oxy)benzaldehyde (16.4 g, 69 mmol) in MeOH (126 mL) was added $NaBH_4$ (2.55 g, 67.4 mmol). After stirring at room temperature for 2 h, the reaction was quenched with $H_2O$. The mixture was concentrated in vacuo then extracted with hexanes. The organic layers were combined, dried with sodium sulfate, filtered and concentrated in vacuo. The residue was purified by silica gel column chromatography (0 to 10% EtOAc in hexanes) to produce (2-((tert-butyldimethylsilyl)oxy)phenyl)methanol.

To a flask containing (2-((tert-butyldimethylsilyl)oxy)phenyl)methanol (1 g, 4.2 mmol) in THF (42 mL) was added dropwise a 1.0 M solution of tBuOK in THF (4.6 mL, 4.6 mmol) and tetrabenzyldiphosphate (2.5 g, 4.6 mmol). The mixture was heated at 60° C. for 1 h. Upon completion, hexanes was added and the contents were filtered. The filtrate was concentrated and the residue was used without further purification.

To a solution of the crude residue dissolved in MeCN (42 mL) was added dropwise HF-pyridine (4.2 mL). After stirring at room temperature for 1 h the mixture was concentrated in vacuo. The residue was purified by silica gel column chromatography (0 to 100% EtOAc in hexanes) to yield dibenzyl (2-hydroxybenzyl)phosphate. MS: (ES) m/z calculated for $C_{21}H_{21}O_5P$ [M+H]$^+$ 385.1, found 385.0.

To a solution of dibenzyl (2-hydroxybenzyl)phosphate (366 mg, 0.95 mmol) in THF (4.8 mL) was added diisopropylethylamine (0.18 mL, 1.0 mmol) and triphosgene (139 mg, 0.47 mmol). After stirring at room temperature for 30 min, the reaction was quenched with $H_2O$. The organic and aqueous layers were separated and the aqueous layer was extracted with EtOAc. The organic layers were combined, dried with sodium sulfate, filtered and concentrated.

To a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (300 mg, 0.48 mmol) in THF (4.8 mL) was added NaH (37 mg, 0.97 mmol). After stirring at room temperature for 20 min, a solution of the crude chloroformate (prepared above) in 1 mL of THF, was added to the mixture. After stirring at room temperature for 16 h, the reaction was quenched with $H_2O$. The organic and aqueous layers were separated, and the aqueous layer was extracted with EtOAc. The organic layers were combined, dried with sodium sulfate, filtered and concentrated in vacuo. The residue was purified by silica gel column chromatography (0 to 100% EtOAc in hexanes) to produce 2-(((bis(benzyloxy)phosphoryl)oxy)methyl)phenyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate.

Step b: To a solution 2-(((bis(benzyloxy)phosphoryl)oxy)methyl)phenyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (500 mg, 0.48 mmol) in EtOAc (2.4 mL) was added 10% Pd/C (51 mg). The mixture was stirred under a H2 balloon for 2 h, then filtered through Celite, concentrated and purified by HPLC (MeCN/$H_2O$, with 0.1% TFA) to yield 2-((phosphonooxy)methyl)phenyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, DMSO-$d_6$) δ 8.12 (d, J=8.1 Hz, 1H), 7.94-8.06 (m, 2H), 7.85 (s, 1H), 7.51 (d, J=7.6 Hz, 1H), 7.35-7.39 (m, 1H), 7.28-7.33 (m, 2H), 7.07-7.20 (m, 3H), 6.90-6.95 (m, 1H), 6.60 (s, 1H), 6.56 (dd, J=8.4, 3.7 Hz, 1H), 5.42 (s, 2H), 4.15 (br s, 2H), 3.59 (br s, 2H), 2.16 (q, J=7.8 Hz, 4H), 1.48 (br s, 6H), 0.90 (t, J=7.5 Hz, 6H). MS: (ES) m/z calculated for $C_{42}H_{38}F_7N_4O_6P$ [M+H]$^+$ 859.2, found 859.2.

Example 20: Synthesis of 2-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carbonyl)benzyl dihydrogen phosphate

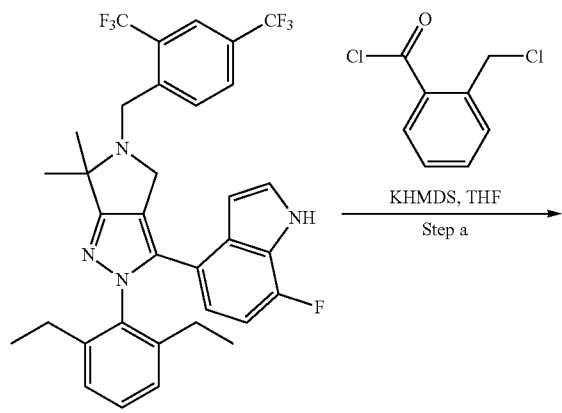

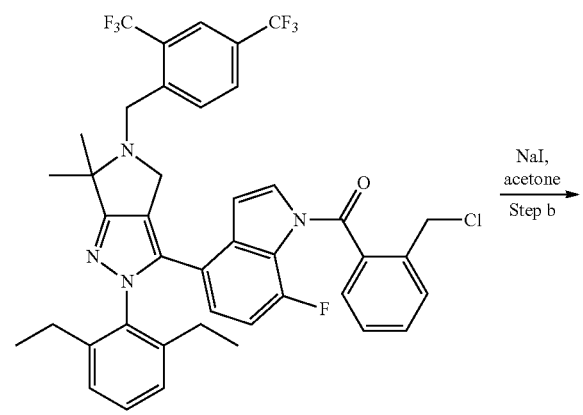

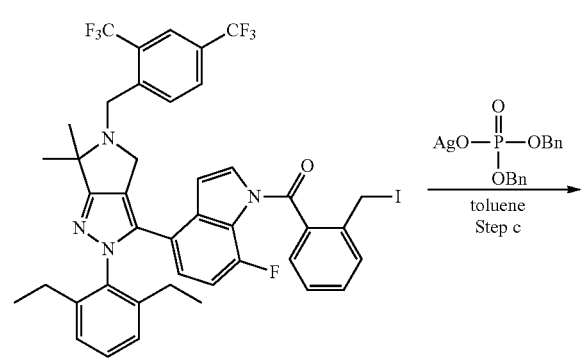

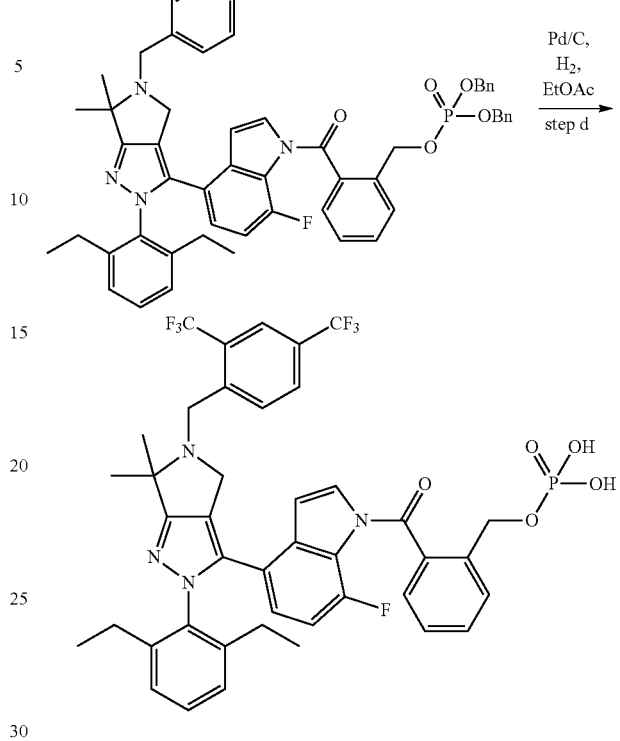

Step a: To a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (500 mg, 0.80 mmol) in THF (8 mL) at −78° C. was added a 0.5 M solution of KHMDS in THF (2.6 mL, 1.3 mmol). After stirring at −78° C. for 30 min, 2-(chloromethyl)benzoyl chloride (0.28 mL, 1.9 mmol) was added to the mixture. After stirring at room temperature for 16 h, the reaction was diluted with EtOAc and washed with satuated aqueous NaHCO$_3$ solution. The aqueous and organic layers were separated, and the aqueous layer was extracted with EtOAc. The organic layers were combined, dried with sodium sulfate, filtered and concentrated. The residue was purified by silica gel column chromatography (0 to 100% EtOAc in hexanes) to yield (4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)(2-(chloromethyl)phenyl)methanone. MS: (ES) m/z calculated for $C_{42}H_{36}ClF_7N_4O$ [M+H]$^+$ 781.3, found 781.0.

Step b: To a solution of (4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)(2-(chloromethyl)phenyl)methanone (194 mg, 0.25 mmol) in acetone (3.1 mL) was added sodium iodide (149 mg, 0.99 mmol). After heating at 70° C. for 2 h, the reaction was diluted with EtOAc and washed with H$_2$O. The aqueous and organic layers were separated, and the aqueous layer was extracted with EtOAc. The organic layers were combined, dried with sodium sulfate, filtered and concentrated to produce (4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)(2-(iodomethyl)phenyl)methanone, which was used in the subsequent step without further purification.

Step c: To a solution of crude (4-(5-(2,4-bis(trifluoromethyl)benzyl)-2-(2,6-diethylphenyl)-6,6-dimethyl-2,4,5,6- tetrahydropyrrolo[3,4-c]pyrazol-3-yl)-7-fluoro-1H-indol-1-yl)(2-(iodomethyl)phenyl)methanone (0.25 mmol) in toluene (1 mL) was added silver dibenzylphosphate (190 mg, 0.49 mmol). After heating the mixture at 110° C. for 3 h, the mixture was filtered through Celite. The filtrate was concentrated and the residue was purified by silica gel column chromatography (0 to 100% EtOAc in hexanes) to provide dibenzyl (2-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carbonyl)benzyl)phosphate.

Step d: To a solution of dibenzyl (2-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carbonyl)benzyl)phosphate (96 mg) in EtOAc (1 mL) was added 10% Pd/C (10 mg, 0.009 mmol). The mixture was stirred under a H2 balloon for 4 h, then filtered through Celite, concentrated and purified by HPLC (MeCN/H$_2$O, with 0.1% TFA) to yield 2-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carbonyl)benzyl dihydrogen phosphate. $^1$H NMR (400 MHz, CD$_3$OD) δ: 8.12 (s, 1H), 8.09 (br s, 2H), 7.74 (d, J=7.7 Hz, 1H), 7.67 (ddd, J=1.4, 7.3, 7.3 Hz, 1H), 7.57 (dd, J=1.4, 7.7 Hz, 1H), 7.49 (ddd, J=1.4, 7.2, 7.2 Hz, 1H), 7.40 (d, J=3.7 Hz, 1H), 7.36 (d, J=7.7 Hz, 1H), 7.20 (d, J=7.7 Hz, 1H), 6.84 (dd, J=8.3, 11.3 Hz, 1H), 6.72 (dd, J=3.8, 8.4 Hz, 1H), 6.67 (dd, J=1.8, 3.8 Hz, 1H), 5.19 (d, J=7.4 Hz, 2H), 4.75 (s, 2H), 4.55 (s, 2H), 2.26 (q, J=7.5 Hz, 4H), 1.93 (s, 6H), 1.03 (t, J=7.5 Hz, 6H). MS: (ES) m/z calculated for C$_{42}$H$_{38}$F$_7$N$_4$O$_5$P [M+H]$^+$ 843.3, found 843.2.

Example 21: Synthesis of ((4-(piperazin-1-ylmethyl)benzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

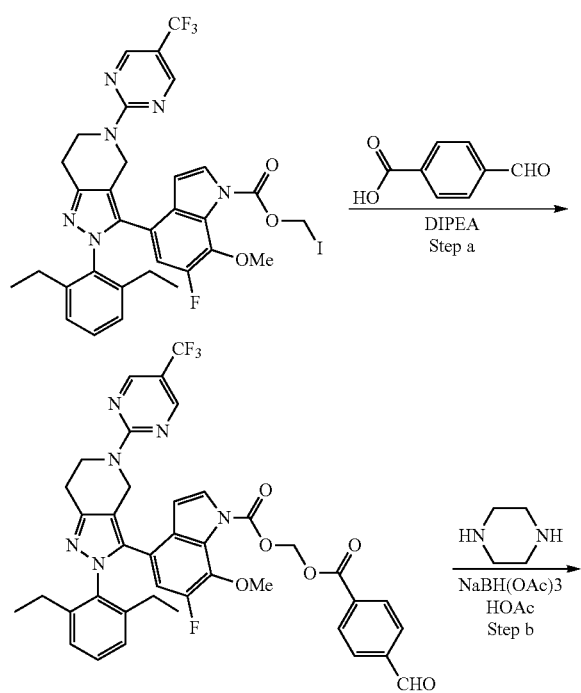

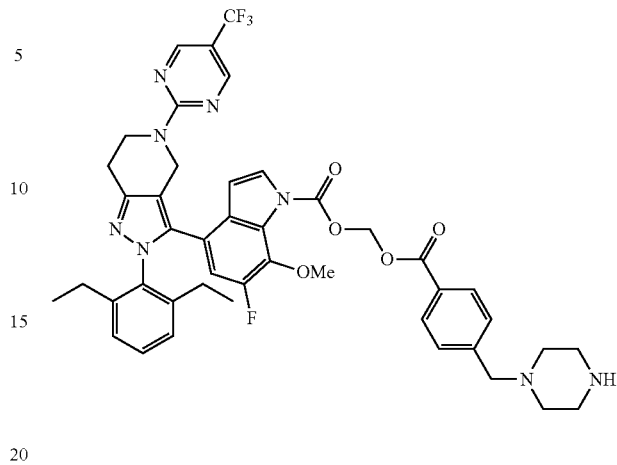

Step a: A mixture of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (840 mg, 1.12 mmol), 4-formylbenzoic acid (252 mg, 1.68 mmol) and diisopropylethylamine (0.74 mL, 4.48 mmol) in dichloromethane (20 mL) was heated to 50° C. for 3 h. The mixture was cooled to room temperature, poured into saturated aqueous NaHCO$_3$ solution and extracted with dichloromethane. The organic layer was separated, dried over Na$_2$SO$_4$, concentrated under reduced pressure and purified by silica gel flash chromatography (0 to 60% EtOAc in hexanes) to afford ((4-formylbenzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. MS: (ES) m/z calculated for C$_{40}$H$_{35}$F$_4$N$_6$O$_6$[M+H]$^+$ 771.2, found 771.2.

Step b: To a 200 mL flask containing piperazine (1.0 g, 11.6 mmol) in dichloromethane (25 mL) at 0° C. was added sequentially acetic acid (40 mL), NaBH(OAc)$_3$ (1.5 g, 7.0 mmol) and ((4-formylbenzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (0.5 g, 0.65 mmol). The mixture was allowed to warm to room temperature and stirred overnight. The mixture was cooled to 0° C. and charged with 2 M HCl solution in ether (20 mL, 40 mmol). The mixture was purified by silica gel flash chromatography (0 to 100% EtOAc in hexanes followed by 0 to 60% MeOH in CH$_2$Cl$_2$). The pure fractions were combined, cooled to 0° C., charged with 2 M HCl solution in ether (10 mL, 20 mmol) and concentrated under reduced pressure to yield the HCl salt of of ((4-(piperazin-1-ylmethyl)benzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. $^1$H NMR (400 MHz, CD$_3$OD) δ 8.58 (s, 2H), 8.21 (d, J=8.4 Hz, 2H), 7.80 (d, J=3.6 Hz, 1H), 7.75 (d, J=8.0 Hz, 2H), 7.33 (t, J=7.8 Hz, 1H), 7.16 (br s, 2H), 6.59-6.66 (m, 2H), 6.30 (s, 2H), 4.32-4.50 (m, 4H), 3.96 (d, J=1.2 Hz, 3H), 3.40-3.60 (m, 9H), 3.28-3.34 (m, 3H), 2.98 (dd, J=5.8, 5.8 Hz, 2H), 2.25 (br s, 4H), 1.00 (br s, 6H); MS (free form): (ES) m/z calculated for C$_{44}$H$_{45}$F$_4$N$_8$O$_5$ [M+H]$^+$ 841.3, found 841.7.

Example 22: Synthesis of ((4-((phosphonooxy)methyl)benzoyl)oxy)methyl 4-(5-(2,4-bis(trifluoromethyl)-benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate
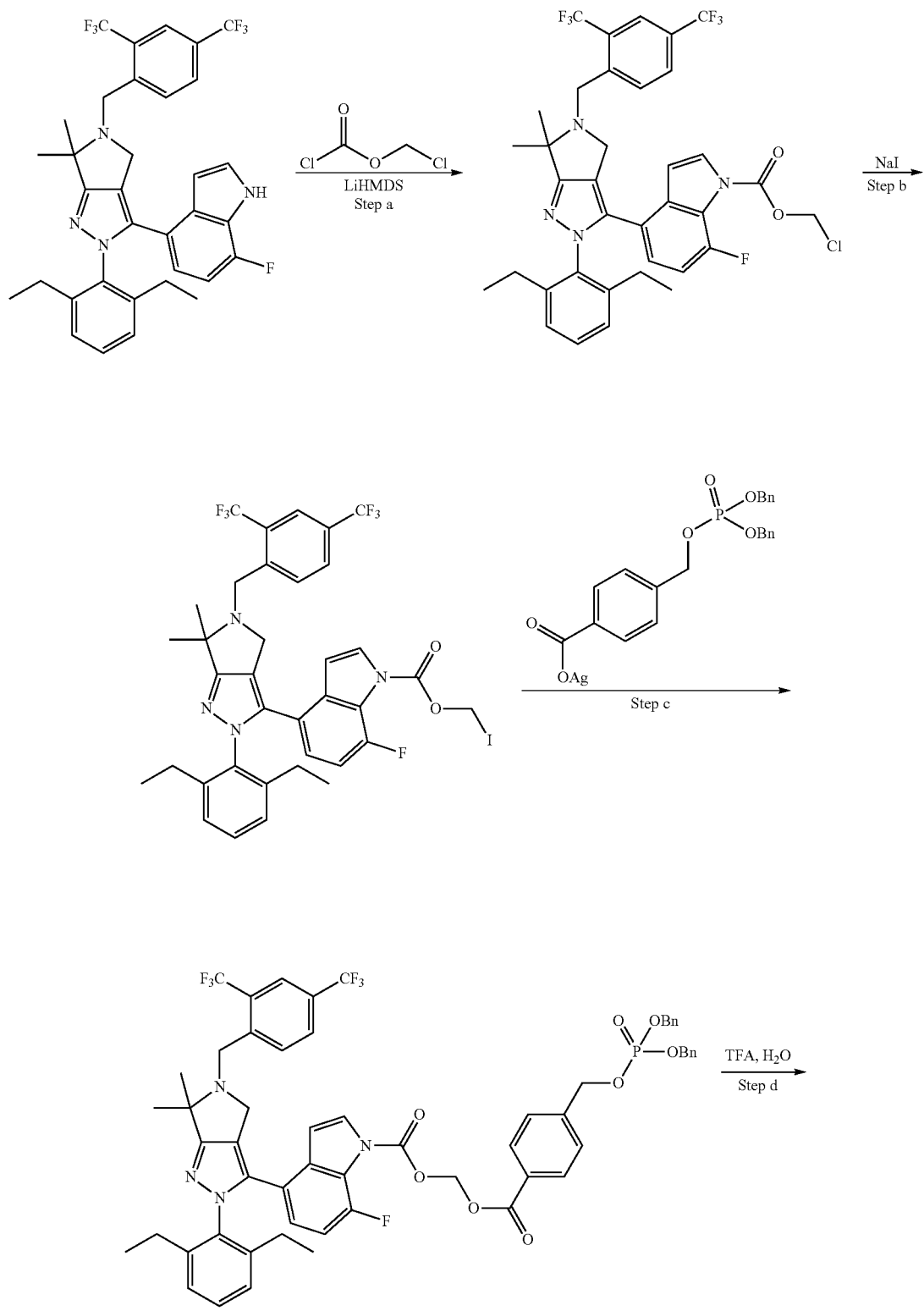

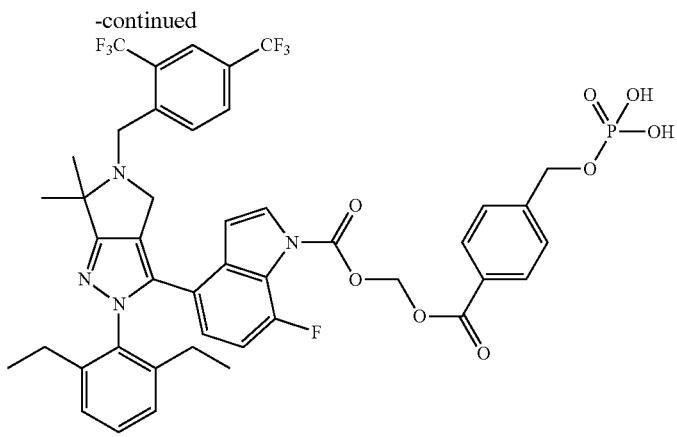

Step a: To a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (3.0 g, 4.76 mmol) in THF (30 mL) at −78° C. was added 1 M LiHMDS solution in toluene (7.61 mL, 7.61 mmol) dropwise. The mixture was stirred at the same temperature for an additional 15 min. Chloromethyl carbonochloridate (0.83 mL, 9.52 mmol) was added to the mixture. The resulting mixture was allowed to warm to room temperature and stirred for 0.5 h. The mixture was quenched with saturated aqueous NH$_4$Cl solution and extracted with EtOAc. The organic layer was separated, washed with saturated aqueous NaHCO$_3$ solution, dried over Na$_2$SO$_4$, concentrated under reduced pressure and purified by silica gel flash chromatography (0 to 40% EtOAc in hexanes) to afford chloromethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for C$_{36}$H$_{33}$ClF$_7$N$_4$O$_2$[M+H]$^+$ 721.1, found 721.0.

Step b: A mixture of chloromethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. (2.5 g, 3.46 mmol) and NaI (6.0 g, 40.0 mmol) in acetone (50 mL) was heated to 45° C. for 7 h. The mixture was cooled to room temperature, poured into saturated aqueous NaHCO$_3$ solution and extracted with EtOAc. The organic layer was separated, dried over Na$_2$SO$_4$, concentrated under reduced pressure and purified by silica gel flash chromatography (0 to 40% EtOAc in hexanes) to afford iodomethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for C$_{36}$H$_{33}$F$_7$IN$_4$O$_2$[M+H]$^+$ 813.2, found 813.2.

Step c: A mixture of iodomethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (156 mg, 0.19 mmol) and ((4-(((bis(benzyloxy)phosphoryl)oxy)methyl)benzoyl)oxy)silver (100 mg, 0.19 mmol) in toluene (10 mL) was heated to 110° C. for 1 h. It was cooled to room temperature, poured into saturated aqueous NaHCO$_3$ solution and extracted with EtOAc. The organic layer was separated, dried over Na$_2$SO$_4$, concentrated under reduced pressure and purified by silica gel flash chromatography (0 to 60% EtOAc in hexanes followed by 0 to 30% EtOAc in CH$_2$Cl$_2$) to afford ((4-(((bis(benzyloxy)phosphoryl)oxy)methyl)-benzoyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for C$_{58}$H$_{53}$F$_7$N$_4$O$_8$P [M+H]$^+$ 1097.3, only fragment of parent MS observed.

Step d: A mixture of ((4-(((bis(benzyloxy)phosphoryl)oxy)methyl)benzoyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (0.10 g, 0.09 mmol) TFA (1 mL), dichloromethane (1 mL) and water (1 mL) was heated to 45° C. for 6 h. It was cooled to room temperature, concentrated under reduced pressure and purified by HPLC (MeCN/H$_2$O, with 0.1% TFA) to afford ((4-((phosphonooxy)methyl)benzoyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate as TFA salt. $^1$H NMR (400 MHz, CD$_3$OD) δ 8.01-8.13 (m, 6H), 7.85 (d, J=3.6 Hz, 1H), 7.54 (d, J=8.4 Hz, 2H), 7.35 (dd, J=7.8, 7.8 Hz, 1H), 7.16 (d, J=8.0 Hz, 2H), 6.81-6.88 (m, 1H), 6.66-6.71 (m, 2H), 6.26 (s, 2H), 5.07 (d, J=7.2 Hz, 2H), 4.70 (br s, 2H), 4.40 (br s, 2H), 3.30 (br s, 2H), 2.16-2.30 (m, 4H), 1.88 (s, 6H), 1.00 (t, J=7.6 Hz, 6H); MS: (ES) m/z calculated for C$_{44}$H$_{41}$F$_7$N$_4$O$_8$P [M+H]$^+$917.3, found 917.1.

Example 23: Synthesis of ((4-(piperazin-1-ylmethyl)benzoyl)oxy)methyl 4-(5-(2,4-bis(trifluoromethyl)-benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

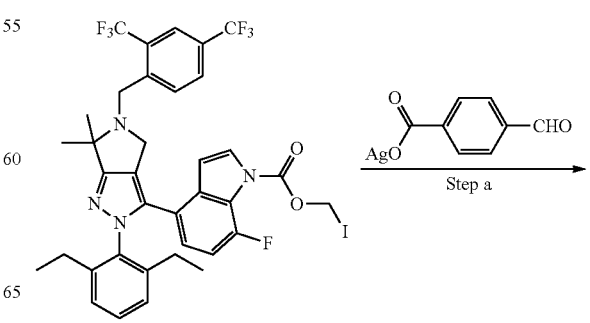

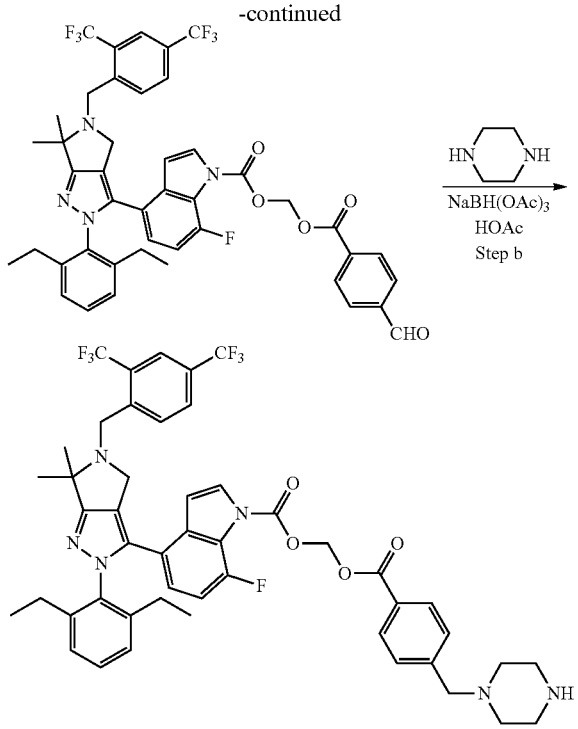

Step a: A mixture of 4-formylbenzoic acid (0.5 g, 3.3 mmol) and LiOH monohydrate (0.15 g, 3.7 mmol) in THF (7.5 mL), MeOH (1 mL) and water (0.5 mL) was stirred at room temperature for 15 minutes. To the mixture was added AgNO$_3$ (0.65 g, 3.8 mmol). The mixture was stirred for an additional 15 minutes and evaporated to dryness under reduced pressure to afford ((4-formylbenzoyl)oxy)silver.

A mixture of iodomethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (0.30 g, 0.37 mmol) and the above ((4-formylbenzoyl)oxy)silver (0.14 g, 0.55 mmol) in toluene (5 mL) was heated to 100° C. for 1 h. It was cooled to room temperature, poured into saturated aqueous NaHCO$_3$ solution and extracted with EtOAc. The organic layer was separated, dried over Na$_2$SO$_4$, concentrated under reduced pressure and purified by silica gel flash chromatography (0 to 60% EtOAc in hexanes) to afford ((4-formylbenzoyl)oxy)methyl 445-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for C$_{44}$H$_{38}$F$_7$N$_4$O$_5$ [M+H]$^+$ 835.3, found 835.3.

Step c: To a vial containing piperazine (0.150 g, 1.74 mmol) in dichloromethane (4 mL) at 0° C. was added acetic acid (3 mL), NaBH(OAc)$_3$ (0.400 g, 1.88 mmol) and ((4-formylbenzoyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (0.060 g, 0.071 mmol) in sequence. The mixture was allowed to warm up to room temperature and stirred overnight. The mixture was cooled to 0° C. and quenched 2 M HCl solution in ether (2 mL, 4 mmol). The mixture was purified by silica gel flash chromatography (0 to 100% MeOH in CH$_2$Cl$_2$). The pure fractions were combined, cooled to 0° C., charged with 2 M HCl solution in ether (2 mL, 4 mmol) and concentrated under reduced pressure to yield HCl salt of ((4-(piperazin-1-ylmethyl)benzoyl)oxy) methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, CD$_3$OD) δ 8.04-8.26 (m, 6H), 7.74-7.90 (m, 3H), 7.35 (dd, J=7.2, 7.2 Hz, 1H), 7.16 (d, J=7.2 Hz, 2H), 6.80-6.90 (m, 2H), 6.66-6.74 (m, 1H), 6.27 (s, 2H), 4.80-5.00 (m, 2H), 4.58 (s, 2H), 4.36 (br s, 1H), 3.63 (br s, 10H), 2.23 (br s, 4H), 2.03 (br s, 6H), 0.99 (t, J=6.4 Hz, 6H); MS: (ES) m/z calculated for C$_{48}$H$_{48}$F$_7$N$_6$O$_4$ [M+H]$^+$ 905.3, found 905.3.

Example 24: Synthesis of ((4-((phosphonooxy)methyl)benzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

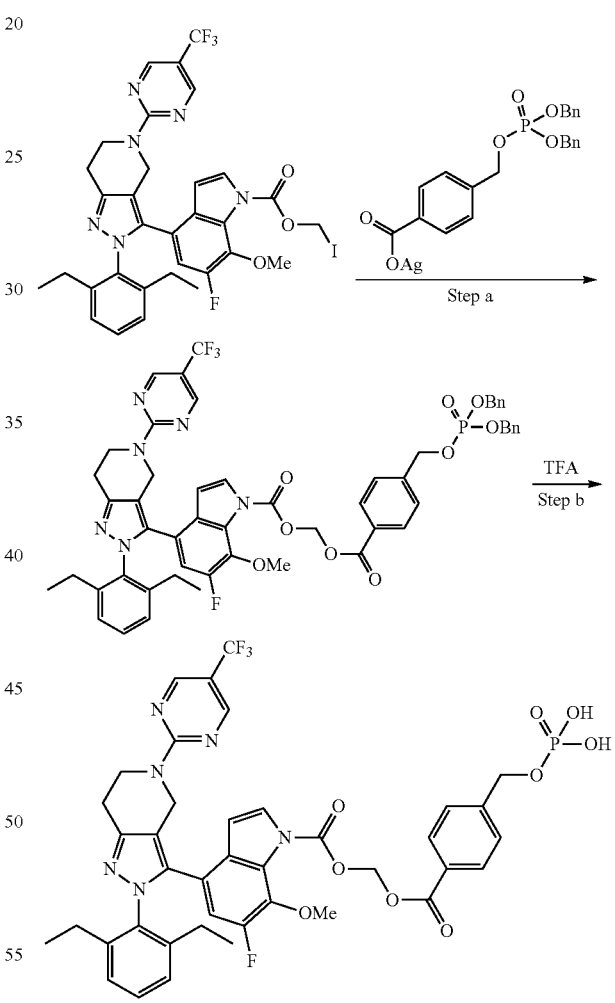

Step a: A mixture of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (0.15 g, 0.20 mmol) and ((4-(((bis(benzyloxy)phosphoryl)oxy)methyl)benzoyl)oxy)silver (0.11 g, 0.21 mmol) in toluene (4 mL) was heated to 110° C. for 1 h. The mixture was cooled to room temperature, poured into into saturated aqueous NaHCO$_3$ solution and extracted with EtOAc. The organic layer was separated, dried over Na₂SO₄, concentrated under reduced pressure and purified by silica gel flash chromatography (0 to 40% EtOAc in CH₂Cl₂) to afford ((4-(((bis(benzyloxy)phosphoryl)oxy)methyl)benzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. MS: (ES) m/z calculated for C₅₄H₅₀F₄N₆O₉P [M+H]⁺ 1033.3, only fragment of parent MS observed.

Step b: A mixture of ((4-(((bis(benzyloxy)phosphoryl)oxy)methyl)benzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (0.08 g, 0.08 mmol), TFA (1 mL), dichloromethane (1 mL) and water (1 mL) was heated to 45° C. for 7 h. It was cooled to room temperature, concentrated under reduced pressure and purified by HPLC (MeCN/H₂O, with 0.1% TFA) to afford ((4-((phosphonooxy)methyl)benzoyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. ¹H NMR (400 MHz, CD₃OD) δ 8.55 (s, 2H), 8.10 (d, J=7.6 Hz, 2H), 7.78 (s, 1H), 7.54 (d, J=8.0 Hz, 2H), 7.32 (dd, J=7.2 Hz, 1H), 7.15 (br s, 2H), 6.57-6.64 (m, 2H), 6.28 (s, 2H), 5.08 (d, J=7.6 Hz, 2H), 4.81 (br s, 2H), 4.36 (br s, 2H), 3.95 (s, 3H), 3.25-3.34 (m, 2H), 2.92-3.00 (m, 2H), 2.20 (br s, 4H), 1.00 (br s, 6H); MS: (ES) m/z calculated for C₄₀H₃₈F₄N₆O₉P [M+H]⁺ 853.2, found 853.0.

Example 25: Synthesis of (glycyloxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

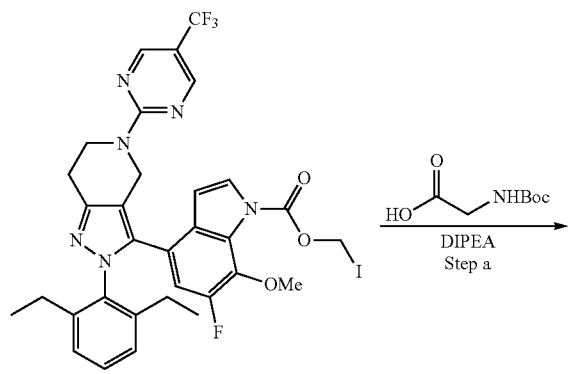

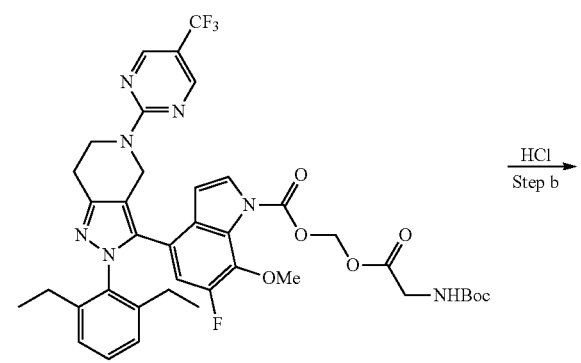

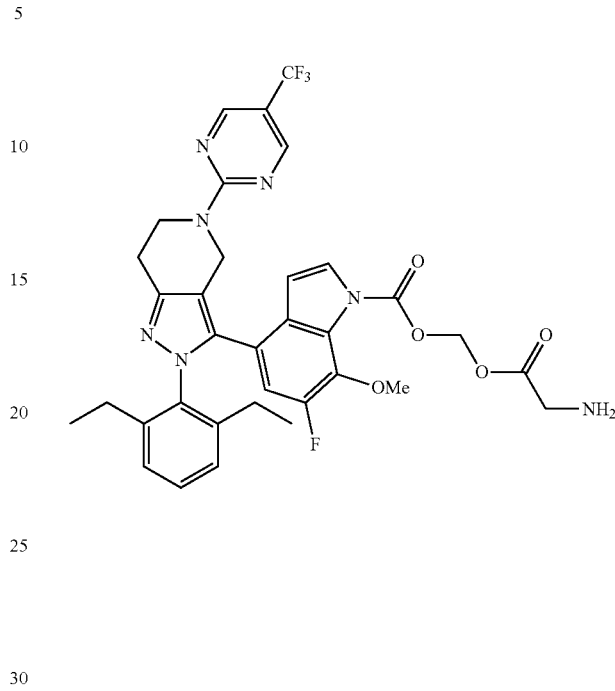

Step a: A mixture of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (0.080 g, 0.10 mmol), (tert-butoxycarbonyl)glycine (0.056 g, 0.32 mmol) and diisopropylethylamine (0.088 mL, 0.53 mmol) in dichloromethane (3 mL) was heated to 45° C. for 1.5 h. It was cooled to room temperature, concentrated under reduced pressure to afford (((tert-butoxycarbonyl)glycyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. MS: (ES) m/z calculated for C₃₉H₄₂F₄N₇O₇ [M+H]⁺ 796.3, found 796.3.

Step b: A mixture of (((tert-butoxycarbonyl)glycyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (~0.10 mmol) and 4 M HCl solution in dioxane (1.5 mL, 6 mmol) in dichloromethane (3 mL) was stirred at room temperature for 1.5 h. The mixture was concentrated under reduced pressure and purified by silica gel flash chromatography (0 to 100% EtOAc in hexanes followed by 0 to 80% MeOH in EtOAc). The pure fractions were combined, cooled to 0° C., charged with 2 M HCl solution in ether (1 mL, 2 mmol) and concentrated under reduced pressure to yield (glycyloxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate as HCl salt. 1H NMR (400 MHz, CD₃OD) δ 8.59 (s, 2H), 7.78-7.83 (m, 1H), 7.34 (dd, J=7.2, 7.2 Hz, 1H), 7.18 (br s, 2H), 6.60-6.68 (m, 2H), 6.17 (s, 2H), 4.83 (br s, 2H), 4.39 (br s, 2H), 4.01 (br s, 2H), 3.97 (s, 3H), 2.96-3.03 (m, 2H), 2.26 (br s, 4H), 1.96-2.03 (m, 2H), 1.20-1.26 (m, 1H), 1.00 (br s, 6H); MS: (ES) m/z calculated for C₃₄H₃₄F₄N₇O₅ [M+H]⁺ 696.2, found 696.2.

Example 26: Synthesis of ((L-valyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

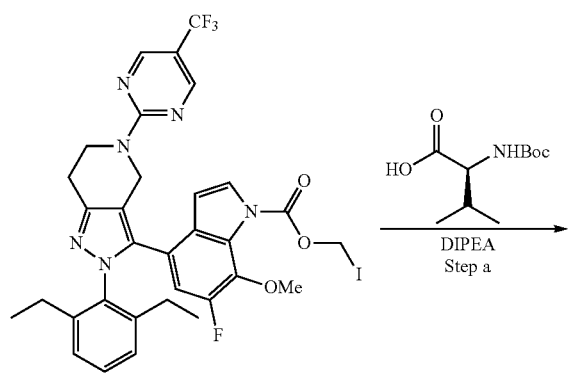

Step a: A mixture of iodomethyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (0.080 g, 0.10 mmol), (tert-butoxycarbonyl)-L-valine (0.07 g, 0.32 mmol) and diisopropylethylamine (0.09 mL, 0.53 mmol) in dichloromethane (3 mL) was stirred at room temperature for 2 h. It was concentrated on a rotary evaporator under reduced pressure and purified by silica gel flash chromatography (0 to 60% EtOAc in hexanes) to afford (((tert-butoxycarbonyl)-L-valyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate; MS: (ES) m/z calculated for $C_{42}H_{48}F_4N_7O_7$ $[M+H]^+$ 838.4, found 838.8.

Step b: A mixture of (((tert-butoxycarbonyl)-L-valyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (31 mg, 0.037 mmol) and 4 M HCl solution in dioxane (0.5 mL, 2 mmol) in dichloromethane (0.5 mL) was stirred at room temperature for 1 h. It was concentrated under reduced pressure and purified by silica gel flash chromatography (0 to 30% MeOH in $CH_2Cl_2$). The pure fractions were combined, cooled to 0° C., charged with 2 M HCl solution in ether (0.5 mL, 2 mmol) and concentrated under reduced pressure to yield ((L-valyl)oxy)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate as HCl salt. 1H NMR (400 MHz, $CD_3OD$) δ 8.60 (s, 2H), 7.81 (s, 1H), 7.36 (dd, J=7.2, 7.2 Hz, 1H), 7.19 (br s, 2H), 6.62-6.72 (m, 2H), 6.24 (d, J=5.6 Hz, 1H), 6.13 (d, J=5.2 Hz, 1H), 5.49 (s, 1H), 4.82 (br s, 2H), 4.41 (br s, 2H), 4.10 (s, 1H), 3.98 (s, 3H), 3.01 (s, 2H), 1.80-2.60 (m, 5H), 0.60-1.40 (m, 14H); MS: (ES) m/z calculated for $C_{37}H_{40}F_4N_7O_5$ $[M+H]^+$ 738.3, found 738.2.

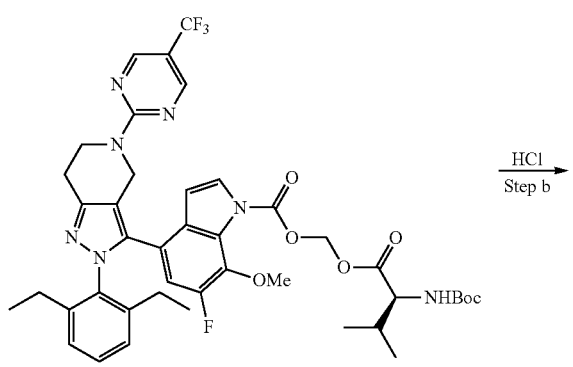

Example 27: Synthesis of (glycyloxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

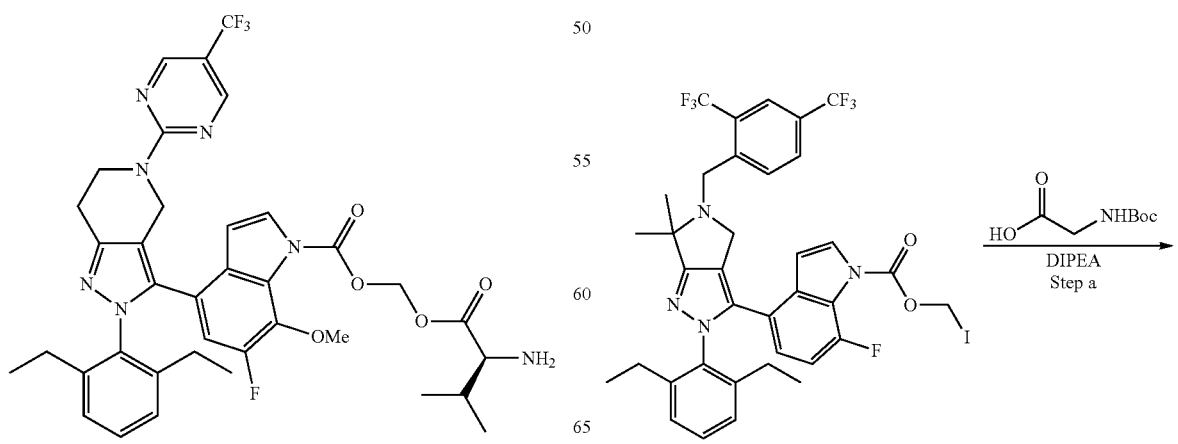

-continued

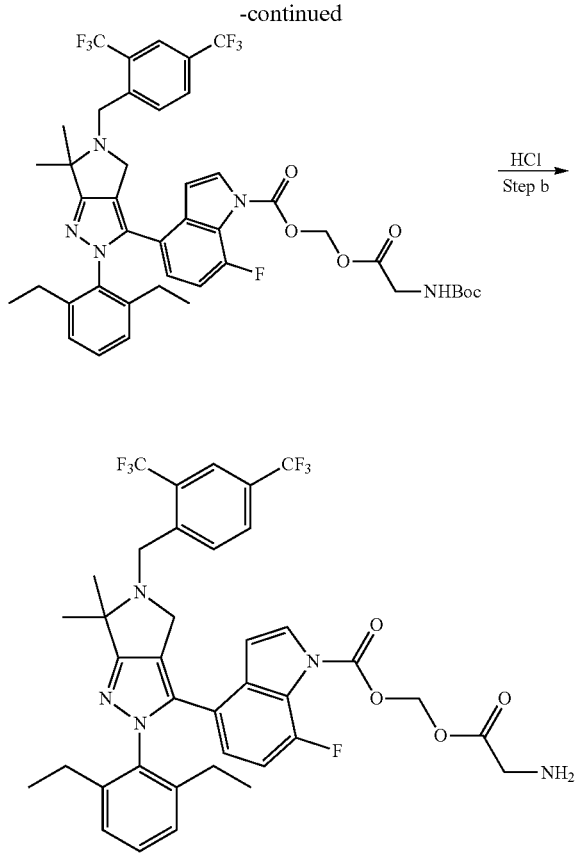

Step a: A mixture of iodomethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (0.06 g, 0.07 mmol), (tert-butoxycarbonyl)glycine (0.04 g, 0.18 mmol) and diisopropylethylamine (0.08 mL, 0.48 mmol) in dichloromethane (1 mL) was stirred at 45° C. for 1.5 h. The mixture was cooled to room temperature and concentrated under reduced pressure to afford (((tert-butoxycarbonyl)glycyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for $C_{43}H_{45}F_7N_5O_6[M+H]^+$ 860.3, found 860.3.

Step b: A mixture of (((tert-butoxycarbonyl)glycyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (~0.07 mmol) and 4 M HCl solution in dioxane (1 mL, 4 mmol) in dioxane (2 mL) was stirred at room temperature for 2 h. The mixture was concentrated under reduced pressure and purified by HPLC (MeCN/H$_2$O, with 0.1% TFA) to yield (glycyloxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate as TFA salt. $^1$H NMR (400 MHz, CDCl$_3$) δ 8.37 (d, J=7.6 Hz, 1H), 7.88-7.94 (m, 2H), 7.59 (d, J=4.0 Hz, 1H), 7.20-7.30 (m, 2H), 7.07 (d, J=7.6 Hz, 2H), 6.58-6.70 (m, 3H), 5.96 (s, 2H), 4.50-4.70 (m, 2H), 4.30 (br s, 2H), 3.79 (s, 2H), 2.19 (br s, 4H), 1.83-2.03 (m, 8H), 0.98 (t, J=7.2 Hz, 6H); MS: (ES) m/z calculated for $C_{38}H_{37}F_7N_5O_4$ [M+H]$^+$ 760.3, found 760.1.

Example 28: Synthesis of (((L-valyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

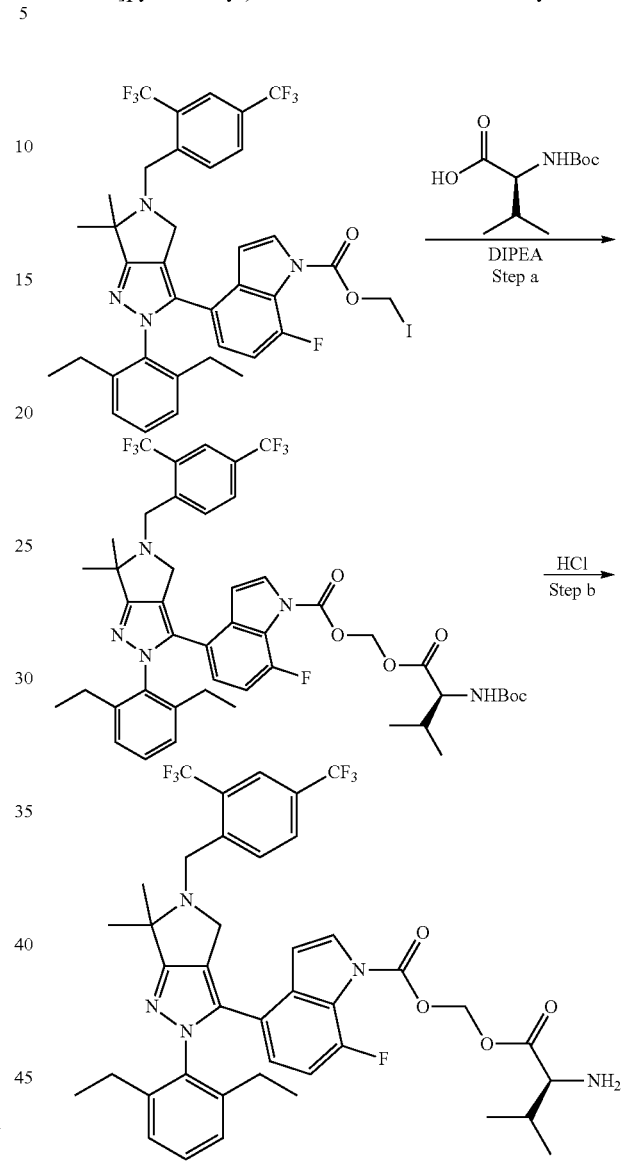

Step a: A mixture of iodomethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (0.10 g, 0.12 mmol), (tert-butoxycarbonyl)-L-valine (0.08 g, 0.37 mmol) and diisopropylethylamine (0.10 mL, 0.61 mmol) in dichloromethane (3 mL) was stirred at 45° C. After 2 h, the mixture was cooled to room temperature, concentrated under reduced pressure and purified by silica gel flash chromatography (0 to 50% EtOAc in hexanes) to afford (((tert-butoxycarbonyl)-L-valyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for $C_{46}H_{51}F_7N_5O_6[M+H]^+$ 902.3, found 902.3.

Step b: To a solution of (((tert-butoxycarbonyl)-L-valyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (25 mg, 0.028 mmol) in dichloromethane (0.3 mL) was added 4 M HCl in dioxane (0.1 mL, 0.4 mmol). The mixture was stirred at room temperature for 3 h and then concentrated under reduced pressure to yield ((L-valyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate as HCl salt. $^1$H NMR (400 MHz, CDCl$_3$) δ 9.33 (s, 1H), 8.99 (s, 2H), 7.99-8.06 (m, 1H), 7.93 (s, 1H), 7.72 (s, 1H), 7.10-7.30 (m, 3H), 6.97 (br s, 1H), 6.68-6.78 (m, 1H), 6.59-6.66 (m, 1H), 6.16-6.22 (m, 1H), 5.90-5.98 (m, 1H), 4.69 (br s, 2H), 4.47 (br s, 1H), 4.03 (s, 1H), 3.60-3.90 (m, 3H), 1.70-2.60 (m, 10H), 0.75-1.34 (m, 12H); MS: (ES) m/z calculated for C$_{41}$H$_{43}$F$_7$N$_5$O$_4$ [M+H]$^+$ 802.3, found 802.2.

Example 29: Synthesis of ((4-((dimethylamino)methyl)benzoyl)oxy)methyl 4-(5-(2,4-bis(trifluoromethyl)-benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

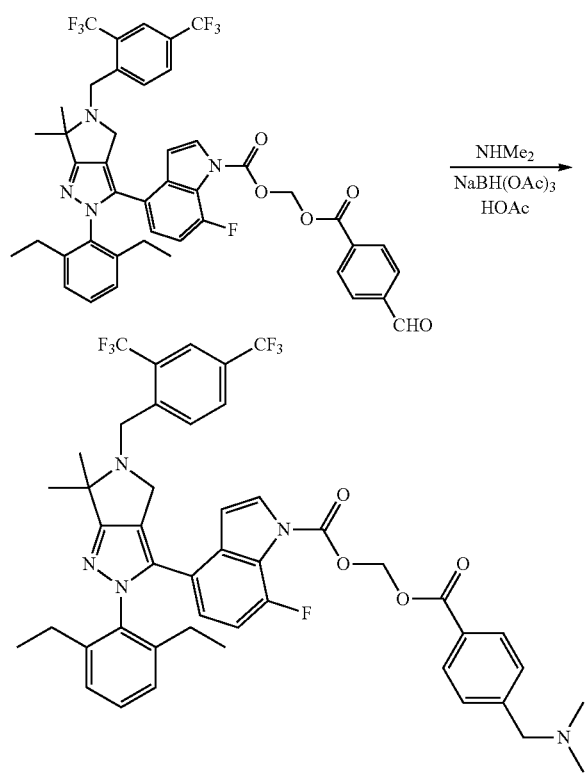

A mixture of dimethylamine (0.40 mL, saturated in dichloromethane), HOAc (0.80 mL), ((4-formylbenzoyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (0.080 g, 0.096 mmol) and NaBH(OAc)$_3$ (0.200 g, 0.94 mmol) in dichloromethane was stirred at room temperature for 1 h. The mixture was poured into saturated aqueous NaHCO$_3$ solution and extracted with EtOAc. The organic layer was separated, dried over Na$_2$SO$_4$, concentrated under reduced pressure and purified by silica gel flash chromatography (0 to 100% EtOAc in hexanes followed by 0 to 30% MeOH in EtOAc) to afford ((4-((dimethylamino)methyl)benzoyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, CDCl$_3$) δ 8.15 (d, J=8.0 Hz, 1H), 8.03 (d, J=7.2 Hz, 2H), 7.86 (s, 1H), 7.75 (d, J=8.0 Hz, 1H), 7.66 (m, 1H), 7.40 (d, J=7.6 Hz, 2H), 7.25 (m, 1H), 7.07 (d, J=7.6 Hz, 2H), 6.77 (m, 1H), 6.62 (m, 1H), 6.56 (m, 1H), 6.23 (s, 2H), 4.12 (s, 2H), 3.63 (s, 2H), 3.47 (s, 2H), 2.23 (s, 6H), 2.10-2.40 (m, 4H), 1.55 (s, 6H), 1.01 (t, J=7.4 Hz, 6H); MS: (ES) m/z calculated for C$_{46}$H$_{45}$F$_7$N$_5$O$_4$ [M+H]$^+$ 864.3, found 864.2.

Example 30: Synthesis of ((dimethylglycyl)oxy)methyl 4-(5-(2,4-bis(trifluoromethyl)-benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

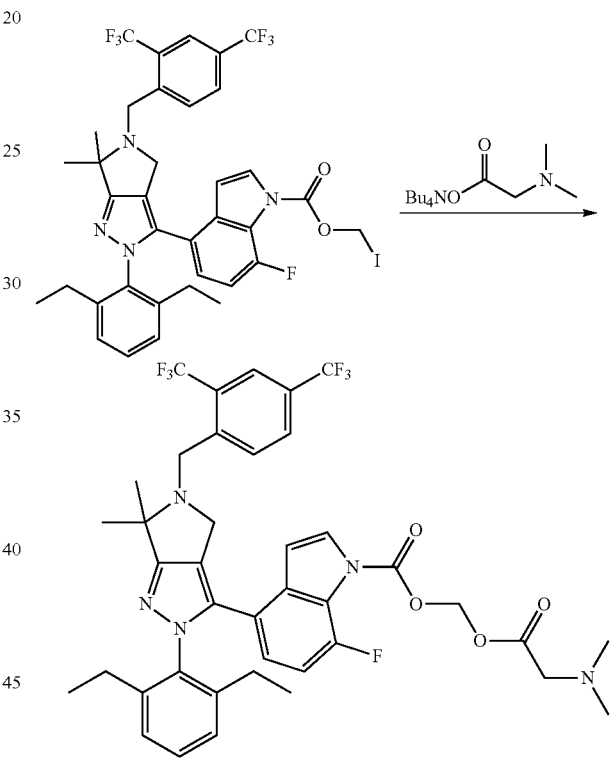

A mixture of iodomethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (0.03 g, 0.04 mmol) and tetrabutylammonium dimethylglycinate (20 mg, 0.06 mmol) in THF (0.6 mL) was stirred at room temperature for 0.5 h. The mixture was concentrated under reduced pressure and purified by HPLC (MeCN/H$_2$O, with 1% HOAc) to yield ((dimethylglycyl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, CD$_3$OD) δ 8.21 (d, J=8.4 Hz, 1H), 7.91-7.96 (m, 2H), 7.80 (d, J=4.0 Hz, 1H), 7.34 (dd, J=7.6, 7.6 Hz, 1H), 7.17 (d, J=7.6 Hz, 2H), 6.81-6.87 (m, 1H), 6.65-6.72 (m, 2H), 6.12 (s, 2H), 4.23 (s, 2H), 4.17 (s, 2H), 3.69 (s, 2H), 2.90 (s, 6H), 2.17-2.36 (m, 4H), 1.57 (s, 6H), 1.02 (t, J=7.4 Hz, 6H); MS: (ES) m/z calculated for C$_{40}$H$_{41}$F$_7$N$_5$O$_4$ [M+H]$^+$ 788.3, found 788.2.

Example 31: Synthesis of ((dimethoxyphosphoryl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate

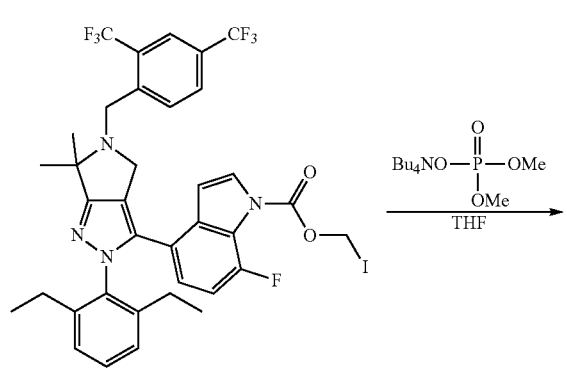

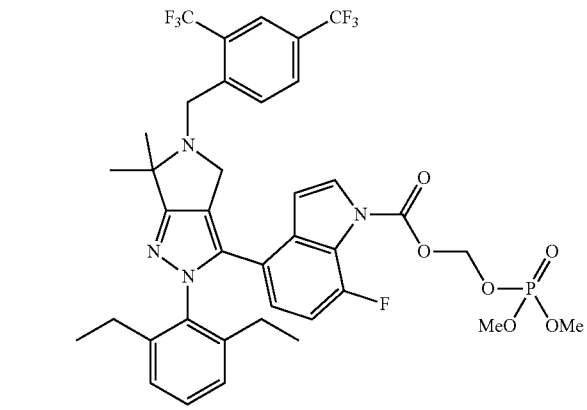

A mixture of iodomethyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (40 mg, 0.037 mmol) and tetrabutylammonium dimethylphosphate (30 mg, 0.08) mmol) in THF (6 mL) was stirred at room temperature for 1.5 h. After completion, the mixture was diluted with EtOAc, washed with brine, and dried over MgSO$_4$. The solvent was removed under reduced pressure and the residue was purified by silica gel flash chromatography (5 to 20% EtOAc in hexanes) to yield ((dimethoxyphosphoryl)oxy)methyl 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, CD$_3$OD) δ 8.13 (d, J=8.2 Hz, 1H), 7.75-7.88 (m, 2H), 7.66-7.68 (m, 1H), 7.23-7.27 (m, 1H), 7.07-7.09 (m, 2H), 6.77 (dd, J=8.4, 11.8 Hz, 1H), 6.59-6.66 (m, 2H), 5.81 (d, J=14.1 Hz, 2H), 4.12 (s, 2H), 3.79 (s, 3H), 3.76 (s, 3H), 3.70 (s, 2H), 2.14-2.38 (m, 4H), 1.56 (s, 6H), 1.02 (t, J=7.6 Hz, 6H). MS: (ES) m/z calculated for C$_{38}$H$_{39}$F$_7$N$_4$O$_6$P [M+H]$^+$ 811.2, found 811.2.

Example 32: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)methanol

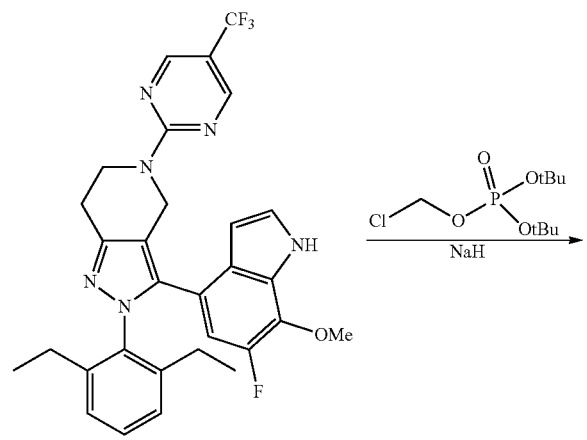

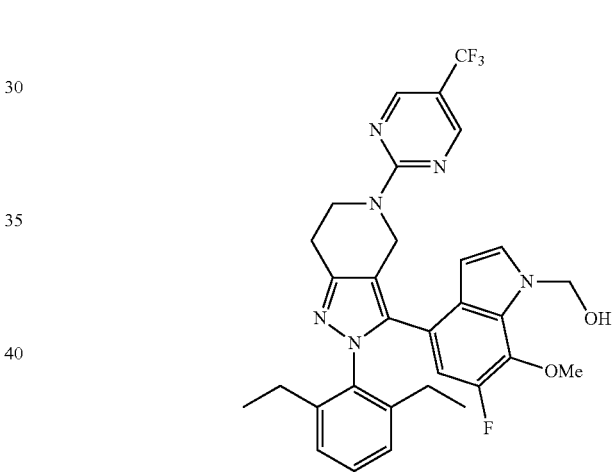

A mixture of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (200 mg, 0.35 mmol), di-tert-butyl (chloromethyl) phosphate (183 mg, 0.35 mmol) and NaH (100 mg, 60% in mineral oil, 2.5 mmol) in DMF (5 mL) was stirred at room temperature for 2 h. The mixture was poured into water and extracted with EtOAc. The organic layer was separated, dried over Na$_2$SO$_4$, concentrated under reduced pressure and purified by silica gel flash chromatography (0 to 80% EtOAc in hexanes) to afford (4-(2-(2,6-diethylphenyl)-5-(5-(trifluoromethyl)pyrimidin-2-yl)methanol. $^1$H NMR (400 MHz, CDCl$_3$) δ 8.48 (s, 2H), 7.24 (dd, J=7.2, 7.2 Hz, 1H), 7.15 (d, J=3.2 Hz, 1H), 7.00-7.10 (m, 2H), 6.44 (d, J=12.8 Hz, 1H), 6.33 (d, J=3.2 Hz, 1H), 5.59 (d, J=8.0 Hz, 2H), 4.80 (s, 2H), 4.35 (s, 2H), 4.11 (d, J=2.4 Hz, 3H), 3.71 (t, J=8.2 Hz, 1H), 3.02 (t, J=5.8 Hz, 2H), 2.30 (br s, 4H), 1.02 (br s, 6H). MS: (ES) m/z calculated for C$_{31}$H$_{31}$F$_4$N$_6$O$_2$ [M+H]$^+$ 595.2, found 595.5.

Example 33: Synthesis of (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl) methyl glycinate hydrochloride

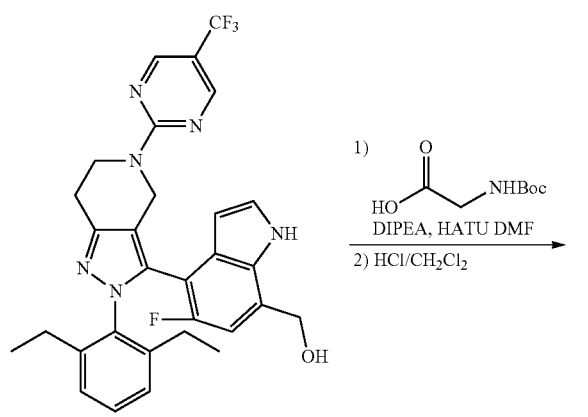

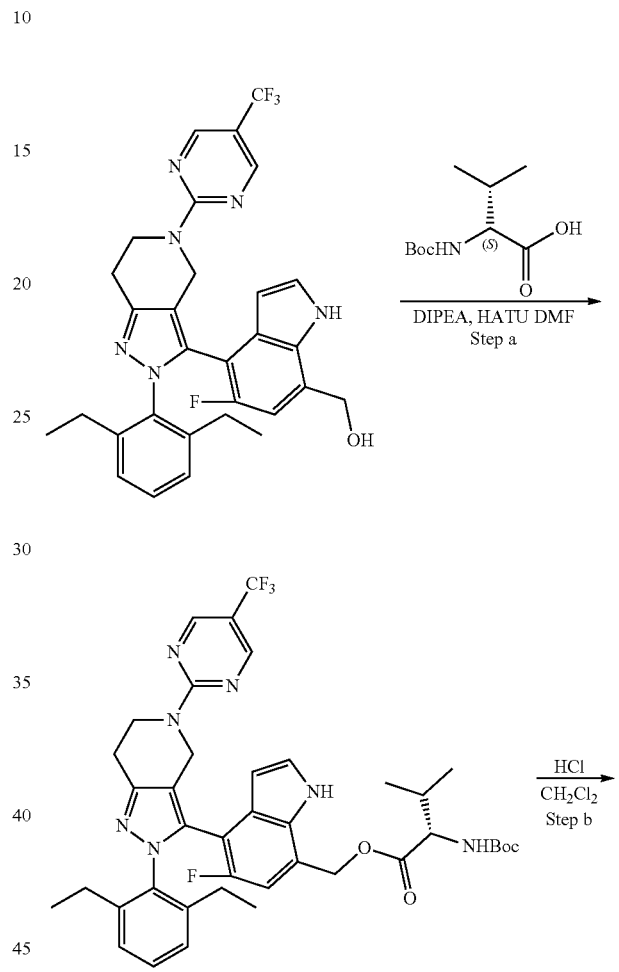

To a vial with DMF (3.0 mL) was charged with (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol (100 mg, 0.18 mmol), (tert-butoxycarbonyl)glycine (61 mg, 0.35 mmol), HATU (134 mg, 0.35 mmol) and diisopropylethylamine (68 mg, 0.52 mmol). The mixture was stirred at room temperature for 24 h. After completion, the reaction was quenched with $H_2O$ and the crude was purified by silica gel chromatography (10 to 50% EtOAc in hexanes) and concentrated in vacuo. The residue was then dissolved in dichloromethane (3.0 mL) and treated with 4 N HCl in dioxane (2.0 mL) at room temperature for 2 h. After completion of the reaction, the solvent was removed and the residue was triturated with dichloromethane to give the (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methyl glycinate hydrochloride. $^1$H NMR (400 MHz, $CD_3OD$) δ 11.07 (bs, 1H), 8.56 (bs, 2H), 7.47-7.50 (m, 1H), 7.19-7.26 (m, 2H), 6.91 (dd, J=1.9, 3.1 Hz, 1H), 6.85 (d, J=10.9 Hz, 1H), 6.40-6.43 (m, 1H), 5.53 (s, 2H), 4.90 (d, J=16.1 Hz, 1H), 4.62 (d, J=16.0 Hz, 1H), 4.42-4.50 (m, 1H), 4.25-4.35 (m, 1H), 3.90 (s, 2H), 3.76 (s, 2H), 3.00 (t, J=5.9 Hz, 2H), 2.43-2.50 (m, 2H), 2.12-2.20 (m, 1H), 1.90-1.98 (m, 1H), 1.22 (t, J=7.8 Hz, 3H), 0.73 (t, J=7.4 Hz, 3H) MS: (ES) m/z calculated for $C_{32}H_{31}F_4N_7O_2$ [M+H]$^+$ 622.3, found 622.2

Example 34: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl-L-valinate hydrochloride

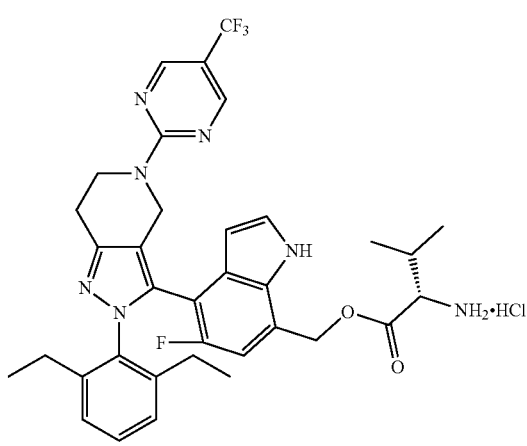

Step a: To a vial with DMF (3.0 mL) was charged with (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol (100 mg, 0.18 mmol), (tert-butoxycarbonyl)valine (77 mg, 0.35 mmol), HATU (134 mg, 0.35 mmol) and diisopropylethylamine (68 mg, 0.53 mmol). The reaction mixture was stirred at 50° C. for 24 h. After completion, the mixture was quenched with H$_2$O and the crude was purified by silica gel chromatography (10 to 50% EtOAc in hexanes) and concentrated in vacuo to give (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl(tert-butoxycarbonyl)-L-valinate. MS: (ES) m/z calculated for C$_{40}$H$_{45}$F$_4$N$_7$O$_4$ [M+H]$^+$ 764.4, found 764.3.

Step b: To a stirred solution of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl (tert-butoxycarbonyl)-L-valinate (60 mg, 0.08 mmol) in dichloromethane (5 mL) was added 4 N HCl in dioxane (0.2 mL, 0.8 mmol). The resulting mixture was stirred at room temperature for 2 h. After completion, the reaction mixture was diluted with water and saturated aqueous NaHCO$_3$, extracted with dichloromethane, washed with brine, and dried over MgSO$_4$. The solvent was removed under reduced pressure and the residue was purified by HPLC (MeCN/H$_2$O, with 0.1% TFA) to give the desired product. The material was converted to HCl salt to give (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl-L-valinate hydrochloride. $^1$H NMR (400 MHz, DMSO-d$_6$) δ 11.65 (bs, 1H), 8.61-8.72 (m, 2H), 8.42 (bs, 2H), 7.56 (bs, 1H), 7.15-7.25 (m, 2H), 6.88-6.98 (m, 2H), 6.33 (s, 1H), 5.42-5.55 (m, 2H), 4.74 (dd, J=6.2, 15.2 Hz, 1H), 4.57 (d, J=15.7 Hz, 1H), 4.35-4.45 (m, 1H), 4.15-4.20 (m, 1H), 3.92-4.05 (m, 1H), 2.85-2.95 (m, 2H), 2.28-2.40 (m, 2H), 2.00-2.20 (m, 2H), 1.85-1.92 (m, 1H), 1.12 (t, J=7.4 Hz, 3H), 0.83-0.90 (m, 6H), 0.61-0.63 (m, 3H). MS: (ES) m/z calculated for C$_{35}$H$_{37}$F$_4$N$_7$O$_2$ [M+H]$^+$ 664.3, found 664.2.

Example 35: Synthesis of 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl (S)-2,5-diaminopentanoate hydrochloride

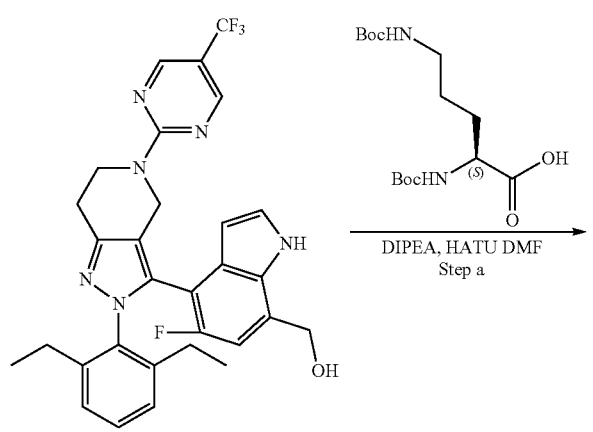

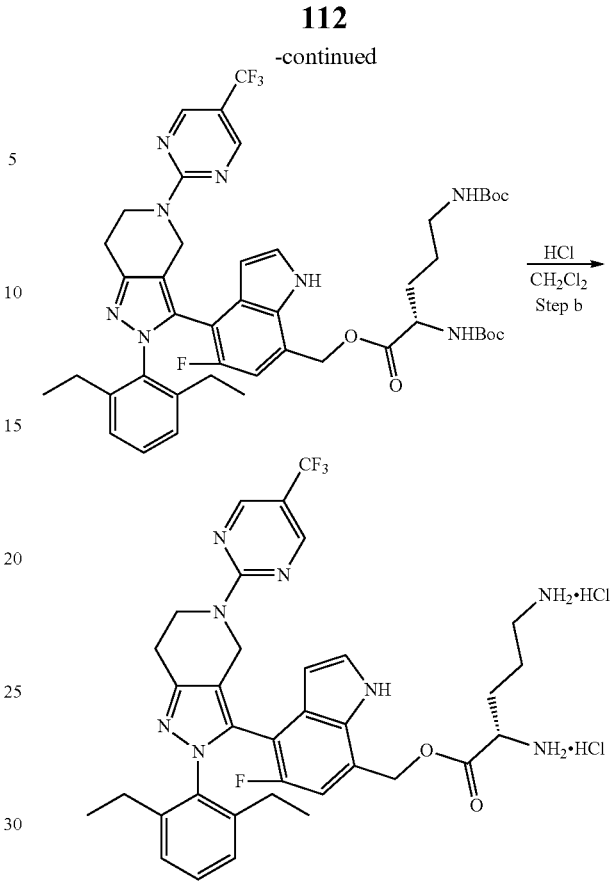

Step a: To a vial with DMF (3.0 mL) was charged with (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol (110 mg, 0.19 mmol), 2,5-bis(tert-butoxycarbonylamino)pentanoic acid (96 mg, 0.29 mmol), HATU (149 mg, 0.39 mmol) and diisopropylethylamine (75 mg, 1.17 mmol). The reaction was stirred at room temperature for 24 h. After completion, the mixture was quenched with H$_2$O and the crude was purified by silica gel chromatography (10 to 100% EtOAc in hexanes) concentrated dried under vacuum to give 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl (S)-2,5-bis((tert-butoxycarbonyl)amino)pentanoate. MS: (ES) m/z calculated for C$_{45}$H$_{54}$F$_4$N$_8$O$_6$ [M+H]$^+$ 879.41, found 879.5

Step b: To a stirred solution of 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl-(S)-2,5-bis((tert-butoxycarbonyl)-amino)pentanoate (75 mg, 3.6 mmol) in dichloromethane (5 mL) was added 4 N HCl in dioxane (0.18 mL, 0.68 mmol). The resulting mixture was stirred at room temperature for 2 h. After completion, the reaction mixture was diluted with H$_2$O and saturated aqueous NaHCO$_3$, extracted with dichloromethane, washed with brine and dried over MgSO$_4$. The solvent was removed under reduced pressure and the residue was purified by HPLC (MeCN/H$_2$O, with 0.1% TFA) to give the desired product. The material was converted to HCl salt to give (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl (S)-2,5-diaminopentanoate hydrochloride. $^1$H NMR (400 MHz, DMSO-d$_6$) δ 11.77 (bs, 1H), 8.50-8.65 (m, 4H), 7.90-8.25 (m, 2H), 7.55

(bs, 1H), 7.15-7.25 (m, 2H), 6.97 (dd, J=1.9, 10.9 Hz, 1H), 6.91 (d, J=7.4 Hz 1H), 6.34 (bs, 1H), 5.35-5.54 (m, 2H), 4.73 (d, J=15.7 Hz, 1H), 4.56 (d, J=16.0 Hz, 1H), 4.38-4.45 (m, 2H), 4.05-4.25 (m, 2H), 2.85-3.00 (m, 2H), 2.75-2.80 (m, 2H), 2.31-2.40 (m, 2H), 1.95-2.10 (m, 1H), 1.65-1.78 (m, 4H), 1.12 (t, J=7.4 Hz, 3H), 0.65 (t, J=7.4 Hz, 3H), MS: (ES) m/z calculated for $C_{35}H_{38}F_4N_8O_2$ [M+H]$^+$ 679.3, found 679.2.

Example 36: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-W-indol-7-yl)methyl L-lysinate hydrochloride

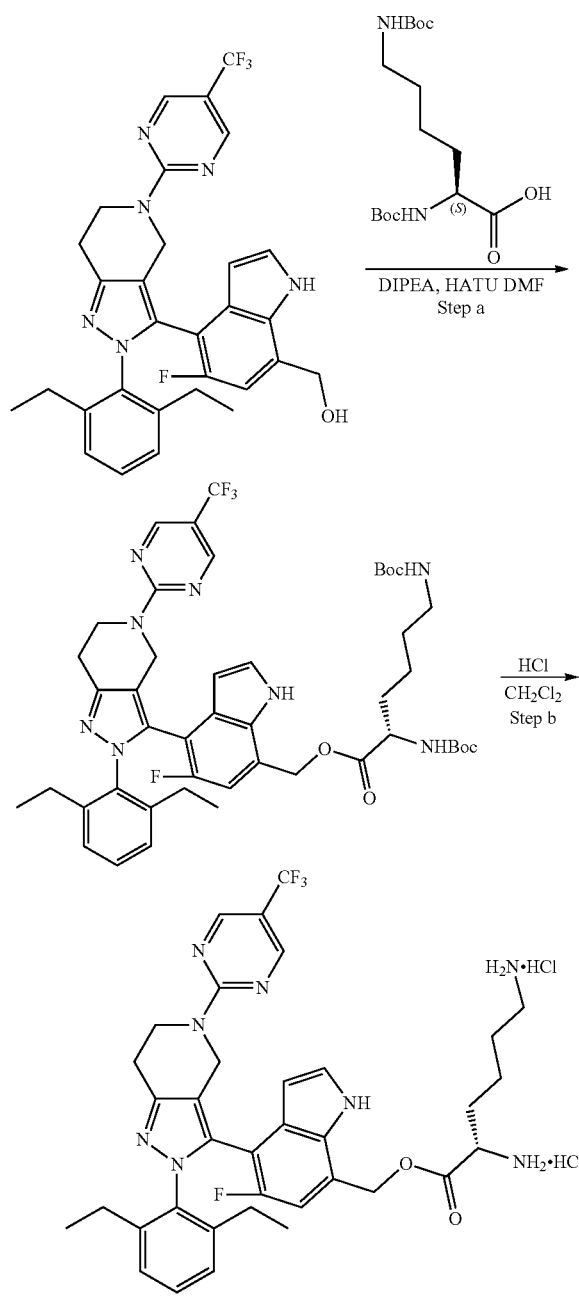

Example 36 was prepared similar to the procedure as described in Example 35 using $N_2,N_6$-bis(tert-butoxycarbonyl)-L-lysine and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-d$_6$) δ 11.71 (bs, 1H), 8.50-8.75 (m, 4H), 7.89 (bs, 2H), 7.56 (t, J=2.8 Hz 1H), 7.15-7.25 (m, 2H), 6.94 (d, J=11.0 Hz, 1H), 6.91 (d, J=7.1 Hz 1H), 6.30-6.35 (m, 1H), 5.38-5.54 (m, 2H), 4.73 (d, J=15.6 Hz, 1H), 4.57 (d, J=15.7 Hz, 1H), 4.35-4.45 (m, 1H), 4.15-4.30 (m, 1H), 4.05-4.15 (m, 2H), 2.85-3.00 (m, 2H), 2.65-2.75 (m, 2H), 2.30-2.42 (m, 2H), 2.00-2.15 (m, 1H), 1.75-1.90 (m, 3H), 1.25-1.60 (m, 3H), 1.12 (t, J=7.4 Hz, 3H), 0.65 (t, J=7.4 Hz, 3H), MS: (ES) m/z calculated for $C_{36}H_{40}F_4N_8O_2$ [M+H]$^+$ 693.3, found 693.3.

Example 37: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl 4-aminobutanoate hydrochloride

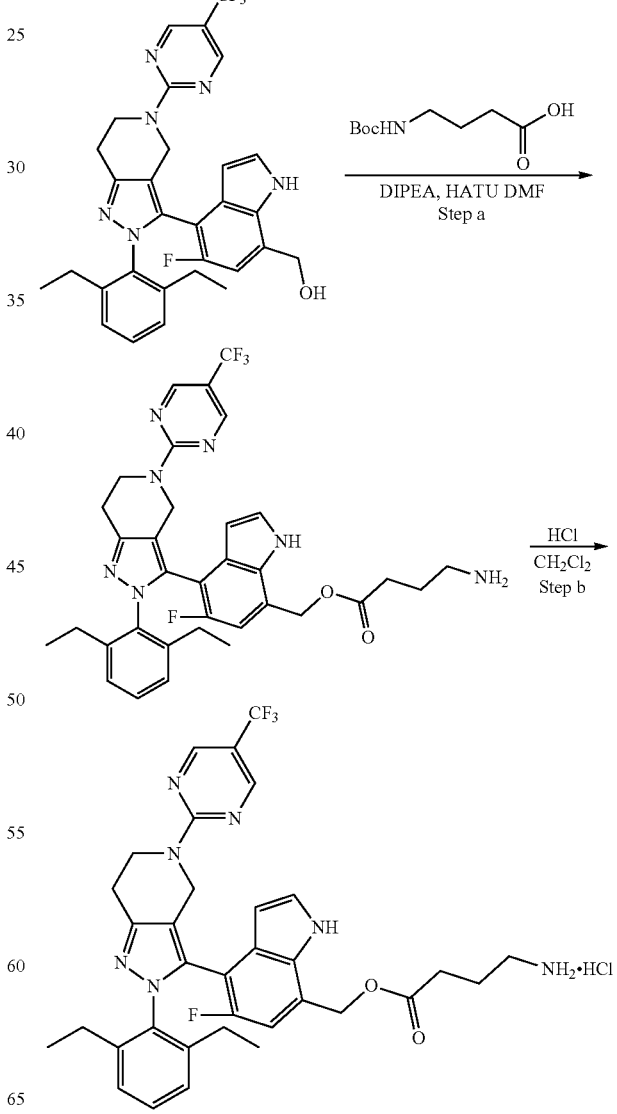

Example 37 was prepared similar to the procedure as described in Example 35 using 4-((tert-butoxycarbonyl)amino)butanoic acid and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol $^1$H NMR (400 MHz, DMSO-$d_6$) δ 11.98 (s, 1H), 8.52-8.72 (m, 2H), 7.79 (bs, 2H), 7.52 (t, J=3.1 Hz 1H), 7.14-7.30 (m, 2H), 6.91 (dd, J=1.6, 7.4 Hz, 1H), 6.84 (d, J=10.9 Hz, 1H), 6.31 (dd, J=1.9, 3.1 Hz, 1H), 5.27 (d, J=3.1 Hz, 2H), 4.74 (d, J=15.6 Hz, 1H), 4.57 (d, J=15.6 Hz, 1H), 4.35-4.50 (m, 2H), 4.15-4.25 (m, 2H), 2.85-3.00 (m, 2H), 2.76-2.84 (m, 2H), 2.31-2.40 (m, 2H), 2.0-2.15 (m, 1H), 1.76-1.90 (m, 3H), 1.12 (t, J=7.4 Hz, 3H), 0.65 (t, J=7.5 Hz, 3H), MS: (ES) m/z calculated for $C_{34}H_{35}F_4N_7O_2$ [M+H]$^+$ 650.3, found 650.3.

Example 38: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl-L-histidinate hydrochloride

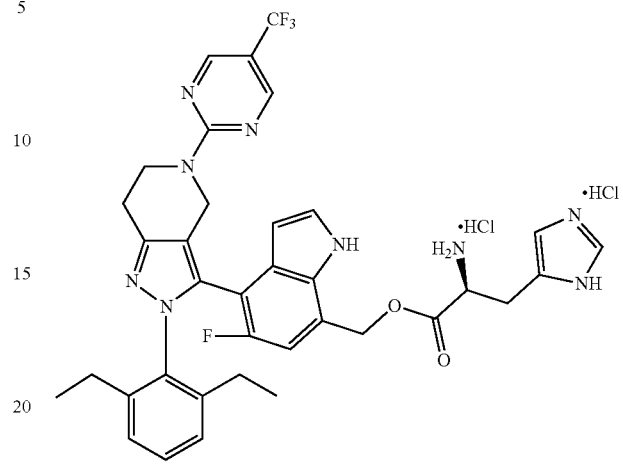

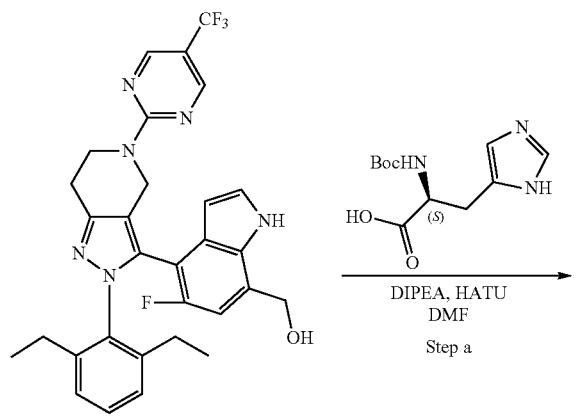

Example 38 was prepared similar to the procedure as described in Example 35 using (tert-butoxycarbonyl)-L-histidine and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-$d_6$) δ 11.76 (br s, 1H), 9.01 (d, J=3.9 Hz 1H), 8.55-8.75 (m, 4H), 7.55 (d, J=2.8 Hz 1H), 7.48 (s, 1H), 7.15-7.25 (m, 2H), 6.90-6.98 (m, 2H), 6.34 (bs, 1H), 5.37-5.54 (m, 2H), 4.75 (dd, J=2.7, 15.6 Hz, 1H), 4.56 (d, J=15.6 Hz, 1H), 4.35-4.45 (m, 2H), 4.15-4.25 (m, 1H), 3.25-3.35 (m, 2H), 2.85-2.95 (m, 3H), 2.30-2.42 (m, 2H), 2.00-2.10 (m, 1H), 1.82-1.90 (m, 1H), 1.13 (t, J=7.8 Hz, 3H), 0.65 (t, J=7.8 Hz, 3H). MS: (ES) m/z calculated for $C_{36}H_{35}F_4N_9O_2$ [M+H]$^+$ 702.3, found 701.9.

Example 39: Synthesis of (S)-3-amino-4-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)-4-oxobutanoic acid hydrochloride

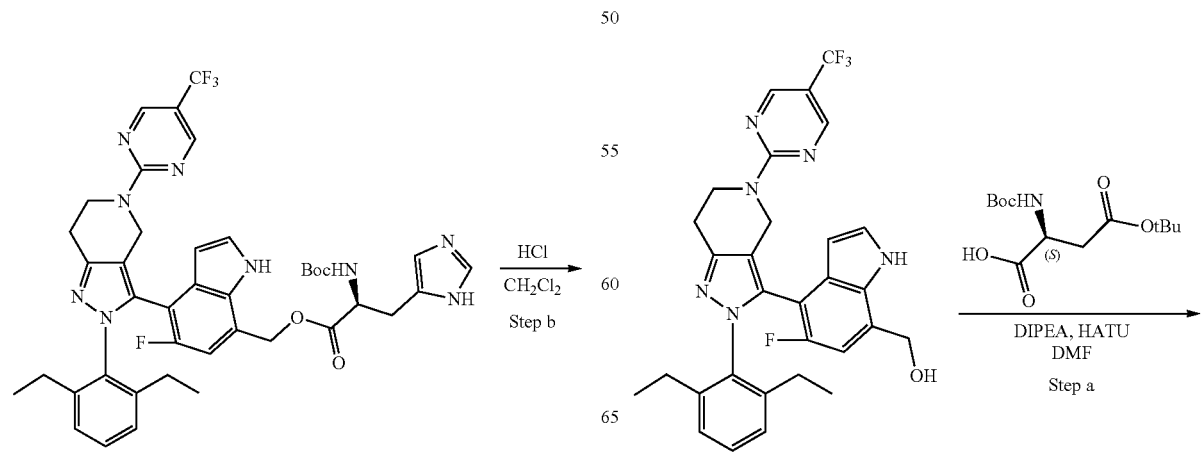

117
-continued

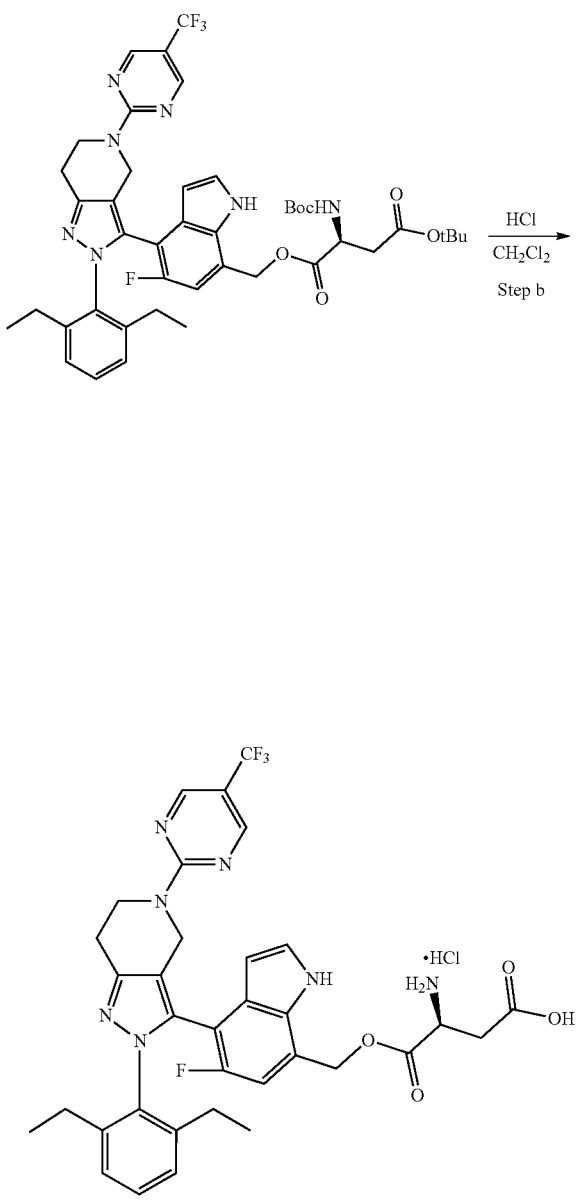

Example 39 was prepared similar to the procedure as described in Example 35 using (S)-4-(tert-butoxy)-2-((tert-butoxycarbonyl)amino)-4-oxobutanoic acid and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-$d_6$) δ 11.65 (bs, 1H), 8.60-8.75 (m, 2H), 8.46 (bs, 3H), 7.52 (t, J=2.9 Hz 1H), 7.15-7.25 (m, 2H), 6.90 (d, J=7.8 Hz, 1H), 6.87 (bs, 1H), 6.31 (bs, 1H), 5.25-5.40 (m, 2H), 4.57 (d, J=15.7 Hz, 1H), 4.35-4.45 (m, 1H), 4.15-4.30 (m, 2H), 3.53 (s, 2H), 2.99 (d, J=5.5 Hz, 1H), 2.85-2.92 (m, 2H), 2.30-2.38 (m, 2H), 2.00-2.15 (m, 1H), 1.82-1.90 (m, 1H), 1.11 (t, J=7.8 Hz, 3H), 0.65 (t, J=7.8 Hz, 3H). MS: (ES) m/z calculated for $C_{34}H_{33}F_4N_7O_2$[M+H]$^+$ 680.3, found 680.1.

118

Example 40: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl L-valylglycinate hydrochloride

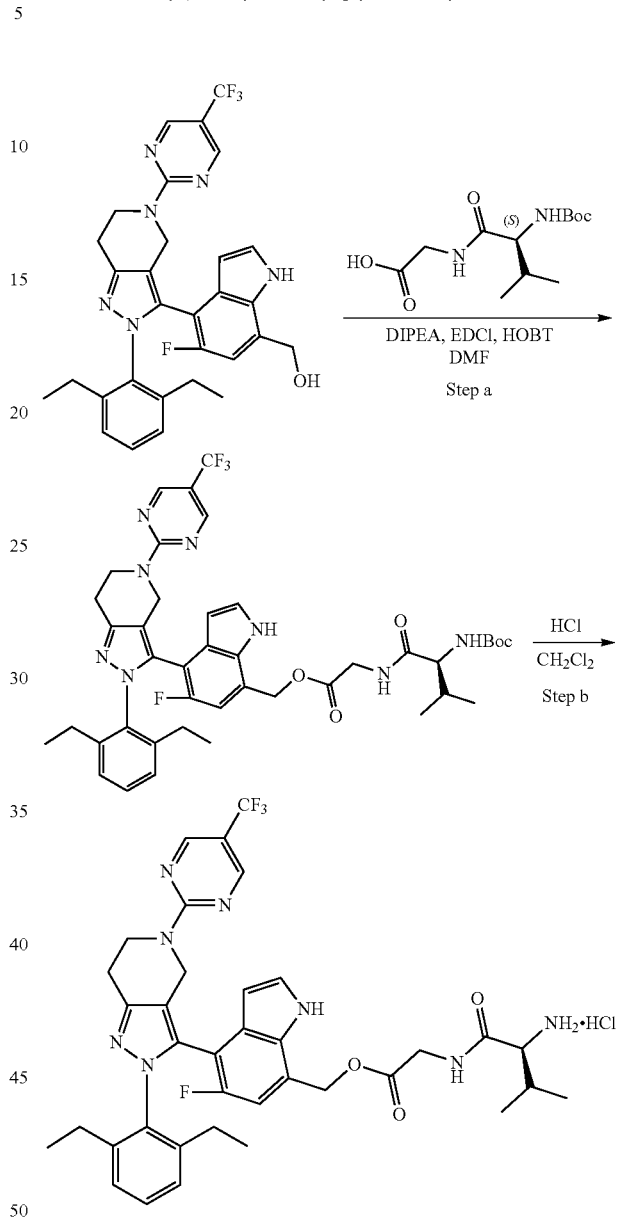

Step a: To a vial with DMF (3.0 mL) was charged with (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol (150 mg, 0.27 mmol), (tert-butoxycarbonyl)-L-valylglycine (145 mg, 0.53 mmol), EDCI (101 mg, 0.53 mmol), HOBT (61 mg, 0.39 mmol) and DIPEA (102 mg, 0.77 mmol). The mixture was stirred at 50° C. for 24 h. After completion of the reaction, the reaction was worked up and the crude was purified by silica gel chromatography (10 to 60% EtOAc in hexanes) to give (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl (tert-butoxycarbonyl)-L-valylglycinate.

Step b: To a stirred solution of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)

methyl-(tert-butoxycarbonyl)-L-valylglycinate (180 mg, 0.02 mmol) in dichloromethane (5 mL) was added 4 N HCl solution in dioxane (0.25 mL, 0.1 mmol). The resulting mixture was stirred at room temperature for 5 h. After completion, the solvent was diluted with water and saturated aqueous NaHCO$_3$, extracted with dichloromethane, washed with brine and dried over Na$_2$SO$_4$. The solvent was removed under reduced presure and the crude was purified by column chromatography (20-100% EtOAc/hexane) to give the desired product, which is converted to HCl salt to give (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl-L-valylglycinate hydrochloride. 1H NMR (400 MHz, DMSO-d$_6$) δ 11.58 (br s, 1H), 8.85 (br s, 1H), 8.60-8.75 (m, 2H), 8.09 (br s, 2H), 7.53 (t, J=3.1 Hz 1H), 7.12-7.25 (m, 2H), 6.90 (d, J=6.3 Hz, 1H), 6.86 (d, J=10.9 Hz, 1H), 6.31 (t, J=2.8 Hz, 1H), 5.25-5.35 (m, 2H), 4.72 (d, J=15.9 Hz, 1H), 4.57 (d, J=16.3 Hz, 1H), 4.40-4.45 (m, 1H), 4.10-4.25 (m, 2H), 3.91 (dd, J=5.1, 17.2 Hz, 1H), 3.59 (t, J=0.8 Hz, 1H), 2.85-2.92 (m, 2H), 2.31-2.40 (m, 2H), 1.90-2.08 (m, 2H), 1.80-1.90 (m, 1H), 1.12 (t, J=7.8 Hz, 3H), 0.80-0.85 (m, 6H), 0.65 (t, J=7.8 Hz, 3H), MS: (ES) m/z calculated for C$_{37}$H$_{40}$F$_4$N$_8$O$_3$ [M+H]$^+$ 721.3, found 721.3.

Example 41: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl L-isoleucinate hydrochloride

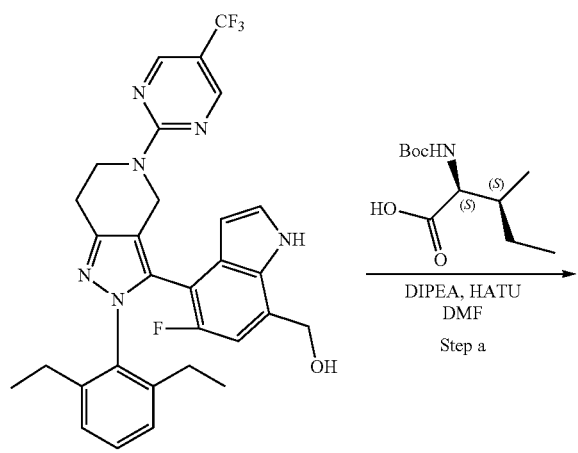

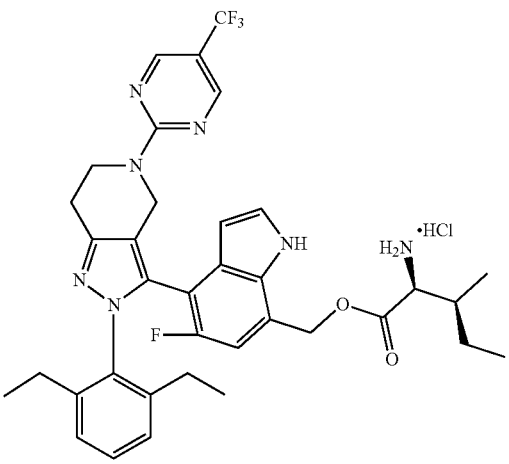

Example 41 was prepared similar to the procedure as described in Example 35 using (tert-butoxycarbonyl)-L-isoleucine and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-d$_6$) δ 11.63 (br s, 1H), 8.60-8.75 (m, 2H), 8.42 (br s, 2H), 7.43-7.60 (m, 1H), 7.14-7.25 (m, 2H), 6.85-6.95 (m, 2H), 6.30-6.35 (m, 1H), 5.38-5.45 (m, 2H), 4.76 (dd, J=5.8, 16.0 Hz, 1H), 4.56 (d, J=15.7 Hz, 1H), 4.35-4.45 (m, 1H), 4.15-4.20 (m, 1H), 3.98-4.05 (m, 1H), 2.82-2.97 (m, 2H), 2.30-2.42 (m, 3H), 2.00-2.10 (m, 1H), 1.80-1.90 (m, 2H), 1.25-1.35 (m, 1H), 1.12 (t, J=7.4 Hz, 3H), 0.72-0.85 (m, 6H), 0.65 (t, J=7.4 Hz, 3H). MS: (ES) m/z calculated for C$_{36}$H$_{39}$F$_4$N$_7$O$_2$[M+H]$^+$ 678.3, found 678.3.

Example 42: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl L-alaninate hydrochloride

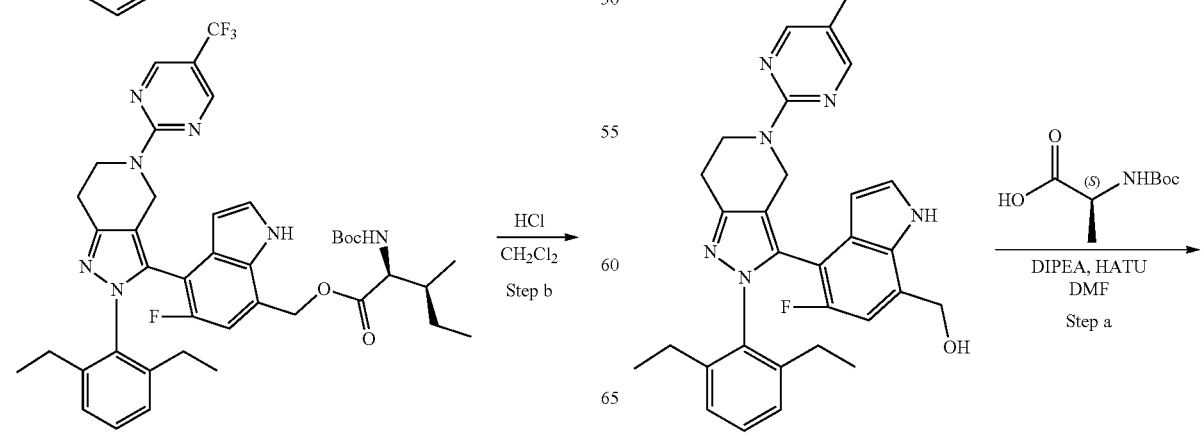

-continued

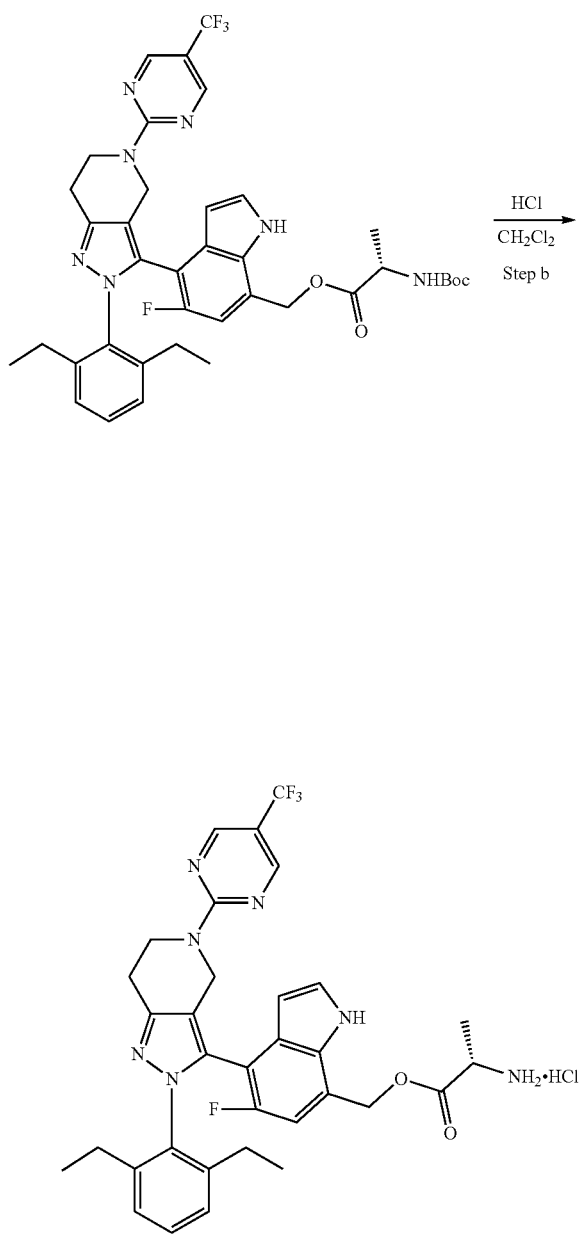

Example 42 was prepared similar to the procedure as described in Example 35 using (tert-butoxycarbonyl)-L-alaninine and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-$d_6$) δ 11.62 (br s, 1H), 8.60-8.75 (m, 2H), 8.35 (br s, 2H), 7.56 (t, J=2.7 Hz, 1H), 7.12-7.25 (m, 2H), 6.85-6.95 (m, 2H), 6.30-6.35 (m, 1H), 5.35-5.50 (m, 2H), 4.73 (d, J=17.0 Hz, 1H), 4.56 (d, J=15.76 Hz, 1H), 4.35-4.45 (m, 1H), 4.15-4.22 (m, 2H), 2.85-2.95 (m, 2H), 2.25-2.40 (m, 2H), 2.00-2.10 (m, 1H), 1.82-1.90 (m, 1H), 1.38 (dd, J=2.4, 7.5 Hz, 3H), 1.12 (t, J=7.8 Hz, 3H), 0.65 (dd, J=7.2, 15.6 Hz, 3H). MS: (ES) m/z calculated for $C_{33}H_{33}F_4N_7O_2$[M+H]$^+$ 636.3, found 636.2.

Example 43: Synthesis of 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl-L-phenylalaninate hydrochloride

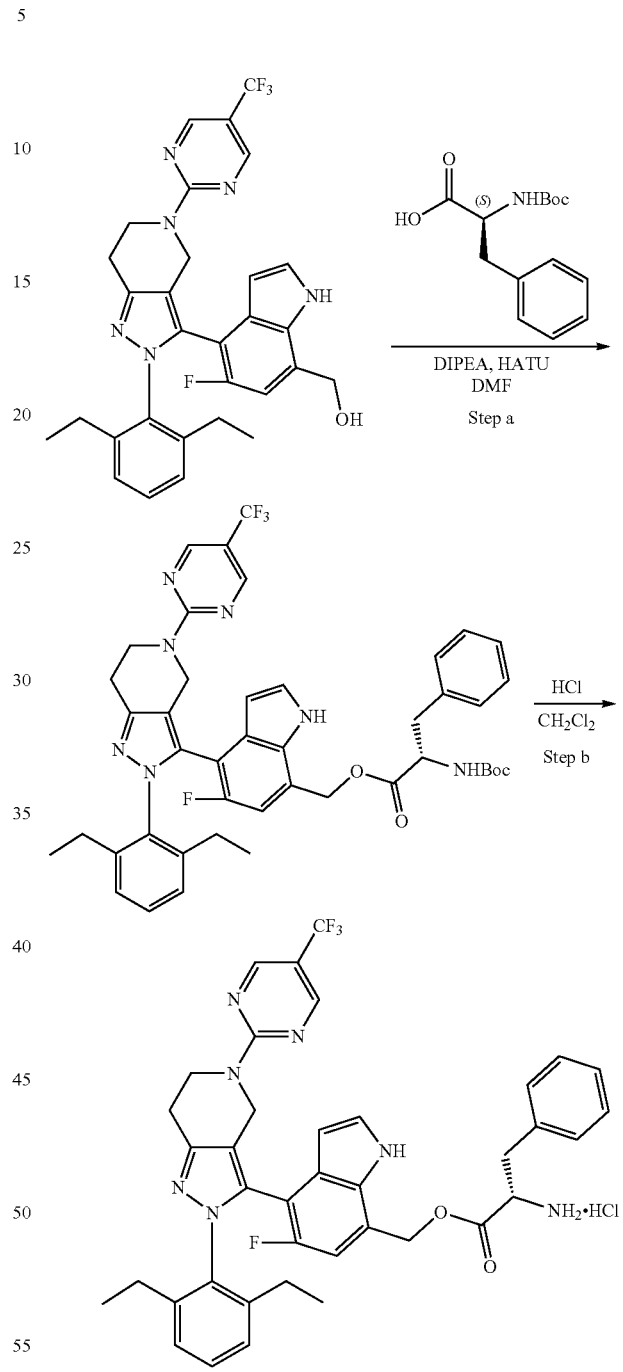

Example 43 was prepared similar to the procedure as described in Example 35 using (tert-butoxycarbonyl)-L-phenylalanine and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-$d_6$) δ 11.55 (br s, 1H), 8.60-8.75 (m, 2H), 8.45-8.52 (m, 2H), 7.52-7.58 (m, 1H), 7.10-7.25 (m, 7H), 6.88-6.95 (m, 1H), 6.71 (dd, J=11.4, 24.3 Hz, 1H), 6.30-6.38 (m, 1H), 5.35-5.45 (m, 2H), 4.73 (d, J=15.9 Hz, 1H), 4.57 (d, J=16.0 Hz, 1H), 4.35-4.45 (m, 2H), 4.15-4.22 (m, 1H), 3.05-3.15 (m, 2H), 2.85-2.95 (m, 2H), 2.30-2.45 (m, 2H), 2.00-2.15 (m, 1H), 1.82-1.90 (m, 1H), 1.13 (t, J=7.4 Hz, 3H), 0.64 (t, J=7.8 Hz, 3H). MS: (ES) m/z calculated for $C_{39}H_{37}F_4N_7O_2$ [M+H]$^+$ 712.3, found 712.2.

Example 44: Synthesis of (S)-2-amino-5-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)-5-oxopentanoic acid hydrochloride

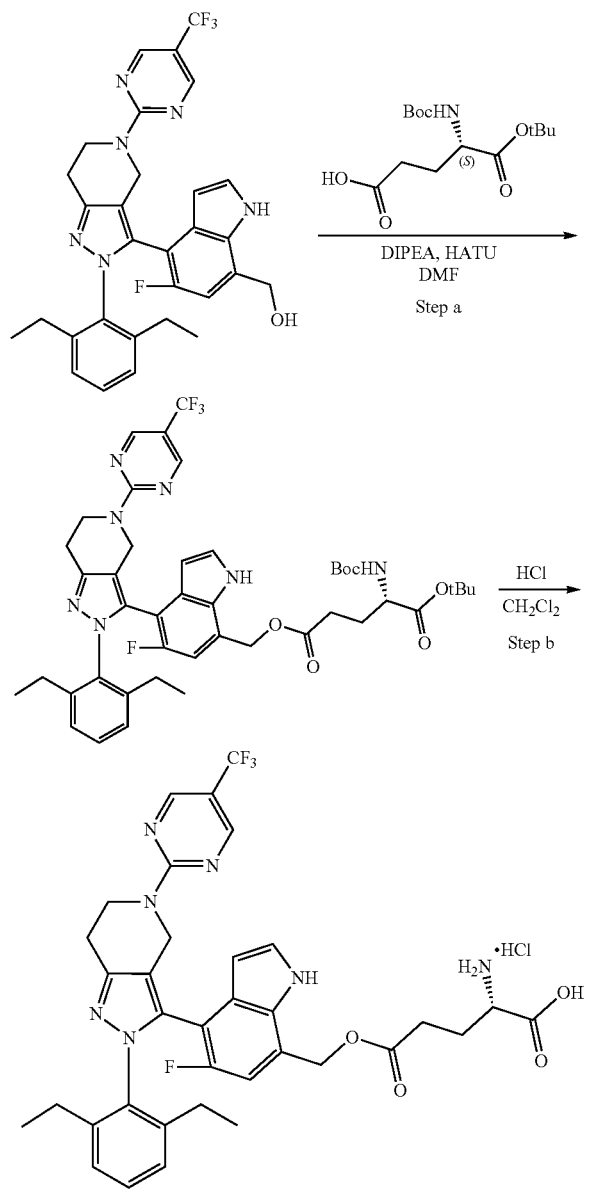

Example 44 was prepared similar to the procedure as described in Example 35 using (S)-5-(tert-butoxy)-4-((tert-butoxycarbonyl)amino)-5-oxopentanoic acid and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-d$_6$) δ 11.61 (br s, 1H), 8.62-8.75 (m, 2H), 8.35-8.45 (m, 3H), 7.52 (t, J=2.7 Hz 1H), 7.12-7.25 (m, 2H), 6.90 (dd, J=7.8, 11.6 Hz, 1H), 6.84 (d, J=11.0 Hz, 1H), 6.31 (q, J=2.0 Hz, 1H), 5.23-5.31 (m, 2H), 4.74 (d, J=16.0 Hz, 1H), 4.57 (d, J=16.0 Hz, 1H), 4.35-4.45 (m, 1H), 3.85-4.00 (m, 2H), 2.85-2.95 (m, 2H), 2.45-2.65 (m, 2H), 2.25-2.40 (m, 2H), 1.85-2.10 (m, 3H), 1.80-1.95 (m, 1H), 1.12 (t, J=7.8 Hz, 3H), 0.64 (t, J=7.8 Hz, 3H). MS: (ES) m/z calculated for $C_{35}H_{35}F_4N_7O_4$ [M+H]$^+$ 694.3, found 694.2.

Example 45: Synthesis of (S)-2-acetamido-5-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)-5-oxopentanoic acid

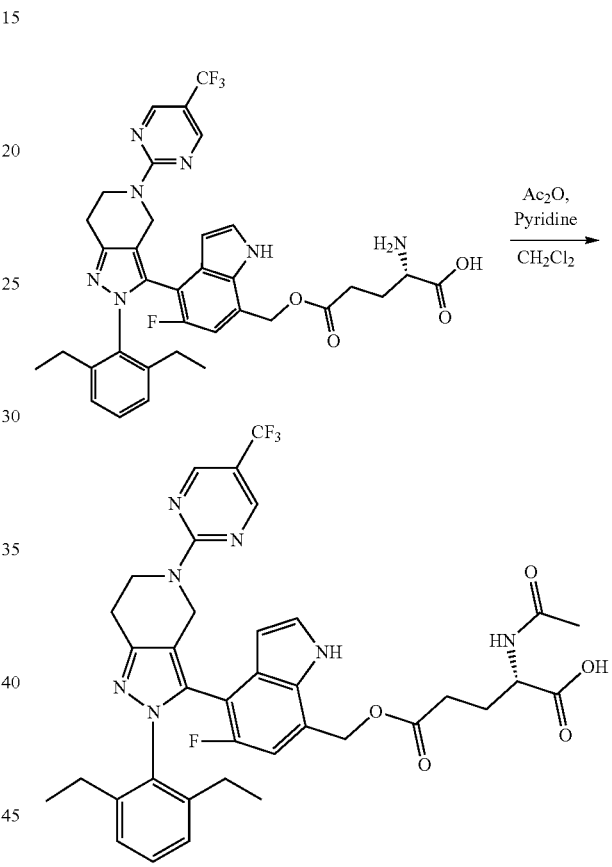

To a stirred solution of (S)-2-amino-5-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)-5-oxopentanoic acid (70 mg, 0.113 mmol) in dichloromethane (3.0 mL) at room temperature were added pyridine (27 mg, 0.4 mmol) and acetic anhydride (30 mg, 0.34 mmol). The reaction mixture was stirred at room temperature for 1 h. After completion, the solvent was removed and the crude material was purified by HPLC (MeCN/H$_2$O, with 0.1% TFA) to give the (S)-2-acetamido-5-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)-5-oxopentanoic acid. $^1$H NMR (400 MHz, DMSO-d$_6$) δ 11.53 (br s, 1H), 8.55-8.80 (m, 2H), 8.12 (d, J=7.8 Hz, 1H), 7.53 (t, J=2.7 Hz, 1H), 7.15-7.25 (m, 2H), 6.91 (d, J=7.5 Hz, 1H), 6.85 (d, J=10.2 Hz, 1H), 6.31 (t, J=10.2 Hz, 1H), 5.25 (d, J=2.7 Hz, 2H), 4.75 (d, J=16.0 Hz, 1H), 4.58 (d, J=16.0 Hz, 1H), 4.37-4.45 (m, 1H), 4.18-4.25 (m, 2H), 3.45-3.85 (m, 1H), 2.85-2.98

(m, 2H), 2.30-2.45 (m, 4H), 1.95-2.10 (m, 2H), 1.85-1.92 (m, 1H), 1.81 (s, 3H), 1.70-1.78 (m, 1H), 1.12 (t, J=7.8 Hz, 3H), 0.65 (t, J=7.8 Hz, 3H), MS: (ES) m/z calculated for $C_{37}H_{37}F_4N_7O_5$ [M+H]$^+$ 736.3, found 736.2.

Example 46: Synthesis of (S)-4-amino-5-((4-(2-(2, 6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)-5-oxopentanoic acid hydrochloride

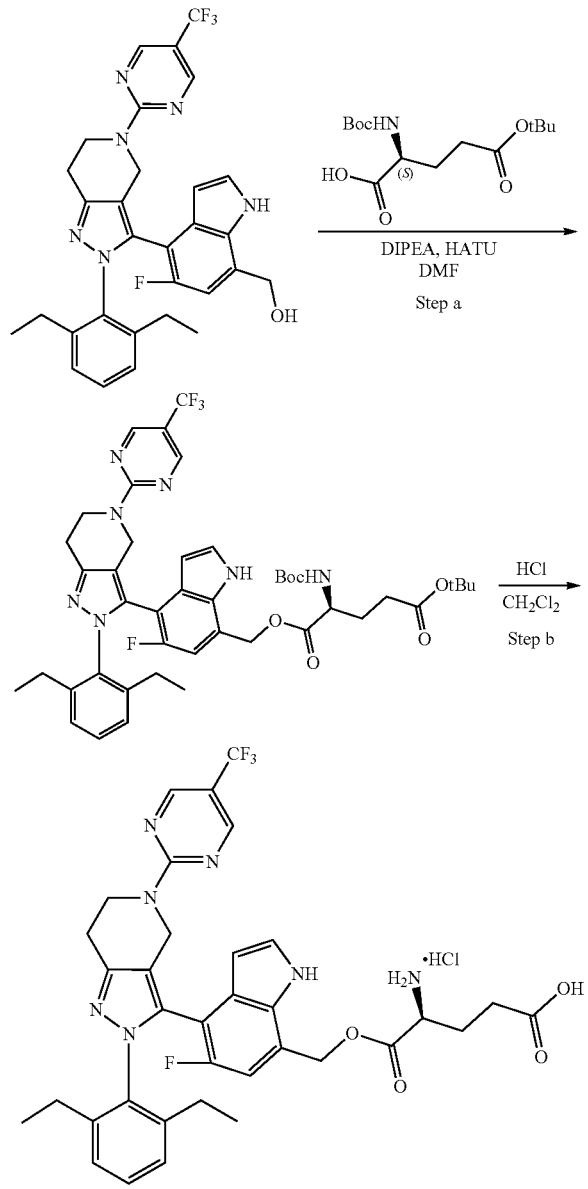

Example 46 was prepared similar to the procedure as described in Example 35 using (S)-5-(tert-butoxy)-2-((tert-butoxycarbonyl)amino)-5-oxopentanoic acid and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-d$_6$) δ 11.56 (br s, 1H), 8.60-8.75 (m, 2H), 8.30-8.45 (m, 2H), 7.56 (t, J=2.7 Hz 1H), 7.15-7.25 (m, 2H), 6.90-6.98 (m, 2H), 6.30- 6.38 (m, 1H), 5.36-5.52 (m, 2H), 4.74 (dd, J=5.6, 16.0 Hz, 1H), 4.57 (d, J=15.7 Hz, 1H), 4.35-4.45 (m, 1H), 4.05-4.25 (m, 2H), 3.35-4.00 (m, 1H), 2.85-2.95 (m, 2H), 2.30-2.45 (m, 4H), 1.95-2.10 (m, 3H), 1.83-1.95 (m, 1H), 1.12 (t, J=7.8 Hz, 3H), 0.65 (dd, J=7.5, 14.9 Hz, 3H), MS: (ES) m/z calculated for $C_{35}H_{35}F_4N_7O_4$ [M+H]$^+$ 694.3, found 694.2.

Example 47: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl glycyl-L-valinate hydrochloride

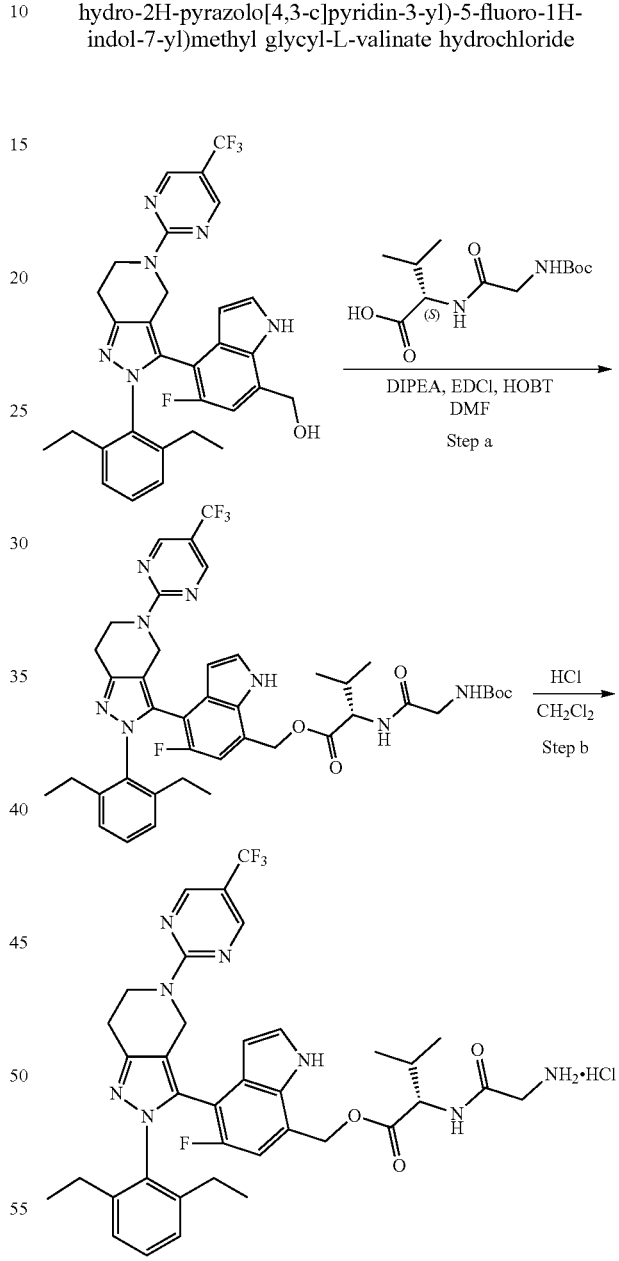

Example 47 was prepared similar to the procedure as described in Example 40 using (tert-butoxycarbonyl)glycyl-L-valine and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1$H NMR (400 MHz, DMSO-d$_6$) δ 11.60 (br s, 1H), 8.60-8.75 (m, 2H), 8.05 (br s, 2H), 7.55 (br s, 1H), 7.14-7.25 (m, 2H), 6.90-6.95 (m, 1H), 6.86 (dd, J=2.0, 11.0 Hz, 1H), 6.32 (t, J=2.3 Hz, 1H), 5.30-5.45 (m, 2H), 4.78 (d, J=3.5 Hz, 1H), 4.74 (d, J=3.1 Hz, 1H), 4.58 (d, J=16.0 Hz, 2H), 4.35-4.45 (m, 2H), 4.15-4.25 (m, 1H), 3.55-3.70 (m, 2H), 2.85-2.96 (m, 2H), 2.30-2.45 (m, 2H), 2.00-2.10 (m, 2H), 1.83-1.90 (m, 1H), 1.12 (t, J=7.5 Hz, 3H), 0.75-0.85 (m, 6H), 0.63 (t, J=7.4 Hz, 3H). MS: (ES) m/z calculated for $C_{37}H_{40}F_4N_8O_3$ $[M+H]^+$ 721.3, found 721.2.

Example 48: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl L-alanyl-L-alaninate hydrochloride

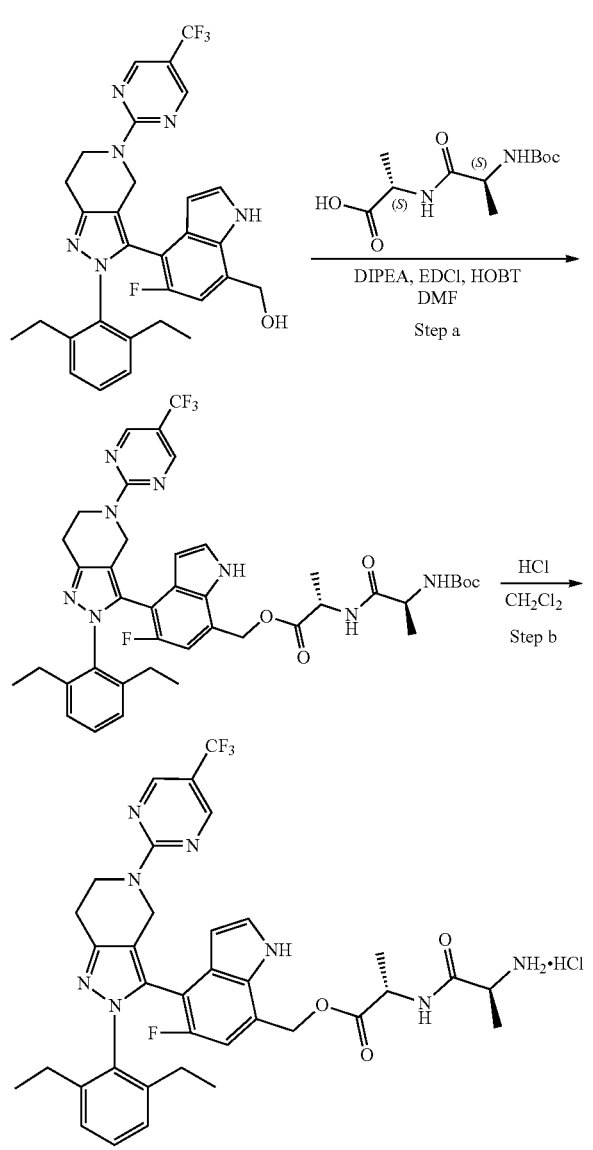

Example 48 was prepared similar to the procedure as described in Example 40 using (tert-butoxycarbonyl)-L-alanyl-L-alanine and (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol. $^1H$ NMR (400 MHz, DMSO-$d_6$) δ 11.58 (br s, 1H), 8.50-8.95 (m, 3H), 8.10 (br s, 2H), 7.53 (br s, 1H), 7.12-7.25 (m, 2H), 6.90 (d, J=7.5 Hz, 1H), 6.84 (dd, J=6.0, 10.6 Hz, 1H), 6.31 (br s, 1H), 5.25-5.38 (m, 2H), 4.73 (d, J=16.5 Hz, 1H), 4.57 (d, J=16.0 Hz, 1H), 4.35-4.45 (m, 2H), 4.15-4.25 (m, 1H), 3.70-3.92 (m, 1H), 2.85-2.95 (m, 2H), 2.30-2.38 (m, 2H), 2.00-2.10 (m, 1H), 1.80-1.87 (m, 1H), 1.30 (t, J=5.6 Hz, 3H), 1.10-1.18 (m, 6H), 0.60-0.66 (m, 3H). MS: (ES) m/z calculated for $C_{36}H_{38}F_4N_8O_3$ $[M+H]^+$ 707.3, found 707.2.

Example 49: Synthesis of 4-(((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)methyl)-5-methyl-1,3-dioxol-2-one

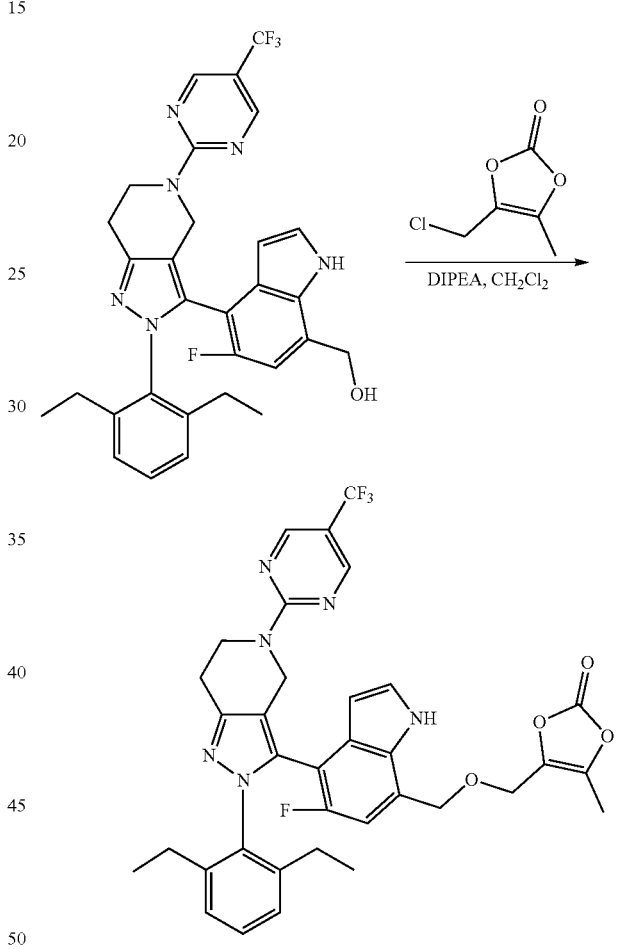

To a stirred solution of (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol (100 mg, 0.18 mmol) in dichloromethane (4.0 mL) at room temperature were added diisopropylethylamine (151 mg, 1.2 mmol) and 4-(chloromethyl)-5-methyl-1,3-dioxol-2-one (150 mg, 0.78 mmol). The reaction was stirred at room temperature for 24 h. After completion, the mixture was quenched with $H_2O$ and the crude was purified by HPLC (MeCN/$H_2O$, with 0.1% TFA) to give the 4-(((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)methyl)-5-methyl-1,3-dioxol-2-one. $^1H$ NMR (400 MHz, CDCl$_3$) δ 9.17 (br s, 1H), 8.47 (br s, 2H), 7.32-7.40 (m, 1H), 7.10-7.35 (m, 2H), 6.85 (d, J=7.4 Hz, 1H), 6.63 (d, J=10.5 Hz, 1H), 6.35-6.45 (m, 1H), 5.49 (d, J=15.1 Hz, 1H), 5.29 (d, J=15.5 Hz, 1H), 4.87 (dd, J=4.3, 16.1 Hz, 1H), 4.66 (dd, J=6.0, 16.5 Hz, 1H), 4.38-4.45 (m, 1H), 4.25-4.35 (m, 1H), 3.04 (t, J=5.8 Hz, 1H), 2.38-2.55 (m, 2H), 2.35 (s, 3H), 2.11-2.25 (m, 2H), 1.85-2.05 (m, 2H), 0.91-1.12 (m, 3H), 0.70-0.89 (m, 3H). MS: (ES) m/z calculated for $C_{35}H_{32}F_4N_6O_4$ [M+H]$^+$ 677.2, found 677.3.

Example 50: Synthesis of (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl dihydrogen phosphate

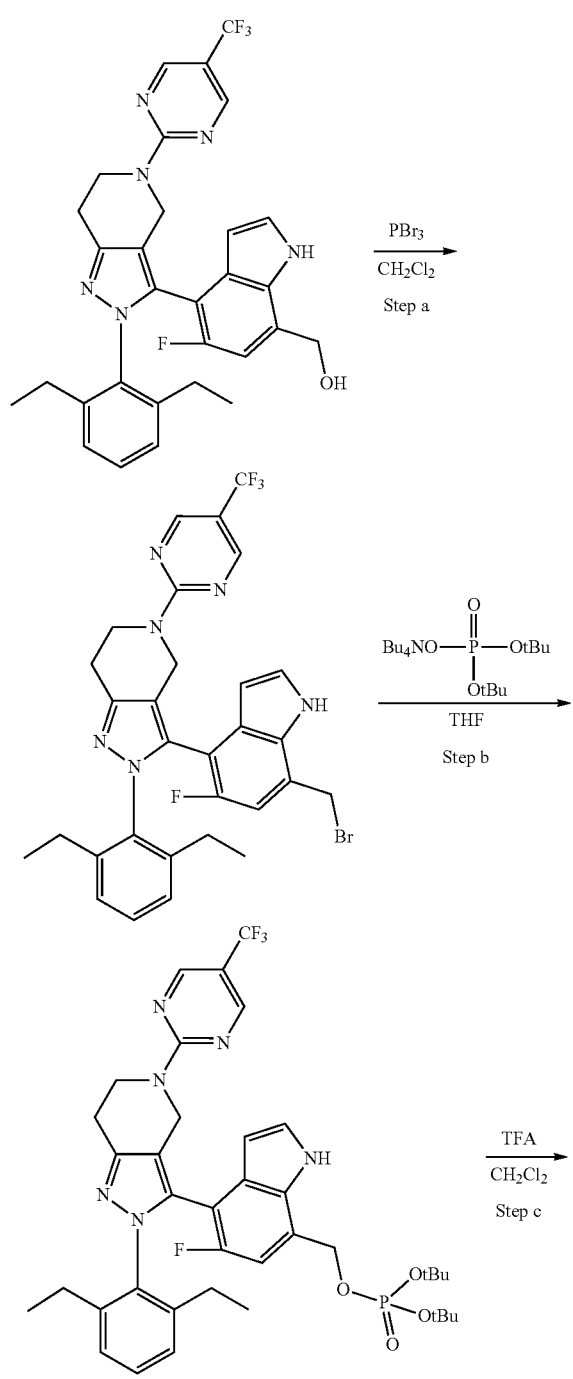

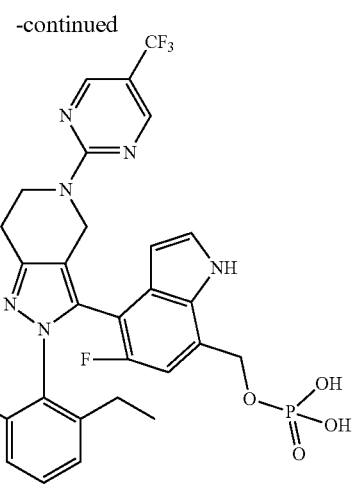

Step a: To a stirred solution of of (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol (100 mg, 0.16 mmol) in dicloromethane (30 mL) at −20° C. was added PBr$_3$ (95 mg, 0.32 mmol). The reaction mixture was allowed to warm to 0° C. and stirred for 2 h. After completion of the reaction, the solvent was removed in vacuo to give 3-(7-(bromomethyl)-5-fluoro-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine which was used directly in the next step without further purification.

Step b: To a stirred solution of 3-(7-(bromomethyl)-5-fluoro-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine (85 mg, 1.24 mmol) in THF (4 mL) was added tetrabutylammonium di-tert-butyl phosphate (91 mg, 0.2 mmol). The reaction mixture was stirred at room temperature for overnight. The reaction mixture was concentrated and the crude was purified by silica gel chromatography (10 to 100% EtOAc in hexanes) to give di-tert-butyl-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl)phosphate. MS: (ES) m/z calculated for $C_{38}H_{45}F_4N_6O_4P$ [M+H]$^+$ 757.32, found 757.3.

Step c: To a stirred solution of di-tert-butyl-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl)phosphate (70 mg, 0.92 mmol) in anhydrous dichloromethane (15 mL) at 0° C. was added TFA (52 mg, 0.46 mmol) dropwise over 5 min. The reaction mixture was stirred at room temperature for 2 h. After completion of the reaction, the solvent was removed in vacuo and the residue was purified by HPLC (MeCN/H$_2$O, with 0.1% TFA) to give (4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methyl dihydrogen phosphate. 1H NMR (400 MHz, CD$_3$OD) δ 8.56 (br s, 2H), 7.43 (d, J=3.2 Hz, 1H), 7.15-7.25 (m, 2H), 6.90 (d, J=5.9 Hz, 1H), 6.81 (d, J=11.3 Hz, 1H), 6.37 (d, J=3.1 Hz, 1H), 5.20-5.30 (m, 2H), 4.91 (d, J=16.1 Hz, 1H), 4.64 (d, J=15.6 Hz, 1H), 4.42-4.50 (m, 1H), 4.30-4.37 (m, 1H), 2.98 (t, J=5.1 Hz, 2H), 2.44 (q, J=7.8 Hz, 2H), 2.12-2.19 (m, 1H), 1.90-1.98 (m, 2H), 1.22 (t, J=7.4 Hz, 3H), 0.72 (t, J=7.4 Hz, 3H), MS: (ES) m/z calculated for $C_{30}H_{29}F_4N_6O_4P$ [M+H]$^+$ 645.2, found 645.6.

Example 51: Synthesis of ((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy)methyl dihydrogen phosphate

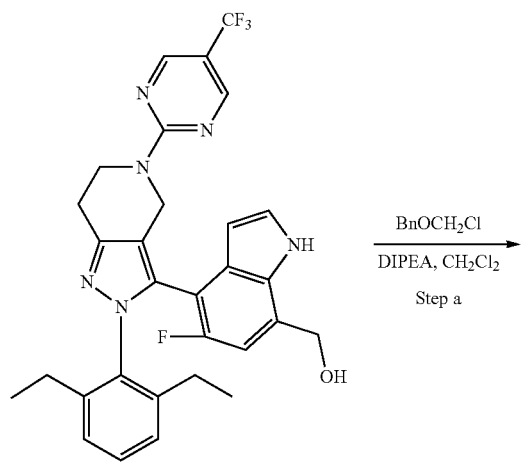

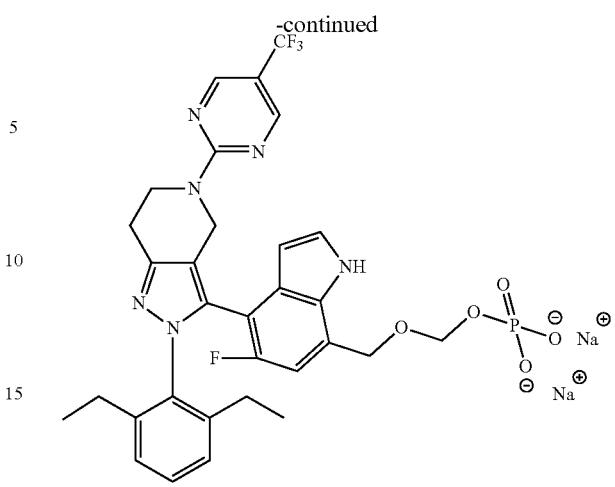

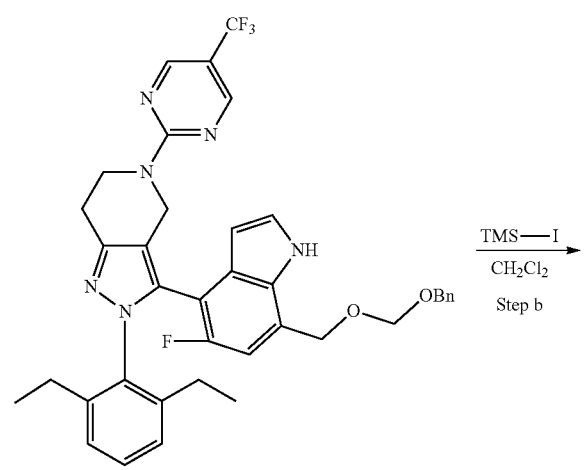

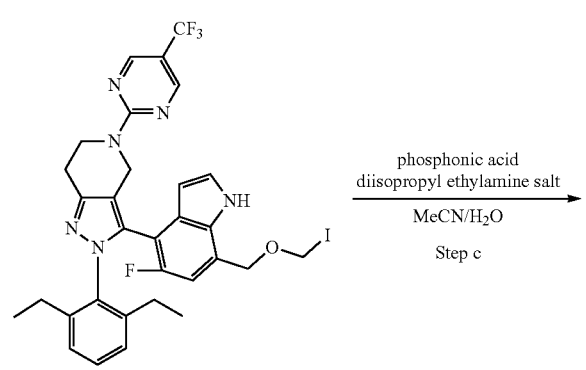

Step a: To a stirred solution of (4-(2-(2,6-diethylphenyl)-5-(4-(trifluoromethyl)phenyl)-4,5,6,7-tetrahydro-2H-pyrazolo[4,3-c]pyridin-3-yl)-5-fluoro-1H-indol-7-yl)methanol (140 mg, 0.25 mmol) in dichloromethane (4 mL) at room temperature was added diisopropylethylamine (77 mg, 0.74 mmol) and ((chloromethoxy)methyl)benzene (77 mg, 0.49 mmol). The reaction mixture was warmed to 50° C. and stirred for 4 h. After completion, the reaction mixture was cooled to room temperature. The mixture was diluted with water and saturated aqueous NaHCO$_3$, extracted with dichloromethane, washed with brine and dried over Na$_2$SO$_4$. The solvent was removed under reduced pressure and the residue was purified by silica gel chromatography (10 to 100% EtOAc in hexanes) to give 3-(7-(((benzyloxy)methoxy)methyl)-5-fluoro-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine. $^1$H NMR (400 MHz, CDCl$_3$) δ 8.82 (br s, 1H), 8.47 (br s, 2H), 7.32-7.40 (m, 4H), 7.12-7.25 (m, 3H), 6.85 (d, J=7.4 Hz, 1H), 6.63 (d, J=10.5 Hz, 1H), 6.35 (t, J=3.1 Hz, 1H), 4.85-4.98 (m, 7H), 4.69 (d, J=16.8 Hz, 1H), 4.65 (s, 2H), 4.40-4.50 (m, 1H), 4.25-4.35 (m, 1H), 3.0-3.12 (m, 1H), 2.45-2.60 (m, 2H), 2.15-2.25 (m, 1H), 1.85-2.05 (m, 1H), 1.12 (t, J=7.4 Hz, 3H), 0.73 (t, J=7.4 Hz, 3H). MS: (ES) m/z calculated for C$_{38}$H$_{36}$F$_4$N$_6$O$_2$ [M+H]$^+$ 685.74, found 685.5.

Step b: To a stirred solution of 3-(7-(((benzyloxy)methoxy)methyl)-5-fluoro-1H-indol-4-yl)-2-(2,6-diethylphenyl)-5-(5-(trifluoromethyl)pyrimidin-2-yl)-4,5,6,7-tetrahydro-2H-pyrazolo[4,3-c]pyridine (140 mg, 0.20 mmol) in dichloromethane (3 mL) was added trimethylsilyl iodide (0.5 mL, 0.51 mmol). The reaction mixture was stirred for 2 h at room temperature. After completion of the reaction, the solvent was removed in vacuo to give 2-(2,6-diethylphenyl)-3-(5-fluoro-7-((iodomethoxy)methyl)-1H-indol-4-yl)-5-(5-(trifluoromethyl)pyrimidin-2-yl)-4,5,6,7-tetrahydro-2H-pyrazolo[4,3-c]pyridine, which was used directly in the next step without further purification.

Step c: To a stirred suspension of phosphonic acid diisopropyl ethylamine salt (482 mg, 1.0 mmol) in MeCN (5 mL) and H$_2$O (5 drops) was added to 2-(2,6-diethylphenyl)-3-(5-fluoro-7-((iodomethoxy)methyl)-1H-indol-4-yl)-5-(5-(trifluoromethyl)pyrimidin-2-yl)-4,5,6,7-tetrahydro-2H-pyrazolo[4,3-c]pyridine (140 mg, 0.19 mmol). The reaction mixture was stirred for 2 h at room temperature. After completion of the reaction, the solvent was removed in vacuo and the mixture was diluted with water and extracted with EtOAc. The solvent was removed under reduced pressure and the residue was purified by HPLC (MeCN/H₂O, with 0.1% NH₄CO₃) and lyophilized to give the ammonium salt of ((4-(2-(2,6-diethylphenyl)-5-(5-[4,3-c]pyridin-3-yl)-5-fluoro-1H-indol-7-yl)methoxy)methyl dihydrogen phosphate. The material was converted to sodium salt by diluting with MeCN (0.6 mL)/H₂O (0.4 mL) and adding 0.1 M NaOH (213 µL, 2 equiv.) and lyophilizing to dryness to give the disodium salt of ((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-5-fluoro-1H-indol-7-yl)methoxy) methyl dihydrogen phosphate. ¹H NMR (400 MHz, D₂O) δ 8.07 (br s, 2H), 7.37 (br s, 1H), 7.07-7.15 (m, 2H), 6.79 (d, J=6.6 Hz, 1H), 6.21 (br s, 2H), 4.87-4.95 (m, 2H), 4.76 (d, J=11.3 Hz, 1H), 4.15-4.25 (m, 2H), 3.60-3.85 (m, 2H), 2.79 (br s, 2H), 2.00-2.25 (m, 4H), 1.65-1.85 (m, 2H), 0.93 (t, J=7.4 Hz, 3H), 0.35-0.50 (m, 3H), MS: (ES) m/z calculated for C₃₁H₃₁F₄N₆O₅P [M+H]⁺ 675.2, found 675.7.

Example 52: Synthesis of 4-((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)methyl)-5-methyl-1,3-dioxol-2-one added at −78° C. The mixture was warmed up to room temperature and stirred for 3 h. After completion, saturated NH₄Cl solution was added, and the mixture was extracted with EtOAc. The organic layers were combined, dried over Na₂SO₄, filtered, and concentrated. The residue was purified by silica gel column chromatography (10 to 30% EtOAc in hexanes) to give 4-((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)methyl)-5-methyl-1,3-dioxol-2-one. ¹H NMR (400 MHz, DMSO-d₆) δ 8.16 (d, J=8.2 Hz, 1H), 8.01 (d, J=8.2 Hz, 1H), 7.97 (br s, 1H), 7.82 (d, J=3.5 Hz, 1H), 7.28 (t, J=7.8 Hz, 1H), 7.13 (d, J=8.1 Hz, 1H), 7.08 (d, J=7.0 Hz, 1H), 6.84 (dd, J=8.06, 13.7 Hz, 1H), 6.54 (dd, J=2.8, 3.6 Hz, 1H), 6.45 (dd, J=4.3, 8.2 Hz, 1H), 4.99 (d, J=4.7 Hz, 1H), 4.45 (d, J=4.7 Hz, 1H), 4.15 (br s, 2H), 3.61 (q, J=3.5 Hz, 1H), 2.33 (s, 3H), 2.20-2.25 (m, 2H), 2.05-2.15 (m, 2H), 1.85-2.05 (m, 1H), 1.47 (s, 6H), 0.90 (t, J=7.4 Hz, 3H), 0.85 (t, J=7.4 Hz, 3H). MS: (ES) m/z calculated for C₃₉H₃₅F₇N₄O₃ [M+H]⁺ 741.3, found 741.2.

Example 53: Synthesis of (5-methyl-2-oxo-1,3-dioxol-4-yl)methyl 4-(5-(2,4-bis(trifluoromethyl)benzyl)-2-(2,6-diethylphenyl)-2,4,5,6-tetrahydro-6,6-dimethylpyrrolo[3,4-c]pyrazol-3-yl)-7-fluoro-1H-indole-1-carboxylate

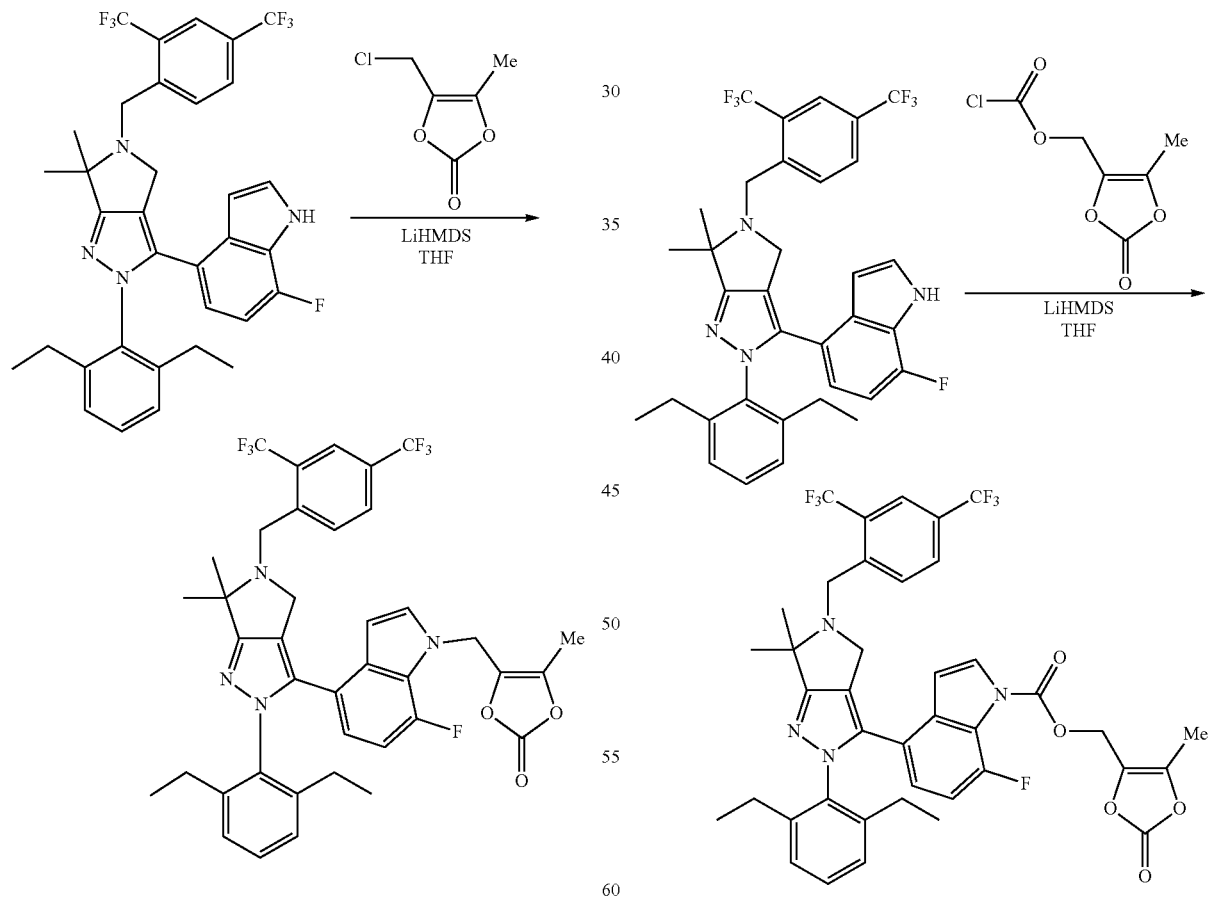

Step a: To a stirred solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole (400 mg, 0.64 mmol) in THF (10 mL) was added 1 M LiHMDS solution in THF (1 mL, 1 mmol) at −78° C. After stirring for 30 min, a solution of 4-(chloromethyl)-5-methyl-1,3-dioxol-2-one (113 mg, 0.76 mmol) in THF (3 mL) was To a 50 mL round bottom flask charged with 4-(hydroxymethyl)-5-methyl-1,3-dioxol-2-one (0.5 g, 3.84 mmol) in anhydrous dichloromethane (6 mL) at −40° C. was added triethylamine (0.77 g, 7.62 mmol) followed by triphosgene (0.88 g, 4.58 mmol) dropwise over 5 min. The reaction mixture was stirred at −40° C. for 1 h then warmed to room temperature for 1 h. After completion, the reaction mixture was diluted with H$_2$O and extracted with dichloromethane. The combined organic layers were dried over Na$_2$SO$_4$, filtered, and concentrated in vacuo to give (5-methyl-2-oxo-1,3-dioxol-4-yl)methyl carbonochloridate which was used directly in the next step without further purification.

Example 53 was prepared similar to the procedure as described in Example 52 using (5-methyl-2-oxo-1,3-dioxol-4-yl)methyl-carbonochloridate and 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole.
$^1$H NMR (400 MHz, CD$_3$OD) δ 8.22 (d, J=6.6 Hz, 1H), 7.90-7.97 (m, 2H), 7.81 (br s, 1H), 7.34 (t, J=7.4 Hz, 1H), 7.16 (d, J=7.4 Hz, 2H), 6.83 (t, J=8.6 Hz, 1H), 6.60-6.75 (m, 2H), 5.24 (s, 2H), 4.23 (br s, 2H), 3.71 (s, 2H), 2.25-2.38 (m, 4H), 2.24 (s, 3H), 1.57 (s, 6H), 1.03 (t, J=7.4 Hz, 6H). MS: (ES) m/z calculated for C$_{40}$H$_{35}$F$_7$N$_4$O$_5$ [M+H]$^+$ 785.2, found 785.1.

Example 54: Synthesis of 4-((4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)methyl)-5-methyl-1,3-dioxol-2-one

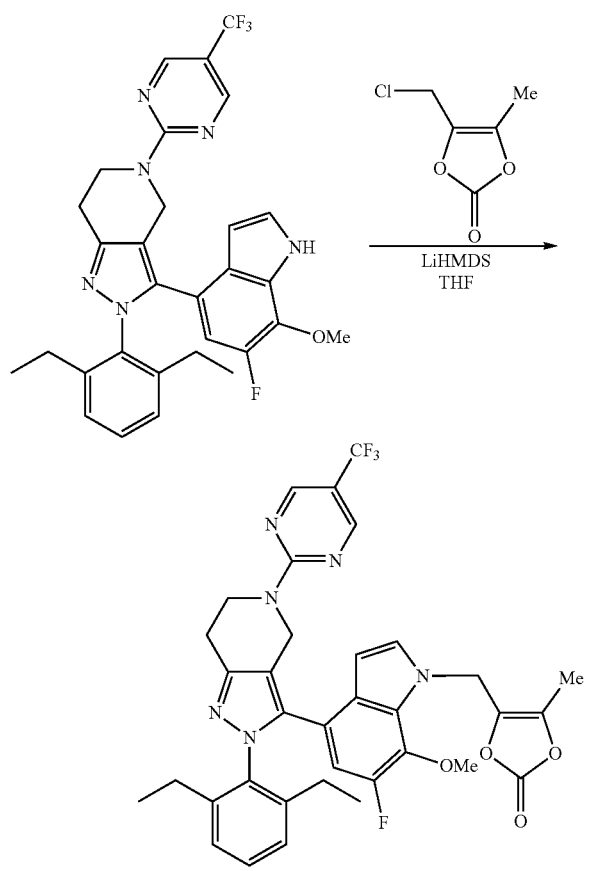

Example 54 was prepared similar to the procedure as described in Example 52 using 4-(chloromethyl)-5-methyl-1,3-dioxol-2-one and 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine $^1$H NMR (400 MHz, CD$_3$OD) δ 8.70 (br s, 2H), 7.86 (s, 1H), 7.28 (t, J=6.9 Hz, 1H), 6.59 (br s, 1H), 6.40 (d, J=13.3 Hz, 1H), 5.02 (br s, 2H), 4.78 (br s, 2H), 4.25-4.60 (m, 2H), 3.79 (s, 3H), 3.30 (br s, 2H), 2.89 (br s, 2H), 2.47 (s, 3H), 2.36 (br s, 4H), 0.67-1.12 (m, 6H). MS: (ES) m/z calculated for C$_{35}$H$_{32}$F$_4$N$_6$O$_4$ [M+H]$^+$ 677.24, found 677.2.

Example 55: Synthesis of (5-methyl-2-oxo-1,3-dioxol-4-yl)methyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate

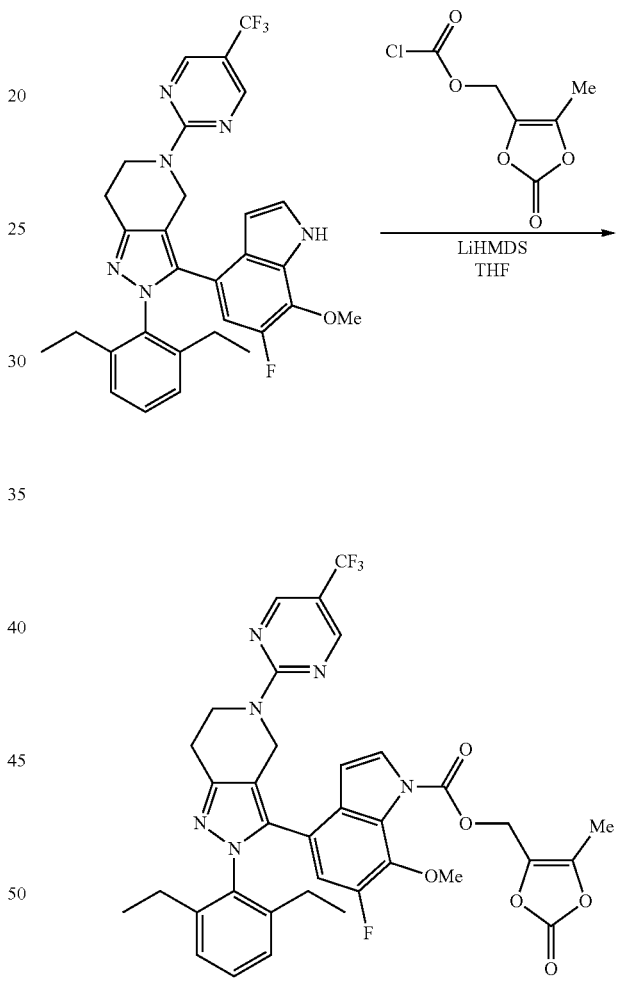

Example 55 was prepared similar to the procedure as described in Example 52 using (5-methyl-2-oxo-1,3-dioxol-4-yl)methyl chloroformate and 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c] pyridine. $^1$H NMR (400 MHz, CD$_3$OD) δ 8.58 (br s, 2H), 7.78 (d, J=1.2 Hz, 1H), 7.32 (t, J=1.2 Hz, 1H), 7.15-7.22 (m, 2H), 6.50-6.65 (m, 2H), 5.28 (s, 2H), 4.38 (br s, 2H), 3.95 (s, 3H), 2.97 (br s, 2H), 2.30-2.40 (m, 6H), 2.26 (s, 3H), 0.98-1.25 (m, 6H). MS: (ES) m/z calculated for C$_{36}$H$_{32}$F$_4$N$_6$O$_6$ [M+H]$^+$ 721.23, found 721.2.

Example 56: Synthesis of 4-((4-(5-(2,4-bis(trifluoromethyl)benzyl)-2-(2,6-diethylphenyl)-2,4,5,6-tetrahydro-6,6-dimethylpyrrolo[3,4-c]pyrazol-3-yl)-7-fluoro-1H-indole-1-carboxyloyloxy)methyl)phenyl dihydrogen phosphate

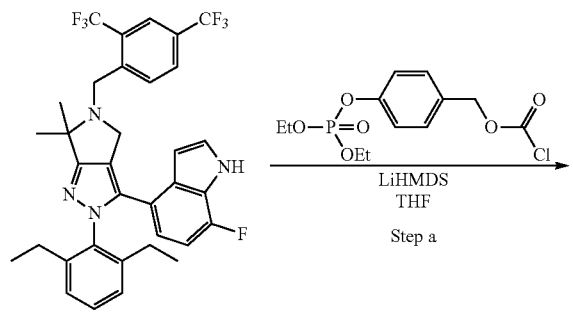

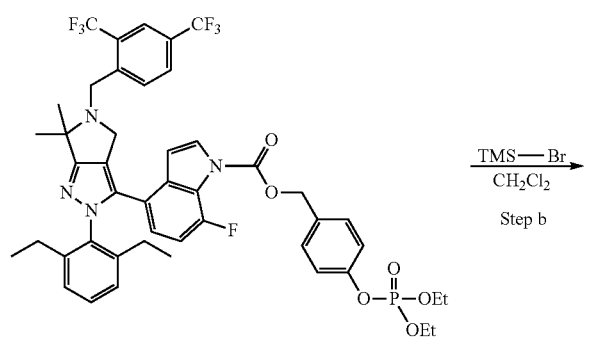

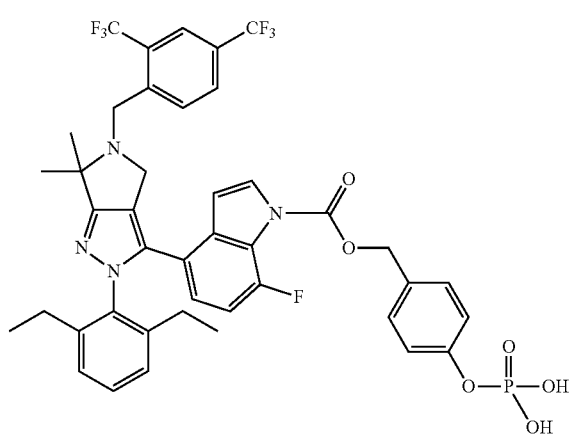

Step a: To a 50 mL round bottom flask charged with 4-(hydroxymethyl)phenol (0.27 g, 1.73 mmol), triethylamine (0.27 g, 1.73 mmol), and anhydrous dichloromethane (6 mL) at 0° C. was added diethylphosphoryl chloride (0.54 g, 4.32 mmol) dropwise over 5 min. The reaction mixture was stirred at room temperature for 16 h. After completion, the mixture was extracted with EtOAc. The organic layers were combined, dried over $Na_2SO_4$, filtered, and concentrated. The residue was purified by silica gel column chromatography (10 to 80% EtOAc in hexanes) to give diethyl 4-(hydroxymethyl)-phenyl phosphate To a stirred solution of diethyl 4-(hydroxymethyl)phenyl phosphate (0.27 g, 1.73 mmol) and triethylamine in anhydrous dichloromethane (10 mL) at 0° C. was added triphosgene (0.54 g, 4.32 mmol) slowly over 5 min. The reaction mixture was stirred at room temperature for 1 h. After completion, the reaction mixture was diluted with $H_2O$ and extracted with dichloromethane. The combined organic layers were dried over $Na_2SO_4$, filtered, and concentrated in vacuo to give 4-((diethoxyphosphoryl)oxy)benzyl carbonochloridate which was used directly in the next step without further purification.

To a solution of 4-(5-(2,4-bis(trifluoromethyl)benzyl)-2-(2,6-diethylphenyl)-2,4,5,6-tetrahydro-6,6-dimethylpyrrolo[3,4-c]pyrazol-3-yl)-7-fluoro-1H-indole (150 mg, 0.23 mmol) in THF (4 mL) was added 1 M LiHMDS solution in THF (0.38 mL, 0.38 mmol) at −78° C. After stirring for 30 min, a solution of 4-((diethoxyphosphoryl)oxy)benzyl carbonochloridate (153 mg, 0.47 mmol) in THF (2 mL) was added at −78° C. The reaction mixture was warmed to room temperature and stirred for 2 h. After completion, saturated aqueous $NH_4Cl$ solution was added, extracted with EtOAc. The organic layers were combined, dried over $Na_2SO_4$, filtered, and concentrated. The residue was purified by silica gel column chromatography (10 to 60% EtOAc in hexanes) to give 4-((diethoxyphosphoryl)oxy)benzyl-4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. MS: (ES) m/z calculated for $C_{46}H_{46}F_7N_4O_6P$ [M+H]$^+$ 915.3, found 915.3.

Step b: To a stirred solution of 4-((diethoxyphosphoryl)oxy)benzyl-4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate (100 mg, 0.11 mmol) in dichloromethane (2.5 mL) was added bromotrimethylsilane (83 mg, 0.55 mmol) at room temperature for 8 h. After completion, the mixture was concentrated to dryness and purified by HPLC (MeCN/$H_2O$, with 0.1% TFA) to give 4-(phosphonooxy)benzyl-4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indole-1-carboxylate. $^1$H NMR (400 MHz, CD$_3$OD) δ 8.13 (s, 1H), 8.06 (s, 2H), 7.82 (d, J=3.5 Hz, 1H), 7.46 (d, J=8.6 Hz, 2H), 7.35 (t, J=7.8 Hz, 1H), 7.22 (d, J=7.9 Hz, 2H), 7.16 (d, J=7.8 Hz, 2H), 6.83 (dd, J=8.2, 12.1 Hz, 1H), 6.65-6.75 (m, 2H), 5.40 (s, 2H), 4.72 (br s, 2H), 4.50 (br s, 2H), 2.15-2.30 (m, 4H), 1.93 (s, 6H), 0.99 (t, J=7.4 Hz, 6H) MS: (ES) m/z calculated for $C_{42}H_{38}F_7N_4O_6P$ [M+H]$^+$ 859.24, found 859.2.

Example 57: Synthesis of 4-(phosphonooxy)benzyl-4-(2-(2,6-diethylphenyl)-5-(5-(trifluoromethyl)-pyrimidin-2-yl)-4,5,6,7-tetrahydro-2H-pyrazolo[4,3-c]pyridin-3-yl)-6-fluoro-7-methoxy-1H-indole-1-carboxylate

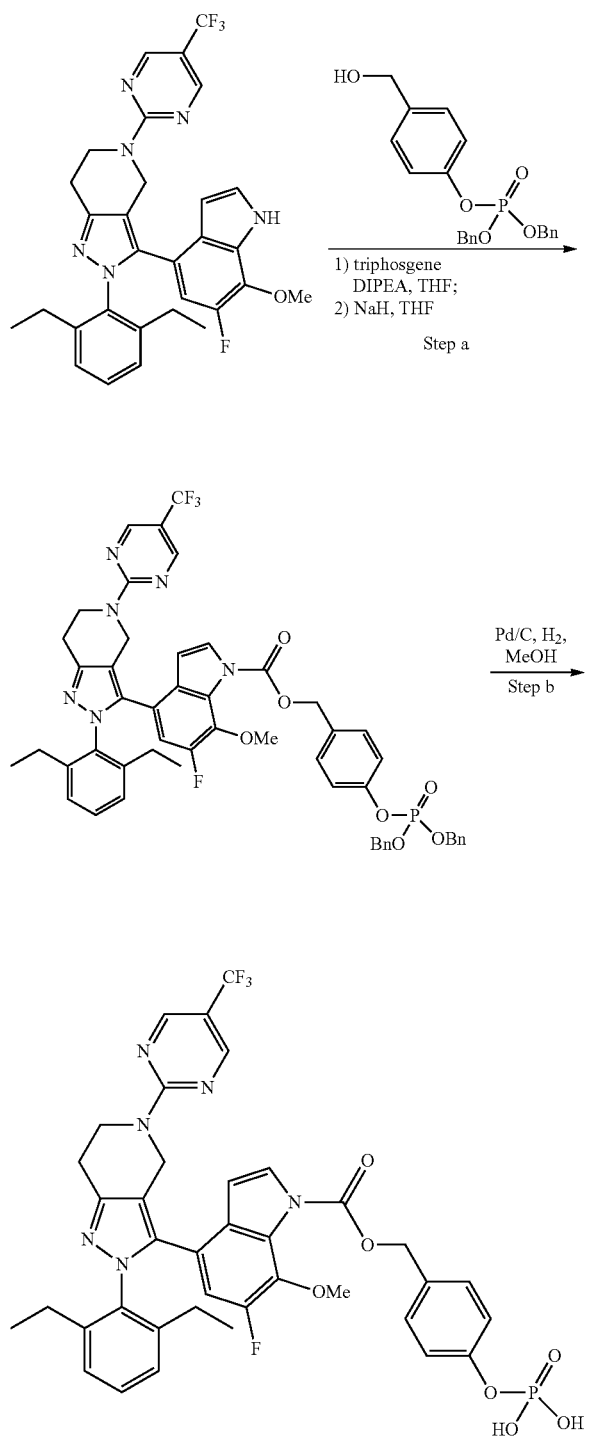

Step a: To a solution of 4-hydroxybenzaldehyde (3.0 g, 24.5 mmol) in 100 mL of THF was added a 1.0 M solution of tBuOK in THF (27.04 mL, 27.04 mmol). The mixture was heated to 70° C. and tetrabenzylphosphate was added (14.5 g, 26.95 mmol). After 1 h at 70° C., hexanes was added to the mixture and the contents were filtered. The filtrate was concentrated in vacuo and the resulting residue was purified by silica gel column chromatography (0 to 100% EtOAc in hexanes) to produce dibenzyl (4-formylphenyl)phosphate. MS: (ES) m/z calculated for $C_{21}H_{19}O_5P$ [M+H]$^+$ 383.1, found 383.2.

To a solution of dibenzyl (4-formylphenyl)phosphate (3.5 g, 9.16 mmol) in 50 mL of THF at −78° C. was added NaBH$_4$ (0.65 g, 18.3 mmol). After stirring at room temperature for 2 h, the mixture was quenched with H$_2$O. The organic and aqueous layers were separated and the aqueous layer was extracted with EtOAc. The combined organic layers were dried with sodium sulfate, filtered and concentrated in vacuo. The residue was purified by silica gel column (0 to 100% EtOAc in hexanes) to provide dibenzyl-4-(hydroxymethyl)phenyl)phosphate. MS: (ES) m/z calculated for $C_{21}H_{21}O_5P$ [M+H]$^+$ 385., found 385.1.

To a solution of dibenzyl-4-(hydroxymethyl)phenyl)phosphate (3.56 g, 9.24 mmol) in 30 mL of THF at 0° C. was added diisopropylethylamine (2.98, 23.1 mmol) and triphosgene (3.0 g, 10.1 mmol). After stirring at 0° C. for 1 h, the reaction was quenched with H$_2$O. The organic and aqueous layers were separated, and the aqueous layer was extracted with EtOAc. The organic layers were combined, dried with sodium sulfate, filtered and concentrated to form the crude chloroformate.

To a solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (250 mg, 0.442 mmol) in 1.2 mL of THF at 0° C. was added NaH (26 mg, 1.05 mmol). After stirring at 0° C. for 30 min, a solution of the crude chloroformate formed above (247 mg, 0.553 mmol) in THF (2 mL) was added to the mixture. The solution was stirred at 0° C. for 1 h then quenched with H$_2$O. The organic and aqueous layers were separated and the aqueous layer was extracted with EtOAc. The organic layers were combined, dried with sodium sulfate, filtered and concentrated in vacuo.

The residue was purified by silica gel column chromatography (0 to 50% EtOAc in hexanes) to give 4-((bis(benzyloxy)phosphoryl)oxy)benzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate.

Step b: To a solution of 4-((bis(benzyloxy)phosphoryl)oxy)benzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate (150 mg, 0.15 mmol) in 7 mL of THF was added 10% Pd/C (50 mg). The mixture was stirred under a H2 balloon for 1 h, then filtered through Celite, concentrated and purified by HPLC (MeCN/H$_2$O, with 0.1% TFA) to give 4-(phosphonooxy)benzyl 4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indole-1-carboxylate. $^1$H NMR (400 MHz, DMSO-d$_6$) δ 7.90 (br s, 1H), 6.99 (d, J=3.5 Hz, 1H), 6.20-6.60 (m, 10H), 5.80 (d, J=3.5 Hz, 1H), 5.69 (d, J=12.5 Hz, 1H), 4.53 (s, 2H), 3.94 (br s, 2H), 3.48 (br s, 2H), 3.0 (s, 3H), 2.08 (br s, 2H), 1.68-1.95 (m, 2H), 0.98-1.45 (m, 6H), MS: (ES) m/z calculated for $C_{38}H_{35}F_4N_6O_7P$ [M+H]$^+$ 795.22, found 795.2.

Example 58: Synthesis of 2-(4-(4-(5-(2,4-bis(trifluoromethyl)benzyl)-2-(2,6-diethylphenyl)-2,4,5,6-tetrahydro-6,6-dimethylpyrrolo-[3,4-c]pyrazol-3-yl)-7-fluoro-1H-indol-1-yl)-2-methyl-4-oxobutan-2-yl)-3,5-dimethylphenyl dihydrogen phosphate

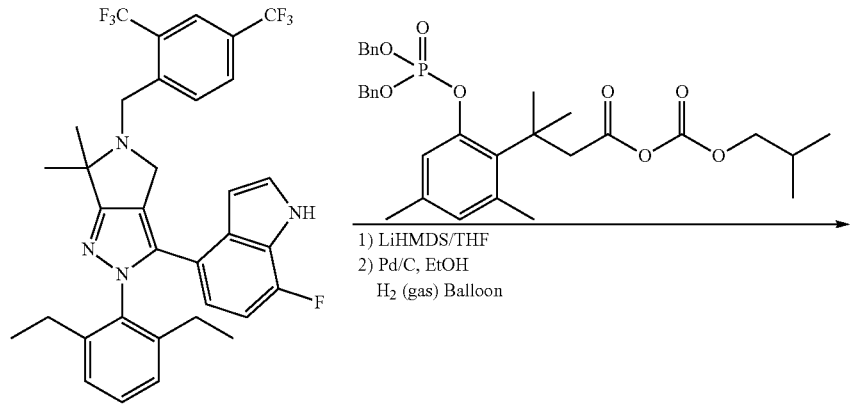

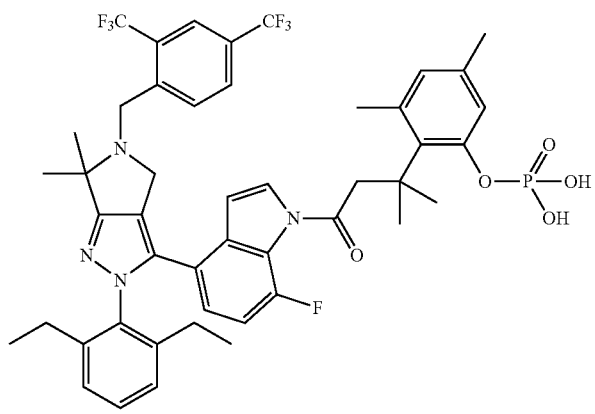

To a solution of 3-(2-((bis(benzyloxy)phosphoryl)oxy)-4,6-dimethylphenyl)-3-methylbutanoic acid (1.0 g, 2.07 mmol) in anhydrous dichloromethane (10 mL) was added diisopropylethylamine followed by isobutyl chloroformate (298 mg, 2.49 mmol) in dichloromethane (10 mL) at 0° C. dropwise over 5 min. The reaction mixture was stirred at room temperature for 2 h. After completion of the reaction, the reaction mixture was diluted with $H_2O$ and extracted with dichloromethane. The combined organic layers were dried over $Na_2SO_4$, filtered, and concentrated in vacuo to give 3-(2-((bis(benzyloxy)phosphoryl)oxy)-4,6-dimethylphenyl)-3-methylbutanoic (isobutyl carbonic) anhydride, which was used directly in the next step without further purification.

To a solution of 4-(5-(2,4-bis(trifluoromethyl)benzyl)-2-(2,6-diethylphenyl)-6,6-(400 mg, 0.63 mmol) in THF (10 mL) was added 1M LiHMDS solution in THF (1.01 mL, 1.01 mmol) at −78° C. After stirring for 30 min, a solution of 3-(2-((bis(benzyloxy)phosphoryl)oxy)-4,6-dimethylphenyl)-3-methylbutanoic (isobutyl carbonic) anhydride (0.46 g, 0.8 mmol) in THF (5 mL) was added at −78° C. and stirred for 1 h. The mixture was warmed to room temperature and stirred for 2 h. After completion, saturated aqueous $NH_4Cl$ solution was added, and the mixture was extracted with EtOAc. The organic layers were combined, dried over $Na_2SO_4$, filtered, and concentrated. The residue was purified by silica gel column chromatography (10 to 60% EtOAc in hexanes) to give dibenzyl (2-(4-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)-2-methyl-4-oxobutan-2-yl)-3,5-dimethylphenyl) phosphate.

To a solution of the resulting phosphate (270 mg, 0.25 mmol) in ethanol (10 mL) was added 10% Pd/C (200 mg) at room temperature. The resulting mixture was stirred under a hydrogen (balloon) atmosphere for 1 h at room temperature. The reaction mixture was filtered through Celite and the filtrate was concentrated under reduced pressure to give 2-(4-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-7-fluoro-1H-indol-1-yl)-2-methyl-4-oxobutan-2-yl)-3,5-dimethylphenyl dihydrogen phosphate. $^1$H NMR (400 MHz, DMSO-$d_6$) δ 12.22 (br s, 1H), 8.47 (d, J=8.2 Hz, 1H), 8.35 (d, J=7.4 Hz, 1H), 8.30 (s, 1H), 8.23 (s, 1H), 7.62 (t, J=8.2 Hz, 1H), 7.44 (d, J=7.0 Hz, 2H), 7.32 (br s, 1H), 7.15 (t, J=10.9 Hz, 1H), 6.82-6.95 (m, 3H), 4.49 (br s, 2H), 3.85-4.05 (m, 4H), 3.66 (br s, 1H), 2.72 (s, 3H), 2.42-2.60 (m, 4H), 2.38 (s, 3H), 1.90 (s, 4H), 1.80 (s, 6H), 1.23 (t, J=7.4 Hz, 6H). MS: (ES) m/z calculated for $C_{47}H_{48}F_7N_4O_5P$ [M+H]$^+$ 913.3, found 913.3.

Example 59: Synthesis of 2-(4-(4-(2-(2,6-diethylphenyl)-5-(5-(trifluoromethyl)pyrimidin-2-yl)-4,5,6,7-tetrahydro-2H-pyrazolo-[4,3-c]pyridin-3-yl)-7-fluoro-1H-indol-1-yl)-2-methyl-4-oxobutan-2-yl)-3,5-dimethylphenyl dihydrogen phosphate

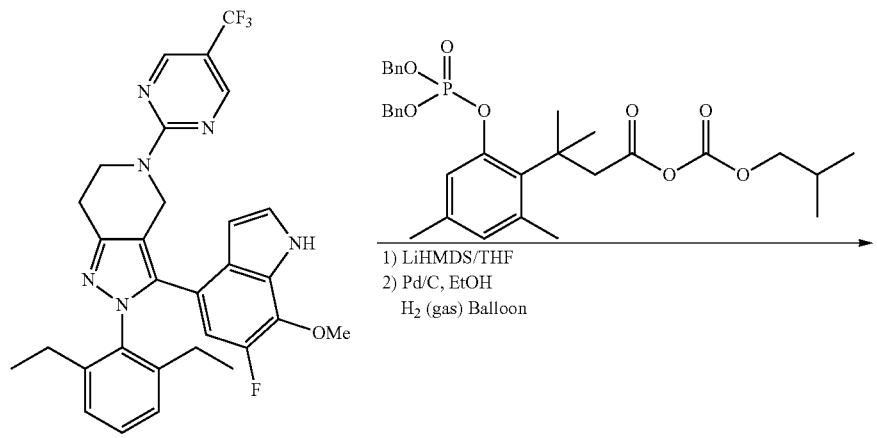

To a solution of 2-(2,6-diethylphenyl)-3-(6-fluoro-7-methoxy-1H-indol-4-yl)-5-(5-(trifluoromethyl)pyrimidin-2-yl)-4,5,6,7-tetrahydro-2H-pyrazolo[4,3-c]pyridine (150 mg, 0.27 mmol) in THF (5 mL) was added 1M LiHMDS in THF (0.43 mL, 0.43 mmol) at −78° C. After stirring for 30 min, a solution of 3-(2-((bis(benzyloxy)phosphoryl)oxy)-4,6-dimethylphenyl)-3-methylbutanoic (isobutyl carbonic) anhydride (193 mg, 0.33 mmol) in THF (2.5 mL) was added at −78° C. and stirred for 1 h. The mixture was warmed to room temperature and stirred for 2 h. After completion of, saturated NH$_4$Cl solution was added, and the mixture was extracted with EtOAc. The organic layers were combined, dried over Na$_2$SO$_4$, filtered, and concentrated. The residue was purified by silica gel column chromatography (10 to 40% EtOAc in hexanes) to give dibenzyl (2-(4-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)-2-methyl-4-oxobutan-2-yl)-3,5-dimethylphenyl)phosphate.

To a solution of the resulting phosphate (120 mg, 0.12 mmol) in ethanol (5 mL) was added 10% Pd/C (100 mg) at

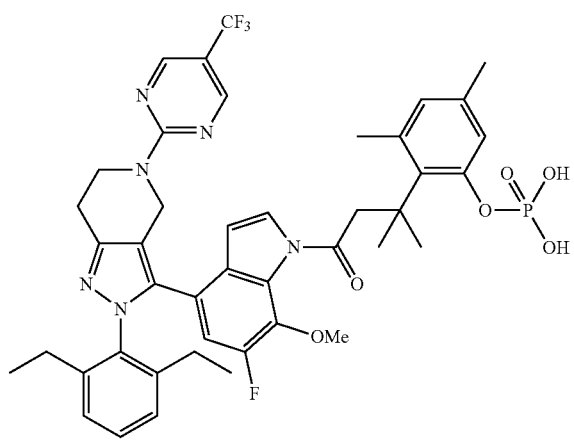

room temperature. The resulting mixture was stirred under a hydrogen (balloon) atmosphere for 1 h at room temperature. The reaction mixture was filtered through Celite and the filtrate was concentrated under reduced pressure to give 2-(4-(4-(2-(2,6-diethylphenyl)-5-(5-(trifluoromethyl)pyrimidin-2-yl)-4,5,6,7-tetrahydro-2H-pyrazolo[4,3-c]pyridin-3-yl)-6-fluoro-7-methoxy-1H-indol-1-yl)-2-methyl-4-oxobutan-2-yl)-3,5-dimethylphenyl dihydrogen phosphate. $^1$H NMR (400 MHz, DMSO-d$_6$) δ 8.74 (br s, 2H), 7.89 (d, J=1.2 Hz, 1H), 7.30-7.38 (m, 1H), 7.21 (br s, 2H), 7.07 (d, J=6.2 Hz, 2H), 6.96 (s, 1H), 6.64 (s, 1H), 6.54 (s, 1H), 6.46-6.50 (m, 2H), 4.76 (bs, 2H), 4.25-4.45 (m, 2H), 3.72 (s, 6H), 2.91 (br s, 2H), 2.46 (br s, 5H), 2.14 (s, 3H), 1.65-2.05 (m, 4H), 0.80-1.20 (m, 6H). MS: (ES) m/z calculated for C$_{43}$H$_{45}$F$_4$N$_6$O$_6$P [M+H]$^+$ 849.31, found 849.2.

Example 60: Synthesis of (4-phosphonooxyphenyl) methyl N-((4-(5-((2,4-bis(trifluoromethyl)-phenyl)methyl)-2-(2,6-diethylphenyl)-6,6-dimethyl-4H-pyrrolo[3,4-c]pyrazol-3-yl)-2,5-difluoro-phenyl)carbamoyl)carbamate

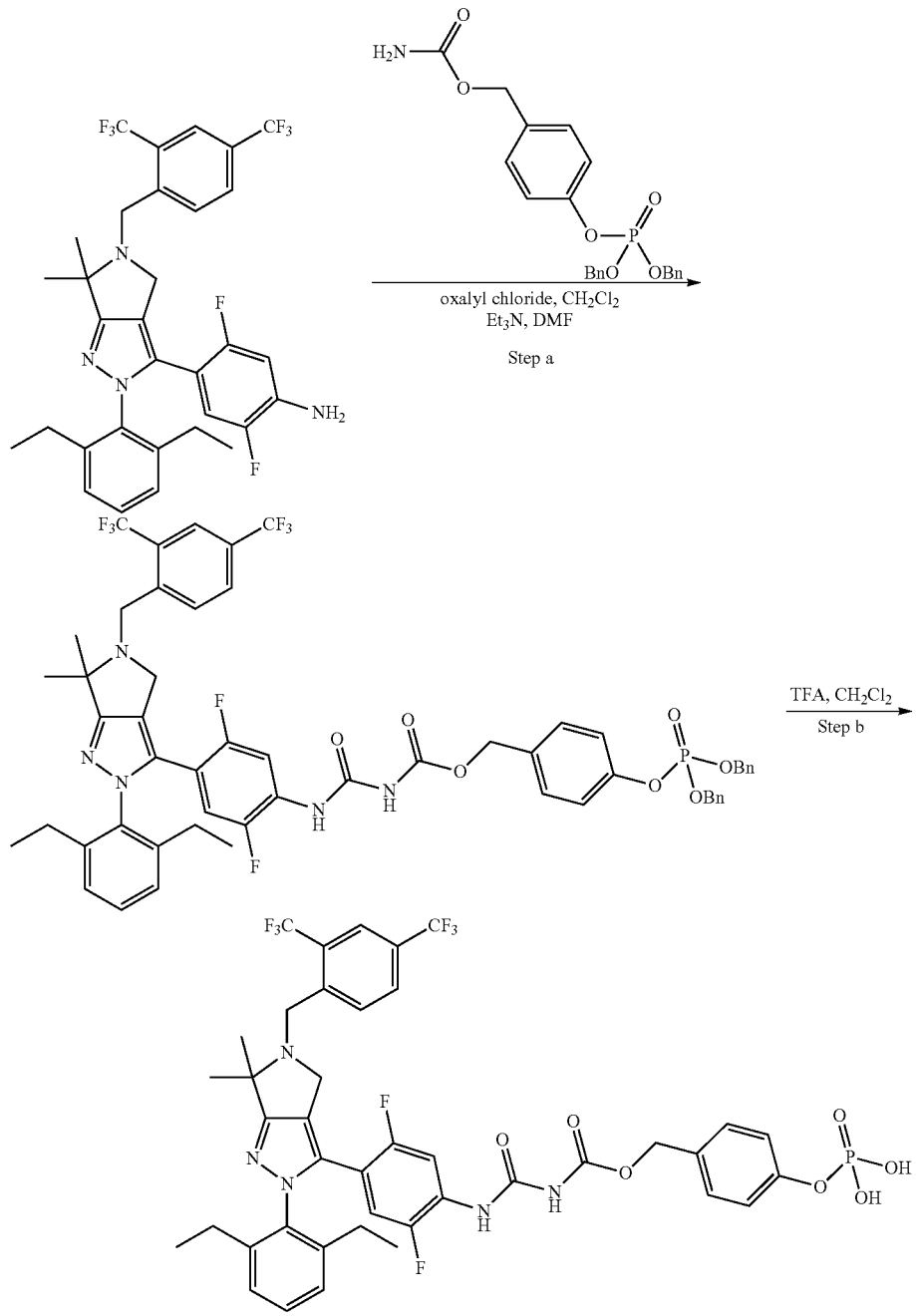

column chromatography (20 to 80% EtOAc in hexanes) to give 4-((bis(benzyloxy)phosphoryl)oxy)benzyl carbamate. MS: (ES) m/z calculated for $C_{22}H_{22}NO_6P$ [M+H]$^+$ 428.1, found 428.1.

To a solution of 4-((bis(benzyloxy)phosphoryl)oxy)benzyl carbamate (700 mg, 1.63 mmol) in dichloromethane (12

Step a: To a solution of dibenzyl-4-(hydroxymethyl)phenyl)phosphate (3.56 g, 9.24 mmol) in 2.4 mL of THF at 0° C. was added diisopropylethylamine (2.98, 23.1 mmol) and triphosgene (3.0 g, 10.1 mmol). After stirring at 0° C. for 1 h, NH$_4$OH (5.0 mL, 41 mmol) was added. The mixture was stirred at room temperature for 16 h then concentrated in vacuo and the resultant residue was purified by silica gel mL) at 0° C. was added oxalyl chloride (0.3 g, 2.45 mmol). After stirring at 0° C. for 1 h, the mixture was heated at 50° C. for 16 h then concentrated in vacuo. The residue was dissolved in THF (2 mL) and added to a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluoroaniline (150 mg, 0.16 mmol) in THF (2 mL). The mixture was stirred at room temperature for 5 h then concentrated in vacuo. The residue was purified by silica gel column chromatography (0 to 100% EtOAc in hexanes) to give (4-dibenzyloxyphosphoryloxy-3-phenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate.

Step b: To a solution of 4-dibenzyloxyphosphoryloxy-3-phenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate (150 mg, 0.14 mmol) in dichloromethane (2 mL) was added dropwise 1:1 mixture of TFA:CH$_2$Cl$_2$ (2 mL) and H$_2$O (0.4 mL) The mixture was heated at 50° C. for 48 h, then concentrated in vacuo. The residue was purified on HPLC (MeCN/H$_2$O, with 0.1% TFA) to yield (4-phosphonooxyphenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluoro-phenyl)carbamoyl)carbamate. $^1$H NMR (400 MHz, DMSO-d$_6$) δ 10.78 (s, 1H), 10.15 (s, 1H), 8.14 (d, J=8.4 Hz, 1H), 7.95-8.08 (m, 3H), 7.35-7.45 (m, 3H), 7.08-7.25 (m, 4H), 6.53 (dd, J=6.7, 11.7 Hz, 1H), 5.11 (s, 2H), 4.12 (br s, 2H), 3.65 (br s, 2H), 2.05-2.25 (m, 4H), 1.43 (s, 6H), 0.96 (t, J=7.4 Hz, 6H). MS: (ES) m/z calculated for C$_{41}$H$_{38}$F$_8$N$_5$O$_7$P [M+H]$^+$ 896.2, found 896.2.

Example 61: 4-(benzyloxy(hydroxy)phosphoryl)oxyphenyl)methyl N-((4-(5-((2,4-bis(trifluoromethyl)phenyl)methyl)-2-(2,6-diethylphenyl)-6,6-dimethyl-4H-pyrrolo[3,4-c]pyrazol-3-yl)-2,5-difluorophenyl)carbamoyl)carbamate

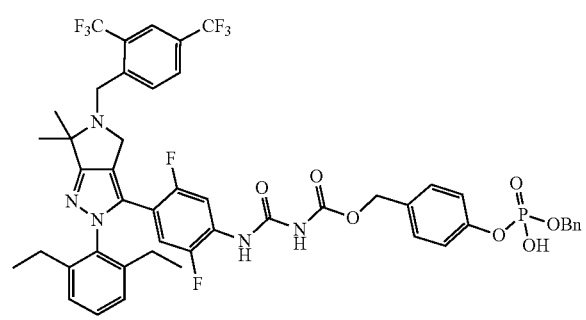 [SMILES: CCc1cccc(CC)c1-n1nc2c(c1-c1cc(F)c(NC(=O)NC(=O)OCc3ccc(OP(=O)(O)OCc4ccccc4)cc3)cc1F)CN(Cc1ccc(C(F)(F)F)cc1C(F)(F)F)C2(C)C]

The step b of Example 60 also gave Example 61. $^1$H NMR (400 MHz, DMSO-d$_6$) δ 10.79 (s, 1H), 10.14 (br s, 1H), 8.14 (d, J=7.0 Hz, 1H), 7.85-8.10 (m, 3H), 7.25-7.40 (m, 7H), 7.20 (d, J=22.2 Hz, 2H), 7.14 (d, J=9.0 Hz, 2H), 6.53 (dd, J=6.7, 11.4 Hz, 1H), 5.13 (s, 2H), 4.99 (d, J=7.9 Hz, 2H), 4.12 (br s, 2H), 3.65 (br s, 2H), 2.10-2.25 (m, 4H), 1.43 (s, 6H), 0.96 (t, J=7.4 Hz, 6H). MS: (ES) m/z calculated for C$_{48}$H$_{44}$F$_8$N$_5$O$_7$P [M+H]$^+$ 986.3, found 986.3.

Example 62: Synthesis of N-((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)carbamoyl)-2-(dimethylamino)acetamide

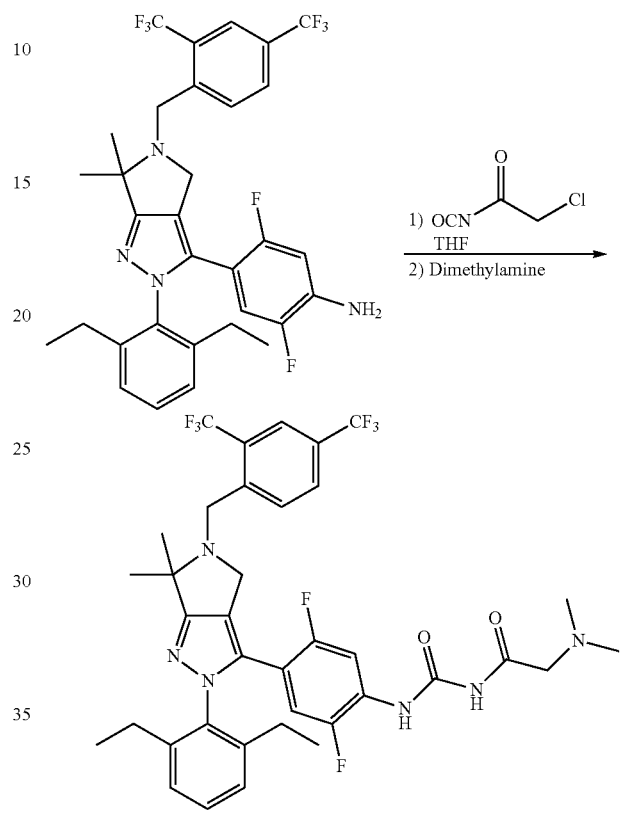

To a stirred solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluoroaniline (400 mg, 0.64 mmol) in THF (5 mL) was added 2-chloroacetyl isocyanate at room temperature. After and stirring for 16 h, the mixture was quenched with H$_2$O and extracted with EtOAc. The combined organic layers were dried with sodium sulfate, filtered and concentrated in vacuo to give N-((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)carbamoyl)-2-chloroacetamide.

To a solution of N-((4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)carbamoyl)-2-chloroacetamide form above (125 mg, 0.17 mmol) in THF (5 mL) was added dimethylamine (0.35 mL, 0.34 mmol) at room temperature. The reaction mixture was stirred for 16 h then concentrated in vacuo. The residue was purified by HPLC (H$_2$O/ACN, 0.1% TFA) to give 5-difluorophenyl)carbamoyl)-2-(400 MHz, DMSO-d$_6$) δ 11.3 (br s, 1H), 10.3 (br s, 1H), 9.85 (br s, 1H), 7.90-8.25 (m, 4H), 7.40-7.45 (m, 1H), 7.20-7.28 (m, 2H), 6.55-6.65 (m, 1H), 4.10-4.35 (m, 3H), 3.70 (br s, 2H), 2.83 (s, 6H), 2.17 (q, J=8.2 Hz, 4H), 1.45 (s, 6H), 0.95 (t, J=7.4 Hz, 6H). MS: (ES) m/z calculated for C$_{37}$H$_{38}$F$_8$N$_6$O$_2$P [M+H]$^+$ 751.3, found 751.2.

Example 63: Synthesis of 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)-3-(pyrrolidin-1-ylmethyl)urea

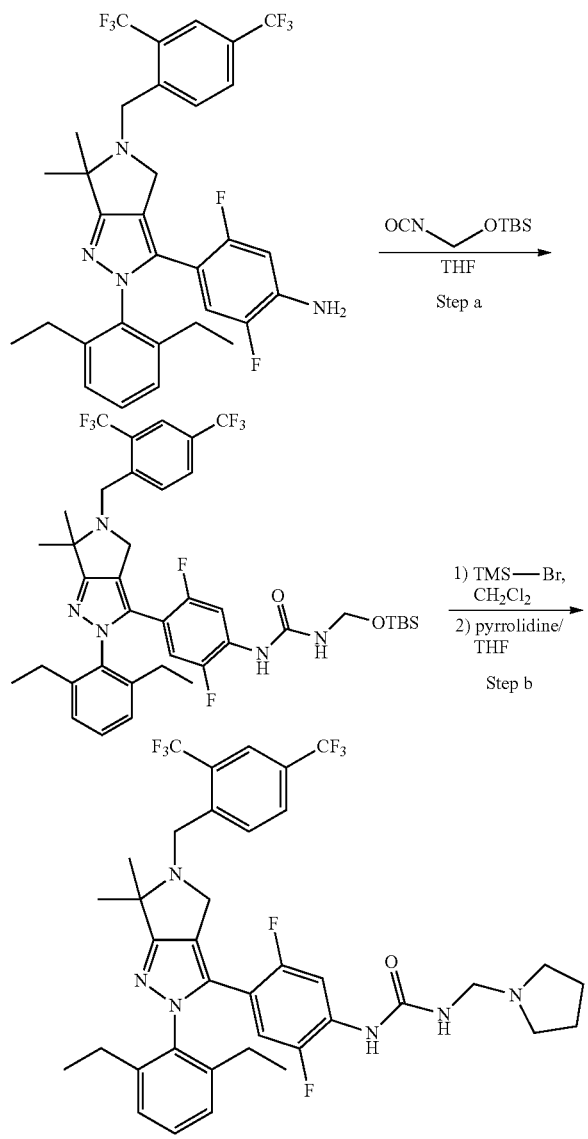

Step a: To a stirred solution of 2-hydroxyacetic acid (5.0 g, 65.7 mmol) in dichloromethane (100 mL) at 0° C., were added imidazole (11.7 g, 164.3 mmol) and TBSCl (19.7 g, 131.4 mmol). The reaction mixture was stirred for 16 h at room temperature. The reaction mixture was quenched with dropwise addition of saturated aqueous NaHCO₃ and extracted with dichloromethane. The organic layer was washed with brine, dried over Na₂SO₄, filtered and concentrated. The crude material was used directly in the next step without further purification.

To a solution of 2-tert-butyldimethylsilyloxy acetic acid (10.0 g, 32.6 mmol) in 50 mL of dichlromethane at 0° C. was added oxalylchloride (8.23 g, 65.3 mmol). The reaction mixture was stirred for 3 h at room temperature, After completion of the reaction, the solvent was removed under reduced pressure and dried under vacuum. The crude material was used directly in the next step.

To a stirred solution of 2-tert-butyldimethylsilyloxy acetyl chloride (5.0 g, 15.4 mmol) in 1:1 mixture of Acetone:H₂O (30 mL) was added NaN₃ (2.5 g, 38.5 mmol) at room temperature and stirred for 2 h. After completion, the solvent was removed under reduced pressure and the mixture was extracted with EtOAc. The combined organic layers were dried with sodium sulfate, filtered and concentrated in vacuo to give 2-tert-butyldimethylsilyloxy acetyl azide. The azide (3.2 g 1.63 mmol) was dissolved in 20 mL of chloroform at room temperature and the mixture was heated at 80° C. for 2 h. The solvent was removed in vacuo and used directly in the next step.

To a solution of tert-butyl(isocyanatomethoxy)dimethylsilane (0.56 g) was dissolved in THF (5 mL) and added to a solution of 4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluoroaniline (1.25 g, 2.0 mmol) in THF (10 mL). The mixture was stirred at room temperature for 5 h then concentrated in vacuo. The residue was purified by silica gel column chromatography (0 to 100% EtOAc in hexanes, with 1% Et₃N) to give 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)-3-(((tert-butyldimethylsilyl)oxy)methyl)urea. MS: (ES) m/z calculated for $C_{40}H_{47}F_8N_5O_2Si$ [M+H]⁺ 810.3, found 810.1.

Step b: To a solution of 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)-3-(((tert-butyldimethylsilyl)oxy)methyl)urea (150 mg, 0.19 mmol) in dichloromethane (3 mL) was added dropwise TMSBr (84 mg, 0.55 mmol) at 0° C. The mixture was stirred at room temperature for 1 h, concentrated in vacuo. This material was dissolved in dichloromethane (4.0 mL) and pyrrolidine (65 mg, 0.92 mmol) was added. The mixture was stirred at room temperature for 4 h then concentrated in vacuo. The residue was purified by HPLC (MeCN/H₂O, with 0.1% TFA) to give 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)-3-(pyrrolidin-1-ylmethyl)urea. ¹H NMR (400 MHz, CD₃OD) δ 8.19 (d, J=5.9, Hz, 1H), 8.00-8.10 (m, 3H), 7.42-7.48 (m, 1H), 7.20-7.35 (m, 2H), 6.45 (dd, J=6.6, 11.7 Hz, 1H), 4.61 (s, 2H), 4.35-4.55 (m, 2H), 3.85-4.20 (m, 2H), 3.45-3.55 (m, 2H), 3.10-3.35 (m, 3H), 2.25 (q, J=7.4 Hz, 4H), 1.90-2.18 (m, 5H), 1.65 (s, 6H), 1.06 (t, J=7.8 Hz, 6H). MS: (ES) m/z calculated for $C_{38}H_{40}F_8N_6O$ [M+H]⁺ 749.3, found 749.2.

Example 64: Synthesis of 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)-3-(hydroxymethyl)urea

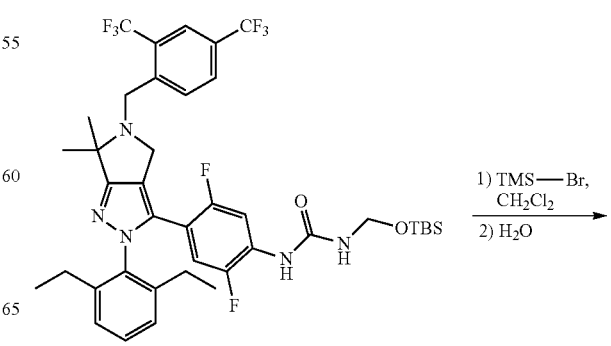

-continued

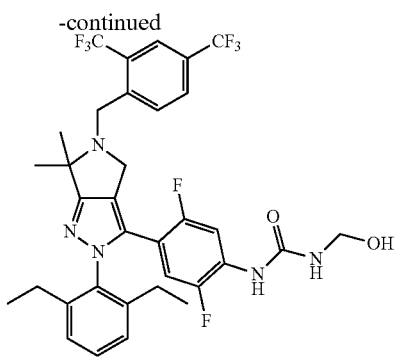

Step a: To a solution of 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)-3-(((tert-butyldimethylsilyl)oxy)methyl)urea (200 mg, 0.24 mmol) in dichloromethane (1.4 mL) was added dropwise TMSBr (0.11 mL, 0.86 mmol). The mixture was stirred at room temperature for 1 h, then concentrated in vacuo and purified by HPLC (MeCN/H$_2$O, with 0.1% TFA) to give 1-(4-(5-(2,4-bis(trifluoromethyl)benzyl)-2-(2,6-diethylphenyl)-6,6-dimethyl-2,4,5,6-tetrahydropyrrolo[3,4-c]pyrazol-3-yl)-2,5-difluorophenyl)-3-(hydroxymethyl)urea. $^1$H NMR (400 MHz, CD$_3$OD) δ 8.00-8.25 (m, 4H), 7.42-7.50 (m, 1H), 7.25-7.30 (m, 2H), 6.36-6.45 (m, 1H), 4.75 (br s, 1H), 4.40-4.70 (m, 5H), 2.25 (q, J=7.4 Hz, 4H), 1.80-1.95 (m, 6H), 1.04 (t, J=3.5 Hz, 6H). MS: (ES) m/z calculated for C$_{34}$H$_{33}$F$_8$N$_5$O$_2$ [M+H]$^+$ 696.3, found 696.3.

Example 65

This example illustrates the evaluation of the biological activity associated with specific compounds of the invention.
Materials and Methods
Cells C5a Receptor Expressing Cells U937 Cells
U937 cells are a monocytic cell line which express C5aR, and are available from ATCC (VA). These cells were cultured as a suspension in RPMI-1640 medium supplemented with 2 mM L-glutamine, 1.5 g/L sodium bicarbonate, 4.5 g/L glucose, 10 mM HEPES, 1 mM sodium pyruvate, and 10% FBS. Cells were grown under 5% CO$_2$/95% air, 100% humidity at 37° C. and subculture twice weekly at 1:6 (cells were cultured at a density range of 1×10$^5$ to 2×10$^6$ cells/mL) and harvested at 1×10$^6$ cells/mL. Prior to assay, cells are treated overnight with 0.5 mM of cyclic AMP (Sigma, OH) and washed once prior to use. cAMP treated U937 cells can be used in C5aR ligand binding and functional assays.
Isolated Human Neutrophils
Optionally, human or murine neutrophils can be used to assay for compound activity. Neutrophils may be isolated from fresh human blood using density separation and centrifigation. Briefly, whole blood is incubated with equal parts 3% dextran and allowed to separate for 45 minutes. After separation, the top layer is layered on top of 15 mls of Ficoll (15 mls of Ficoll for every 30 mls of blood suspension) and centrifuged for 30 minutes at 400×g with no brake. The pellet at the bottom of the tube is then isolated and resuspended into PharmLyse RBC Lysis Buffer (BD Biosciences, San Jose, Calif.) after which the sample is again centrifuged for 10 minutes at 400×g with brake. The remaining cell pellet is resuspended as appropriate and consists of isolated neutrophils.
Assays Inhibition of C5aR Ligand Binding cAMP treated U937 cells expressing C5aR were centrifuged and resuspended in assay buffer (20 mM HEPES pH 7.1, 140 mM NaCl, 1 mM CaCl$_2$, 5 mM MgCl$_2$, and with 0.1% bovine serum albumin) to a concentration of 3×10$^6$ cells/mL. Binding assays were set up as follows. 0.1 mL of cells was added to the assay plates containing 5 μL of the compound, giving a final concentration of ~2-10 μM each compound for screening (or part of a dose response for compound IC$_{50}$ determinations). Then 0.1 mL of $^{125}$I labeled C5a (obtained from Perkin Elmer Life Sciences, Boston, Mass.) diluted in assay buffer to a final concentration of ~50 μM, yielding~30,000 cpm per well, was added, the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 μl; Microscint 20, Packard Instruments) was added to each well, the plates were sealed and radioactivity measured in a Topcount scintillation counter (Packard Instruments). Control wells containing either diluent only (for total counts) or excess C5a (1 μg/mL, for non-specific binding) were used to calculate the percent of total inhibition for compound. The computer program Prism from GraphPad, Inc. (San Diego, Ca) was used to calculate IC$_{50}$ values. IC$_{50}$ values are those concentrations required to reduce the binding of radiolabeled C5a to the receptor by 50%. (For further descriptions of ligand binding and other functional assays, see Dairaghi, et al., *J. Biol. Chem.* 274: 21569-21574 (1999), Penfold, et al., Proc. Natl. Acad. Sci. USA. 96:9839-9844 (1999), and Dairaghi, et al., *J. Biol. Chem.* 272:28206-28209 (1997)).

Calcium Mobilization

Optionally, compounds may be further assayed for their ability to inhibit calcium flux in cells. To detect the release of intracellular stores of calcium, cells (e.g., cAMP stimulated U937 or neutrophils) are incubated with 3 μM of INDO-1AM dye (Molecular Probes; Eugene, Oreg.) in cell media for 45 minutes at room temperature and washed with phosphate buffered saline (PBS). After INDO-1AM loading, the cells are resuspended in flux buffer (Hank's balanced salt solution (HBSS) and 1% FBS). Calcium mobilization is measured using a Photon Technology International spectrophotometer (Photon Technology International; New Jersey) with excitation at 350 nm and dual simultaneous recording of fluorescence emission at 400 nm and 490 nm. Relative intracellular calcium levels are expressed as the 400 nm/490 nm emission ratio. Experiments are performed at 37° C. with constant mixing in cuvettes each containing 10$^6$ cells in 2 mL of flux buffer. The chemokine ligands may be used over a range from 1 to 100 nM. The emission ratio is plotted over time (typically 2-3 minutes). Candidate ligand blocking compounds (up to 10 μM) are added at 10 seconds, followed by chemokines at 60 seconds (i.e., C5a; R&D Systems; Minneapolis, Minn.) and control chemokine (i.e., SDF-1α; R&D Systems; Minneapolis, Minn.) at 150 seconds.
Chemotaxis Assays
Optionally, compounds may be further assayed for their ability to inhibit chemotaxis in cells. Chemotaxis assays are performed using 5 µm pore polycarbonate, polyvinylpyrrolidone-coated filters in 96-well chemotaxis chambers (Neuroprobe; Gaithersburg, Md.) using chemotaxis buffer (Hank's balanced salt solution (HMS) and 1% FBS). C5aR ligands (i.e., C5a, R&D Systems; Minneapolis, Minn.) are use to evaluate compound mediated inhibition of C5aR mediated migration. Other chemokines (i.e., SDF-1α; R&D Systems; Minneapolis, Minn.) are used as specificity controls. The lower chamber is loaded with 29 µl of chemokine (i.e., 0.03 nM C5a) and varying amounts of compound; the top chamber contains 100,000 U937 or neutrophil cells in 20 µl. The chambers are incubated 1.5 hours at 37° C., and the number of cells in the lower chamber quantified either by direct cell counts in five high powered fields per well or by the CyQuant assay (Molecular Probes), a fluorescent dye method that measures nucleic acid content and microscopic observation.

Identification of Inhibitors of C5aR

Assay

To evaluate small organic molecules that prevent the C5a receptor from binding ligand, an assay was employed that detected radioactive ligand (i.e, C5a) binding to cells expressing C5aR on the cell surface (for example, cAMP stimulated U937 cells or isolated human neutrophils). For compounds that inhibited binding, whether competitive or not, fewer radioactive counts are observed when compared to uninhibited controls.

Equal numbers of cells were added to each well in the plate. The cells were then incubated with radiolabeled C5a. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

$$\% \text{ inhibition} = (1 - [(\text{sample } cpm) - (\text{nonspecific } cpm)] / [(\text{total } cpm) - (\text{nonspecific } cpm)]) \times 100.$$

Dose Response Curves

To ascertain a candidate compound's affinity for C5aR as well as confirm its ability to inhibit ligand binding, inhibitory activity was titered over a $1 \times 10^{-10}$ to $1 \times 10^{-4}$ M range of compound concentrations. In the assay, the amount of compound was varied; while cell number and ligand concentration were held constant.

In Vivo Efficacy Models

The compounds of interest can be evaluated for potential efficacy in treating a C5a mediated conditions by determining the efficacy of the compound in an animal model. In addition to the models described below, other suitable animal models for studying the compound of interest can be found in Mizuno, M. et al., *Expert Opin. Investig. Drugs* (2005), 14(7), 807-821, which is incorporated herein by reference in its entirety.

Models of C5a Induced Leukopenia

C5a Induced Leukopenia in a Human C5aR Knock-in Mouse Model

To study the efficacy of compounds of the instant invention in an animal model, a recombinant mouse can be created using standard techniques, wherein the genetic sequence coding for the mouse C5aR is replaced with sequence coding for the human C5aR, to create a hC5aR-KI mouse. In this mouse, administration of hC5a leads to upregulation of adhesion molecules on blood vessel walls which bind blood leukocytes, sequestering them from the blood stream. Animals are administered 20 ug/kg of hC5a and 1 minute later leukocytes are quantified in peripheral blood by standard techniques. Pretreatment of mice with varying doses of the present compounds can almost completely block the hC5a induced leukopenia.

C5a Induced Leukopenia in a Cynomolgus Model

To study the efficacy of compounds of the instant invention in a non-human primate model model, C5a induced leucopenia is studied in a cynomolgus model. In this model administration of hC5a leads to upregulation of adhesion molecules on blood vessel walls which bind blood leukocytes, hence sequestering them from the blood stream. Animals are administered 10 ug/kg of hC5a and 1 minute later leukocytes are quantified in peripheral blood.

Mouse Model of ANCA Induced Vasculitis

On day 0 hC5aR-KI mice are intraveneously injected with 50 mg/kg purified antibodiy to myeloperoxidase (Xiao et al, *J. Clin. Invest.* 110: 955-963 (2002)). Mice are further dosed with oral daily doses of compounds of the invention or vehicle for seven days, then mice are sacrificed and kidneys collected for histological examination. Analysis of kidney sections can show significantly reduced number and severity of crescentic and necrotic lesions in the glomeruli when compared to vehicle treated animals.

Mouse Model of Choroidal Neovascularization

To study the efficacy of compounds of the instant invention in treatment of age related macular degeneration (AMD) the bruch membrane in the eyes of hC5aR-KI mice are ruptured by laser photocoagulation (Nozika et al, *PNAS* 103: 2328-2333 (2006). Mice are treated with vehicle or a daily oral or appropriate intra-vitreal dose of a compound of the invention for one to two weeks. Repair of laser induced damage and neovascularization are assessed by histology and angiography.

Rheumatoid Arthritis Models

Rabbit Model of Destructive Joint Inflammation

To study the effects of candidate compounds on inhibiting the inflammatory response of rabbits to an intra-articular injection of the bacterial membrane component lipopolysaccharide (LPS), a rabbit model of destructive joint inflammation is used. This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al, *J. Immunol.* 169(11):6435-6444 (2002)).

A rabbit LPS study is conducted essentially as described in Podolin, et al. ibid., female New Zealand rabbits (approximately 2 kilograms) are treated intra-articularly in one knee with LPS (10 ng) together with either vehicle only (phosphate buffered saline with 1% DMSO) or with addition of candidate compound (dose 1=50 µM or dose 2=100 µM) in a total volume of 1.0 mL. Sixteen hours after the LPS injection, knees are lavaged and cells counts are performed. Beneficial effects of treatment were determined by histopathologic evaluation of synovial inflammation. Inflammation scores are used for the histopathologic evaluation: 1—minimal, 2—mild, 3—moderate, 4—moderate-marked.
Evaluation of a Compound in a Rat Model of Collagen Induced Arthritis A 17 day developing type II collagen arthritis study is conducted to evaluate the effects of a candidate compound on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3): 857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 mg/mL bovine type II collagen at the base of the tail and two sites on the back on days 0 and 6 of this 17 day study. A candidate compound is dosed daily in a sub-cutaneous manner from day 0 till day 17 at a efficacious dose. Caliper measurements of the ankle joint diameter were taken, and reducing joint swelling is taken as a measure of efficacy.

Rat Model of Sepsis

To study the effect of compounds of interest on inhibiting the generalized inflammatory response that is associated with a sepsis like disease, the Cecal Ligation and Puncture (CLP) rat model of sepsis is used. A Rat CLP study is conducted essentially as described in Fujimura N, et al. (*American Journal Respiratory Critical Care Medicine* 2000; 161: 440-446). Briefly described here, Wistar Albino Rats of both sexes weighing between 200-250 g are fasted for twelve hours prior to experiments. Animals are kept on normal 12 hour light and dark cycles and fed standard rat chow up until 12 hours prior to experiment. Then animals are split into four groups; (i) two sham operation groups and (ii) two CLP groups. Each of these two groups (i.e., (i) and (ii)) is split into vehicle control group and test compound group. Sepsis is induced by the CLP method. Under brief anesthesia a midline laparotomy is made using minimal dissection and the cecum is ligated just below the ileocaecal valve with 3-0 silk, so the intestinal continuity is maintained. The antimesinteric surface of the cecum is perforated with an 18 gauge needle at two locations 1 cm apart and the cecum is gently squeezed until fecal matter is extruded. The bowel is then returned to the abdomen and the incision is closed. At the end of the operation, all rats are resuscitated with saline, 3 ml/100 g body weight, given subcutaneously. Postoperatively, the rats are deprived of food, but have free access to water for the next 16 hours until they are sacrificed. The sham operated groups are given a laparotomy and the cecum is manipulated but not ligated or perforated. Beneficial effects of treatment are measured by histopathological scoring of tissues and organs as well as measurement of several key indicators of hepatic function, renal function, and lipid peroxidation. To test for hepatic function aspartate transaminase (AST) and alanine transaminase (ALT) are measured. Blood urea nitrogen and creatinine concentrations are studied to assess renal function. Pro-inflammatory cytokines such as TNF-alpha and IL-1 beta are also assayed by ELISA for serum levels.

Mouse SLE Model of Experimental Lupus Nephritis.

To study the effect of compounds of interest on a Systemic Lupus Erythematosus (SLE), the MRL/lpr murine SLE model is used. The MRL/Mp-Tmfrsf6$^{lpr/lpr}$ strain (MRL/lpr) is a commonly used mouse model of human SLE. To test compounds efficacy in this model male MRL/lpr mice are equally divided between control and C5aR antagonists groups at 13 weeks of age. Then over the next 6 weeks compound or vehicle is administered to the animals via osmotic pumps to maintain coverage and minimize stress effects on the animals. Serum and urine samples are collected bi-weekly during the six weeks of disease onset and progression. In a minority of these mice glomerulosclerosis develops leading to the death of the animal from renal failure. Following mortality as an indicator of renal failure is one of the measured criteria and successful treatment will usually result in a delay in the onset of sudden death among the test groups. In addition, the presence and magnitude of renal disease may also be monitored continuously with blood urea nitrogen (BUN) and albuminuria measurements. Tissues and organs were also harvested at 19 weeks and subjected to histopathology and immunohistochemistry and scored based on tissue damage and cellular infiltration.

Rat Model of COPD

Smoke induced airway inflammation in rodent models may be used to assess efficacy of compounds in Chronic Obstructive Pulmonary Disease (COPD). Selective antagonists of chemokines have shown efficacy in this model (see, Stevenson, et al., *Am. J. Physiol Lung Cell Mol Physiol.* 288 L514-L522, (2005)). An acute rat model of COPD is conducted as described by Stevenson et al. A compound of interest is administered either systemically via oral or IV dosing; or locally with nebulized compound. Male Sprague-Dawley rats (350-400 g) are placed in Perspex chambers and exposed to cigarette smoke drawn in via a pump (50 mL every 30 seconds with fresh air in between). Rats are exposed for a total period of 32 minutes. Rats are sacrificed up to 7 days after initial exposure. Any beneficial effects of treatment are assessed by a decrease inflammatory cell infiltrate, decreases in chemokine and cytokine levels.

In a chronic model, mice or rats are exposed to daily tobacco smoke exposures for up to 12 months. Compound is administered systemically via once daily oral dosing, or potentially locally via nebulized compound. In addition to the inflammation observed with the acute model (Stevensen et al.), animals may also exhibit other pathologies similar to that seen in human COPD such as emphysema (as indicated by increased mean linear intercept) as well as altered lung chemistry (see Martorana et al, *Am. J. Respir. Crit Care Med.* 172(7): 848-53.

Mouse EAE Model of Multiple Sclerosis

Experimental autoimmune encephalomyelitis (EAE) is a model of human multiple sclerosis. Variations of the model have been published, and are well known in the field. In a typical protocol, C57BL/6 (Charles River Laboratories) mice are used for the EAE model. Mice are immunized with 200 ug myelin oligodendrocyte glycoprotein (MOG) 35-55 (Peptide International) emulsified in Complete Freund's Adjuvant (CFA) containing 4 mg/ml *Mycobacterium tuberculosis* (Sigma-Aldrich) s.c. on day 0. In addition, on day 0 and day 2 animals are given 200 ng of pertussis toxin (Calbiochem) i.v. Clinical scoring is based on a scale of 0-5: 0, no signs of disease; 1, flaccid tail; 2, hind limb weakness; 3, hind limb paralysis; 4, forelimb weakness or paralysis; 5, moribund. Dosing of the compounds of interest to be assessed can be initiated on day 0 (prophylactic) or day 7 (therapeutic, when histological evidence of disease is present but few animals are presenting clinical signs) and dosed once or more per day at concentrations appropriate for their activity and pharmacokinetic properties, e.g. 100 mg/kg s.c. Efficacy of compounds can be assessed by comparisons of severity (maximum mean clinical score in presence of compound compared to vehicle), or by measuring a decrease in the number of macrophages (F4/80 positive) isolated from spinal cords. Spinal cord mononuclear cells can be isolated via discontinuous Percoll-gradient. Cells can be stained using rat anti-mouse F4/80-PE or rat IgG2b-PE (Caltag Laboratories) and quantitated by FACS analysis using 10 ul of Polybeads per sample (Polysciences).

Mouse Model of Kidney Transplantation

Transplantation models can be performed in mice, for instance a model of allogenic kidney transplant from C57BL/6 to BALB/c mice is described in Faikah Gueler et al, JASN Express, Aug. 27, 2008. Briefly, mice are anesthetized and the left donor kidney attached to a cuff of the aorta and the renal vein with a small caval cuff, and the ureters removed en block. After left nephrectomy of the recipient, the vascular cuffs are anastomosed to the recipient abdominal aorta and vena cava, respectively, below the level of the native renal vessels. The ureter is directly anastomosed into the bladder. Cold ischemia time is 60 min, and warm ischemia time is 30 min. The right native kidney can be removed at the time of allograft transplantation or at post-transplantation day 4 for long-term survival studies. General physical condition of the mice is monitored for evidence of rejection. Compound treatment of animals can be started before surgery or immediately after transplantation, eg by sub cut injection once daily. Mice are studied for renal function and survival. Serum creatinine levels are measured by an automated method (Beckman Analyzer, Krefeld, Germany).

Mouse Model of Ischemia/Reperfusion

A mouse model of ischemia/reperfusion injury can be performed as described by Xiufen Zheng et al, *Am. J. Pathol*, Vol 173:4, October, 2008. Briefly, CD1 mice aged 6-8 weeks are anesthetized and placed on a heating pad to maintain warmth during surgery. Following abdominal incisions, renal pedicles are bluntly dissected and a microvascular clamp placed on the left renal pedicle for 25-30 minutes. Following ischemia the clamps are removed along with the right kidney, incisions sutured, and the animals allowed to recover. Blood is collected for serum creatinine and BUN analysis as an indicator of kidney health. Alternatively animal survival is monitored over time. Compound can be administered to animals before and/or after the surgery and the effects on serum creatinine, BUN or animal survival used as indicators of compound efficacy.

Mouse Model of Tumor Growth

C57BL/6 mice 6-16 weeks of age are injected subcutaneously with 1×105 TC-1 cells (ATCC, VA) in the right or left rear flank. Beginning about 2 weeks after cell injection, tumors are measured with calipers every 2-4 d until the tumor size required the mice are killed. At the time of sacrifice animals are subjected to a full necropsy and spleens and tumors removed. Excised tumors are measured and weighed. Compounds may be administered before and/or after tumor injections, and a delay or inhibition of tumor growth used to assess compound efficacy.

Intermediates 1 to 4 are potent C5aR antagonists with $IC_{50} \leq 5$ nM in the chemotaxis assay using U937 cells as described in Example 65. Characterization data for Examples 1-64 are provided in Table 1 (below).

TABLE 1

Structure, Characterization Data of Specific Embodiments

| Example No. | Structure | MS: (ES) m/z [M + H]$^+$ | $R_t$ (min) |
| --- | --- | --- | --- |
| 1 | 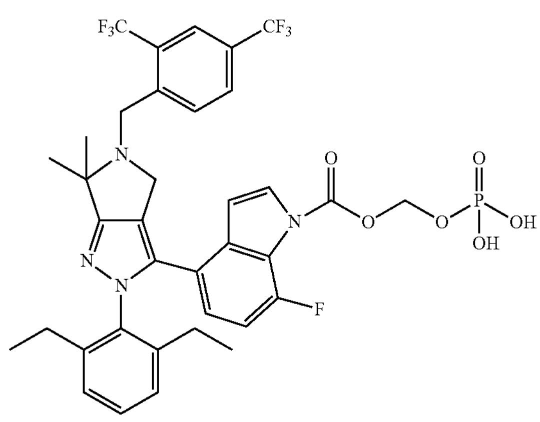 [SMILES: CCc1cccc(CC)c1-n1nc2c(c1-c1ccc(F)c3c1ccn3C(=O)OCOP(=O)(O)O)CN(Cc1ccc(C(F)(F)F)cc1C(F)(F)F)C2(C)C] | 783.2 | 2.37 (Method A) |

TABLE 1-continued
Structure, Characterization Data of Specific Embodiments
| Example No. | Structure | MS: (ES) m/z [M + H]+ | R$_t$ (min) |
|---|---|---|---|
| 2 | 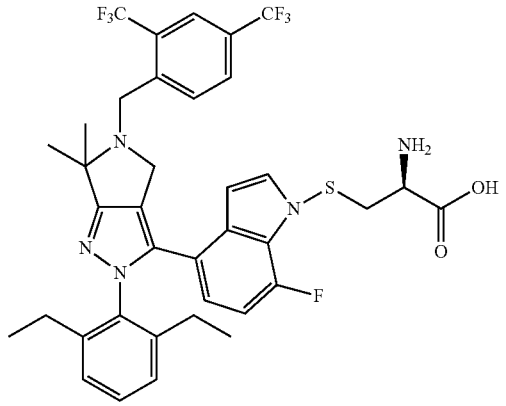 [SMILES: CCc1cccc(CC)c1-n1nc2c(c1-c1ccc(F)c3c1ccn3SC[C@@H](N)C(=O)O)CN(Cc1ccc(C(F)(F)F)cc1C(F)(F)F)C2(C)C] | 748.2 | 2.67 (method A) |
| 3 | 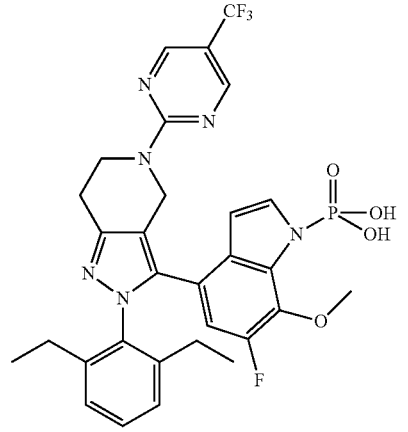 [SMILES: CCc1cccc(CC)c1-n1nc2c(c1-c1cc(F)c(OC)c3c1ccn3P(=O)(O)O)CN(c1ncc(C(F)(F)F)cn1)CC2] | 645.4 | 3.45 (Method A) |
| 4 | 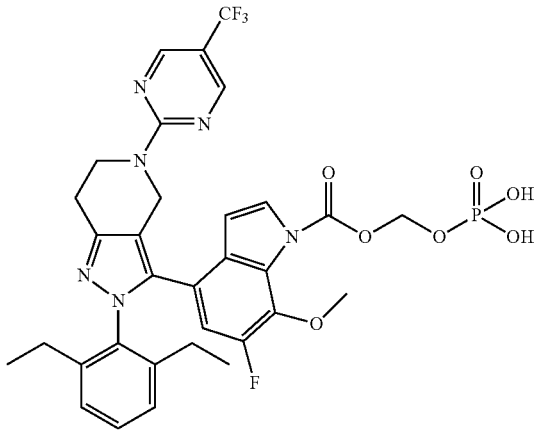 [SMILES: CCc1cccc(CC)c1-n1nc2c(c1-c1cc(F)c(OC)c3c1ccn3C(=O)OCOP(=O)(O)O)CN(c1ncc(C(F)(F)F)cn1)CC2] | 719.2 | 2.50 (Method A) |

TABLE 1-continued
Structure, Characterization Data of Specific Embodiments
| Example No. | Structure | MS: (ES) m/z [M + H]⁺ | R$_t$ (min) |
|---|---|---|---|
| 5 | 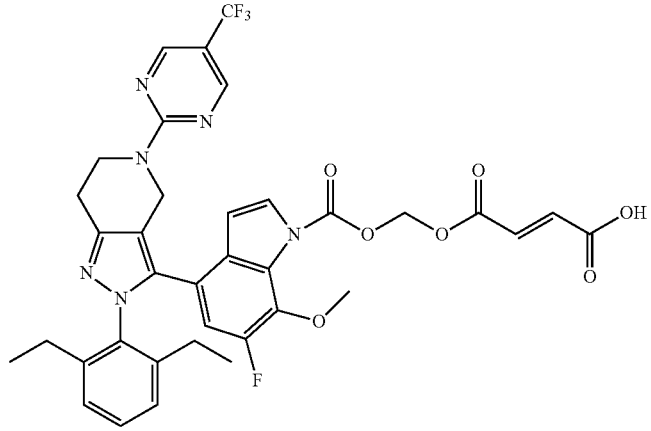 [SMILES: CCc1cccc(CC)c1-n1nc2c(c1-c1cc(F)c(OC)c3c1ccn3C(=O)OCOC(=O)/C=C/C(=O)O)CN(c1ncc(C(F)(F)F)cn1)CC2] | 737.2 | 3.07 (Method A) |
| 6 | 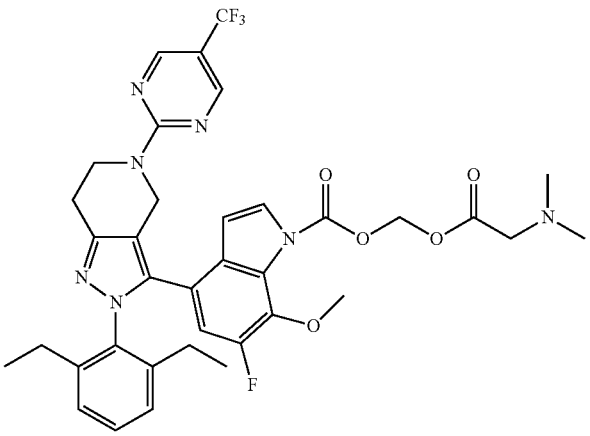 [SMILES: CCc1cccc(CC)c1-n1nc2c(c1-c1cc(F)c(OC)c3c1ccn3C(=O)OCOC(=O)CN(C)C)CN(c1ncc(C(F)(F)F)cn1)CC2] | 724.2 | 2.95 (Method A) |
| 7 | 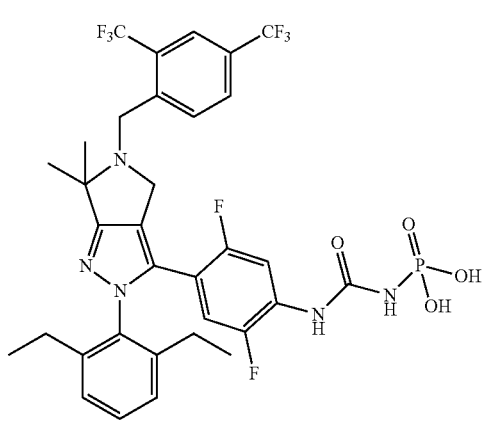 [SMILES: CCc1cccc(CC)c1-n1nc2c(c1-c1cc(F)c(NC(=O)NP(=O)(O)O)cc1F)CN(Cc1ccc(C(F)(F)F)cc1C(F)(F)F)C2(C)C] | 746.2 | 3.60 (Method A) |

TABLE 1-continued

Structure, Characterization Data of Specific Embodiments

| Example No. | Structure | MS: (ES) m/z [M + H]+ | R$_t$ (min) |
|---|---|---|---|
| 8 | 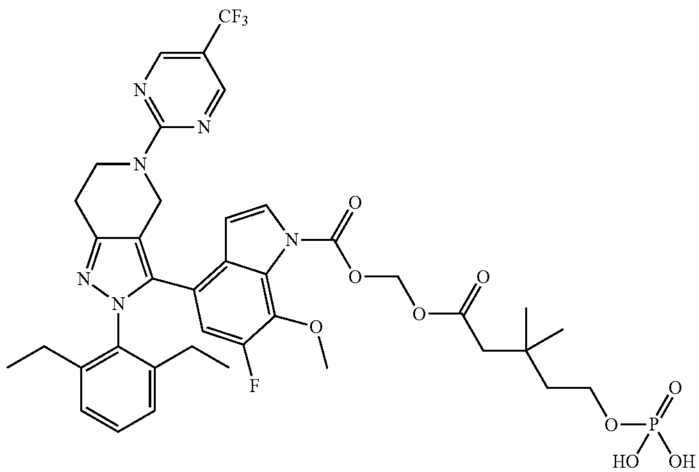 [SMILES: CCc1cccc(CC)c1-n1nc2c(c1-c1cc(F)c(OC)c3c1ccn3C(=O)OCOC(=O)CC(C)(C)CCOP(=O)(O)O)CN(c1ncc(C(F)(F)F)cn1)CC2] | 847.2 | 3.11 (Method A) |
| 9 | 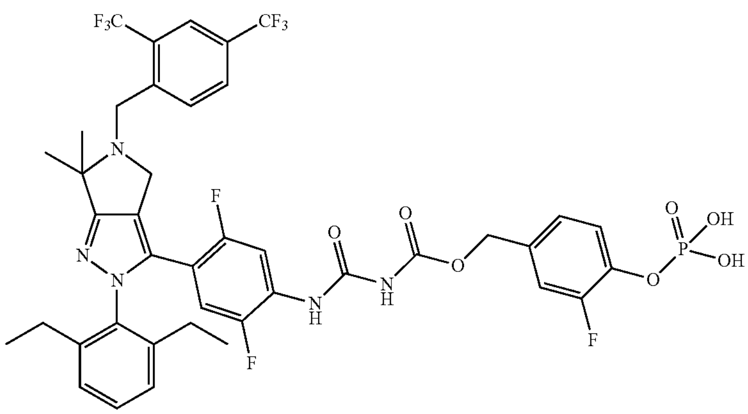 [SMILES: CCc1cccc(CC)c1-n1nc2c(c1-c1cc(F)c(NC(=O)NC(=O)OCc3ccc(OP(=O)(O)O)c(F)c3)cc1F)CN(Cc1ccc(C(F)(F)F)cc1C(F)(F)F)C2(C)C] | 914.1 | 2.68 (Method A) |
| 10 | 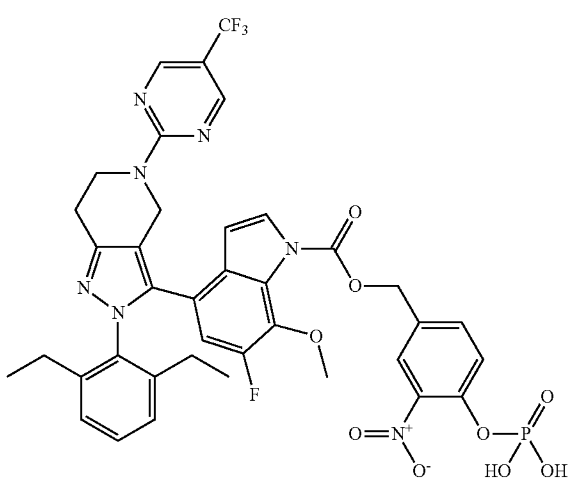 [SMILES: CCc1cccc(CC)c1-n1nc2c(c1-c1cc(F)c(OC)c3c1ccn3C(=O)OCc1ccc(OP(=O)(O)O)c([N+](=O)[O-])c1)CN(c1ncc(C(F)(F)F)cn1)CC2] | 840.0 | 2.73 (Method A) |

TABLE 1-continued

Structure, Characterization Data of Specific Embodiments

| Example No. | Structure | MS: (ES) m/z [M + H]+ | R_t (min) |
|---|---|---|---|
| 11 | 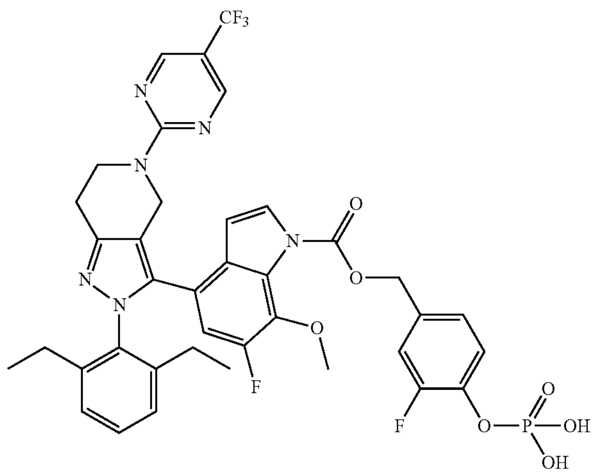 [SMILES: CCc1cccc(CC)c1-n1nc2c(c1-c1cc(F)c(OC)c3c1ccn3C(=O)OCc1ccc(OP(=O)(O)O)c(F)c1)CN(c1ncc(C(F)(F)F)cn1)CC2] | 813.2 | 2.76 (Method A) |
| 12 | 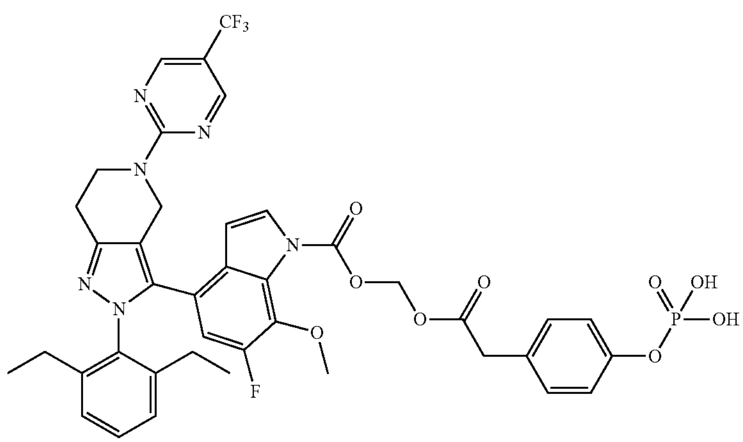 [SMILES: CCc1cccc(CC)c1-n1nc2c(c1-c1cc(F)c(OC)c3c1ccn3C(=O)OCOC(=O)Cc1ccc(OP(=O)(O)O)cc1)CN(c1ncc(C(F)(F)F)cn1)CC2] | 853.0 | 2.85 (Method A) |
| 13 | 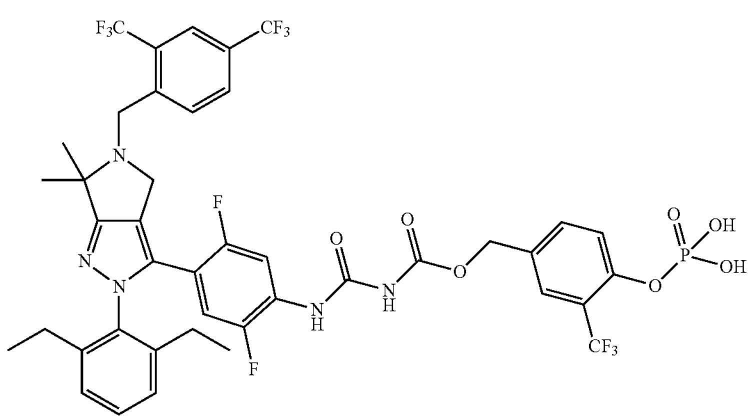 [SMILES: CCc1cccc(CC)c1-n1nc2c(c1-c1cc(F)c(NC(=O)NC(=O)OCc3ccc(OP(=O)(O)O)c(C(F)(F)F)c3)cc1F)CN(Cc1ccc(C(F)(F)F)cc1C(F)(F)F)C2(C)C] | 964.0 | 2.89 (Method A) |

TABLE 1-continued

Structure, Characterization Data of Specific Embodiments

| Example No. | Structure | MS: (ES) m/z [M + H]+ | R_t (min) |
|---|---|---|---|
| 14 | 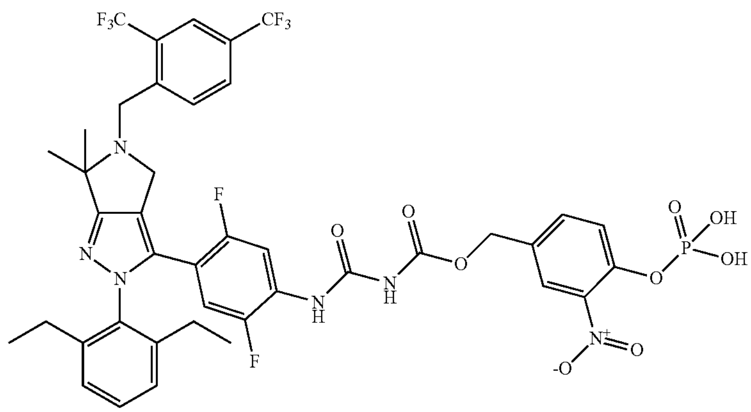 | 941.0 | 2.68 (Method A) |
| 15 | 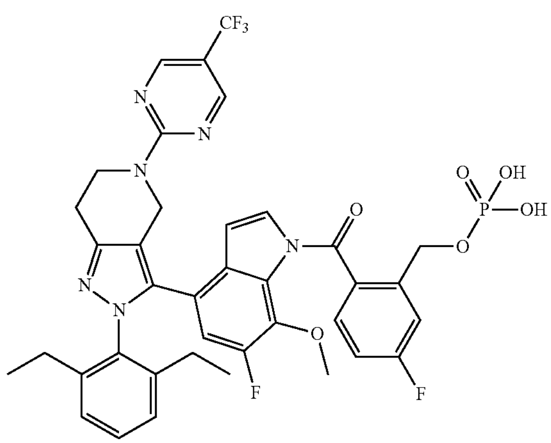 [SMILES: CCc1cccc(CC)c1-n1nc2c(c1-c1cc(F)c(OC)c3c1ccn3C(=O)c1ccc(F)cc1COP(=O)(O)O)CN(c1ncc(C(F)(F)F)cn1)CC2] | 797.1 | 2.92 (Method A) |
| 16 | 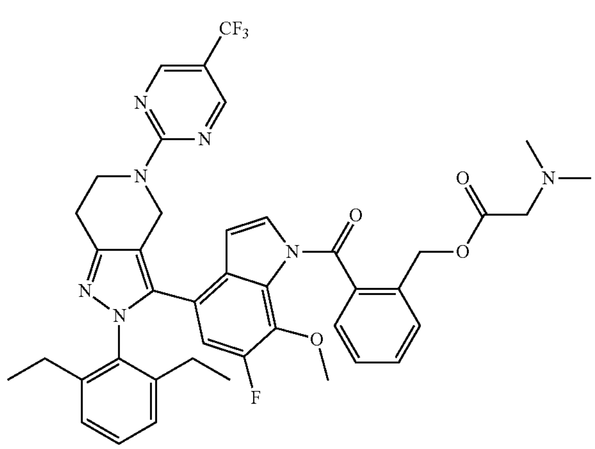 [SMILES: CCc1cccc(CC)c1-n1nc2c(c1-c1cc(F)c(OC)c3c1ccn3C(=O)c1ccccc1COC(=O)CN(C)C)CN(c1ncc(C(F)(F)F)cn1)CC2] | 784.2 | 3.18 (Method A) |

TABLE 1-continued

Structure, Characterization Data of Specific Embodiments

| Example No. | Structure | MS: (ES) m/z [M + H]+ | R_t (min) |
|---|---|---|---|
| 17 | 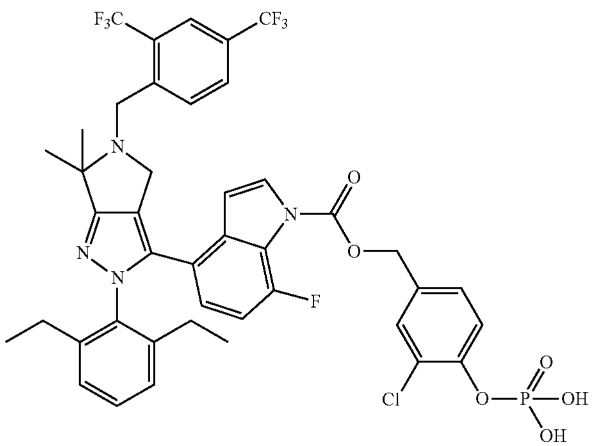 [SMILES: CCc1cccc(CC)c1-n1nc2c(c1-c1ccc(F)c3c1ccn3C(=O)OCc1ccc(OP(=O)(O)O)c(Cl)c1)CN(Cc1ccc(C(F)(F)F)cc1C(F)(F)F)C2(C)C] | 893.1 | 2.83 (Method A) |
| 18 | 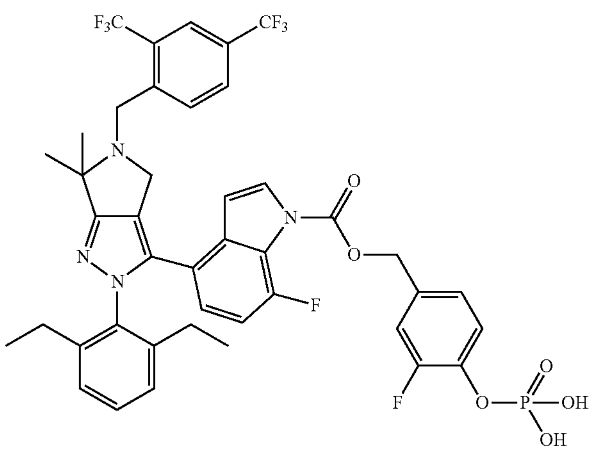 [SMILES: CCc1cccc(CC)c1-n1nc2c(c1-c1ccc(F)c3c1ccn3C(=O)OCc1ccc(OP(=O)(O)O)c(F)c1)CN(Cc1ccc(C(F)(F)F)cc1C(F)(F)F)C2(C)C] | 877.1 | 2.77 (Method A) |
| 19 | 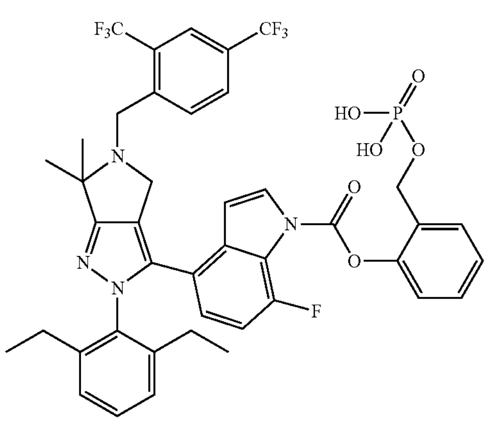 [SMILES: CCc1cccc(CC)c1-n1nc2c(c1-c1ccc(F)c3c1ccn3C(=O)Oc1ccccc1COP(=O)(O)O)CN(Cc1ccc(C(F)(F)F)cc1C(F)(F)F)C2(C)C] | 859.2 | 2.86 (Method A) |

TABLE 1-continued
Structure, Characterization Data of Specific Embodiments
| Example No. | Structure | MS: (ES) m/z [M + H]+ | R$_t$ (min) |
|---|---|---|---|
| 21 | 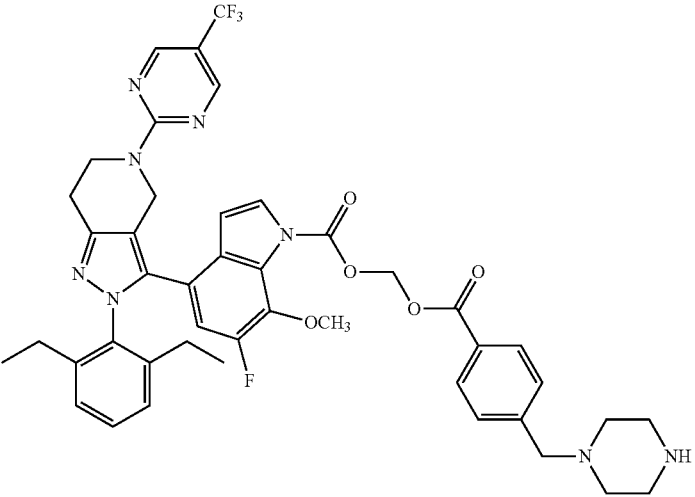 [SMILES: CCc1cccc(CC)c1-n1nc2c(c1-c1cc(F)c(OC)c3c1ccn3C(=O)OCOC(=O)c1ccc(CN3CCNCC3)cc1)CN(c1ncc(C(F)(F)F)cn1)CC2] | 841.2 | 3.86 (Method B) |
| 21 | 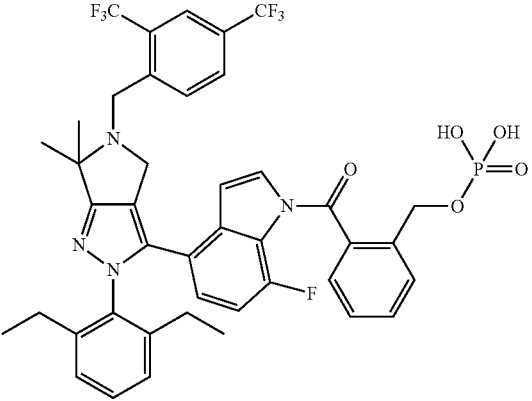 [SMILES: CCc1cccc(CC)c1-n1nc2c(c1-c1ccc(F)c3c1ccn3C(=O)c1ccccc1COP(=O)(O)O)CN(Cc1ccc(C(F)(F)F)cc1C(F)(F)F)C2(C)C] | 843.2 | 2.95 (Method A) |
| 22 | 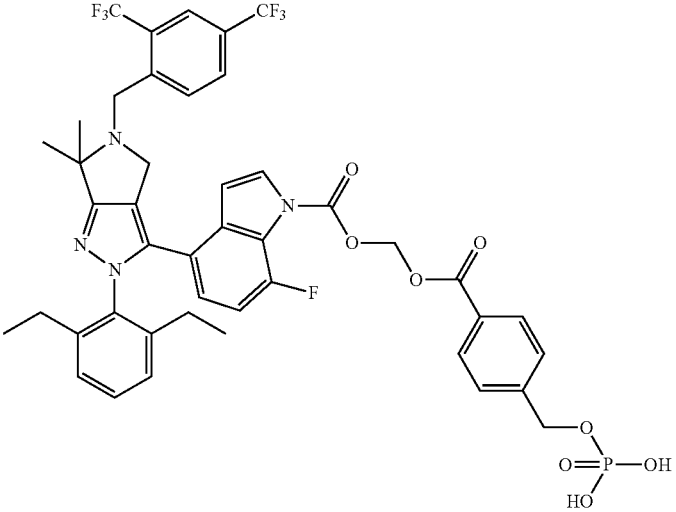 [SMILES: CCc1cccc(CC)c1-n1nc2c(c1-c1ccc(F)c3c1ccn3C(=O)OCOC(=O)c1ccc(COP(=O)(O)O)cc1)CN(Cc1ccc(C(F)(F)F)cc1C(F)(F)F)C2(C)C] | 917.1 | 3.67 (Method B) |

TABLE 1-continued

Structure, Characterization Data of Specific Embodiments

| Example No. | Structure | MS: (ES) m/z [M + H]⁺ | R_t (min) |
|---|---|---|---|
| 23 | 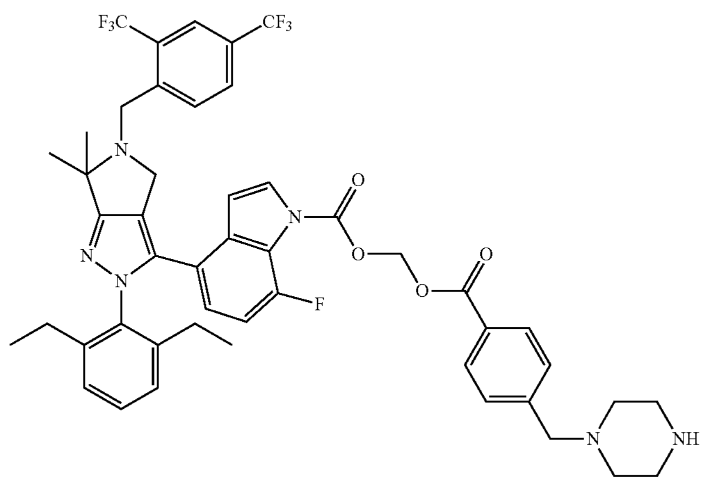 [SMILES: CCc1cccc(CC)c1-n1nc2c(c1-c1ccc(F)c3c1ccn3C(=O)OCOC(=O)c1ccc(CN3CCNCC3)cc1)CN(Cc1ccc(C(F)(F)F)cc1C(F)(F)F)C2(C)C] | 905.3 | 4.71 (Method C) |
| 24 | 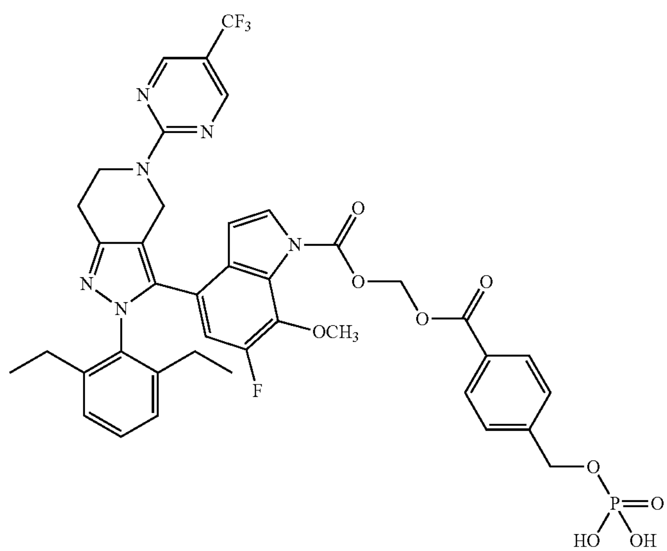 [SMILES: CCc1cccc(CC)c1-n1nc2c(c1-c1cc(F)c(OC)c3c1ccn3C(=O)OCOC(=O)c1ccc(COP(=O)(O)O)cc1)CN(c1ncc(C(F)(F)F)cn1)CC2] | 853.0 | 3.51 (Method B) |
| 25 | 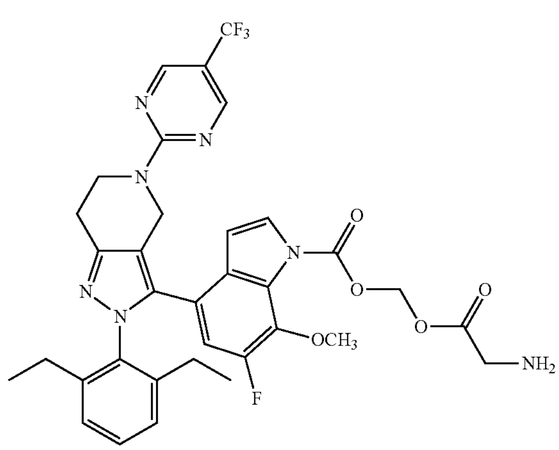 [SMILES: CCc1cccc(CC)c1-n1nc2c(c1-c1cc(F)c(OC)c3c1ccn3C(=O)OCOC(=O)CN)CN(c1ncc(C(F)(F)F)cn1)CC2] | 696.2 | 3.67 (Method B) |

TABLE 1-continued

Structure, Characterization Data of Specific Embodiments

| Example No. | Structure | MS: (ES) m/z [M + H]+ | R_t (min) |
| --- | --- | --- | --- |
| 26 | 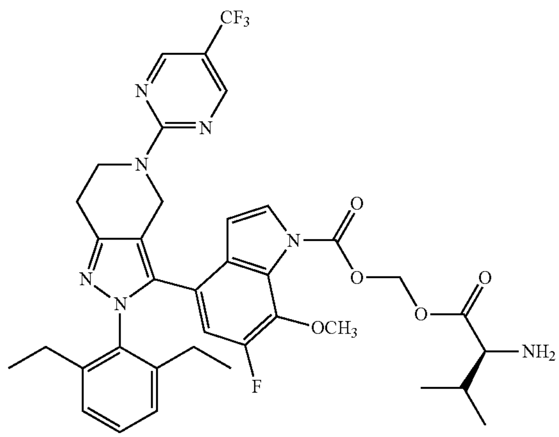 [SMILES: CCc1cccc(CC)c1-n1nc2c(c1-c1cc(F)c(OC)c3c1ccn3C(=O)OCOC(=O)[C@@H](N)C(C)C)CN(c1ncc(C(F)(F)F)cn1)CC2] | 738.2 | 3.34 (Method B) |
| 27 | 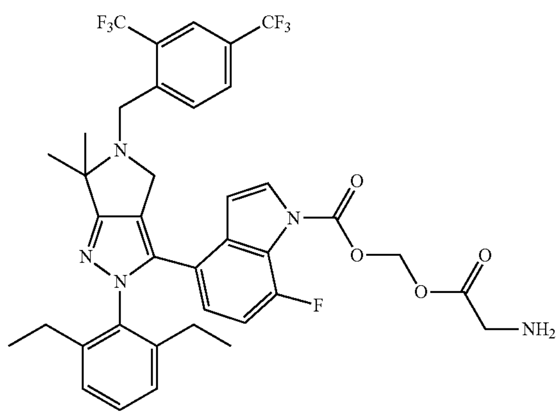 [SMILES: CCc1cccc(CC)c1-n1nc2c(c1-c1ccc(F)c3c1ccn3C(=O)OCOC(=O)CN)CN(Cc1ccc(C(F)(F)F)cc1C(F)(F)F)C2(C)C] | 760.1 | 3.54 (Method B) |
| 28 | 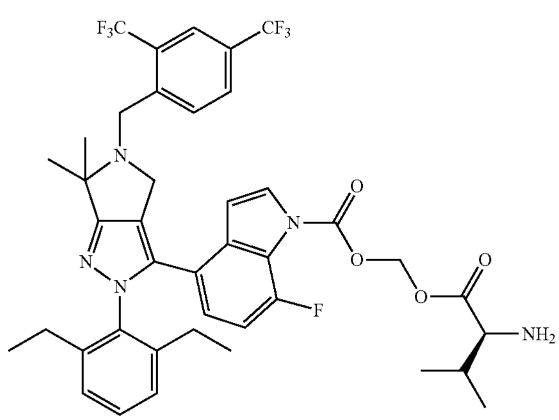 [SMILES: CCc1cccc(CC)c1-n1nc2c(c1-c1ccc(F)c3c1ccn3C(=O)OCOC(=O)[C@@H](N)C(C)C)CN(Cc1ccc(C(F)(F)F)cc1C(F)(F)F)C2(C)C] | 802.2 | 3.55 (Method B) |

TABLE 1-continued
Structure, Characterization Data of Specific Embodiments
| Example No. | Structure | MS: (ES) m/z [M + H]+ | R_t (min) |
|---|---|---|---|
| 29 | 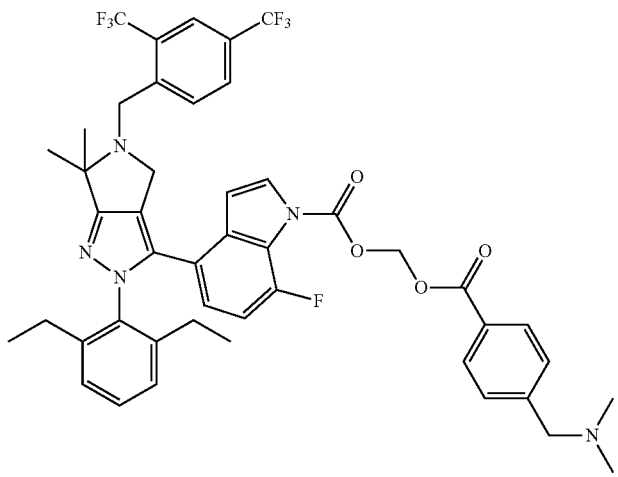 [SMILES: CCc1cccc(CC)c1-n1nc2c(c1-c1ccc(F)c3c1ccn3C(=O)OCOC(=O)c1ccc(CN(C)C)cc1)CN(Cc1ccc(C(F)(F)F)cc1C(F)(F)F)C2(C)C] | 864.2 | 3.84 (Method B) |
| 30 | 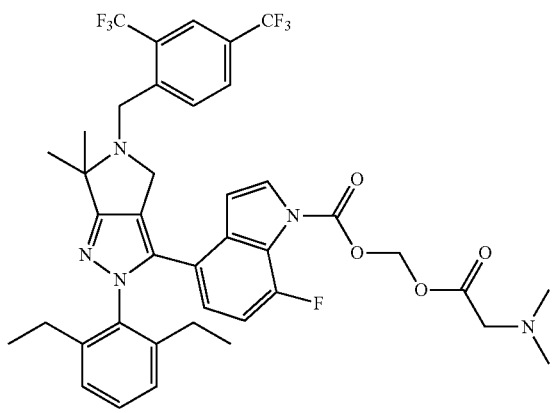 [SMILES: CCc1cccc(CC)c1-n1nc2c(c1-c1ccc(F)c3c1ccn3C(=O)OCOC(=O)CN(C)C)CN(Cc1ccc(C(F)(F)F)cc1C(F)(F)F)C2(C)C] | 788.2 | 4.96 (Method C) |
| 31 | 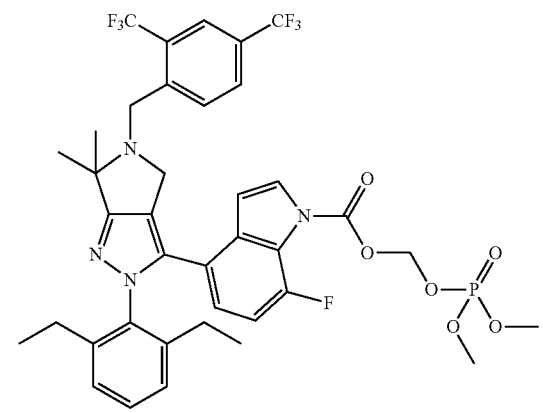 [SMILES: CCc1cccc(CC)c1-n1nc2c(c1-c1ccc(F)c3c1ccn3C(=O)OCOP(=O)(OC)OC)CN(Cc1ccc(C(F)(F)F)cc1C(F)(F)F)C2(C)C] | 811.2 | 5.36 (Method A) |

TABLE 1-continued

Structure, Characterization Data of Specific Embodiments

| Example No. | Structure | MS: (ES) m/z [M + H]+ | R$_t$ (min) |
|---|---|---|---|
| 32 | 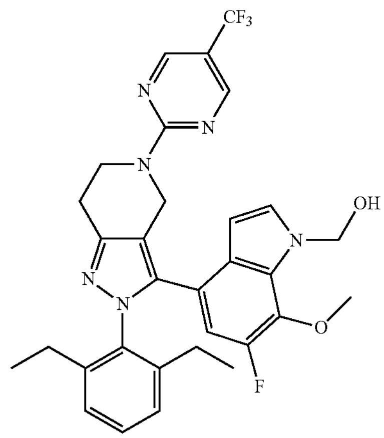 [SMILES: CCc1cccc(CC)c1-n1nc2c(c1-c1cc(F)c(OC)c3c1ccn3CO)CN(c1ncc(C(F)(F)F)cn1)CC2] | 595.5 | 4.88 (Method C) |
| 33 | 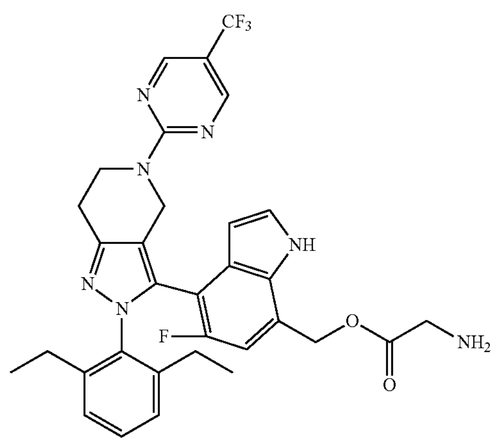 [SMILES: CCc1cccc(CC)c1-n1nc2c(c1-c1c(F)cc(COC(=O)CN)c3[nH]ccc13)CN(c1ncc(C(F)(F)F)cn1)CC2] | 622.2 | 2.51 (Method A) |
| 34 | 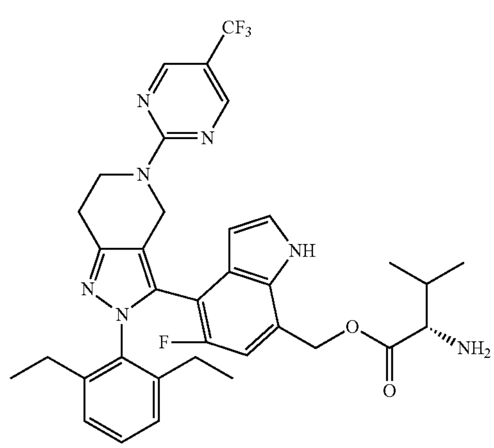 [SMILES: CCc1cccc(CC)c1-n1nc2c(c1-c1c(F)cc(COC(=O)[C@@H](N)C(C)C)c3[nH]ccc13)CN(c1ncc(C(F)(F)F)cn1)CC2] | 664.2 | 2.68 (Method A) |

TABLE 1-continued

Structure, Characterization Data of Specific Embodiments

| Example No. | Structure | MS: (ES) m/z [M + H]+ | R$_t$ (min) |
|---|---|---|---|
| 35 | 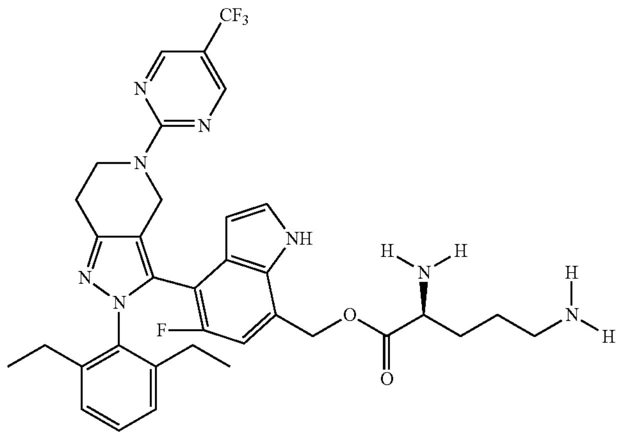 [SMILES: CCc1cccc(CC)c1-n1nc2c(c1-c1c(F)cc(COC(=O)[C@@H](N)CCCN)c3[nH]ccc13)CN(c1ncc(C(F)(F)F)cn1)CC2] | 679.2 | 2.27 (Method A) |
| 36 | 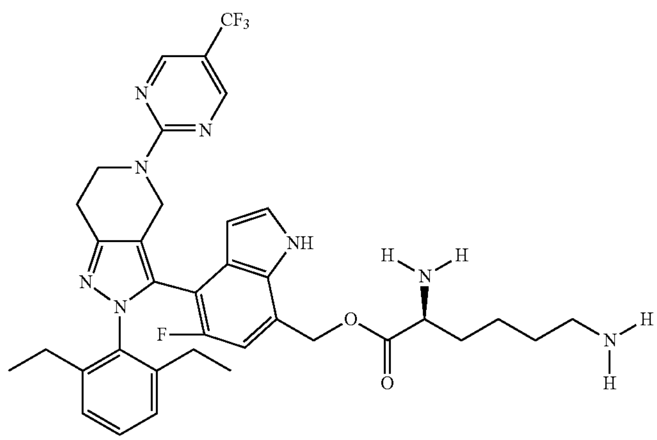 [SMILES: CCc1cccc(CC)c1-n1nc2c(c1-c1c(F)cc(COC(=O)[C@@H](N)CCCCN)c3[nH]ccc13)CN(c1ncc(C(F)(F)F)cn1)CC2] | 693.3 | 2.09 (Method A) |
| 37 | 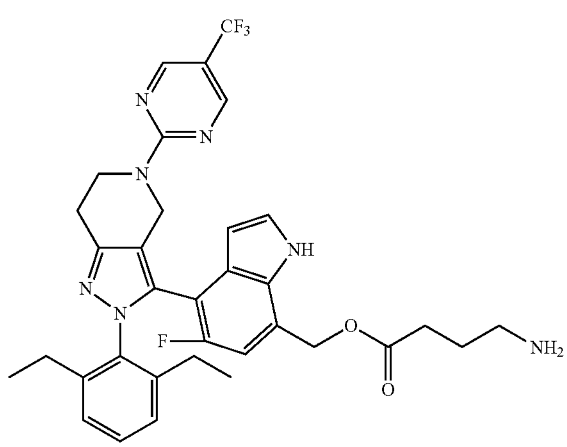 [SMILES: CCc1cccc(CC)c1-n1nc2c(c1-c1c(F)cc(COC(=O)CCCN)c3[nH]ccc13)CN(c1ncc(C(F)(F)F)cn1)CC2] | 650.3 | 2.60 (Method A) |

TABLE 1-continued
Structure, Characterization Data of Specific Embodiments
| Example No. | Structure | MS: (ES) m/z [M + H]+ | R_t (min) |
|---|---|---|---|
| 38 | 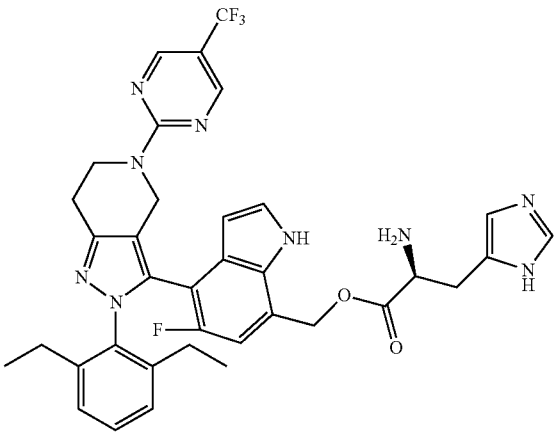 [SMILES: CCc1cccc(CC)c1-n1nc2c(c1-c1c(F)cc(COC(=O)[C@@H](N)Cc3cnc[nH]3)c3[nH]ccc13)CN(c1ncc(C(F)(F)F)cn1)CC2] | 701.9 | 2.10 (Method A) |
| 39 | 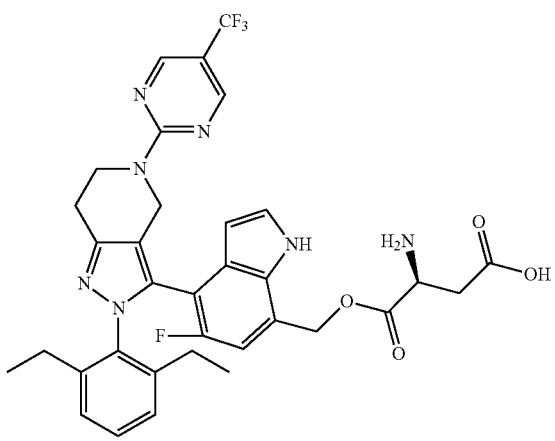 [SMILES: CCc1cccc(CC)c1-n1nc2c(c1-c1c(F)cc(COC(=O)[C@@H](N)CC(=O)O)c3[nH]ccc13)CN(c1ncc(C(F)(F)F)cn1)CC2] | 680.1 | 2.55 (Method A) |
| 40 | 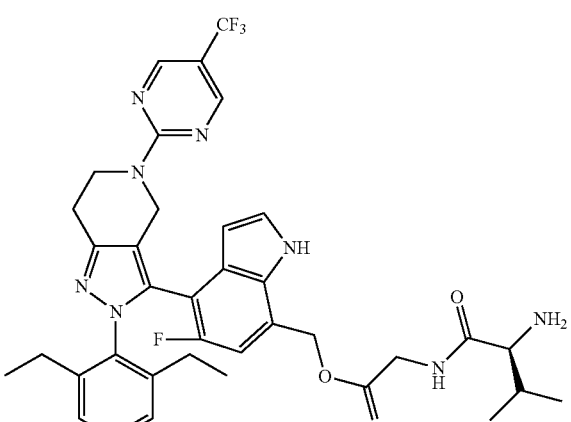 | 721.2 | 2.62 (Method A) |

TABLE 1-continued

Structure, Characterization Data of Specific Embodiments

| Example No. | Structure | MS: (ES) m/z [M + H]+ | R_t (min) |
|---|---|---|---|
| 41 | 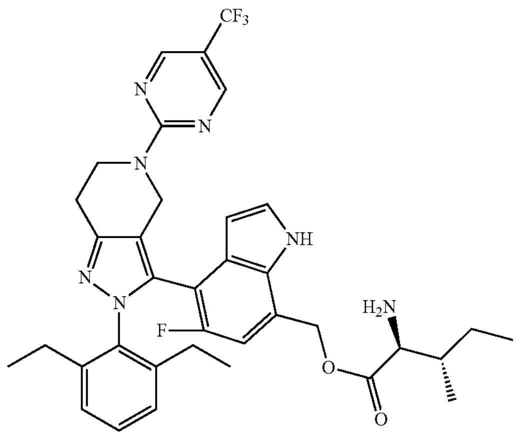 [SMILES: CCc1cccc(CC)c1-n1nc2c(c1-c1c(F)cc(COC(=O)[C@@H](N)[C@@H](C)CC)c3[nH]ccc13)CN(c1ncc(C(F)(F)F)cn1)CC2] | 678.3 | 2.64 (Method A) |
| 42 | 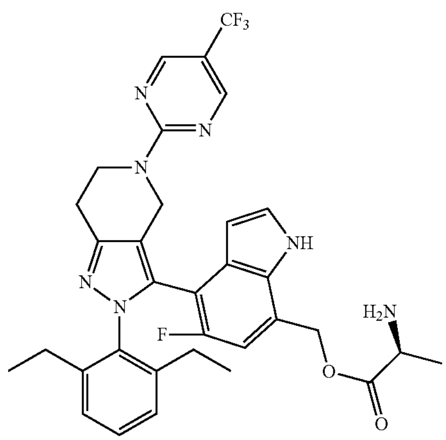 [SMILES: CCc1cccc(CC)c1-n1nc2c(c1-c1c(F)cc(COC(=O)[C@H](C)N)c3[nH]ccc13)CN(c1ncc(C(F)(F)F)cn1)CC2] | 636.2 | 2.50 (Method A) |
| 43 | 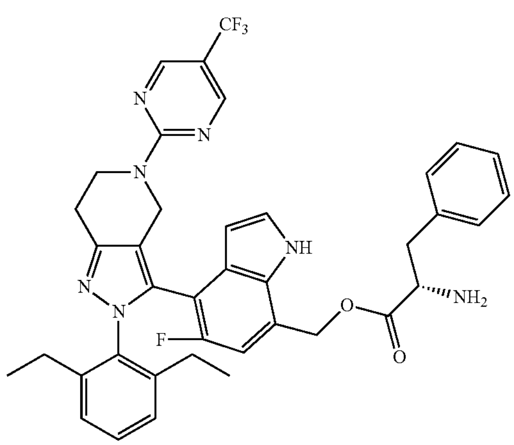 [SMILES: CCc1cccc(CC)c1-n1nc2c(c1-c1c(F)cc(COC(=O)[C@@H](N)Cc3ccccc3)c3[nH]ccc13)CN(c1ncc(C(F)(F)F)cn1)CC2] | 712.2 | 2.80 (Method A) |

TABLE 1-continued
Structure, Characterization Data of Specific Embodiments
| Example No. | Structure | MS: (ES) m/z [M + H]+ | R$_t$ (min) |
|---|---|---|---|
| 44 | 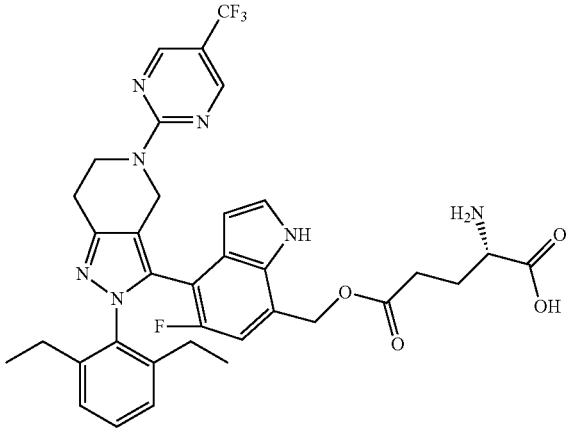 [SMILES: CCc1cccc(CC)c1-n1nc2c(c1-c1c(F)cc(COC(=O)CC[C@H](N)C(=O)O)c3[nH]ccc13)CN(c1ncc(C(F)(F)F)cn1)CC2] | 694.2 | 2.43 (Method A) |
| 45 | 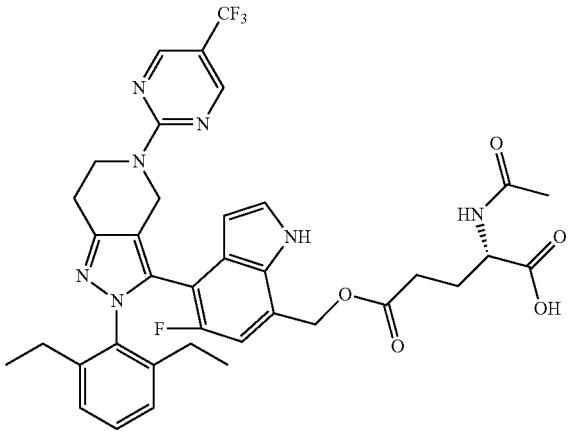 [SMILES: CCc1cccc(CC)c1-n1nc2c(c1-c1c(F)cc(COC(=O)CC[C@H](NC(C)=O)C(=O)O)c3[nH]ccc13)CN(c1ncc(C(F)(F)F)cn1)CC2] | 736.2 | 2.87 (Method A) |
| 46 | 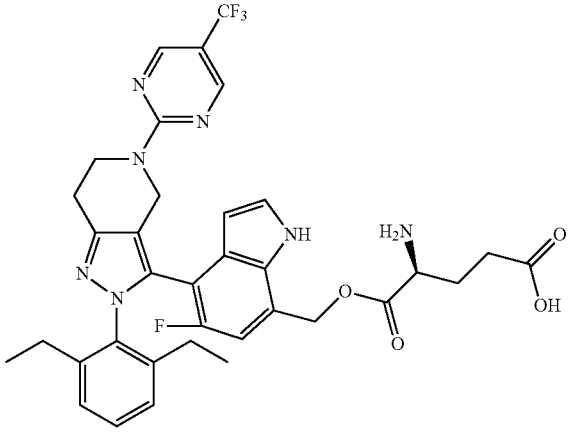 [SMILES: CCc1cccc(CC)c1-n1nc2c(c1-c1c(F)cc(COC(=O)[C@@H](N)CCC(=O)O)c3[nH]ccc13)CN(c1ncc(C(F)(F)F)cn1)CC2] | 694.2 | 2.45 (Method A) |

TABLE 1-continued

Structure, Characterization Data of Specific Embodiments

| Example No. | Structure | MS: (ES) m/z [M + H]⁺ | $R_t$ (min) |
|---|---|---|---|
| 47 | 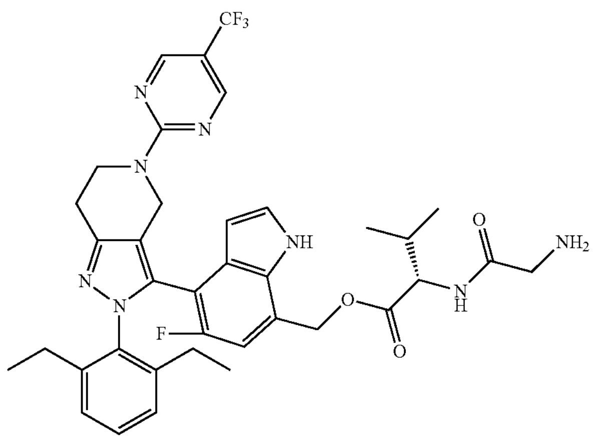 [SMILES: CCc1cccc(CC)c1-n1nc2c(c1-c1c(F)cc(COC(=O)[C@@H](NC(=O)CN)C(C)C)c3[nH]ccc13)CN(c1ncc(C(F)(F)F)cn1)CC2] | 721.2 | 2.56 (Method A) |
| 48 | 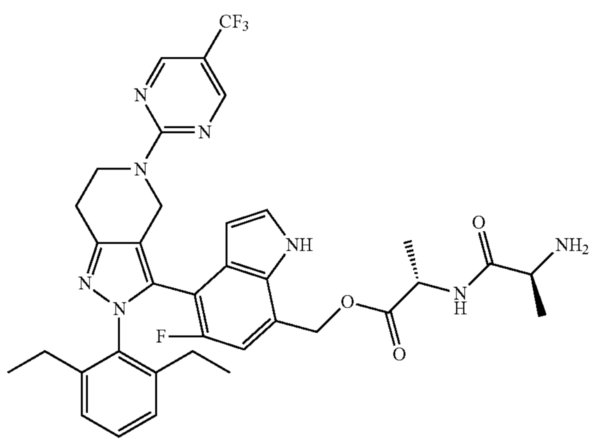 [SMILES: CCc1cccc(CC)c1-n1nc2c(c1-c1c(F)cc(COC(=O)[C@H](C)NC(=O)[C@H](C)N)c3[nH]ccc13)CN(c1ncc(C(F)(F)F)cn1)CC2] | 707.2 | 2.50 (Method A) |
| 49 | 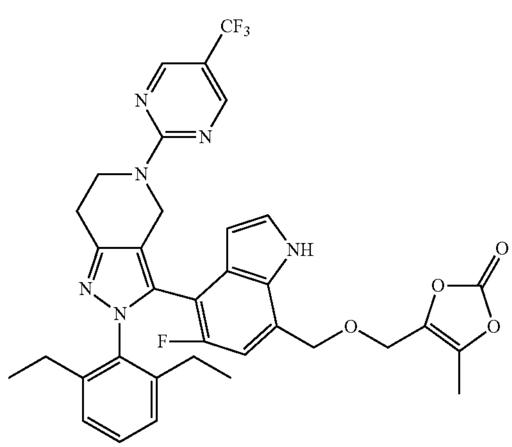 [SMILES: CCc1cccc(CC)c1-n1nc2c(c1-c1c(F)cc(COCc3oc(=O)oc3C)c3[nH]ccc13)CN(c1ncc(C(F)(F)F)cn1)CC2] | 677.7 | 3.25 (Method A) |

TABLE 1-continued

Structure, Characterization Data of Specific Embodiments

| Example No. | Structure | MS: (ES) m/z [M + H]+ | R$_t$ (min) |
|---|---|---|---|
| 50 | 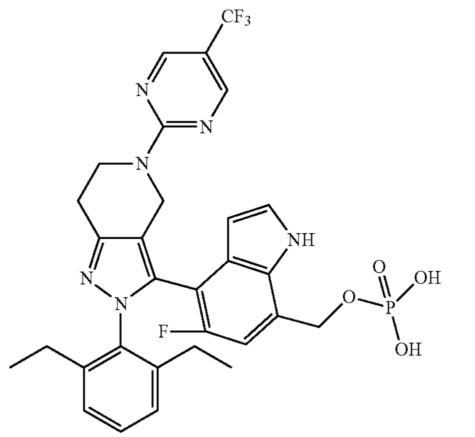 [SMILES: CCc1cccc(CC)c1-n1nc2c(c1-c1c(F)cc(COP(=O)(O)O)c3[nH]ccc13)CN(c1ncc(C(F)(F)F)cn1)CC2] | 645.6 | 2.60 (Method A) |
| 51 | 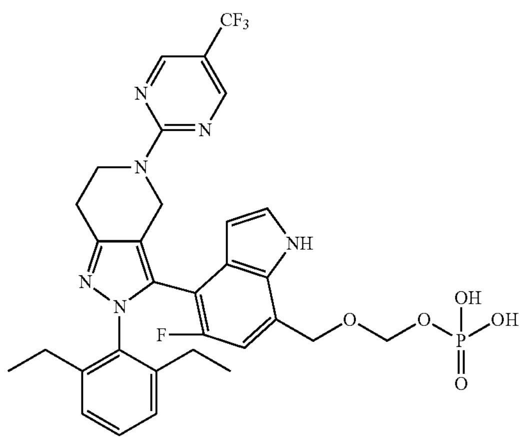 [SMILES: CCc1cccc(CC)c1-n1nc2c(c1-c1c(F)cc(COCOP(=O)(O)O)c3[nH]ccc13)CN(c1ncc(C(F)(F)F)cn1)CC2] | 675.7 | 2.39 (Method A) |
| 52 | 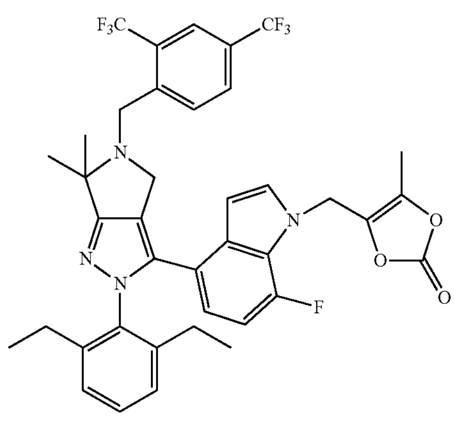 [SMILES: CCc1cccc(CC)c1-n1nc2c(c1-c1ccc(F)c3c1ccn3Cc1oc(=O)oc1C)CN(Cc1ccc(C(F)(F)F)cc1C(F)(F)F)C2(C)C] | 741.2 | 2.95 (Method A) |

TABLE 1-continued
Structure, Characterization Data of Specific Embodiments
| Example No. | Structure | MS: (ES) m/z [M + H]+ | R_t (min) |
|---|---|---|---|
| 53 | 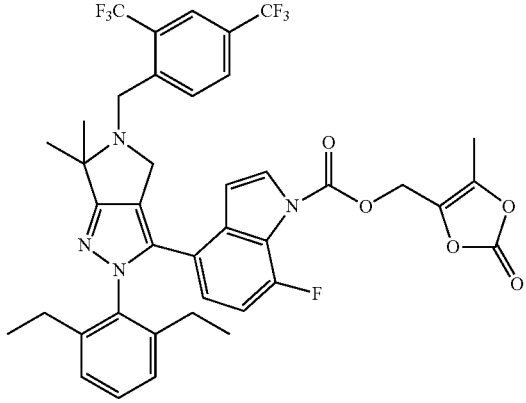 [SMILES: CCc1cccc(CC)c1-n1nc2c(c1-c1ccc(F)c3c1ccn3C(=O)OCc1oc(=O)oc1C)CN(Cc1ccc(C(F)(F)F)cc1C(F)(F)F)C2(C)C] | 785.1 | 3.83 (Method A) |
| 54 | 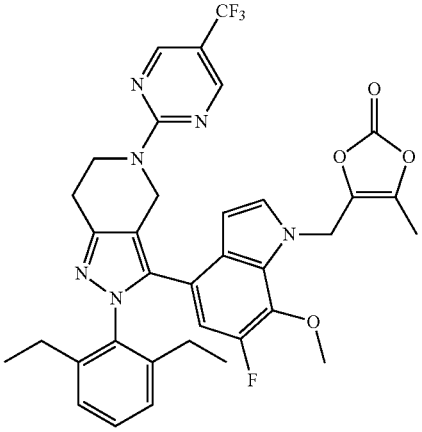 [SMILES: CCc1cccc(CC)c1-n1nc2c(c1-c1cc(F)c(OC)c3c1ccn3Cc1oc(=O)oc1C)CN(c1ncc(C(F)(F)F)cn1)CC2] | 677.2 | 2.40 (Method A) |
| 55 | 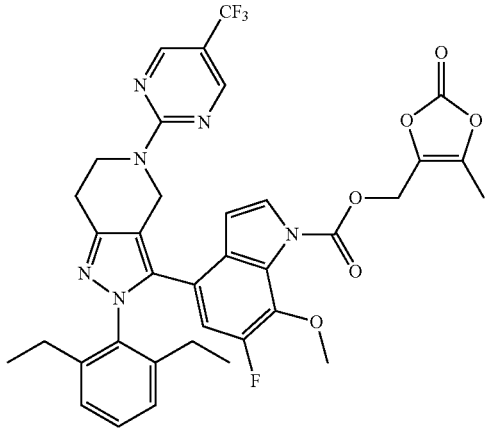 [SMILES: CCc1cccc(CC)c1-n1nc2c(c1-c1cc(F)c(OC)c3c1ccn3C(=O)OCc1oc(=O)oc1C)CN(c1ncc(C(F)(F)F)cn1)CC2] | 721.2 | 2.35 (Method A) |

TABLE 1-continued
Structure, Characterization Data of Specific Embodiments
| Example No. | Structure | MS: (ES) m/z [M + H]+ | R$_t$ (min) |
|---|---|---|---|
| 56 | 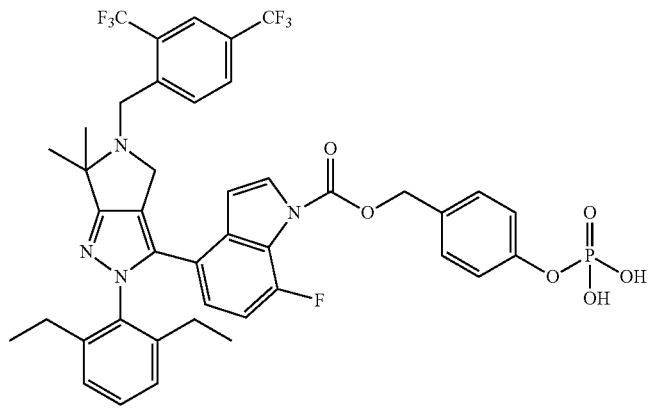 [SMILES: CCc1cccc(CC)c1-n1nc2c(c1-c1ccc(F)c3c1ccn3C(=O)OCc1ccc(OP(=O)(O)O)cc1)CN(Cc1ccc(C(F)(F)F)cc1C(F)(F)F)C2(C)C] | 859.2 | 4.05 (Method A) |
| 57 | 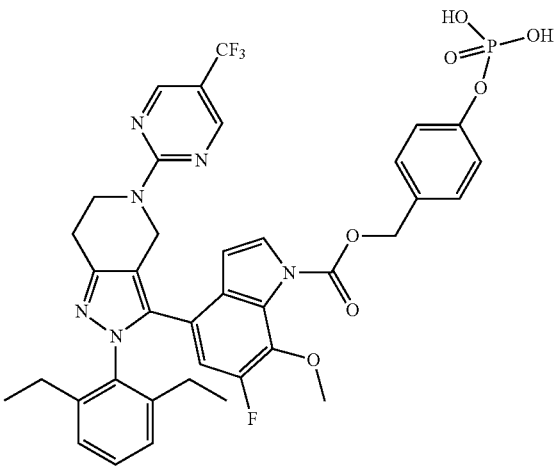 [SMILES: CCc1cccc(CC)c1-n1nc2c(c1-c1cc(F)c(OC)c3c1ccn3C(=O)OCc1ccc(OP(=O)(O)O)cc1)CN(c1ncc(C(F)(F)F)cn1)CC2] | 795.2 | 2.82 (Method A) |
| 58 | 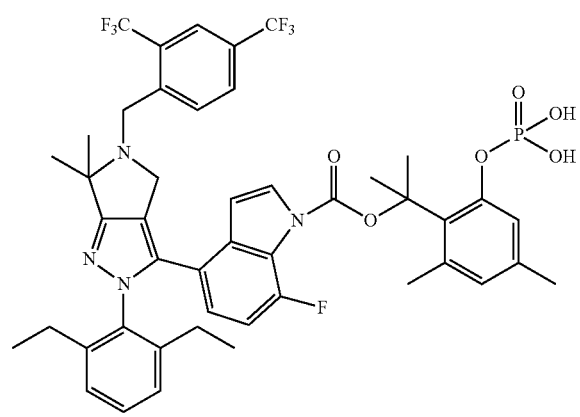 [SMILES: CCc1cccc(CC)c1-n1nc2c(c1-c1ccc(F)c3c1ccn3C(=O)OC(C)(C)c1c(C)cc(C)cc1OP(=O)(O)O)CN(Cc1ccc(C(F)(F)F)cc1C(F)(F)F)C2(C)C] | 913.3 | 3.06 (Method A) |

TABLE 1-continued

Structure, Characterization Data of Specific Embodiments

| Example No. | Structure | MS: (ES) m/z [M + H]+ | R<sub>t</sub> (min) |
|---|---|---|---|
| 59 | 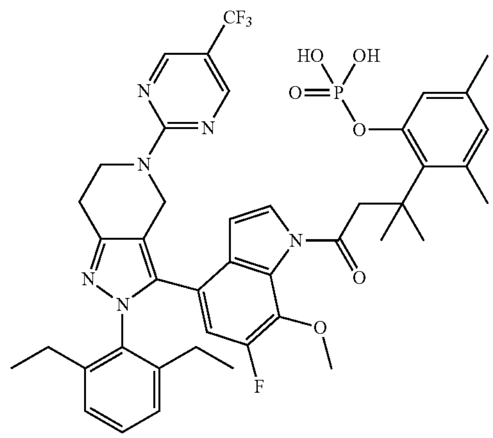 [SMILES: CCc1cccc(CC)c1-n1nc2c(c1-c1cc(F)c(OC)c3c1ccn3C(=O)CC(C)(C)c1c(C)cc(C)cc1OP(=O)(O)O)CN(c1ncc(C(F)(F)F)cn1)CC2] | 849.2 | 3.16 (Method A) |
| 60 | 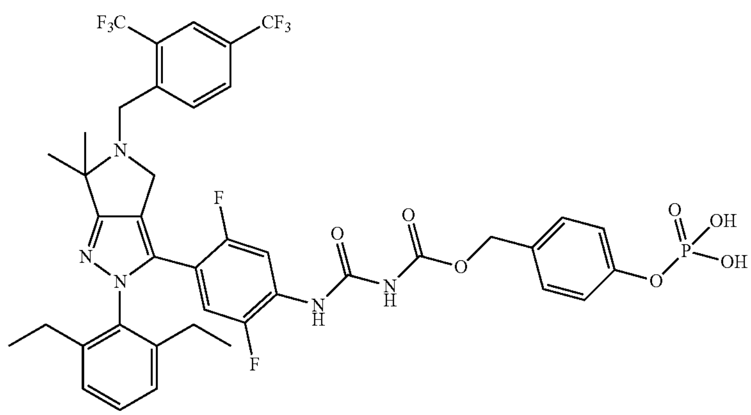 [SMILES: CCc1cccc(CC)c1-n1nc2c(c1-c1cc(F)c(NC(=O)NC(=O)OCc3ccc(OP(=O)(O)O)cc3)cc1F)CN(Cc1ccc(C(F)(F)F)cc1C(F)(F)F)C2(C)C] | 896.2 | 2.56 (Method A) |
| 61 | 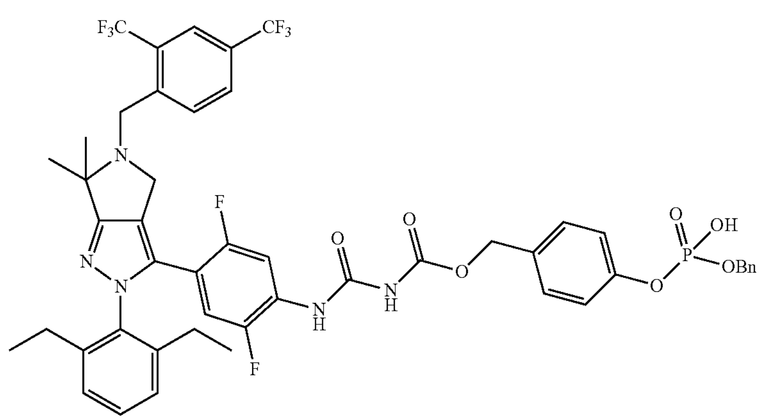 [SMILES: CCc1cccc(CC)c1-n1nc2c(c1-c1cc(F)c(NC(=O)NC(=O)OCc3ccc(OP(=O)(O)OCc4ccccc4)cc3)cc1F)CN(Cc1ccc(C(F)(F)F)cc1C(F)(F)F)C2(C)C] | 986.3 | 2.93 (Method A) |

TABLE 1-continued

Structure, Characterization Data of Specific Embodiments

| Example No. | Structure | MS: (ES) m/z [M + H]+ | R$_t$ (min) |
|---|---|---|---|
| 62 | 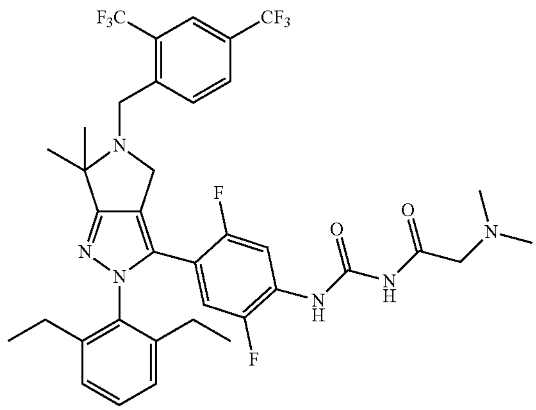 [SMILES: CCc1cccc(CC)c1-n1nc2c(c1-c1cc(F)c(NC(=O)NC(=O)CN(C)C)cc1F)CN(Cc1ccc(C(F)(F)F)cc1C(F)(F)F)C2(C)C] | 751.2 | 3.05 (Method A) |
| 63 | 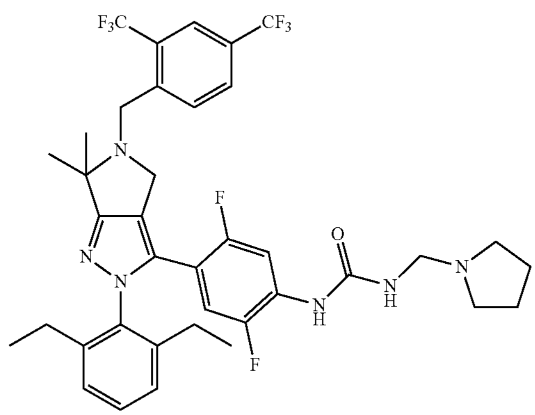 [SMILES: CCc1cccc(CC)c1-n1nc2c(c1-c1cc(F)c(NC(=O)NCN3CCCC3)cc1F)CN(Cc1ccc(C(F)(F)F)cc1C(F)(F)F)C2(C)C] | 749.2 | 4.65 (Method A) |
| 64 | 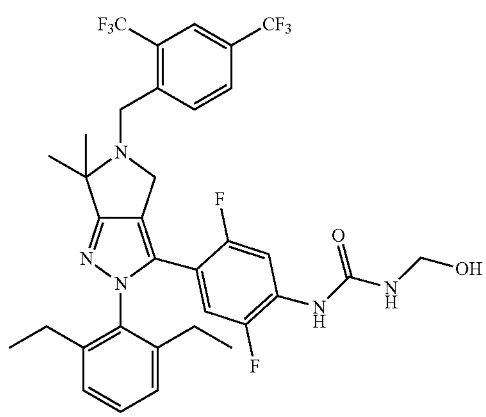 [SMILES: CCc1cccc(CC)c1-n1nc2c(c1-c1cc(F)c(NC(=O)NCO)cc1F)CN(Cc1ccc(C(F)(F)F)cc1C(F)(F)F)C2(C)C] | 696.3 | 4.69 (Method A) |

Reverse Phase HPLC Conditions Used for Determination of Retention Times in Table 1:
- Column: ZORBAX (SB-C18 2.1×50 mm, 5 μm)
- Mobile phase A: 95% H$_2$O, 5% MeCN (with 0.1% Formic Acid)
- Mobile phase B: 5% H$_2$O, 95% MeCN (with 0.1% Formic Acid)
- Flow rate: 1.0 mL/min
- Gradient: 20 to 100% B in 5.5 min (Method A)
- 0 to 100% B in 4.5 min (Method B)
- 0 to 100% B in 5.5 min (Method C)

Intravenous Injections in Rats

Male rats, weighing between 0.22 to 0.25 Kg, were purchased from Charles River Laboratories (Hollister, Calif.) and were acclimated before use. All compounds were prepared in solution formulations and administered to animals through intravenous dosing. Compounds of example 1 and example 4 were prepared in 31.6% DMA/36.8% EtOH/31.6% PG and each animal received 1 mL/Kg. Blood (0.2 mL) were sampled through the jugular vein or cardiac punctures (for terminal points only) at pre-dose, 2, 5, 10, 15, and 30 min, 1, 2, 4, 6, and 8 hours post-dose for i.v. dosing.

Blood samples were collected into chilled polypropylene tubes containing potassium EDTA as anticoagulant and plasma was collected through centrifugation (Eppendorf Centrifuge 5417R) at 10,000 rpm and 4° C. for 6 minutes and stored at −20° C. until analysis.

Figure 2:
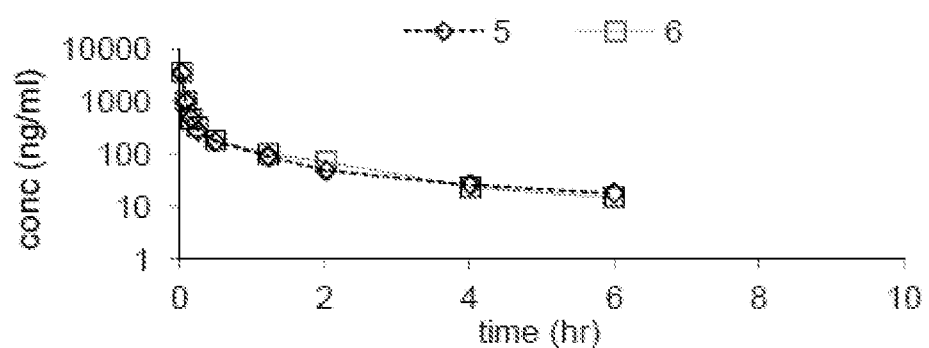
FIG. 2 shows release of active compound intermediate 1 from the compound of Example 4 (0.5 mg/kg mole equiv., AUC=753 ng.hr/mL)

Plasma samples (50 µL) were extracted with 200 µL acetonitrile containing internal standard on a linear shaker for 10 min and then centrifuged at 4450 rpm for 10 min at 4° C. (Allegra X-15R centrifuge, Beckman Coulter, Inc., Fullerton, Calif.). One hundred µL of the resulting supernatant was transferred into a new plate and mixed with 100 µL 0.1% formic acid in water for LC-MS/MS analysis. Good amount of active drugs were released after intravenous injection for both compounds in male rats as illustrated by FIGS. 1 and 2.

While particular embodiments of this invention are described herein, upon reading the description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A compound of any one of Formulae (IA), (IB), (IC), (IIA), (IIB) or (IIC):

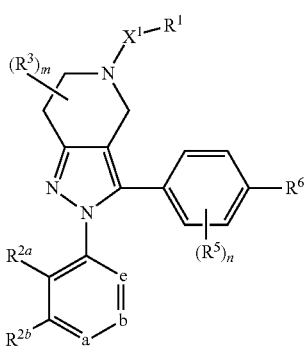

IA

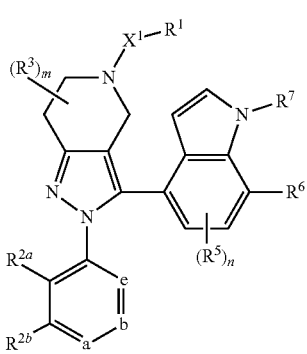

IB

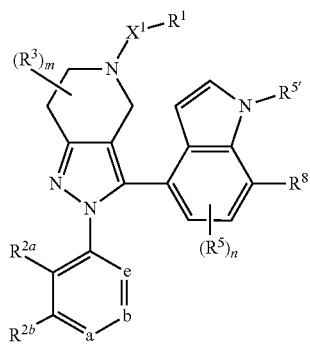

IC

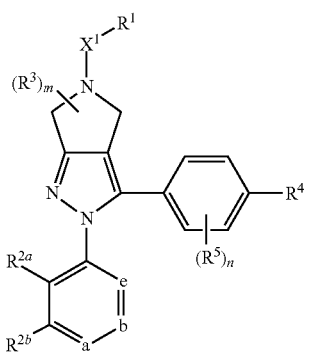

IIA

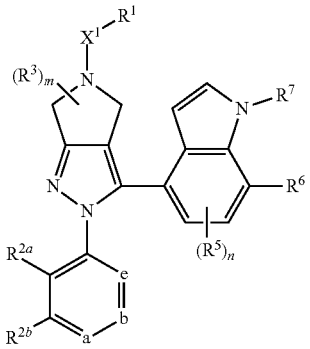

IIB

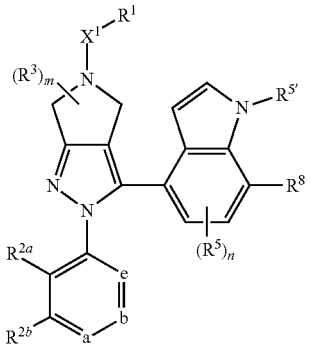

IIC or a pharmaceutically acceptable salt thereof, wherein, ring vertex a is N or $C(R^{2c})$, ring vertex b is N or $C(R^{2d})$, and ring vertex a is N or $C(R^{2e})$, wherein no more than one of a, b and e is N;

$X^1$ is selected from the group consisting of a bond, $C_{1-8}$ alkylene, C(O), C(O)—$C_{1-4}$ alkylene, and $S(O)_2$;

$R^1$ is selected from the group consisting of
a) 5- to 10-membered heteroaryl having from 1 to 4 heteroatoms as ring vertices selected from N, O and S;
b) $C_{6-10}$ aryl;
c) $C_{3-8}$ cycloalkyl;
d) 4- to 8-membered heterocycloalkyl having from 1 to 2 heteroatoms as ring vertices selected from N, O and S; and
e) $C_{1-8}$ alkyl, $C_{1-8}$ alkoxy, $C_{1-8}$ haloalkyl, —C(O)NR$^{1a}$R$^{1b}$, and —CO$_2$R$^{1a}$; wherein R$^{1a}$ and R$^{1b}$ are each independently selected from the group consisting of hydrogen, $C_{1-8}$ alkyl, $C_{6-10}$ aryl, and —$C_{1-6}$ alkylene—$C_{6-10}$ aryl;
wherein the group —X$^1$—R$^1$ is unsubstituted or substituted with 1 to 5 R$^x$ substituents;
$R^{2a}$ and $^{2e}$ are each independently selected from the group consisting of hydrogen, $C_{1-6}$ alkyl, $C_{1-6}$ alkoxy, $C_{1-6}$ haloalkyl, —O—$C_{1-6}$ haloalkyl, —S—$C_{1-6}$ alkyl, —$C_{1-6}$ alkyl—O—$C_{1-6}$ alkyl, —$C_{1-6}$ alkyl—S—$C_{1-6}$ alkyl, CN, and halogen, and at least one of R$^{2a}$ and $^{2e}$ is other than hydrogen;
$R^{2b}$, $R^{2c}$, and $R^{2d}$ are each independently selected from the group consisting of hydrogen, $C_{1-6}$ alkyl, $C_{1-6}$ alkoxy, $C_{1-6}$ haloalkyl, —O—$C_{1-6}$ haloalkyl, —S—$C_{1-6}$ alkyl, —$C_{1-6}$ alkyl—O—$C_{1-6}$ alkyl, —$C_{1-6}$ alkyl—S—$C_{1-6}$ alkyl, cyano, and halogen;
each $R^3$ is independently selected from the group consisting of hydroxyl, $C_{1-4}$ alkyl, $C_{1-4}$ haloalkyl and $C_{1-4}$ hydroxyalkyl, and optionally two $R^3$ groups on the same carbon atom are combined to form oxo (=O), and optionally two $R^3$ groups and the carbon atoms they are attached to form a 3-6 membered ring with 0-2 hetereoatoms as ring members selected from O, N, and S;
$R^4$ is a member selected from the group consisting of: —NHP$^1$, —NHC(O)NHP$^1$, —CH$_2$NHP$^1$ and —CH$_2$NHC(O)NHP$^1$;
each $R^5$ is independently selected from the group consisting of $C_{1-8}$ alkyl, $C_{1-8}$ alkoxy, $C_{1-8}$ haloalkyl, $C_{1-8}$ haloalkoxy, $C_{1-8}$ hydroxyalkyl, halogen, OH, CN, C(O)R$^{5a}$ and CO$_2$R$^{5a}$;
$R^{5'}$ is a member selected from the group consisting of hydrogen, $C_{1-8}$ alkyl, $C_{1-8}$ haloalkyl, $C_{1-8}$ hydroxyalkyl, C(O)R$^{5a}$ and CO$_2$R$^{5a}$; wherein each R$^{5a}$ is independently selected from the group consisting of hydrogen, $C_{1-4}$ alkyl, and $C_{1-4}$ haloalkyl;
$R^6$ is a member selected from the group consisting of hydrogen, $C_{1-6}$ alkyl, $C_{1-6}$ alkoxy, $C_{1-6}$ haloalkyl, —O—$C_{1-6}$ haloalkyl, —S—$C_{1-6}$ alkyl, —$C_{1-6}$ alkyl—O—$C_{1-6}$ alkyl, —$C_{1-6}$ alkyl—S—$C_{1-6}$ alkyl, cyano, and halogen;
$R^7$ is P$^1$; and
$R^8$ is —CH$_2$OP$^1$;
each P$^1$ is
(i) selected from the group consisting of:

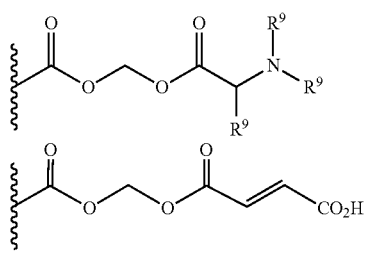

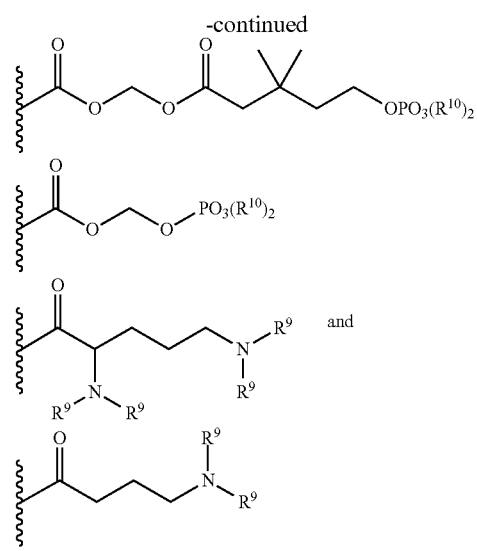

wherein each $R^9$ is independently selected from the group consisting of H and $C_{1-3}$ alkyl; and
each $R^{10}$ is independently selected from the group consisting of H, $C_{1-3}$ alkyl, phenyl, and benzyl;
(ii) selected from the group consisting of:

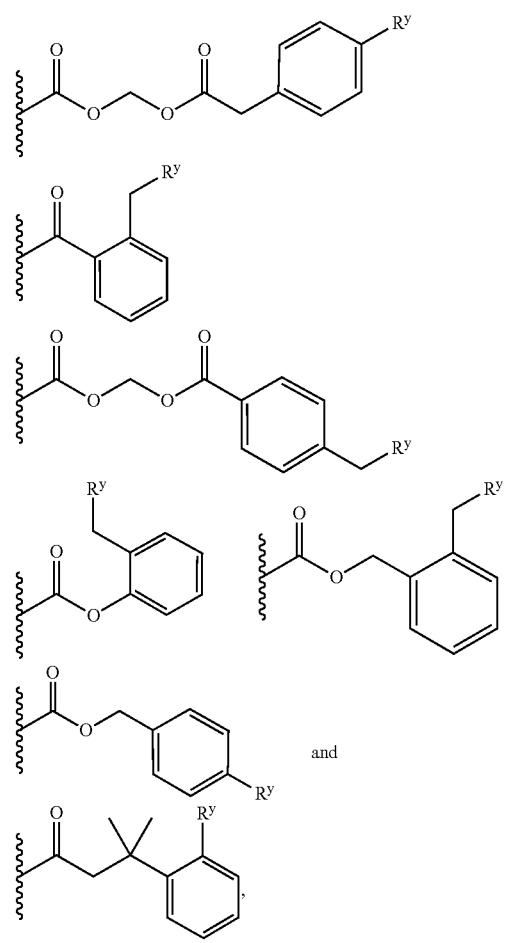

wherein
each $R^y$ is independently selected from the group consisting of
—OP(O)(OR$^{y1}$)$_2$, —OC(O)CH$_2$N(R$^{y2}$)$_2$, —N(R$^{y2}$)$_2$, and piperazine;
each $R^{y1}$ is independently selected form the group consisting of H, C$_{1-3}$ alkyl, and benzyl;
each $R^{y2}$ is independently H or C$_{1-3}$ alkyl; and
each phenyl ring bearing an $R^y$ or —CH$_2$R$^y$ substituent is further substituted with from 0 to 3 members independently selected from the group consisting of nitro, halogen, CN, CF$_3$, C$_{1-4}$ alkyl, C$_{1-4}$ alkoxy, C$_{1-4}$ haloalkyl, C$_{1-4}$ haloalkoxy, and C$_{1-4}$ hydroxyalkyl;
(iii) selected from the group consisting of —CH$_2$OH, —P(O)(OR$^{10}$)$_2$, and
—CH$_2$—O—P(O)(OR$^{10}$)$_2$, wherein each R$^{10}$ is independently selected from the group consisting of H, C$_{1-3}$ alkyl, phenyl, and benzyl;
(iv) selected from the group consisting of an amino acid, a dipeptide, and a tripeptide; or
(v) selected from the group consisting of:

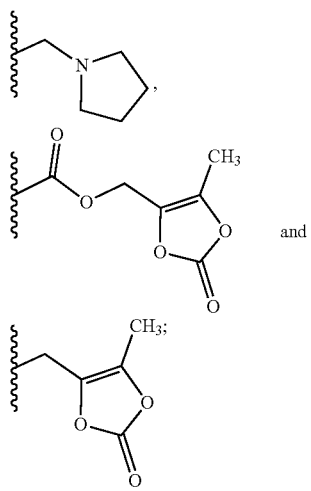

each $R^x$ is independently selected from the group consisting of halogen, CN, C$_{1-4}$ alkyl, C$_{1-4}$ alkoxy, C$_{1-4}$ haloalkyl, C$_{1-4}$ haloalkoxy, C$_{1-4}$ hydroxyalkyl, C$_{2-4}$ alkenyl, C$_{3-6}$ cycloalkyl, CO$_2$—C$_{1-4}$ alkyl, and CONH$_2$;
the subscript m is 0, 1, 2, 3 or 4; and
the subscript n is 0, 1, 2 or 3.

2. The compound of claim 1, or a pharmaceutically acceptable salt thereof, wherein P$^1$ is selected from the group consisting of:

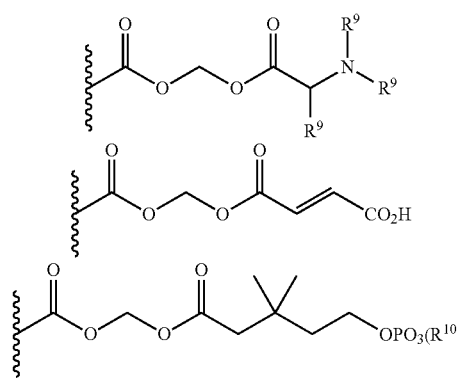

-continued

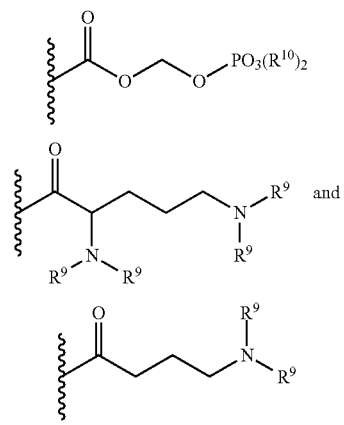

wherein each R$^9$ is independently selected from the group consisting of H and C$_{1-3}$ alkyl; and
each R$^{10}$ is independently selected from the group consisting of H, C$_{1-3}$ alkyl, phenyl, and benzyl.

3. The compound of claim 1, or a pharmaceutically acceptable salt thereof, wherein P$^1$ is selected from the group consisting of:

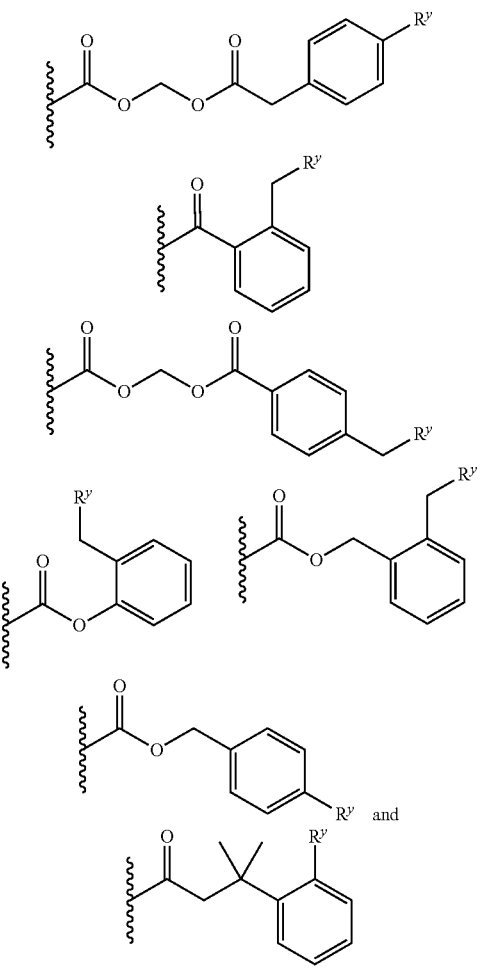

wherein
each $R^y$ is independently selected from the group consisting of
—OP(O)(OR$^{y1}$)$_2$, —OC(O)CH$_2$N(R$^{y2}$)$_2$, —N(R$^{y2}$)$_2$, and piperazine;
each $R^{y1}$ is independently selected form the group consisting of H, C$_{1-3}$ alkyl, and benzyl;
each $R^{y2}$ is independently H or C$_{1-3}$ alkyl; and
each phenyl ring bearing an R$^y$ or —CH$_2$R$^y$ substituent is further substituted with from 0 to 3 members independently selected from the group consisting of nitro, halogen, CN, CF$_3$, C$_{1-4}$ alkyl, C$_{1-4}$ alkoxy, C$_{1-4}$ haloalkyl, C$_{1-4}$ haloalkoxy, and C$_{1-4}$ hydroxyalkyl.

4. The compound of claim 1, or a pharmaceutically acceptable salt thereof, wherein P$^1$ is selected from the group consisting of —CH$_2$OH, —P(O)(OR$^{10}$), and —CH$_2$—O—P(O)(OR$^{10}$)$_2$, wherein each R$^{10}$ is independently selected from the group consisting of H, C$_{1-3}$ alkyl, phenyl, and benzyl.

5. The compound of claim 1, or a pharmaceutically acceptable salt thereof, wherein P$^1$ is selected from the group consisting of an amino acid, a dipeptide, and a tripeptide.

6. The compound of claim 1, where said amino acid, dipeptide, or tripeptide moieties are independently selected from the group consisting of glycine, alanine, valine, leucine, isoleucine, lysine, cysteine, aspartate, glutamate, histidine, and phenylalanine, wherein the N atom of each amino acid unit may be methylated or acylated.

7. The compound of claim 1, or a pharmaceutically acceptable salt thereof, wherein P$^1$ is selected from the group consisting of:

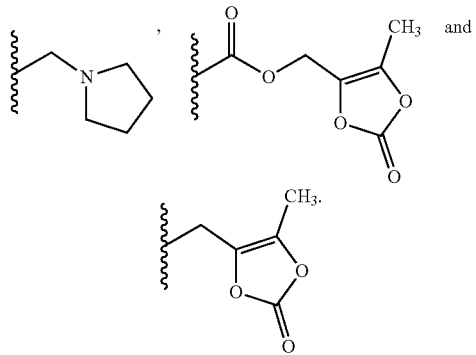

8. The compound of claim 1, or a pharmaceutically acceptable salt thereof, wherein X$^1$ is C(O)—C$_{1-4}$ alkylene or S(O)$_2$.

9. The compound of claim 1, or a pharmaceutically acceptable salt thereof, wherein R$^1$ is a 5- to 10-membered heteroaryl having from 1 to 4 heteroatoms as ring vertices selected from N, O and S; and wherein the group —X$^1$—R$^1$ is optionally substituted with 1 to 4 R$^x$ substituents.

10. The compound of claim 9, wherein R$^1$ is selected from the group consisting of pyrazolyl, pyridyl, pyrimidinyl, imidazolyl, thiazolyl, thiadiazolyl and pyrazinyl; and wherein the group —X$^1$—R$^1$ is optionally substituted with 1 to 4 R$^x$ substituents.

11. The compound of claim 1, or a pharmaceutically acceptable salt thereof, wherein R$^1$ is C$_{6-10}$ aryl; and wherein the group —X$^1$—R$^1$ is optionally substituted with 1 to 4 R$^x$ substituents.

12. The compound of claim 11, wherein R$^1$ is phenyl; and wherein the group —X$^1$—R$^1$ is optionally substituted with 1 to 4 R$^x$ substituents.

13. The compound of claim 1, or a pharmaceutically acceptable salt thereof, wherein R$^1$ is C$_{3-8}$ cycloalkyl; and wherein the group —X$^1$—R$^1$ is optionally substituted with 1 to 4 R$^x$ substituents.

14. The compound of claim 13, wherein R$^1$ is selected from the group consisting of cyclobutyl, cyclopentyl and cyclohexyl; and wherein the group —X$^1$—R$^1$ is optionally substituted with 1 to 4 R$^x$ substituents.

15. The compound of claim 1, or a pharmaceutically acceptable salt thereof, wherein R$^1$ is a 4- to 8-membered heterocycloalkyl having from 1 to 2 heteroatoms as ring vertices selected from N, O and S; and wherein the group —X$^1$—R$^1$ is optionally substituted with 1 to 4 R$^x$ substituents.

16. The compound of claim 15, wherein R$^1$ is selected from the group consisting of oxetanyl, tetrahydrofuranyl, tetrahydropyranyl and morpholinyl; and wherein the group —X$^1$—R$^1$ is optionally substituted with 1 to 4 R$^x$ substituents.

17. The compound of claim 1, or a pharmaceutically acceptable salt thereof, wherein R$^1$ is selected from the group consisting of C$_{1-8}$ alkyl, C$_{1-8}$ alkoxy, C$_{1-8}$ haloalkyl, —C(O)NR$^{1a}$R$^{1b}$, and —CO$_2$R$^{1a}$; wherein R$^{1a}$ and R$^{1b}$ are each independently selected from the group consisting of hydrogen, C$_{1-8}$ alkyl, C$_{6-10}$ aryl, and —C$_{1-6}$ alkylene—C$_{6-10}$ aryl; and wherein the group —X$^1$—R$^1$ is optionally substituted with 1 to 4 R$^x$ substituents.

18. The compound of claim 1, or a pharmaceutically acceptable salt thereof, wherein R$^1$ is selected from the group consisting of phenyl, pyridyl, pyrimidinyl, and pyrazinyl; and wherein the group —X$^1$—R$^1$ is optionally substituted with 1 to 4 R$^x$ substituents.

19. The compound of claim 1, or a pharmaceutically acceptable salt thereof, wherein ring vertices a and b are CH; R$^{2b}$ is H; ring vertex e is C(R$^{2e}$), and R$^{2a}$ and R$^{2e}$ are independently selected from the group consisting of C$_{1-6}$ alkyl, C$_{1-6}$ alkoxy, C$_{1-6}$ haloalkyl, —O—C$_{1-6}$ haloalkyl, —S—C$_{1-6}$ alkyl, —C$_{1-6}$ alkyl—O—C$_{1-6}$ alkyl, —C$_{1-6}$ alkyl—S—C$_{1-6}$ alkyl, CN, and halogen.

20. The compound of claim 1, or a pharmaceutically acceptable salt thereof, wherein ring vertices a and b are CH; R$^{2b}$ is H; ring vertex e is C(R$^{2e}$), and R$^{2a}$ and R$^{2e}$ are independently selected from the group consisting of C$_{1-6}$ alkyl, C$_{1-6}$ alkoxy and halogen.

21. The compound of claim 1, or a pharmaceutically acceptable salt thereof, wherein n is 0, 1 or 2 and each R$^5$, when present, is selected from the group consisting of F, Cl, CN, C$_{1-4}$ alkyl and C$_{1-4}$ alkoxy.

22. The compound of claim 1, or a pharmaceutically acceptable salt thereof, wherein n is 0, 1 or 2 and each R$^5$, when present, is selected from the group consisting of F, Cl, CN, CH$_3$ and OCH$_3$.

23. The compound of claim 1, or a pharmaceutically acceptable salt thereof, wherein m is 0, 1 or 2 and each R$^3$, when present, is C$_{1-4}$ alkyl.

24. The compound of claim 1, or a pharmaceutically acceptable salt thereof, wherein R$^1$ is selected from the group consisting of phenyl or pyridyl, wherein the group —X$^1$—R$^1$ is optionally substituted with 1 to 4 R$^x$ substituents; ring vertices a and b are CH; R$^{2b}$ is H; ring vertex e is C(R$^{2e}$), and R$^{2a}$ and R$^{2e}$ are independently selected from the group consisting of C$_{1-6}$ alkyl, C$_{1-6}$ alkoxy and halogen; m is 0, 1 or 2 and each R$^3$, when present, is CH$_3$, n is 0, 1 or 2 and each $R^5$, when present, is selected from the group consisting of F, Cl, CN, $CH_3$ and $OCH_3$.
25. The compound of claim 1, or a pharmaceutically acceptable salt thereof, wherein $R^1$ is selected from the group consisting of
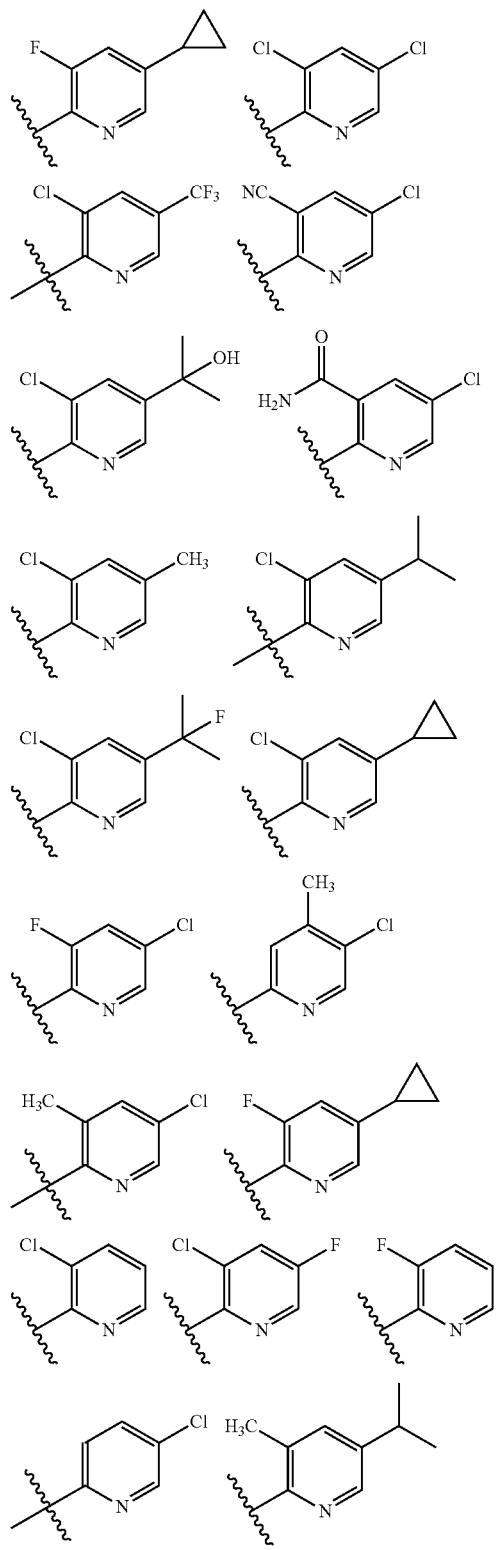
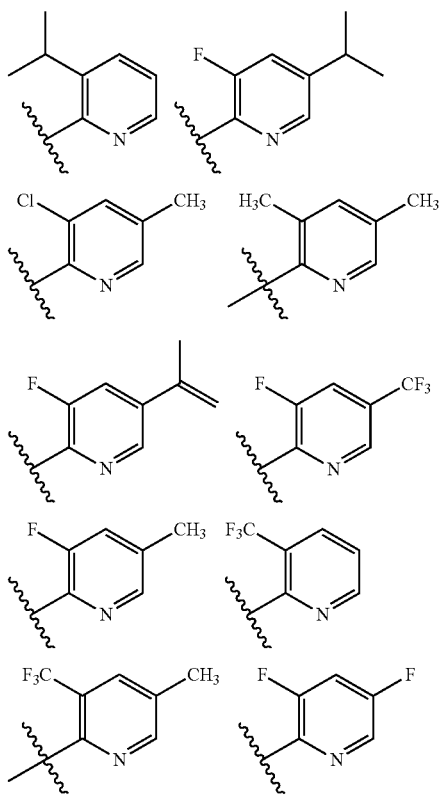
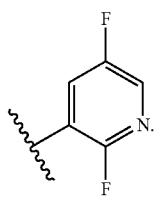
26. The compound of claim 1, or a pharmaceutically acceptable salt thereof, wherein $-X^1-R^1$ is selected from the group consisting of:
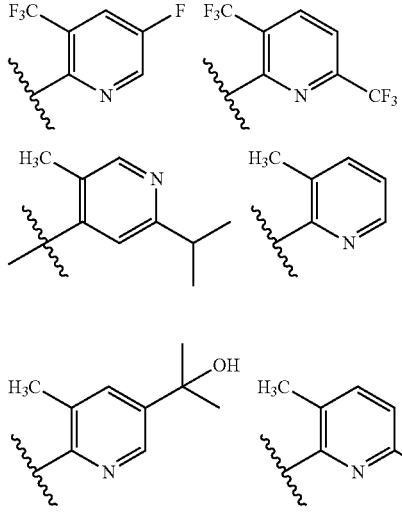

-continued
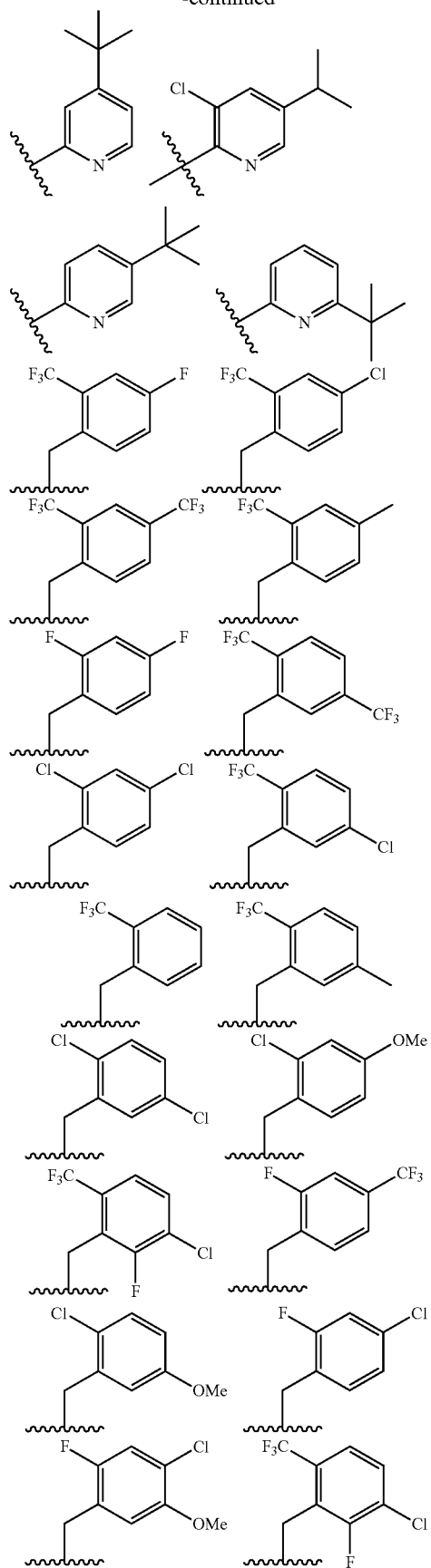
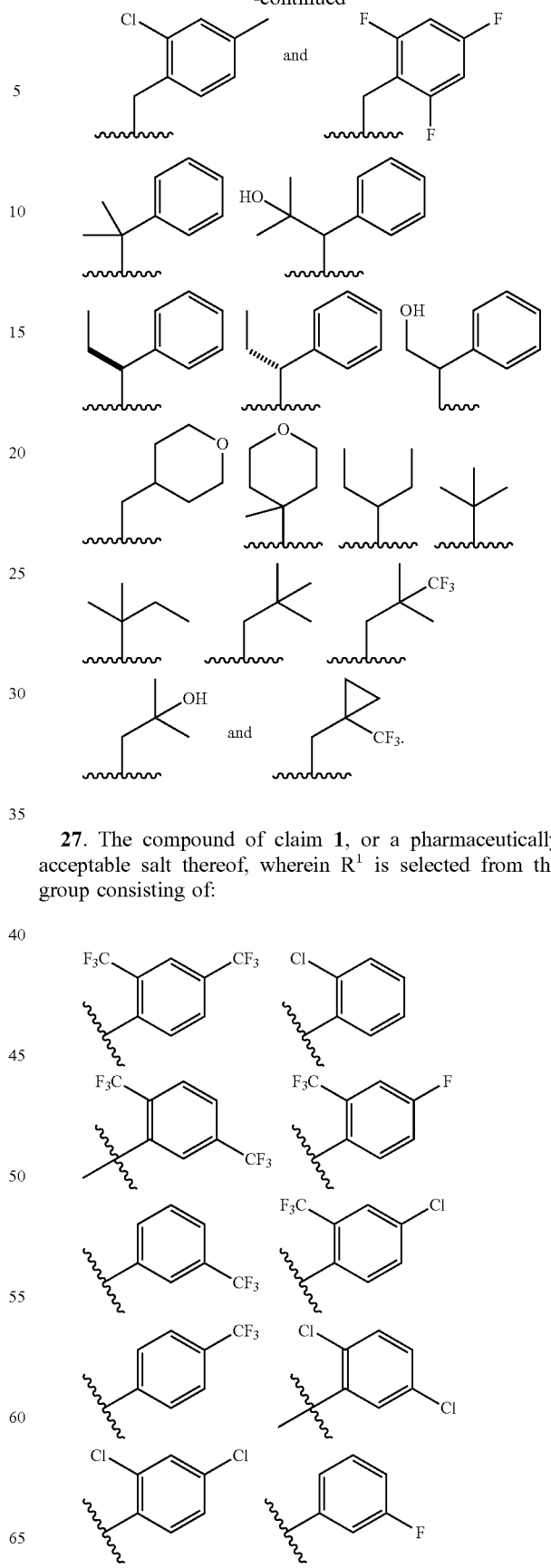
27. The compound of claim 1, or a pharmaceutically acceptable salt thereof, wherein $R^1$ is selected from the group consisting of:

-continued
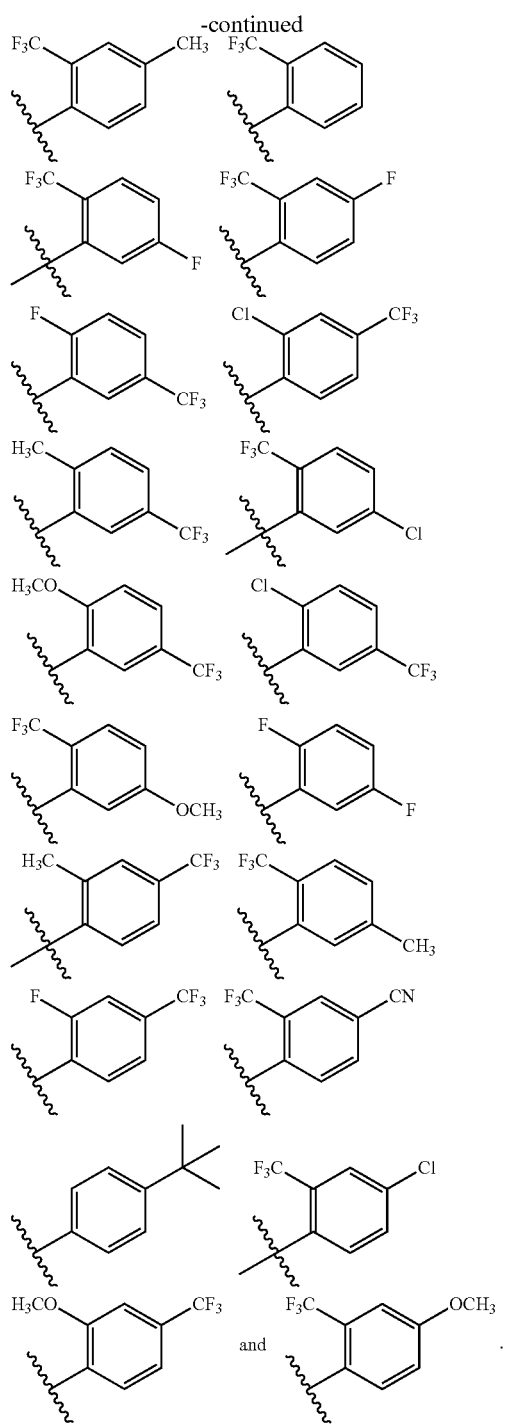
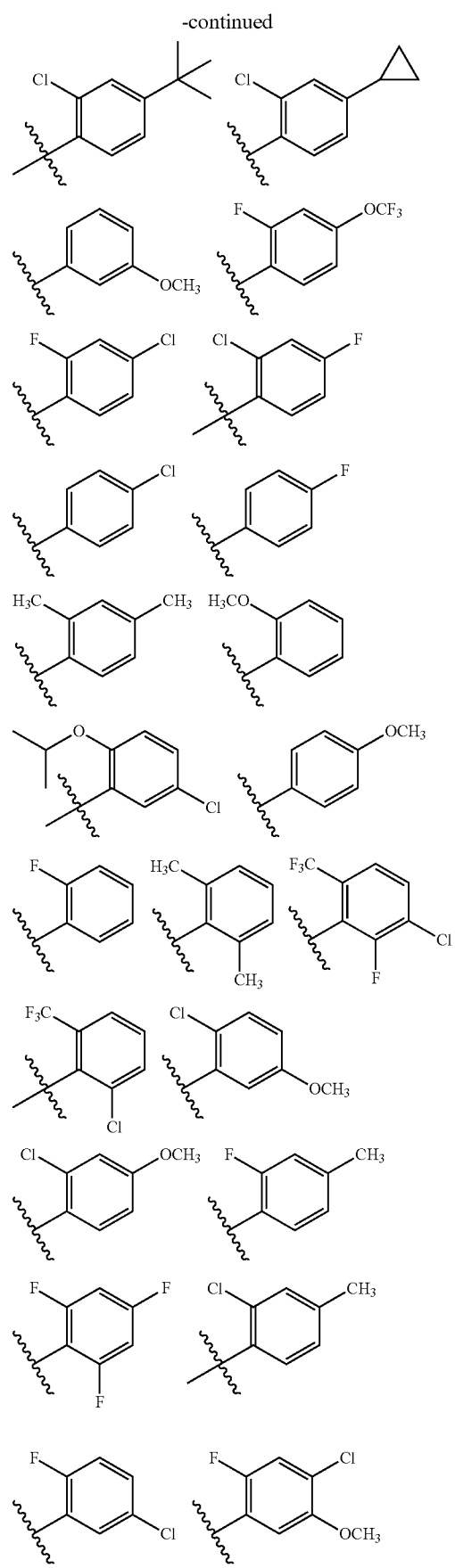
28. The compound of claim 1, or a pharmaceutically acceptable salt thereof, wherein $R^1$ is selected from the group consisting of:
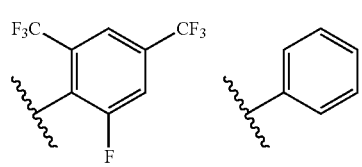

-continued

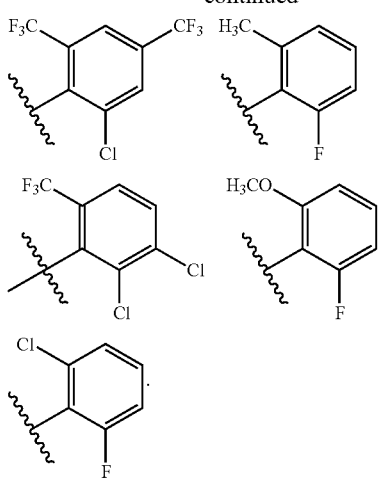

29. The compound of claim 1, or a pharmaceutically acceptable salt thereof, wherein $R^1$ is selected from the group consisting of:

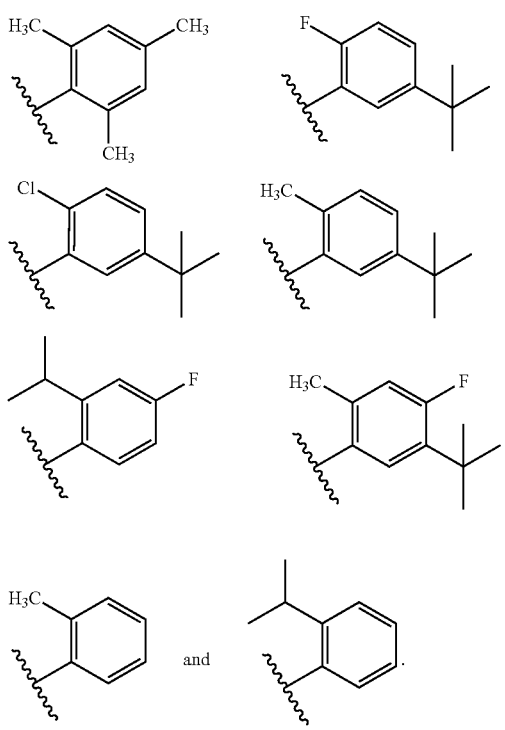

30. The compound of claim 1, or a pharmaceutically acceptable salt thereof, wherein is selected from the group consisting of

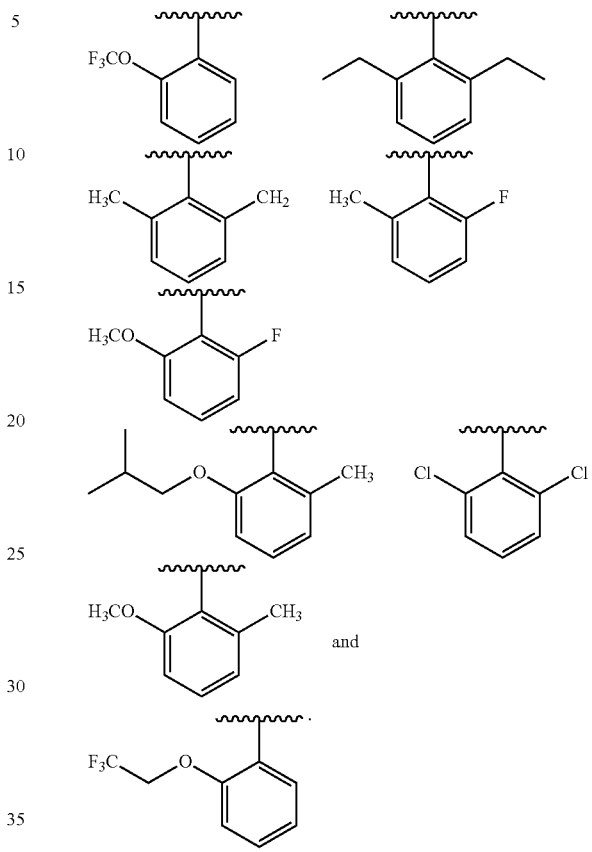

31. The compound of claim 1, or a pharmaceutically acceptable salt thereof, wherein n is 0.

32. The compound of claim 1, or a pharmaceutically acceptable salt thereof, wherein n is 2 and the two $R^3$ groups are on the same carbon atom and are combined to form oxo (=O).

33. A pharmaceutical composition comprising a compound of claim 1, or a pharmaceutically acceptable salt thereof and a pharmaceutically acceptable carrier.

34. The pharmaceutical composition of claim 33, formulated for oral, intravenous, transdermal or subcutaneous administration.

35. The pharmaceutical composition of claim 33, further comprising one or more additional therapeutic agents.

36. The pharmaceutical composition of claim 35, wherein the one or more additional therapeutic agent is selected from the group consisting of corticosteroids, steroids, immunosuppressants, Immunoglobulin G agonists, Dipeptidyl peptidase IV inhibitors, Lymphocyte function antigen-3 receptor antagonists, Interleukin-2 ligands, Interleukin-1 beta ligand inhibitors, IL-2 receptor alpha subunit inhibitors, HGF gene stimulators, IL-6 antagonists, IL-5 antagonists, Alpha 1 antitrypsin stimulators, Cannabinoid receptor antagonists, Histone deacetylase inhibitors, AKT protein kinase inhibitors, CD20 inhibitors, Abl tyrosine kinase inhibitors, JAK tyrosine kinase inhibitors, TNF alpha ligand inhibitors, Hemoglobin modulators, TNF antagonists, proteasome inhibitors, CD3 modulators, Hsp 70 family inhibitors, Immunoglobulin agonists, CD30 antagonists, tubulin

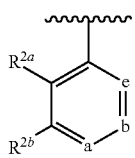

antagonists, Sphingosine-1-phosphate receptor-1 agonists, connective tissue growth factor ligand inhibitors, caspase inhibitors, adrenocorticotrophic hormone ligands, Btk tyrosine kinase inhibitors, Complement C1s subcomponent inhibitors, Erythropoietin receptor agonists, B-lymphocyte stimulator ligand inhibitors, Cyclin-dependent kinase-2 inhibitors, P-selectin glycoprotein ligand-1 stimulators, mTOR inhibitors, Elongation factor 2 inhibitors, Cell adhesion molecule inhibitors, Factor XIII agonists, Calcineurin inhibitors, Immunoglobulin G1 agonists, Inosine monophosphate dehydrogenase inhibitors, Complement C1s subcomponent inhibitors, Thymidine kinase modulators, Cytotoxic T-lymphocyte protein-4 modulators, Angiotensin II receptor antagonists, Angiotensin II receptor modulators, TNF superfamily receptor 12A antagonists, CD52 antagonists, Adenosine deaminase inhibitors, T-cell differentiation antigen CD6 inhibitors, FGF-7 ligands, dihydroorotate dehydrogenase inhibitors, Syk tyrosine kinase inhibitors, Interferon type I receptor antagonists, Interferon alpha ligand inhibitors, Macrophage migration inhibitory factor inhibitors, Integrin alpha-V/beta-6 antagonists, Cysteine protease stimulators, p38 MAP kinase inhibitors, TP53 gene inhibitors, Shiga like toxin I inhibitors, Fucosyltransferase 6 stimulators, Interleukin 22 ligands, IRS1 gene inhibitors, Protein kinase C stimulators, Protein kinase C alpha inhibitors, CD74 antagonists, Immunoglobulin gamma Fc receptor IIB antagonists, T-cell antigen CD7 inhibitors, CD95 antagonists, N acetylmannosamine kinase stimulators, Cardiotrophin-1 ligands, Leukocyte elastase inhibitors, CD40 ligand receptor antagonists, CD40 ligand modulators, IL-17 antagonists, TLR-2 antagonists, Mannan-binding lectin serine protease-2 (MASP-2) inhibitors, Factor B inhibitors, Factor D inhibitors, C3aR modulators, C5aR2 modulators, T cell receptor antagonists, PD-1 inhibitors, PD-L1 inhibitors, TIGIT inhibitors, TIM-3 inhibitors, LAG-3 inhibitors, VISTA inhibitors, STING agonists, IDO inhibitors, adenosine receptor modulators, CD39 inhibitors, CD73 inhibitors, antagonists of the chemokine receptors, especially CXCR1, CXCR2, CXCR3, CXCR4, CXCR7, CCR1, CCR2, CCR3, CCR4, CCR5, CCR7, CCR7, CCR9, CX3CR1 and CXCR6, and combinations thereof.

37. The pharmaceutical composition of claim 35, wherein the one or more additional therapeutic agent is selected from the group consisting of obinutuzumab, rituximab, ocrelizumab, cyclophosphamide, prednisone, hydrocortisone, hydrocortisone acetate, cortisone acetate, tixocortol pivalate, prednisolone, methylprednisolone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, halometasone, alclometasone dipropionate, beclomethasone, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide and prednicarbate, GB-0998, immuglo, begelomab, alefacept, aldesleukin, gevokizumab, daclizumab, basiliximab, inolimomab, beperminogene perplasmid, sirukumab, tocilizumab, clazakizumab, mepolizumab, fingolimod, panobinostat, triciribine, nilotinib, imatinib, tofacitinib, momelotinib, peficitinib, itacitinib, infliximab, PEG-bHb-CO, etanercept, ixazomib, bortezomib, muromonab, otelixizumab, gusperimus, brentuximab vedotin, Ponesimod, KRP-203, FG-3019, emricasan, corticotropin, ibrutinib, cinryze, conestat, methoxy polyethylene glycol-epoetin beta, belimumab, blisibimod, atacicept, seliciclib, neihulizumab, everolimus, sirolimus, denileukin diftitox, LMB-2, natalizumab, catridecacog, ciclosporin, tacrolimus, voclosporin, voclosporin, canakinumab, mycophenolate, mizoribine, CE-1145, TK-DLI, abatacept, belatacept, olmesartan medoxomil, sparsentan, TXA-127, BIM-023, alemtuzumab, pentostatin, itolizumab, palifermin, leflunomide, PRO-140, cenicriviroc, fostamatinib, anifrolumab, sifalimumab, BAX-069, BG-00011, losmapimod, QPI-1002, ShigamAbs, TZ-101, F-652, reparixin, ladarixin, PTX-9908, aganirsen, APH-703, sotrastaurin, sotrastaurin, milatuzumab, SM-101, T-Guard, APG-101, DEX-M74, cardiotrophin-1, tiprelestat, ASKP-1240, BMS-986004, HPH-116, KD-025, OPN-305, TOL-101, defibrotide, pomalidomide, Thymoglobulin, laquinimod, remestemcel-L, Equine antithymocyte immunoglobulin, Stempeucel, LIV-Gamma, Octagam 10%, t2c-001, 99mTc-sestamibi, Clairyg, Prosorba, pomalidomide, laquinimod, teplizumab, FCRx, solnatide, foralumab, ATIR-101, BPX-501, ACP-01, ALLO-ASC-DFU, irbesartan+propagermanium, ApoCell, cannabidiol, RGI-2001, saratin, anti-CD3 bivalent antibody-diphtheria toxin conjugate, NOX-100, LT-1951, OMS721, ALN-CCS, ACH-4471, AMY-101, Acthar gel, and CD4+CD25+ regulatory T-cells, MEDI7814, P32, P59, pembrolizumab, nivolumab, atezolizumab, avelumab, durvalumab, CCX354, CCX721, CCX9588, CCX140, CCX872, CCX598, CCX6239, CCX587, CCX624, CCX282, CCX025, CCX507, CCX430, CCX765, CCX758, CCX771, CCX662, CCX650, and combinations thereof.

38. A method of treating a human suffering from or susceptible to a disease or disorder involving pathologic activation of C5a receptors, comprising administering to the mammal a therapeutically effective amount of a compound of claim 1.

39. The method of claim 38, wherein the disease or disorder is selected from the group consisting of neutropenia, neutrophilia, Wegener's granulomatosis, microscopic polyangiitis, C3-glomerulopathy, C3-glomerulonephritis, dense deposit disease, membranoproliferative glomerulonephritis, Kawasaki disease, sepsis, septic shock, Hemolytic uremic syndrome, atypical hemolytic uremic syndrome (aHUS), Alzheimer's disease, multiple sclerosis, stroke, inflammatory bowel disease, chronic obstructive pulmonary disorder, inflammation associated with burns, lung injury, osteoarthritis, atopic dermatitis, chronic urticaria, ischemia-reperfusion injury, acute respiratory distress syndrome, systemic inflammatory response syndrome, multiple organ dysfunction syndrome, Uveitis, tissue graft rejection, hyperacute rejection of transplanted organs, myocardial infarction, coronary thrombosis, vascular occlusion, post-surgical vascular reocclusion, artherosclerosis, polypoidal choroidal vasculopathy, traumatic central nervous system injury, ischemic heart disease, rheumatoid arthritis, systemic lupus erythematosus, Guillain-Barre syndrome, pancreatitis, lupus nephritis, lupus glomerulonephritis, psoriasis, Crohn's disease, vasculitis, ANCA vasculitis, irritable bowel syndrome, dermatomyositis, multiple sclerosis, bronchial asthma, pemphigus, pemphigoid, scleroderma, myasthenia gravis, autoimmune hemolytic and thrombocytopenic states, Goodpasture's syndrome, immuno vasculitis, Graft versus host disease, Paroxysmal nocturnal hemoglobinuria, Sjoegrens syndrome, insulin-dependent diabetes, mellitus, lupus nephropathy, Heyman nephritis, membranous nephritis, glomerulonephritis, IGA nephropathy, Membranoproliferative glomerulonephritis, Antiphospholipid syndrome, Age related macular degeneration; Dry age related macular degeneration, Wet age related macular degeneration, Motor neurone disease, contact sensitivity responses, hidradenitis suppurativa, and inflammation resulting from contact of blood with artificial surfaces.
40. The compound of claim 1, or a pharmaceutically acceptable salt thereof, having the structure selected from
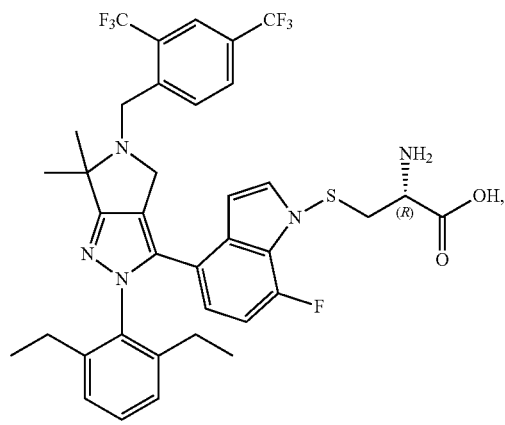
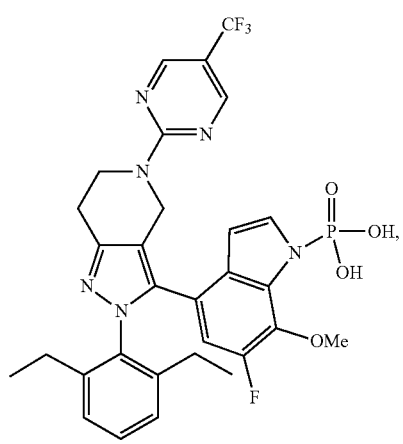
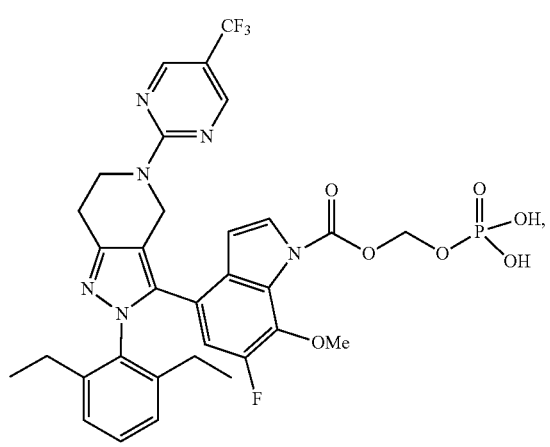
-continued
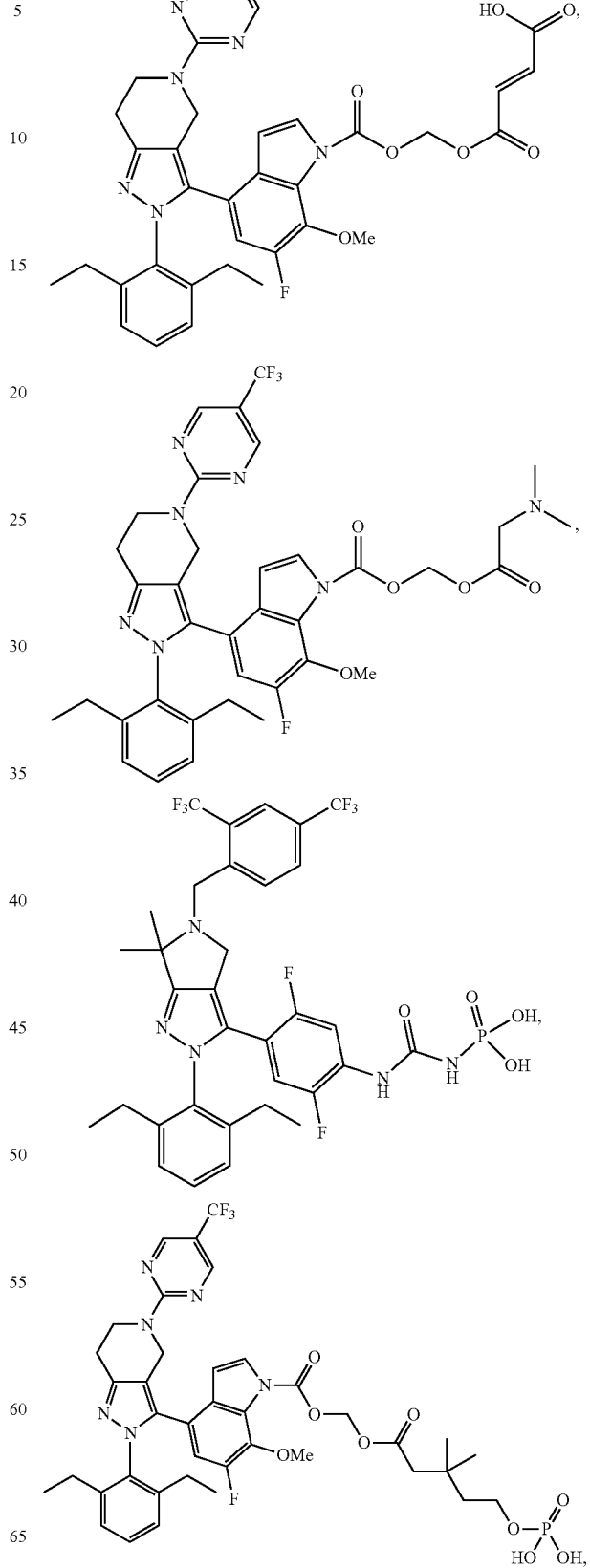

221
-continued
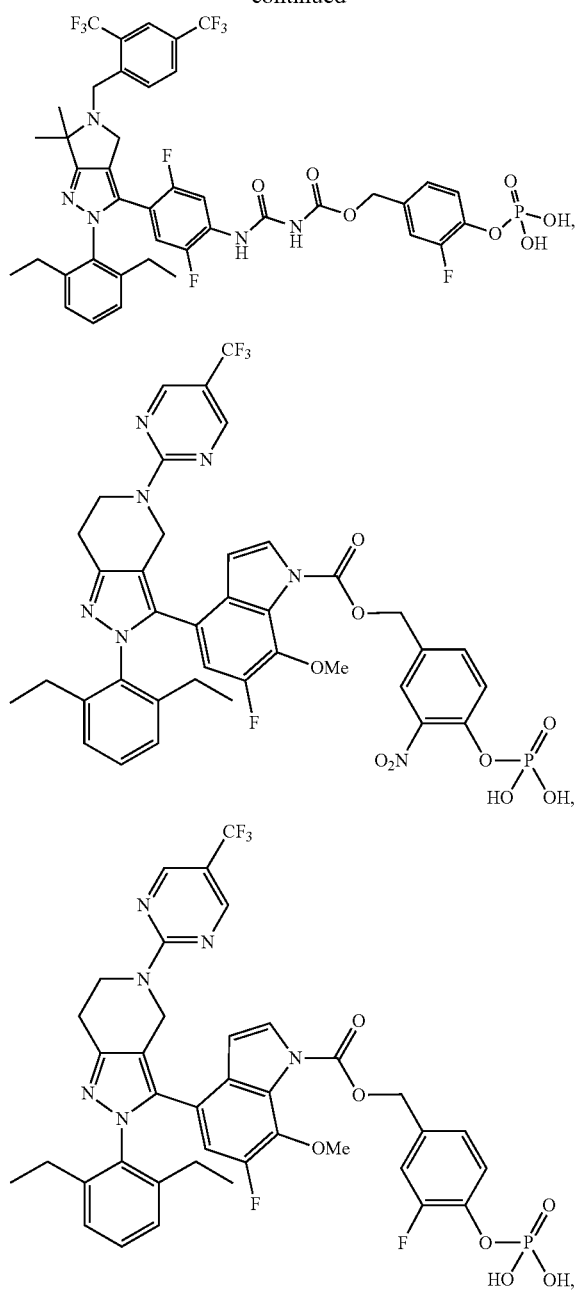
222
-continued
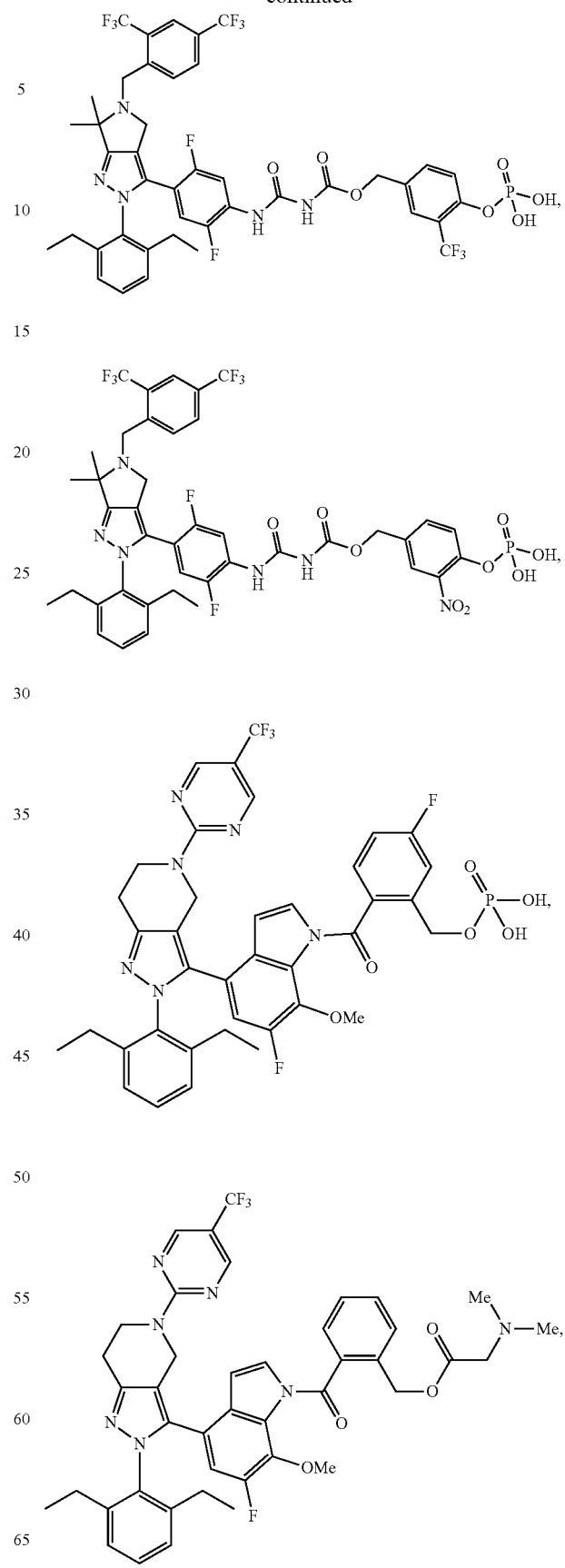

223
-continued
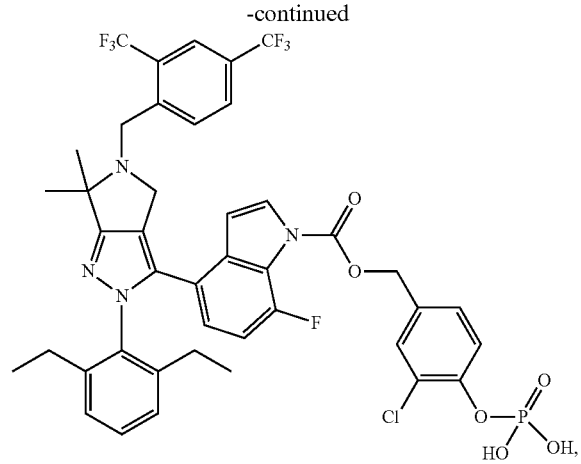
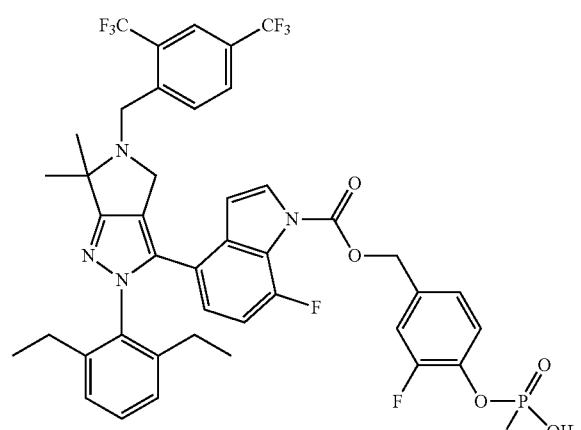
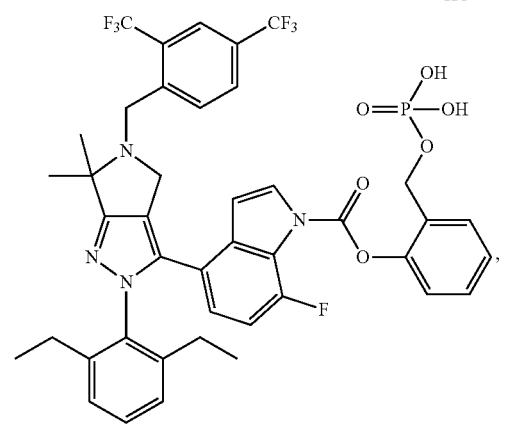
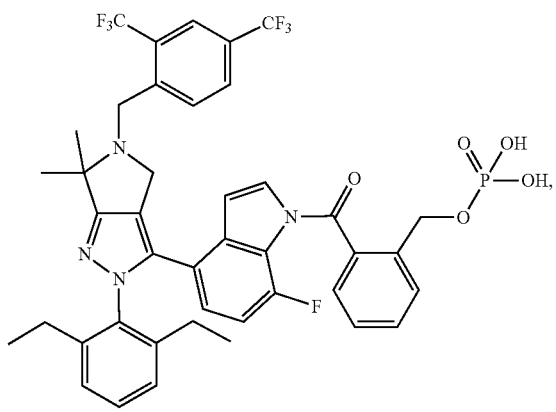
224
-continued
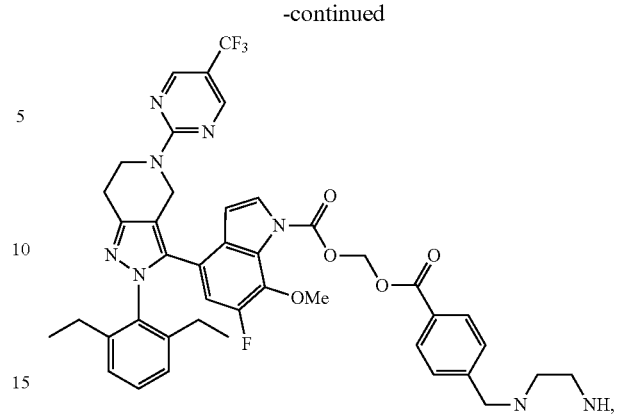
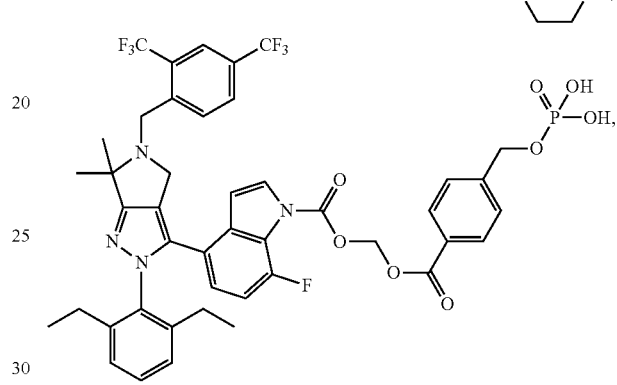
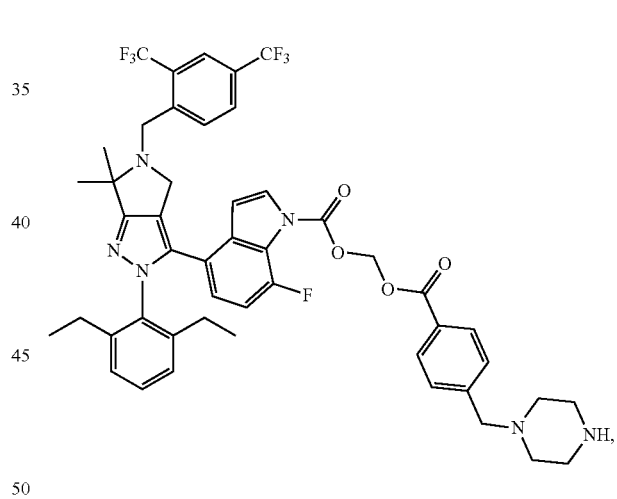
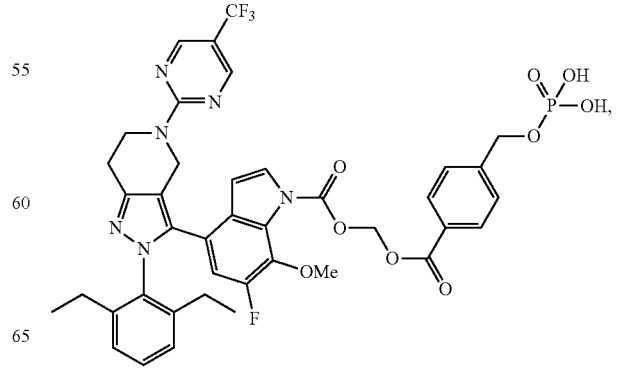

225
-continued
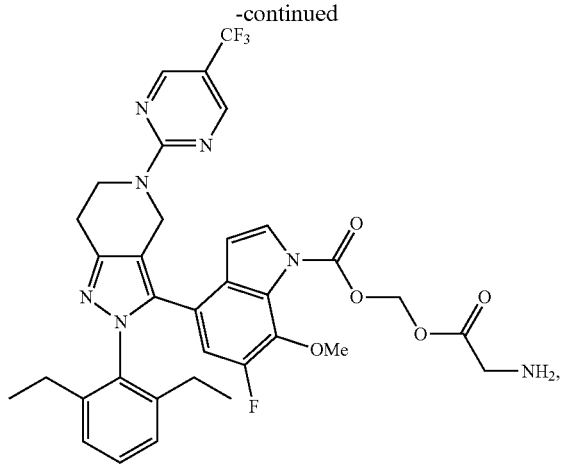
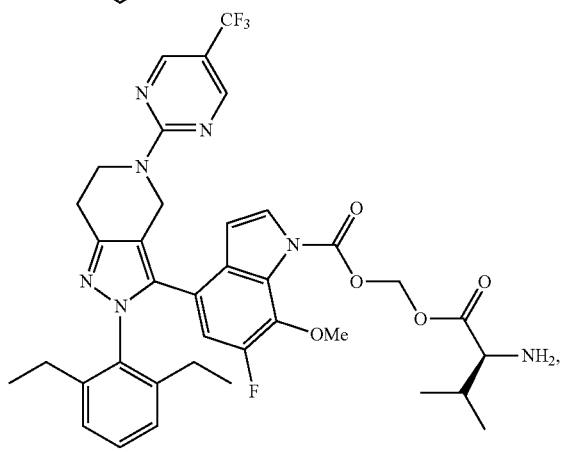
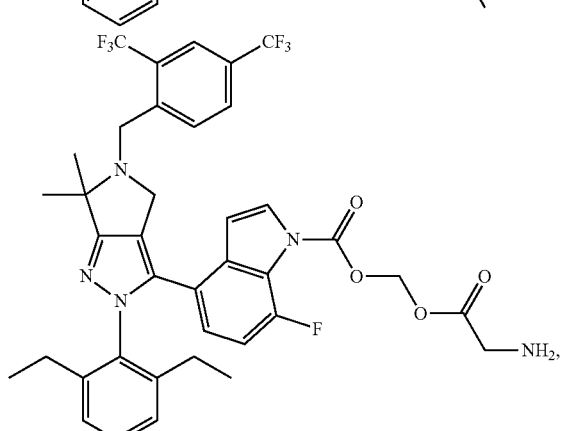
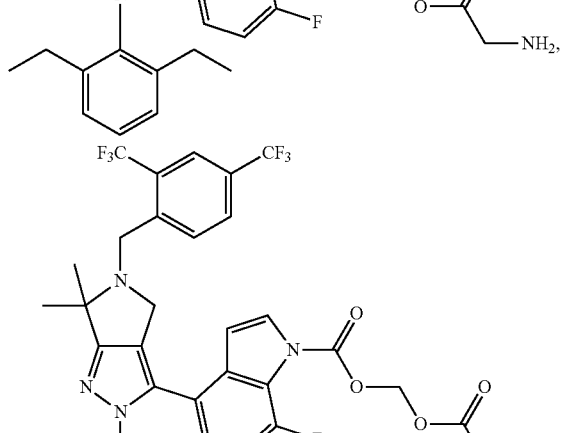
226
-continued
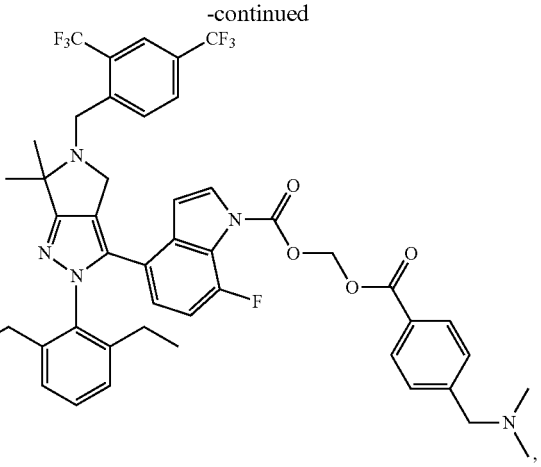
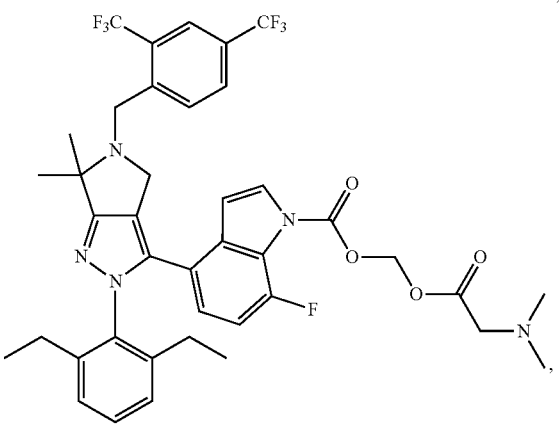
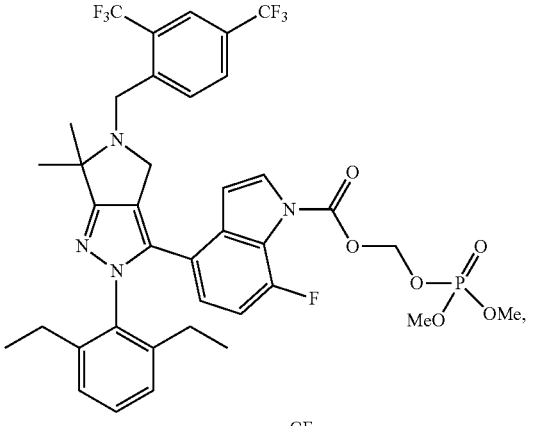
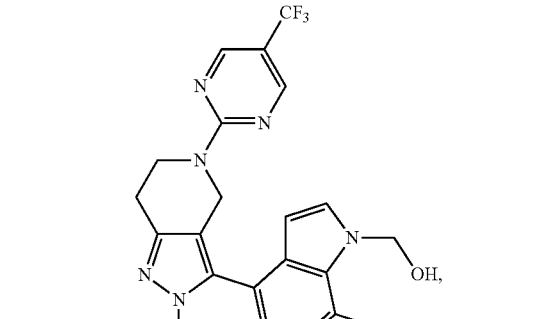

227
-continued
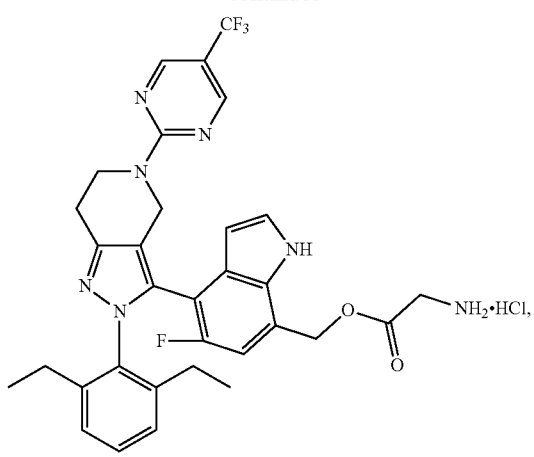
228
-continued
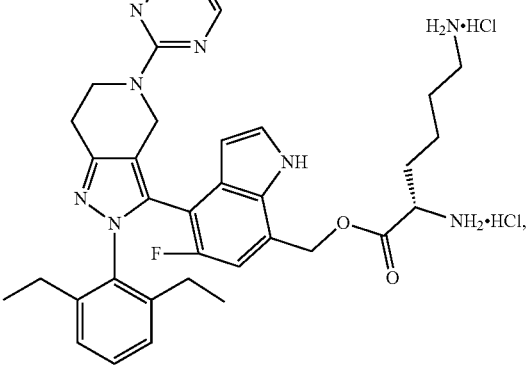
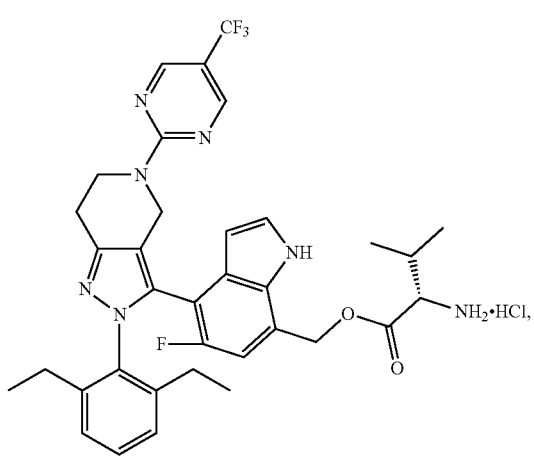
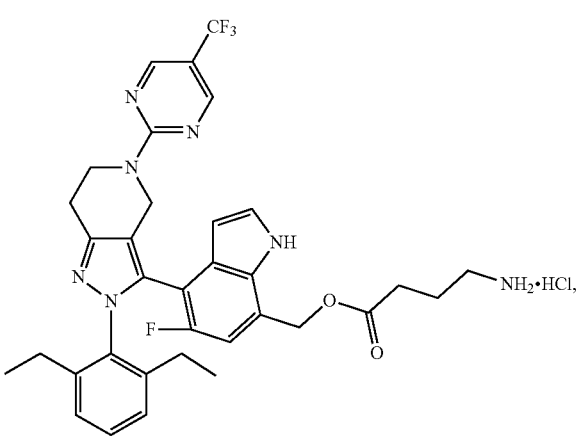
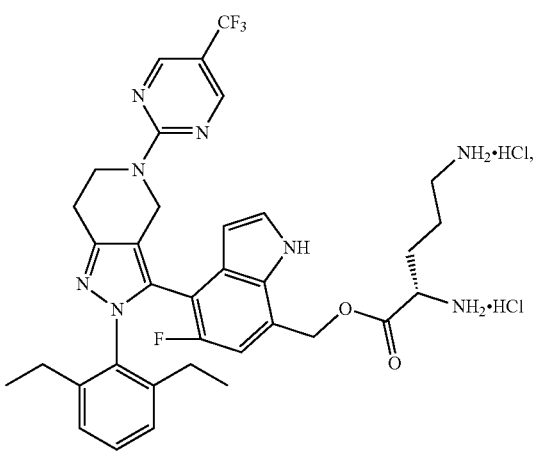
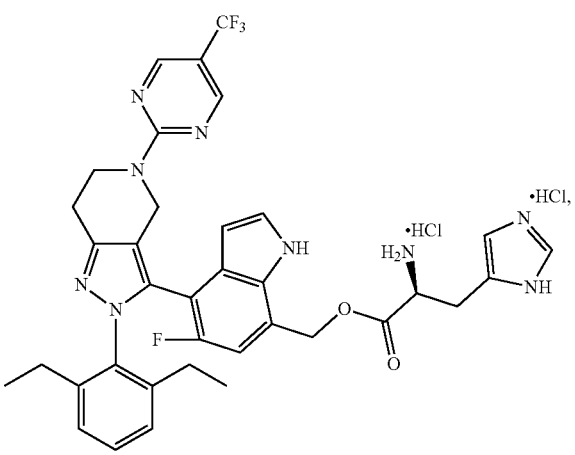

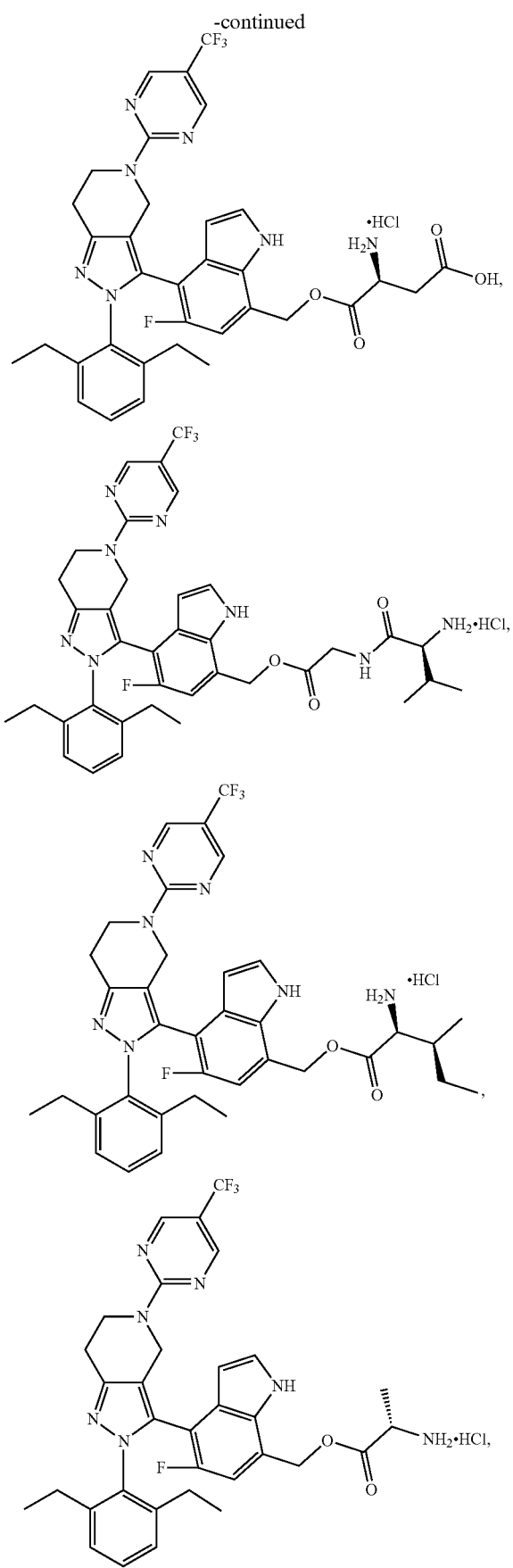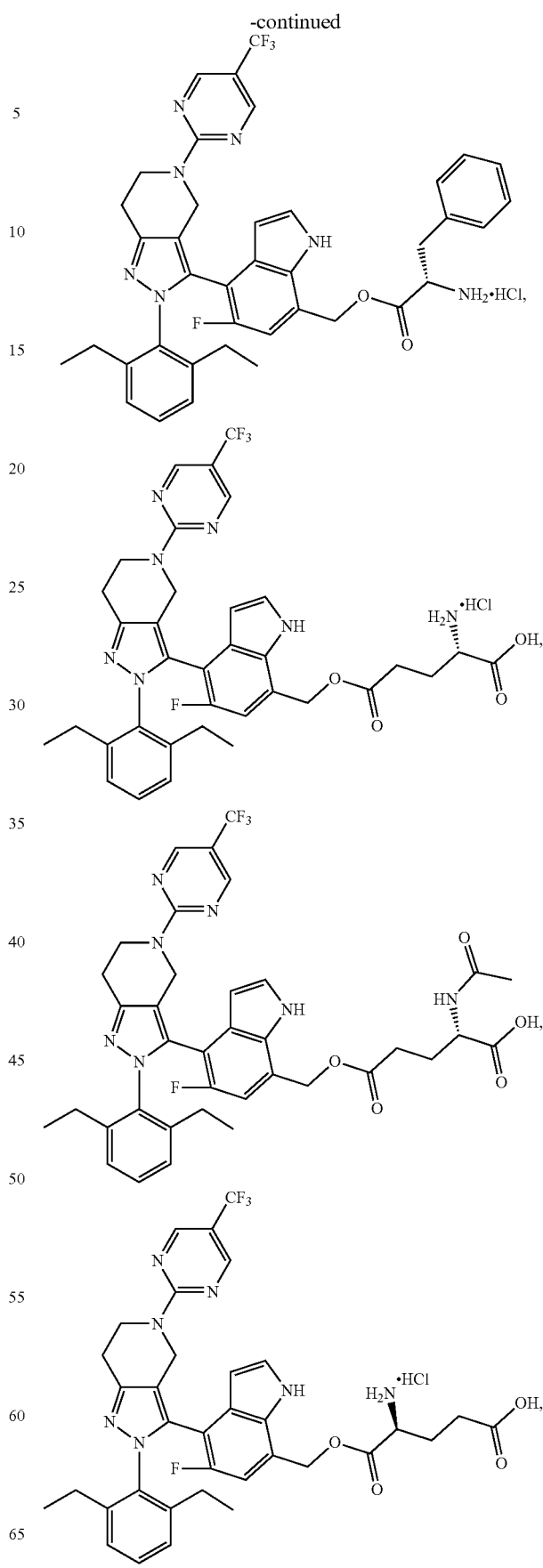

231
-continued
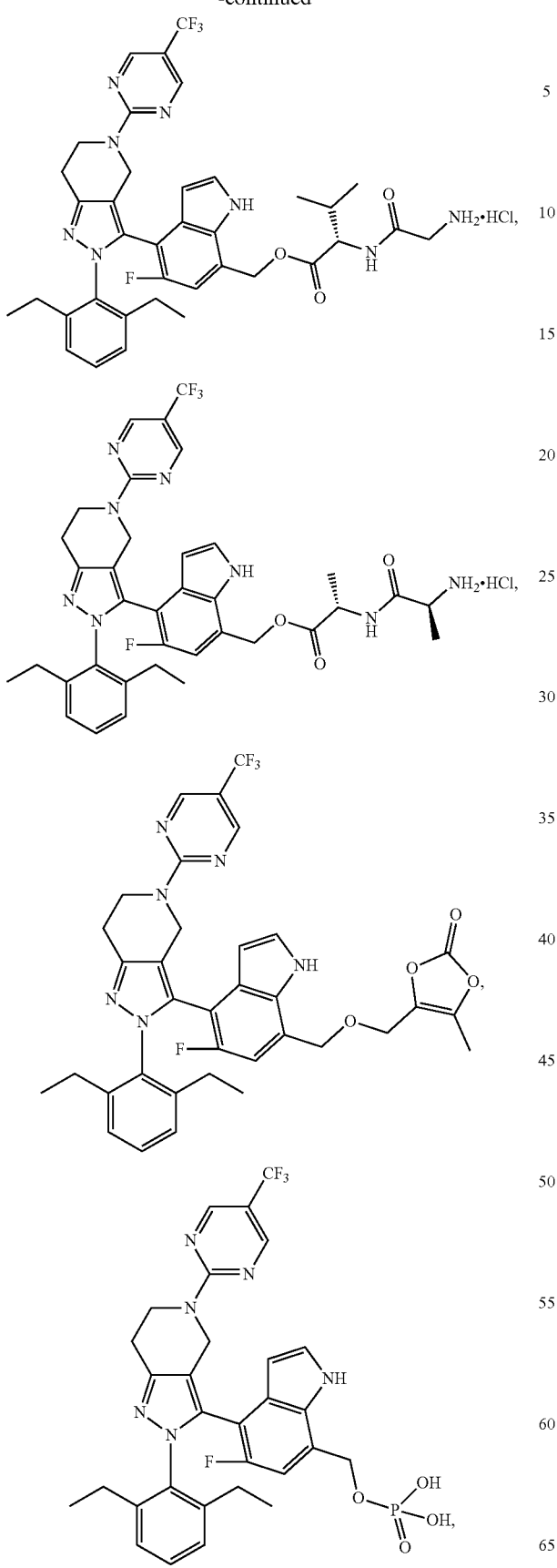
232
-continued
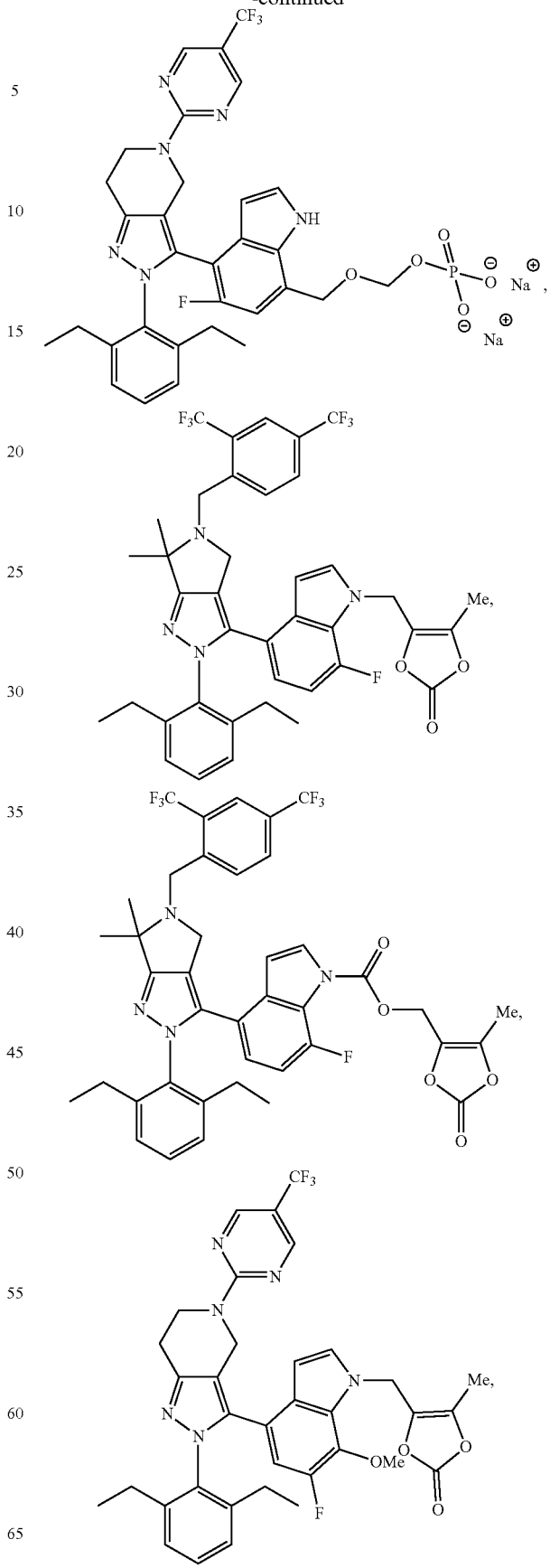

233
-continued
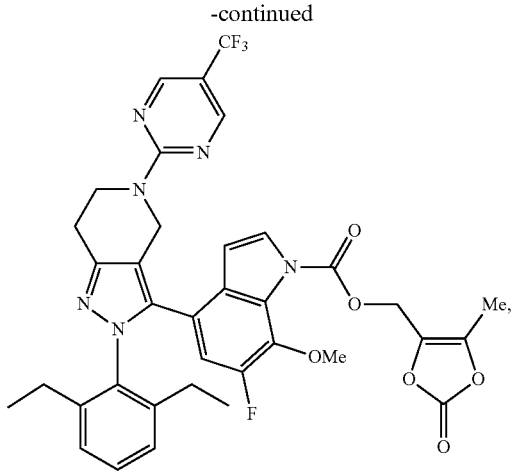
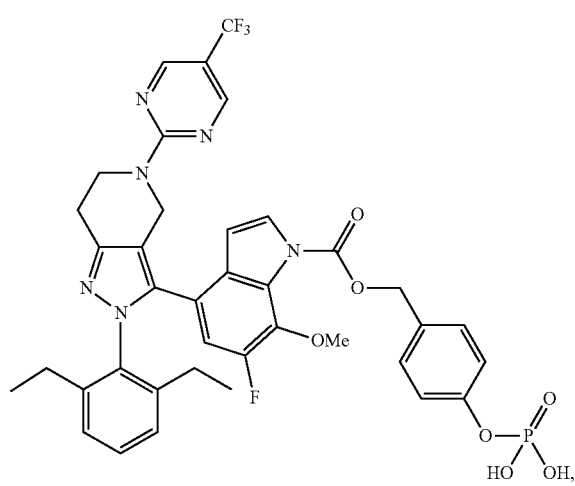
234
-continued
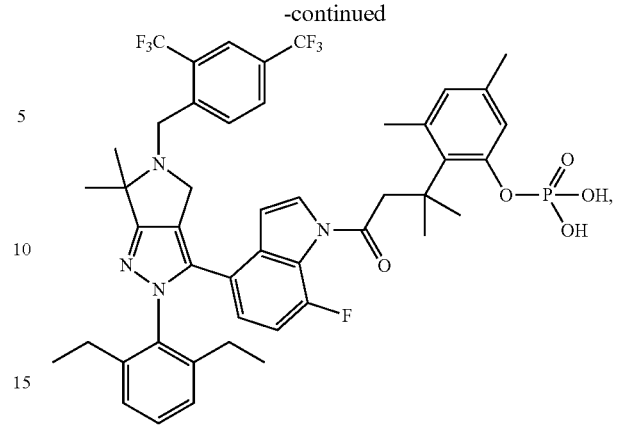
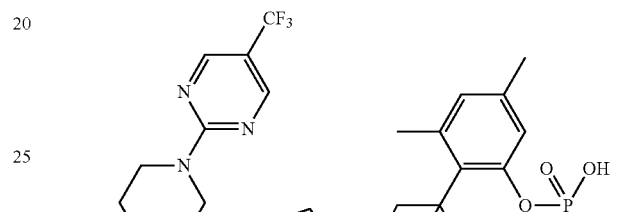
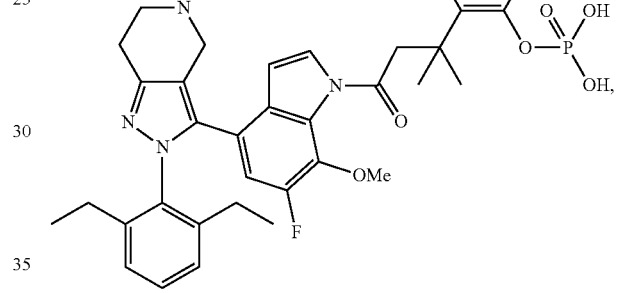
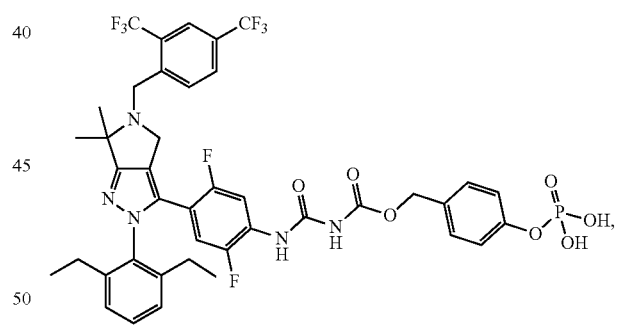
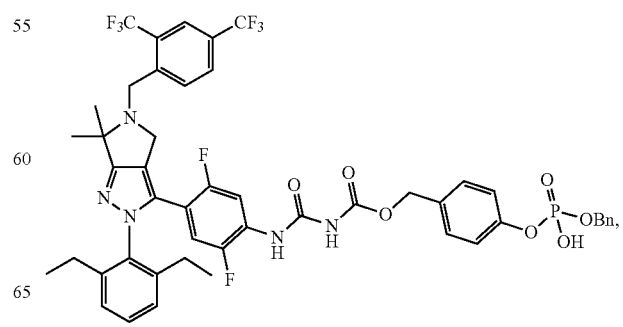

-continued
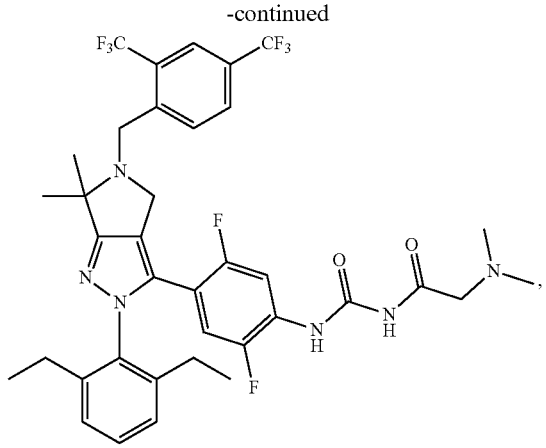
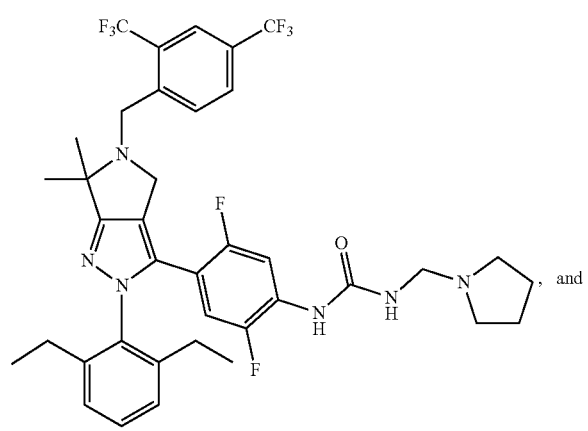, and
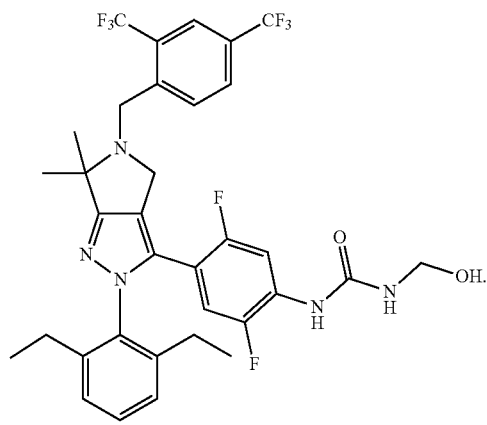
41. The compound of claim 40, or a pharmaceutically acceptable salt thereof, having the structure
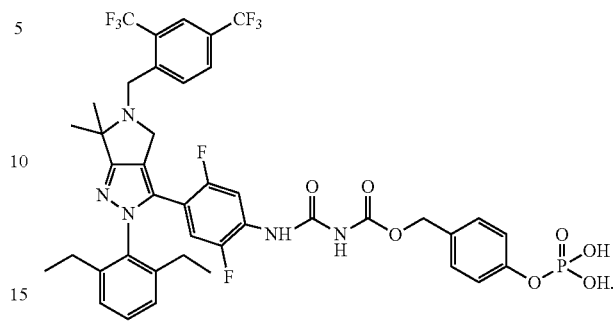
42. The compound of claim 40, or a pharmaceutically acceptable salt thereof, having the structure
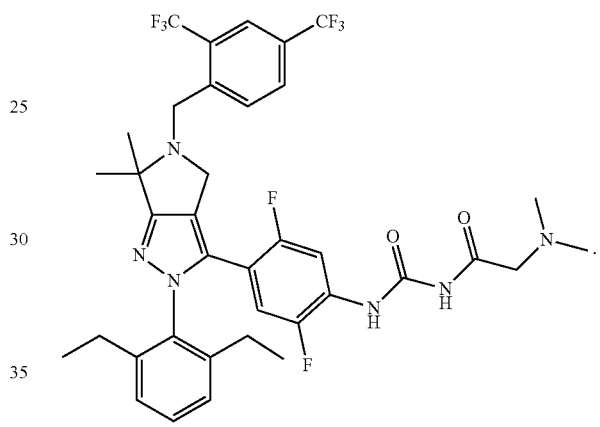
43. The compound of claim 40, or a pharmaceutically acceptable salt thereof, having the structure
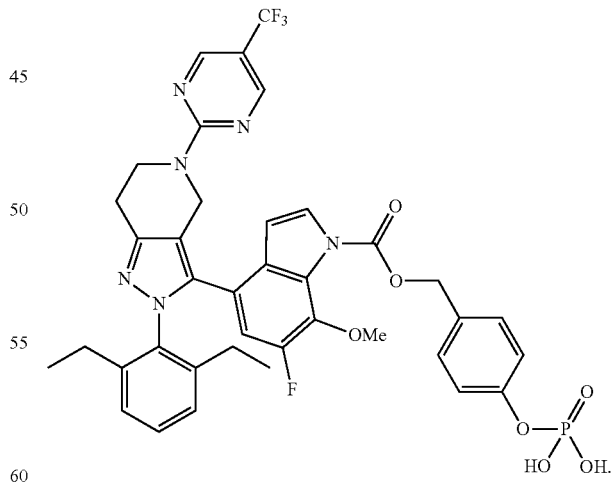
* * * * *